US012674179B2

(12) United States Patent
Pettitt et al.

(10) Patent No.: US 12,674,179 B2
(45) Date of Patent: Jul. 7, 2026

(54) ANTI-CANCER VACCINES AND RELATED THERAPY

(71) Applicant: The Institute of Cancer Research: Royal Cancer Hospital, London (GB)

(72) Inventors: Stephen Pettitt, London (GB); Christopher Lord, London (GB); Marco Punta, London (GB); Alan Melcher, London (GB)

(73) Assignee: The Institute of Cancer Research: Royal Cancer Hospital, London (GB)

( * ) Notice: Subject to any disclaimer, the term of this patent is extended or adjusted under 35 U.S.C. 154(b) by 770 days.

(21) Appl. No.: 17/921,837

(22) PCT Filed: Apr. 28, 2021

(86) PCT No.: PCT/EP2021/061184
§ 371 (c)(1),
(2) Date: Oct. 27, 2022

(87) PCT Pub. No.: WO2021/219750
PCT Pub. Date: Nov. 4, 2021

(65) Prior Publication Data
US 2023/0173048 A1     Jun. 8, 2023

(30) Foreign Application Priority Data

Apr. 28, 2020     (GB) ...................................... 2006254

(51) Int. Cl.
| | |
|---|---|
| *A61K 40/42* | (2025.01) |
| *A61K 35/17* | (2015.01) |
| *A61K 40/11* | (2025.01) |
| *A61K 40/31* | (2025.01) |
| *A61P 35/00* | (2006.01) |
| *C12N 15/86* | (2006.01) |
| *C12N 15/90* | (2006.01) |

(52) U.S. Cl.
CPC .............. *C12N 15/86* (2013.01); *A61K 35/17* (2013.01); *A61K 40/11* (2025.01); *A61K 40/31* (2025.01); *A61K 40/4201* (2025.01); *A61P 35/00* (2018.01); *C12N 15/902* (2013.01)

(58) Field of Classification Search
None
See application file for complete search history.

(56) References Cited

U.S. PATENT DOCUMENTS

| | | | | |
|---|---|---|---|---|
| 7,097,977 | B1 * | 8/2006 | Takeda | .................... A61P 35/00 435/325 |
| 2012/0040366 | A1 * | 2/2012 | Holt | ..................... C12Q 1/6886 530/391.1 |
| 2019/0224236 | A1 * | 7/2019 | Riddell | .................. A61K 40/32 |

FOREIGN PATENT DOCUMENTS

| | | |
|---|---|---|
| JP | 2019-516754 | 6/2019 |
| JP | 2019-517577 | 6/2019 |
| WO | WO 2017/202949 A1 | 11/2017 |
| WO | WO 2017/205810 A1 | 11/2017 |
| WO | WO 2020/022902 A1 | 1/2020 |

OTHER PUBLICATIONS

Afghahi et al., Tumour BRCA1 Reversion Mutation Arising during Neoadjuvant Platinum-Based Chemotherapy in Triple-Negative Breast Cancer Is Associated with Therapy Resistance. *Clin Cancer Res* 23:3365-3370, 2017 (Author manuscript version, 16 pages).

Alsop et al., BRCA mutation frequency and patterns of treatment response in BRCA mutation-positive women with ovarian cancer: a report from the Australian Ovarian Cancer Study Group. *J Clin Oncol* 30:2654-2663. 2012.

Bailey et al., Genomic analyses identify molecular subtypes of pancreatic cancer. *Nature* 531:47-52, 2016.

Banda et al., Somatic Reversion of Germline BRCA2 Mutation Confers Resistance to Poly(ADP-ribose) Polymerase Inhibitor Therapy. *JCO Precision Oncology*, 1-6, 2018.

Barber et al., Secondary mutations in BRCA2 associated with clinical resistance to a PARP inhibitor. *J Pathol* 229:422-429, 2013.

Bhargava et al., Regulation of Single-Strand Annealing and its Role in Genome Maintenance. *Trends in Genetics* 32:566-575, 2016.

Cancer Genome Atlas Network, Comprehensive molecular portraits of human breast tumours. *Nature* 490:61-70, 2012.

Cancer Genome Atlas Research Network, Integrated genomic analyses of ovarian carcinoma. *Nature* 474:609-615, 2011.

Carneiro et al., Acquired Resistance to Poly (ADP-ribose) Polymerase Inhibitor Olaparib in BRCA2-Associated Prostate Cancer Resulting From Biallelic BRCA2 Reversion Mutations Restores Both Germline and Somatic Loss-of-Function Mutations. *JCO Precision Oncology*, 1-8, 2018.

Cheng et al., Polyclonal BRCA2 Reversion Mutations Detected in Circulating Tumor DNA After Platinum Chemotherapy in a Patient with Metastatic Prostate Cancer. *JCO Precision Oncology* 1-5, 2018.

(Continued)

*Primary Examiner* — Michail A Belyavsky
(74) *Attorney, Agent, or Firm* — Klarquist Sparkman, LLP

(57) ABSTRACT

The present invention provides an anti-cancer vaccine comprising: (i) at least one peptide comprising the amino acid sequence of a neoantigen encoded by a mutant homologous recombination (HR) DNA repair gene selected from the group: BRCA1, BRCA2, PALB2, CDK12, RAD51B, RAD51C and RAD51D, wherein the mutant gene comprises a reversion mutation; and/or (ii) at least one polynucleotide encoding the at least one peptide of (i). Also provided are engineered T cells that recognise said neoantigen. Related methods and medical uses of the vaccine and/or engineered T cell are provided, including for the treatment of cancers, such as homologous recombination (HR) deficient cancers that acquire PARP inhibitor resistance or platinum resistance by development of reversion mutations in an HR DNA repair gene selected from the group: BRCA1, BRCA2, PALB2, CDK12, RAD51B, RAD51C and RAD51D.

9 Claims, 11 Drawing Sheets

Specification includes a Sequence Listing.

(56)             References Cited

OTHER PUBLICATIONS

Christie et al., Reversion of BRCA1/2 Germline Mutations Detected in Circulating Tumour DNA From Patients With High-Grade Serous Ovarian Cancer. *J Clin Oncol* 35:1274-1280, 2017.

Cline et al., BRCA Challenge: BRCA Exchange as a global resource for variants in BRCA1 and BRCA2. *PLoS Genet* 14:e1007752, 2018 (17 pages).

Cruz et al., RAD51 foci as a functional biomarker of homologous recombination repair and PARP inhibitor resistance in germline BRCA-mutated breast cancer. *Ann Oncol* 29:1203-1210, 2018.

Davies et al., HRDetect is a predictor of BRCA1 and BRCA2 deficiency based on mutational signatures. *Nat Med* 23:517-525, 2017.

Dréan et al., Modeling Therapy Resistance in BRCA1/2-Mutant Cancers. *Mol Cancer Ther* 16:2022-2034, 2017.

Edwards et al., Resistance to therapy caused by intragenic deletion in BRCA2. *Nature* 451:1111-1115, 2008.

Esashi et al., Stabilization of RAD51 nucleoprotein filaments by the C-terminal region of BRCA2. *Nat Struct Mol Biol* 14:468-474, 2007.

Futreal, et al., BRCA1 mutations in primary breast and ovarian carcinomas. *Science* 266:120-122, 1994.

Goodall et al., Circulating Cell-Free DNA to Guide Prostate Cancer Treatment with PARP Inhibition. *Cancer Discov* 7:1006-1017, 2017.

Gornstein et al., BRCA2 Reversion Mutation Associated With Acquired Resistance to Olaparib in Estrogen Receptor-positive Breast Cancer Detected by Genomic Profiling of Tissue and Liquid Biopsy. *Clin Breast Cancer* 18:184-188, 2018.

Gourraud et al., HLA diversity in the 1000 genomes dataset. *PLoS ONE* 9:e97282, 2014 (8 pages).

Grasso et al., The mutational landscape of lethal castration-resistant prostate cancer. *Nature* 487:239-243, 2012.

Holter et al., Germline BRCA Mutations in a Large Clinic-Based Cohort of Patients With Pancreatic Adenocarcinoma. *Journal of Clinical Oncology* 33:3124-3129, 2015.

Ikeda et al., Genetic reversion in an acute myelogenous leukemia cell line from a Fanconi anemia patient with biallelic mutations in BRCA2. *Cancer Res* 63:2688-2694, 2003.

Jurtz, et al., NetMHCpan-4.0: Improved Peptide-MHC Class I Interaction Predictions Integrating Eluted Ligand and Peptide Binding Affinity Data. *J Immunol* 199:3360-3368, 2017.

Khalique et al., Longitudinal analysis of a secondary BRCA2 mutation using digital droplet PCR. *J Pathol Clin Res*, 6:3-11, 2018.

Kondrashova et al., Secondary Somatic Mutations Restoring and Associated with Acquired Resistance to the PARP Inhibitor Rucaparib in High-Grade Ovarian Carcinoma. *Cancer Discov* 7:984-998, 2017.

Lancaster et al., BRCA2 mutations in primary breast and ovarian cancers. *Nat Genet* 13:238-240, 1996.

Landrum et al., ClinVar: improving access to variant interpretations and supporting evidence. *Nucleic acids research* 46:D1062-D1067, 2017.

Lin et al., BRCA Reversion Mutations in Circulating Tumour DNA Predict Primary and Acquired Resistance to the PARP Inhibitor Rucaparib in High-Grade Ovarian Carcinoma. *Cancer Discov* 9:210-219, 2019.

Livingstone and Barton, Protein sequence alignments: a strategy for the hierarchical analysis of residue conservation. *Comput Appl Biosci* 9:745-756, 1993.

Lord and Ashworth, BRCAness revisited. *Nat Rev Cancer* 16:110-120, 2016.

Lord and Ashworth, PARP inhibitors: Synthetic lethality in the clinic. *Science* 355:1152-1158, 2017.

Marty et al., MHC-I Genotype Restricts the Oncogenic Mutational Landscape. *Cell* 171:1272-1283, 2017.

Mayor et al., BRCA1 reversion mutation acquired after treatment identified by liquid biopsy. *Gynecol Oncol Rep* 21:57-60, 2017.

Meijer et al., Direct Ex Vivo Observation of Homologous Recombination Defect Reversal After DNA-Damaging Chemotherapy in Patients With Metastatic Breast Cancer. *JCO Precision Oncology*, 1-12, 2019.

Norquist et al., Secondary somatic mutations restoring BRCA1/2 predict chemotherapy resistance in hereditary ovarian carcinomas. *J Clin Oncol* 29:3008-3015, 2011.

Patch et al., Whole-genome characterization of chemoresistant ovarian cancer. *Nature* 521:489-494, 2015.

Patel et al., Characterisation of homologous recombination deficiency in paired primary and recurrent high-grade serous ovarian cancer. *Br J Cancer* 119:1060-1066, 2018.

Pishvaian et al., BRCA2 secondary mutation-mediated resistance to platinum and PARP inhibitor-based therapy in pancreatic cancer. *Br J Cancer* 116:1021-1026, 2017.

Powell et al., eggNOG v4.0: nested orthology inference across 3686 organisms. *Nucleic acids research* 42:D231-D239, 2014.

Punta et al., The immunogenic potential of recurrent cancer drug resistance mutations: an in silico study. *Front. Immunol.* 11:524968, 2019 (15 pages).

Quigley et al., Analysis of Circulating Cell-Free DNA Identifies Multiclonal Heterogeneity of Reversion Mutations Associated with Resistance to PARP Inhibitors. *Cancer Discov* 7:999-1005, 2017.

Sakai et al., Functional restoration of BRCA2 protein by secondary BRCA2 mutations in BRCA2-mutated ovarian carcinoma. *Cancer Res* 69:6381-6386, 2009.

Sakai et al., Secondary mutations as a mechanism of cisplatin resistance in BRCA2-mutated cancers. *Nature* 451:1116-1120, 2008.

Shroff et al., Rucaparib Monotherapy in Patients With Pancreatic Cancer and a Known Deleterious Mutation. *JCO Precis Oncol*, 1-15, 2018.

Sinha et al., Risky business: Microhomology-mediated end joining. *Mutat Res* 788:17-24, 2016.

Spurdle et al., ENIGMA-Evidence-based network for the interpretation of germline mutant alleles: An international initiative to evaluate risk and clinical significance associated with sequence variation in BRCA1 and BRCA2 genes. *Hum Mutat* 33:2-7, 2011.

Staaf et al., Whole-genome sequencing of triple-negative breast cancers in a population-based clinical study. *Nat Med* 25:1526-1533, 2019.

Swisher et al., Secondary BRCA1 mutations in BRCA1-mutated ovarian carcinomas with platinum resistance. *Cancer Res* 68:2581-2586, 2008 (Author manuscript version, 13 pages).

Ter Brugge et al., Mechanisms of Therapy Resistance in Patient-Derived Xenograft Models of BRCA1-Deficient Breast Cancer. *J Natl Cancer Inst* 108:djw148, 2016 (12 pages).

Tutt, Inhibited, trapped or adducted: the optimal selective synthetic lethal mix for BRCAness. *Annals of oncology* 29:18-21, 2018.

Tutt et al., Carboplatin in BRCA1/2-mutated and triple-negative breast cancer BRCAness subgroups: the TNT Trial. *Nat Med* 24:628-637, 2018.

Waddell et al., Whole genomes redefine the mutational landscape of pancreatic cancer. *Nature* 518:495-501, 2015.

Wang et al., The BRCA1-Δ11q Alternative Splice Isoform Bypasses Germline Mutations and Promotes Therapeutic Resistance to PARP Inhibition and Cisplatin. *Cancer Res* 76:2778-2790, 2016.

Weigelt et al., Diverse BRCA1 and BRCA2 Reversion Mutations in Circulating Cell-Free DNA of Therapy-Resistant Breast or Ovarian Cancer. *Clin Cancer Res* 23:6708-6720, 2017.

Yates et al., Ensembl 2016. *Nucleic acids research* 44:D710-D716, 2016.

Yun and Hiom, CtIP-BRCA1 modulates the choice of DNA double-strand-break repair pathway throughout the cell cycle. *Nature* 459:460-463, 2009.

Hsu et al., "Vaccination of Patients with B-cell Lymphoma Using Autologous Antigen-pulsed Dendritic Cells." *Nature Medicine* 2(1):52-58, 1996.

Jennings et al., "Potentiating Oncolytic Virus-Induced Immune-Mediated Tumour Cell Killing Using Histone Deacetylase Inhibition." *Molecular Therapy* 27(6):1139-52, 2019.

Ott et al., "An Immunogenic Personal Neoantigen Vaccine for Patients with Melanoma." *Nature* 547(7662):217-221, 2017.

(56) References Cited

OTHER PUBLICATIONS

Pettitt and Lord, "Dissecting PARP Inhibitor Resistance with Functional Genomics." *Current Opinion in Genetics & Development* 54:55-63, 2019.
Prestwich et al., "Tumour Infection by Oncolytic Reovirus Primes Adaptive Antitumour Immunity." *Clinical Cancer Research* 14(22):7358-66, 2008 (Author manuscript version, 19 pages).
Walton et al., "CRISPR/Cas9-Derived Models of Ovarian High Grade Serous Carcinoma Targeting Brca1, Pten and Nf1, and Correlation with Platinum Sensitivity." *Scientific Reports* 7(1):16827, 2017 (11 pages).
Walton et al., "CRISPR/Cas9-Mediated Trp53 and Brca2 Knockout to Generate Improved Murine Models of Ovarian High-Grade Serous Carcinoma." *Cancer Research* 76(20):6118-6129, 2016.
Da Cunha Colombo Bonadio et al., "Homologous recombination deficiency in ovarian cancer: a review of its epidemiology and management," *Clinics,* 73(suppl 1):e450s, 2018 (6 pages).
Jayasinghe et al., "Systematic Analysis of Splice-Site-Creating Mutations in Cancer," *Cell Reports,* vol. 23, pp. 270-281, 2018.

Li et al., "Prospects for combining immune checkpoint blockade with PARP inhibition," *Journal of Hematology & Oncology,* 12:98, 2019 (12 pages).
Pettitt et al., "Clinical BRCA1/2 Reversion Analysis Identifies Hotspot Mutations and Predicted Neoantigens Associated with Therapy Resistance," *Cancer Discovery,* vol. 10, No. 10, pp. 1475-1488, 2020.
Pettitt et al., "Targeting neoantigens associated with BRCA1/2 reversion mutations," Basser Center for BRCA 10th Annual Scientific Symposium, available after May 5, 2022 (poster, 1 page).
Shoemaker et al., "Targeting 'Retired Antigens' for Cancer Immunoprevention," *Cancer Prevention Research* 10(11):607-608, Nov. 2017.
Official Action issued in JP 2022-566009 on Apr. 15, 2025 (7 pages).
Noordermeer and Van Attikum, "PARP Inhibitor Resistance: A Tug-of-War in BRCA-Mutated Cells," *Trends in Cell Biology,* vol. 29, No. 10, pp. 820-834, 2019.
Notice of Reasons for Refusal issued for Japanese Application No. 2022-566009, dated Feb. 3, 2026 (6 pages; includes English translation).

* cited by examiner

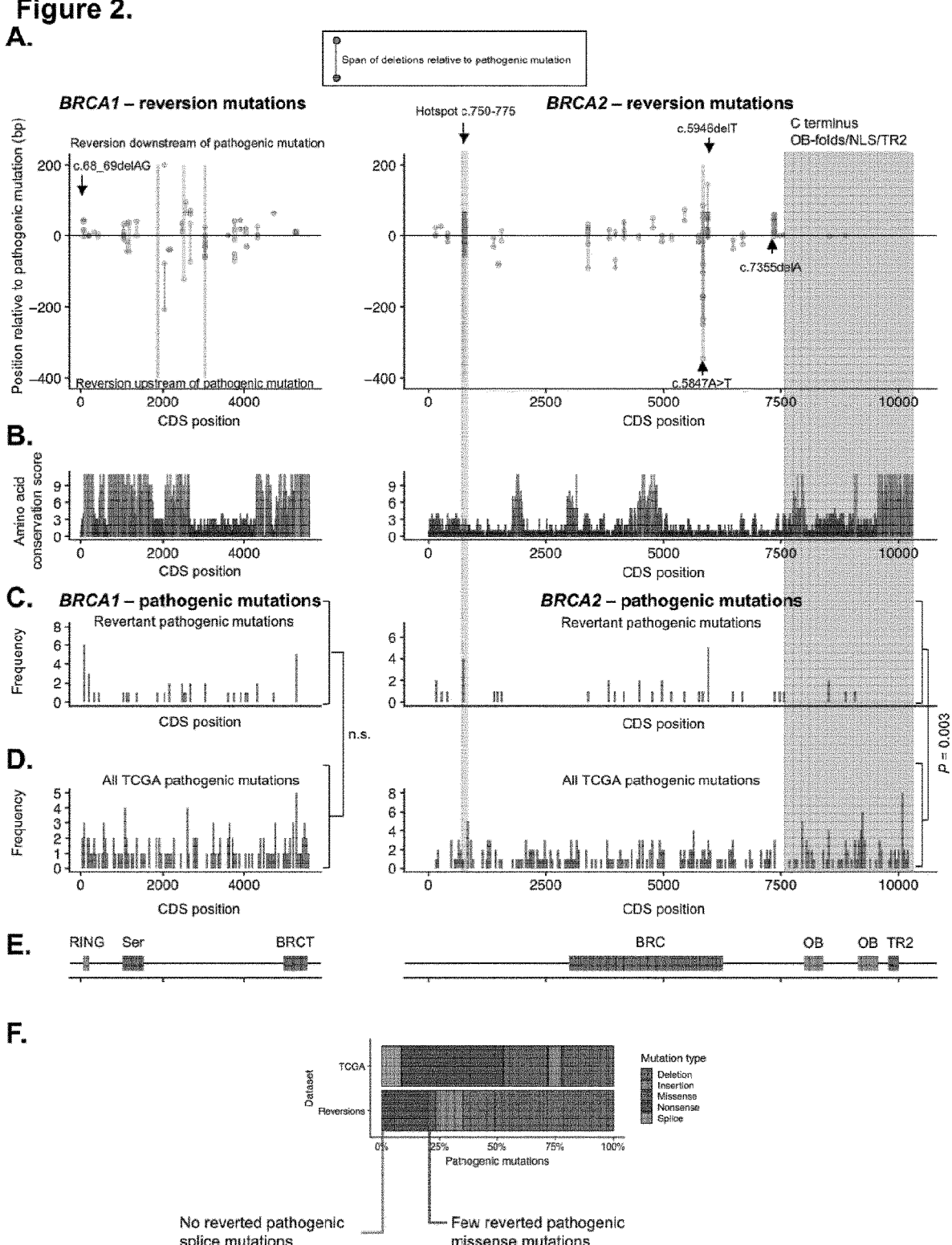

Span of deletions relative to pathogenic mutation

BRCA1 – reversion mutations

Reversion downstream of pathogenic mutation c.68_69delAG

Reversion upstream of pathogenic mutation

Position relative to pathogenic mutation (bp)

CDS position

BRCA2 – reversion mutations

Hotspot c.750-775 c.5946delT

C terminus
OB-folds/NLS/TR2 c.7355delA c.5847A>T

CDS position

B.

Amino acid conservation score

CDS position

C.  BRCA1 – pathogenic mutations

Revertant pathogenic mutations

Frequency

CDS position

BRCA2 – pathogenic mutations

Revertant pathogenic mutations

CDS position

D.

All TCGA pathogenic mutations

Frequency

CDS position

All TCGA pathogenic mutations

CDS position n.s.

P = 0.003

E.

RING   Ser          BRCT

BRC          OB    OB  TR2

F.

Dataset

TCGA

Reversions

0%   25%   50%   75%   100%

Pathogenic mutations

Mutation type
Deletion
Insertion
Missense
Nonsense
Splice

No reverted pathogenic
splice mutations

Few reverted pathogenic
missense mutations

SEQ ID NO:          G>T substitution leading to
                    premature STOP codon (TAA)

Reference *BRCA2* sequence:          1228  CCTGCAGAAGAATCTGAACATAAAAACAACAATTACGAACCAAAC
Pathogenic mutant allele (p.E49X):   1229  CCTGCAGAA⬚TAA⬚TCTGAACATAAAAACAACAATTACGAACCAAAC
Reversion allele (alignment 1):      1230  CCTGCAGAA----------------------------TACGAACCAAAC
Reversion allele (alignment 2)       1230  CCTGCAGAATA----------------------------CGAACCAAAC Reversion (deletion) with flanking TA microhomology

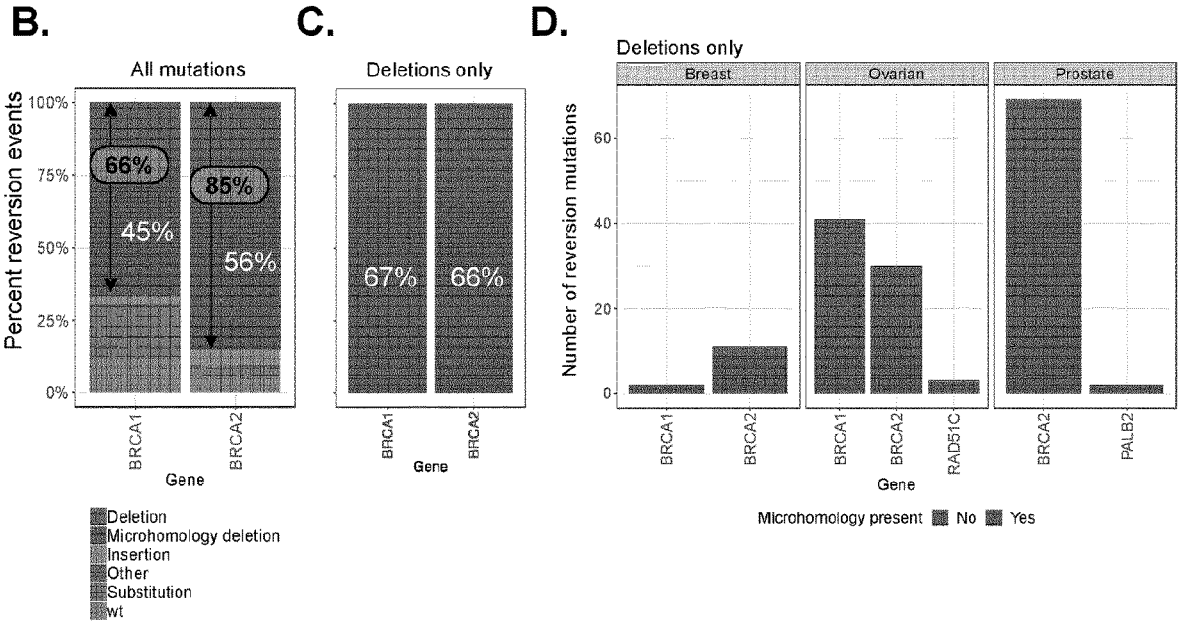

B. All mutations

C. Deletions only

D. Deletions only

Legend:
Deletion
Microhomology deletion
Insertion
Other
Substitution
wt

Microhomology present ■ No ■ Yes

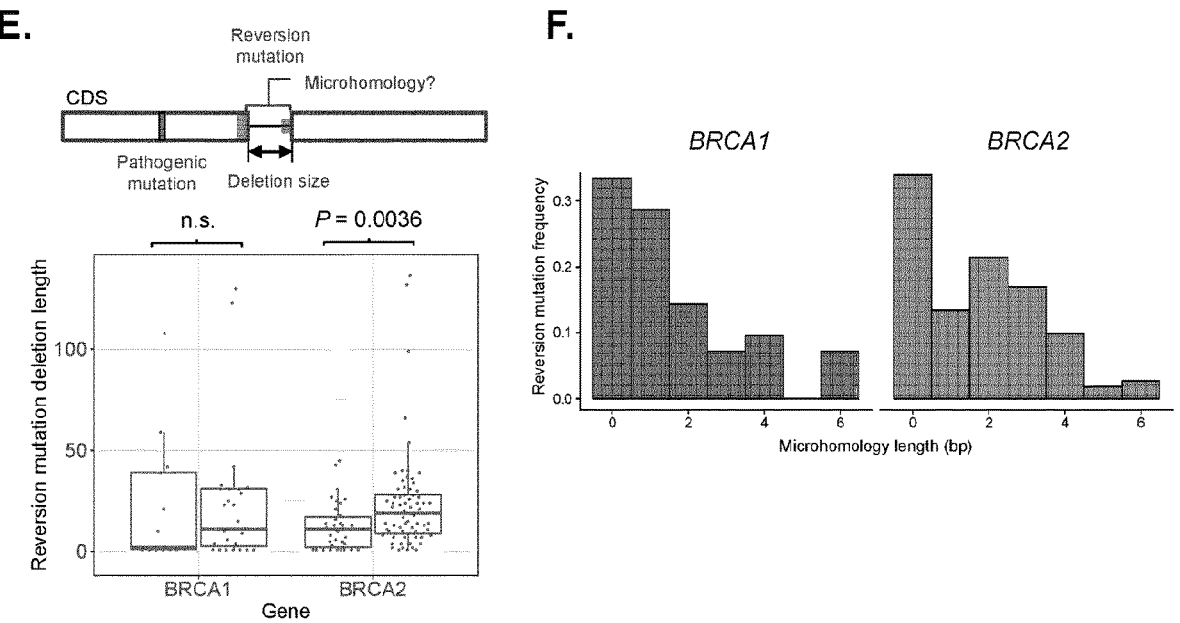

E.

F.

Microhomology present 🔲 No 🔲 Yes

Figure 4.
A.
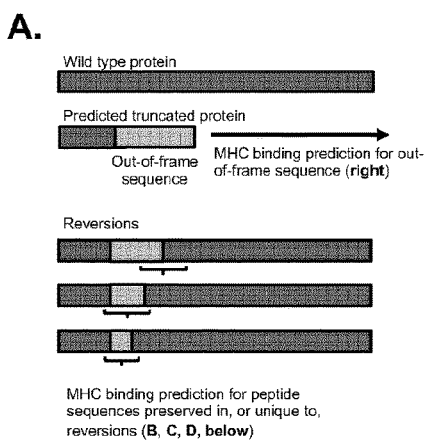
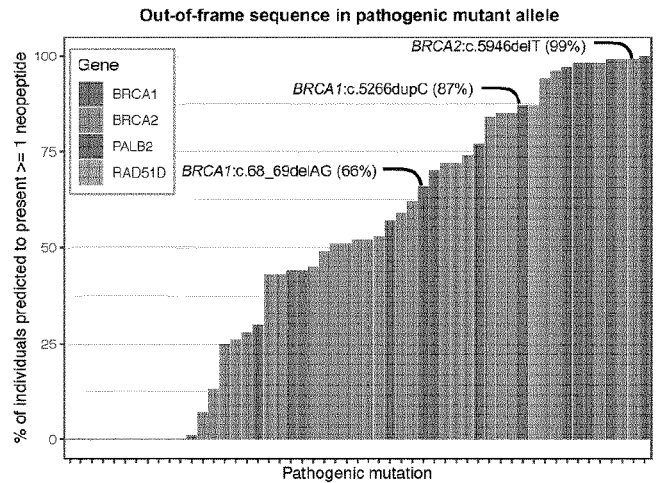
B.
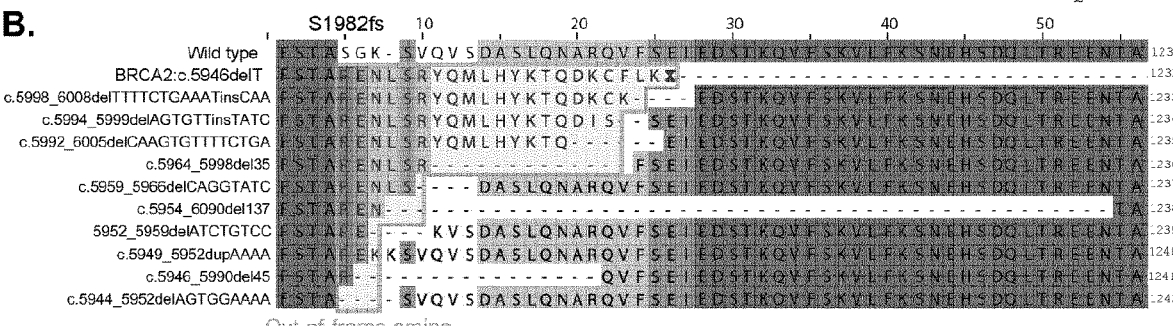
C.
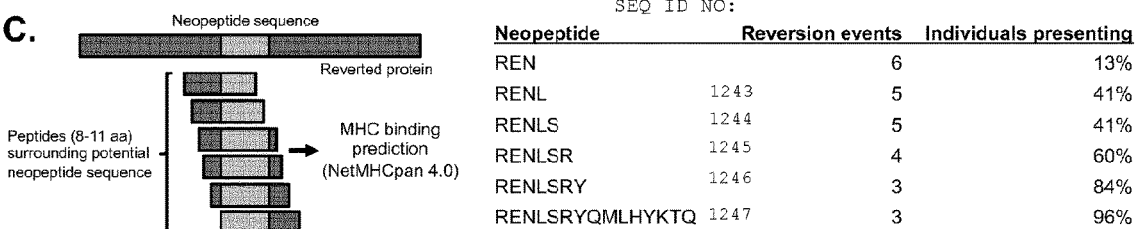
| Neopeptide | SEQ ID NO: | Reversion events | Individuals presenting |
|---|---|---|---|
| REN | | 6 | 13% |
| RENL | 1243 | 5 | 41% |
| RENLS | 1244 | 5 | 41% |
| RENLSR | 1245 | 4 | 60% |
| RENLSRY | 1246 | 3 | 84% |
| RENLSRYQMLHYKTQ | 1247 | 3 | 96% |
D.
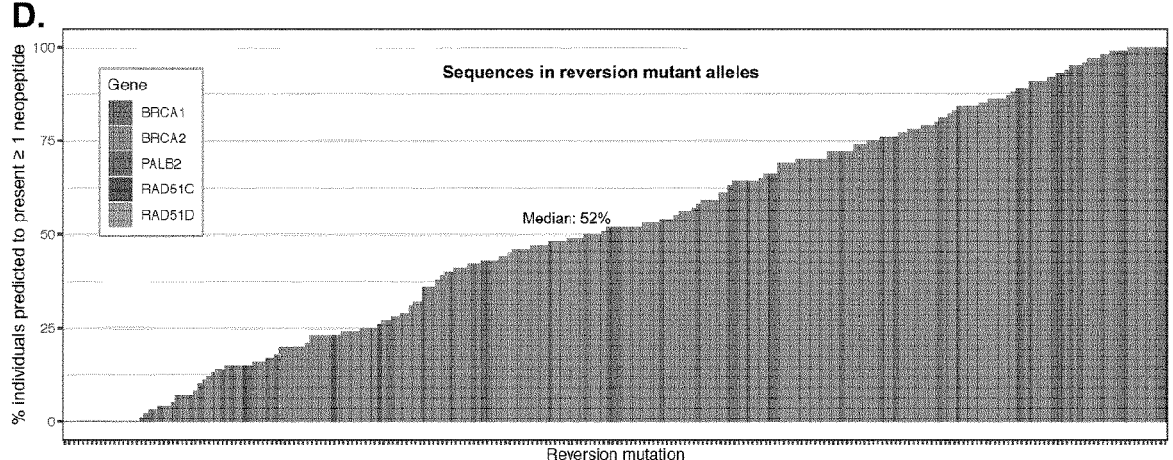

Figure 7.
A.
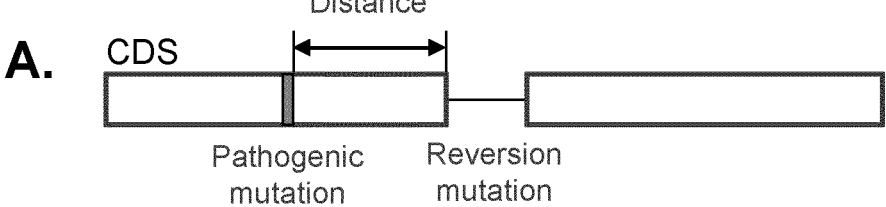
B.
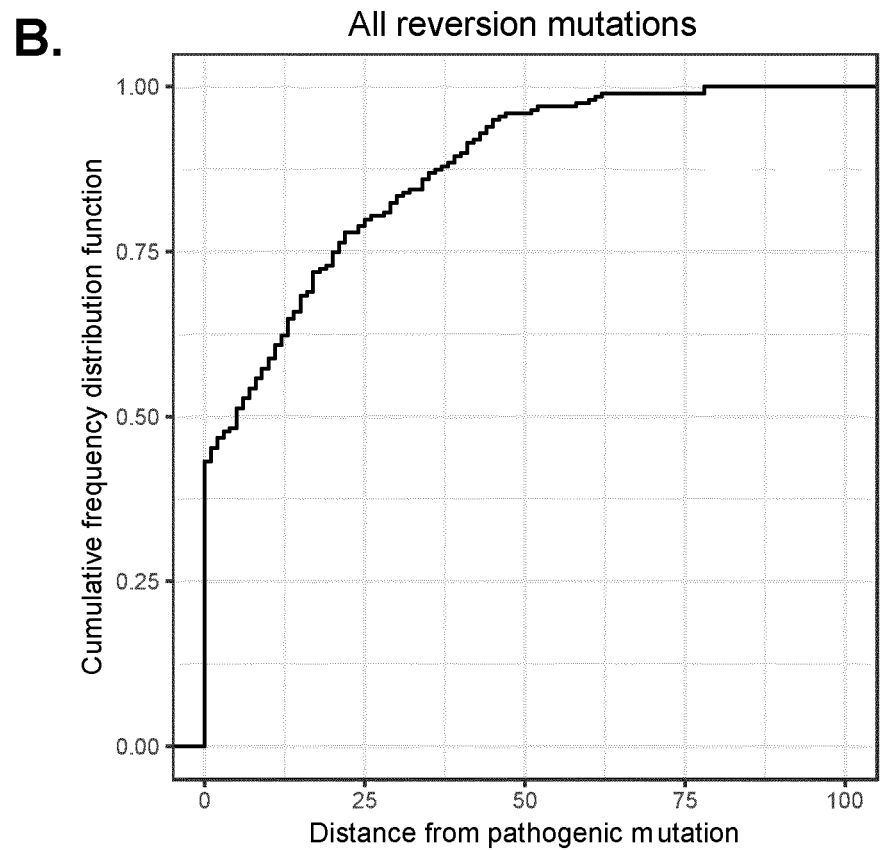

B

| Gene | Mutation |
|------|----------|
| BRCA2 | c.5444_5447delCTAG |
| BRCA2 | c.5614A>T |
| BRCA1 | c.4327C>T |
| BRCA1 | c.427G>T |
| BRCA1 | c.4041_4042delAG |
| BRCA1 | c.2475delC |
| BRCA1 | c.3770_3771delAG |
| BRCA2 | c.145G>T |
| BRCA2 | c.5946delT |
| BRCA1 | c.188T>A |
| BRCA1 | c.5266dupC |
| BRCA1 | c.4065_4068delTCAA |
| BRCA2 | c.767_771delCAAAT |
| BRCA1 | c.2162_2163delTT |

A

HLA-A02:01 netMHC prediction

| Peptide | %Rank_EL | BindLevel | SEQ ID NO: |
|---|---|---|---|
| GIAPLLPSV | 0.013 | SB | 325 |
| SQMEKIPLL | 0.017 | SB | 934 |
| KIMSGLEKV | 0.03 | SB | 463 |
| SLLGIAPLL | 0.046 | SB | 889 |
| ILVSHLSEL | 0.076 | SB | 47 |
| MLHYKTQEI | 0.645 | WB | 72 |
| KTQDISSEI | 1.88 | WB | 70 |
| RTQENLLSL | 0.893 | WB | 807 |

B

SEQUENCE LISTING

<160> NUMBER OF SEQ ID NOS: 1247

<210> SEQ ID NO 1
<211> LENGTH: 9
<212> TYPE: PRT
<213> ORGANISM: Homo sapiens

<400> SEQUENCE: 1

Ile Leu Val Ser His Leu Ser Gly Val
1               5

<210> SEQ ID NO 2
<211> LENGTH: 10
<212> TYPE: PRT
<213> ORGANISM: Homo sapiens

<400> SEQUENCE: 2

Gly Val Asp Gln Gly Thr Cys Leu His Lys
1               5                   10

<210> SEQ ID NO 3
<211> LENGTH: 8
<212> TYPE: PRT
<213> ORGANISM: Homo sapiens

<400> SEQUENCE: 3

Asn Ala Met Gln Lys Ile Leu Val
1               5

<210> SEQ ID NO 4
<211> LENGTH: 9
<212> TYPE: PRT
<213> ORGANISM: Homo sapiens

<400> SEQUENCE: 4

Met Gln Lys Ile Leu Val Ser His Leu
1               5

<210> SEQ ID NO 5
<211> LENGTH: 10
<212> TYPE: PRT
<213> ORGANISM: Homo sapiens

<400> SEQUENCE: 5

Lys Ile Leu Val Ser His Leu Ser Gly Val
1               5                   10

<210> SEQ ID NO 6
<211> LENGTH: 9
<212> TYPE: PRT
<213> ORGANISM: Homo sapiens

<400> SEQUENCE: 6

Ala Arg Asn Leu Leu Leu Trp Ala Leu
1               5

<210> SEQ ID NO 7
<211> LENGTH: 9
<212> TYPE: PRT
<213> ORGANISM: Homo sapiens

<400> SEQUENCE: 7

Arg Glu Ser Pro Gly Gln Lys Asp Leu
1               5

-continued

```
<210> SEQ ID NO 8
<211> LENGTH: 10
<212> TYPE: PRT
<213> ORGANISM: Homo sapiens

<400> SEQUENCE: 8

Ser Thr Gly Met Asp Gly Thr Ala Val Trp
1               5                   10

<210> SEQ ID NO 9
<211> LENGTH: 9
<212> TYPE: PRT
<213> ORGANISM: Homo sapiens

<400> SEQUENCE: 9

Thr Gly Met Asp Gly Thr Ala Val Trp
1               5

<210> SEQ ID NO 10
<211> LENGTH: 9
<212> TYPE: PRT
<213> ORGANISM: Homo sapiens

<400> SEQUENCE: 10

Ala Phe Ile Ile His Pro Trp His Arg
1               5

<210> SEQ ID NO 11
<211> LENGTH: 10
<212> TYPE: PRT
<213> ORGANISM: Homo sapiens

<400> SEQUENCE: 11

Gly Glu Gly Ala Phe Ile Ile His Pro Trp
1               5                   10

<210> SEQ ID NO 12
<211> LENGTH: 11
<212> TYPE: PRT
<213> ORGANISM: Homo sapiens

<400> SEQUENCE: 12

Arg Ser Thr Gly Met Asp Gly Thr Ala Val Trp
1               5                   10

<210> SEQ ID NO 13
<211> LENGTH: 9
<212> TYPE: PRT
<213> ORGANISM: Homo sapiens

<400> SEQUENCE: 13

Gln Gly Ala Arg Asn Leu Leu Leu Trp
1               5

<210> SEQ ID NO 14
<211> LENGTH: 9
<212> TYPE: PRT
<213> ORGANISM: Homo sapiens

<400> SEQUENCE: 14

Gln His Ala His Arg Ser Thr Gly Met
1               5

<210> SEQ ID NO 15
```

```
<211> LENGTH: 10
<212> TYPE: PRT
<213> ORGANISM: Homo sapiens

<400> SEQUENCE: 15

Gly Ala Phe Ile Ile His Pro Trp His Arg
1               5                   10

<210> SEQ ID NO 16
<211> LENGTH: 8
<212> TYPE: PRT
<213> ORGANISM: Homo sapiens

<400> SEQUENCE: 16

Phe Ile Ile His Pro Trp His Arg
1               5

<210> SEQ ID NO 17
<211> LENGTH: 9
<212> TYPE: PRT
<213> ORGANISM: Homo sapiens

<400> SEQUENCE: 17

Trp Ala Leu His Gln His Ala His Arg
1               5

<210> SEQ ID NO 18
<211> LENGTH: 8
<212> TYPE: PRT
<213> ORGANISM: Homo sapiens

<400> SEQUENCE: 18

His Ala His Arg Ser Thr Gly Met
1               5

<210> SEQ ID NO 19
<211> LENGTH: 10
<212> TYPE: PRT
<213> ORGANISM: Homo sapiens

<400> SEQUENCE: 19

Lys Arg Ala Arg Glu Ser Pro Gly Gln Lys
1               5                   10

<210> SEQ ID NO 20
<211> LENGTH: 9
<212> TYPE: PRT
<213> ORGANISM: Homo sapiens

<400> SEQUENCE: 20

Arg Ala Arg Glu Ser Pro Gly Gln Lys
1               5

<210> SEQ ID NO 21
<211> LENGTH: 9
<212> TYPE: PRT
<213> ORGANISM: Homo sapiens

<400> SEQUENCE: 21

Glu Gly Ala Phe Ile Ile His Pro Trp
1               5

<210> SEQ ID NO 22
<211> LENGTH: 10
<212> TYPE: PRT
```

```
<213> ORGANISM: Homo sapiens

<400> SEQUENCE: 22

Ala Ala Arg Cys Leu Asp Arg Gly Gln Trp
1               5                   10

<210> SEQ ID NO 23
<211> LENGTH: 8
<212> TYPE: PRT
<213> ORGANISM: Homo sapiens

<400> SEQUENCE: 23

Gly Ala Arg Asn Leu Leu Leu Trp
1               5

<210> SEQ ID NO 24
<211> LENGTH: 10
<212> TYPE: PRT
<213> ORGANISM: Homo sapiens

<400> SEQUENCE: 24

Ala Arg Cys Leu Asp Arg Gly Gln Trp Leu
1               5                   10

<210> SEQ ID NO 25
<211> LENGTH: 9
<212> TYPE: PRT
<213> ORGANISM: Homo sapiens

<400> SEQUENCE: 25

Gly Glu Gly Ala Phe Ile Ile His Pro
1               5

<210> SEQ ID NO 26
<211> LENGTH: 11
<212> TYPE: PRT
<213> ORGANISM: Homo sapiens

<400> SEQUENCE: 26

Glu Gly Ala Phe Ile Ile His Pro Trp His Arg
1               5                   10

<210> SEQ ID NO 27
<211> LENGTH: 9
<212> TYPE: PRT
<213> ORGANISM: Homo sapiens

<400> SEQUENCE: 27

Lys Asp Leu Gln Gly Ala Arg Asn Leu
1               5

<210> SEQ ID NO 28
<211> LENGTH: 10
<212> TYPE: PRT
<213> ORGANISM: Homo sapiens

<400> SEQUENCE: 28

Gly Ala Arg Asn Leu Leu Leu Trp Ala Leu
1               5                   10

<210> SEQ ID NO 29
<211> LENGTH: 9
<212> TYPE: PRT
<213> ORGANISM: Homo sapiens
```

```
<400> SEQUENCE: 29

Leu Gln Gly Ala Arg Asn Leu Leu Leu
1               5

<210> SEQ ID NO 30
<211> LENGTH: 9
<212> TYPE: PRT
<213> ORGANISM: Homo sapiens

<400> SEQUENCE: 30

Thr Ala Arg Glu Asn Leu Ser Arg Tyr
1               5

<210> SEQ ID NO 31
<211> LENGTH: 9
<212> TYPE: PRT
<213> ORGANISM: Homo sapiens

<400> SEQUENCE: 31

Arg Glu Asn Leu Ser Arg Tyr Gln Met
1               5

<210> SEQ ID NO 32
<211> LENGTH: 9
<212> TYPE: PRT
<213> ORGANISM: Homo sapiens

<400> SEQUENCE: 32

Lys Thr Gln Asp Lys Cys Phe Leu Lys
1               5

<210> SEQ ID NO 33
<211> LENGTH: 9
<212> TYPE: PRT
<213> ORGANISM: Homo sapiens

<400> SEQUENCE: 33

Ser Thr Ala Arg Glu Asn Leu Ser Arg
1               5

<210> SEQ ID NO 34
<211> LENGTH: 9
<212> TYPE: PRT
<213> ORGANISM: Homo sapiens

<400> SEQUENCE: 34

Ile Phe Ser Thr Ala Arg Glu Asn Leu
1               5

<210> SEQ ID NO 35
<211> LENGTH: 10
<212> TYPE: PRT
<213> ORGANISM: Homo sapiens

<400> SEQUENCE: 35

Ser Thr Ala Arg Glu Asn Leu Ser Arg Tyr
1               5                   10

<210> SEQ ID NO 36
<211> LENGTH: 8
<212> TYPE: PRT
<213> ORGANISM: Homo sapiens

<400> SEQUENCE: 36
```

```
Ser Arg Tyr Gln Met Leu His Tyr
1               5

<210> SEQ ID NO 37
<211> LENGTH: 10
<212> TYPE: PRT
<213> ORGANISM: Homo sapiens

<400> SEQUENCE: 37

Asn Thr Cys Gly Ile Phe Ser Thr Ala Arg
1               5                   10

<210> SEQ ID NO 38
<211> LENGTH: 10
<212> TYPE: PRT
<213> ORGANISM: Homo sapiens

<400> SEQUENCE: 38

Ala Arg Glu Asn Leu Ser Arg Tyr Gln Met
1               5                   10

<210> SEQ ID NO 39
<211> LENGTH: 9
<212> TYPE: PRT
<213> ORGANISM: Homo sapiens

<400> SEQUENCE: 39

Leu Ser Arg Tyr Gln Met Leu His Tyr
1               5

<210> SEQ ID NO 40
<211> LENGTH: 9
<212> TYPE: PRT
<213> ORGANISM: Homo sapiens

<400> SEQUENCE: 40

Glu Asn Leu Ser Arg Tyr Gln Met Leu
1               5

<210> SEQ ID NO 41
<211> LENGTH: 8
<212> TYPE: PRT
<213> ORGANISM: Homo sapiens

<400> SEQUENCE: 41

Asn Leu Ser Arg Tyr Gln Met Leu
1               5

<210> SEQ ID NO 42
<211> LENGTH: 10
<212> TYPE: PRT
<213> ORGANISM: Homo sapiens

<400> SEQUENCE: 42

Phe Ser Thr Ala Arg Glu Asn Leu Ser Arg
1               5                   10

<210> SEQ ID NO 43
<211> LENGTH: 9
<212> TYPE: PRT
<213> ORGANISM: Homo sapiens

<400> SEQUENCE: 43

Ser Arg Tyr Gln Met Leu His Tyr Lys
1               5
```

-continued

```
<210> SEQ ID NO 44
<211> LENGTH: 10
<212> TYPE: PRT
<213> ORGANISM: Homo sapiens

<400> SEQUENCE: 44

Arg Glu Asn Leu Ser Arg Tyr Gln Met Leu
1               5                   10

<210> SEQ ID NO 45
<211> LENGTH: 10
<212> TYPE: PRT
<213> ORGANISM: Homo sapiens

<400> SEQUENCE: 45

Asn Leu Ser Arg Tyr Gln Met Leu His Tyr
1               5                   10

<210> SEQ ID NO 46
<211> LENGTH: 10
<212> TYPE: PRT
<213> ORGANISM: Homo sapiens

<400> SEQUENCE: 46

Gly Val Asp Gln Gly Thr Cys Leu Thr Lys
1               5                   10

<210> SEQ ID NO 47
<211> LENGTH: 9
<212> TYPE: PRT
<213> ORGANISM: Homo sapiens

<400> SEQUENCE: 47

Ile Leu Val Ser His Leu Ser Glu Leu
1               5

<210> SEQ ID NO 48
<211> LENGTH: 8
<212> TYPE: PRT
<213> ORGANISM: Homo sapiens

<400> SEQUENCE: 48

Asn Ala Met Gln Lys Ile Cys Leu
1               5

<210> SEQ ID NO 49
<211> LENGTH: 11
<212> TYPE: PRT
<213> ORGANISM: Homo sapiens

<400> SEQUENCE: 49

Ser Glu Leu Ile Lys Glu Pro Val Ser Thr Lys
1               5                   10

<210> SEQ ID NO 50
<211> LENGTH: 10
<212> TYPE: PRT
<213> ORGANISM: Homo sapiens

<400> SEQUENCE: 50

Ala Arg Glu Ser Pro Gly Gln Lys Glu Ile
1               5                   10
```

<210> SEQ ID NO 51
<211> LENGTH: 10
<212> TYPE: PRT
<213> ORGANISM: Homo sapiens

<400> SEQUENCE: 51

Ala Arg Glu Ser Pro Gly Arg Lys Ile Phe
1               5                   10

<210> SEQ ID NO 52
<211> LENGTH: 9
<212> TYPE: PRT
<213> ORGANISM: Homo sapiens

<400> SEQUENCE: 52

Glu Ser Pro Gly Arg Lys Ile Phe Arg
1               5

<210> SEQ ID NO 53
<211> LENGTH: 9
<212> TYPE: PRT
<213> ORGANISM: Homo sapiens

<400> SEQUENCE: 53

Gly Gln Lys Glu Ile Phe Arg Gly Leu
1               5

<210> SEQ ID NO 54
<211> LENGTH: 10
<212> TYPE: PRT
<213> ORGANISM: Homo sapiens

<400> SEQUENCE: 54

Gly Arg Lys Ile Phe Arg Gly Leu Glu Ile
1               5                   10

<210> SEQ ID NO 55
<211> LENGTH: 9
<212> TYPE: PRT
<213> ORGANISM: Homo sapiens

<400> SEQUENCE: 55

Lys Glu Ile Phe Arg Gly Leu Glu Ile
1               5

<210> SEQ ID NO 56
<211> LENGTH: 9
<212> TYPE: PRT
<213> ORGANISM: Homo sapiens

<400> SEQUENCE: 56

Arg Ala Arg Glu Ser Pro Gly Arg Lys
1               5

<210> SEQ ID NO 57
<211> LENGTH: 9
<212> TYPE: PRT
<213> ORGANISM: Homo sapiens

<400> SEQUENCE: 57

Arg Glu Ser Pro Gly Gln Lys Glu Ile
1               5

<210> SEQ ID NO 58
<211> LENGTH: 10

-continued

```
<212> TYPE: PRT
<213> ORGANISM: Homo sapiens

<400> SEQUENCE: 58

Arg Glu Ser Pro Gly Gln Lys Glu Ile Phe
1               5               10

<210> SEQ ID NO 59
<211> LENGTH: 8
<212> TYPE: PRT
<213> ORGANISM: Homo sapiens

<400> SEQUENCE: 59

Arg Glu Ser Pro Gly Arg Lys Ile
1               5

<210> SEQ ID NO 60
<211> LENGTH: 9
<212> TYPE: PRT
<213> ORGANISM: Homo sapiens

<400> SEQUENCE: 60

Arg Glu Ser Pro Gly Arg Lys Ile Phe
1               5

<210> SEQ ID NO 61
<211> LENGTH: 10
<212> TYPE: PRT
<213> ORGANISM: Homo sapiens

<400> SEQUENCE: 61

Ser Pro Gly Arg Lys Ile Phe Arg Gly Leu
1               5               10

<210> SEQ ID NO 62
<211> LENGTH: 9
<212> TYPE: PRT
<213> ORGANISM: Homo sapiens

<400> SEQUENCE: 62

Gly Ile Phe Ser Thr Ala Arg Glu Lys
1               5

<210> SEQ ID NO 63
<211> LENGTH: 10
<212> TYPE: PRT
<213> ORGANISM: Homo sapiens

<400> SEQUENCE: 63

Ala Arg Glu Lys Val Ser Asp Ala Ser Leu
1               5               10

<210> SEQ ID NO 64
<211> LENGTH: 10
<212> TYPE: PRT
<213> ORGANISM: Homo sapiens

<400> SEQUENCE: 64

Ala Arg Glu Asn Leu Ser Asp Ala Ser Leu
1               5               10

<210> SEQ ID NO 65
<211> LENGTH: 9
<212> TYPE: PRT
<213> ORGANISM: Homo sapiens
```

-continued

```
<400> SEQUENCE: 65

Glu Asn Leu Ser Arg Phe Ser Glu Ile
1               5

<210> SEQ ID NO 66
<211> LENGTH: 10
<212> TYPE: PRT
<213> ORGANISM: Homo sapiens

<400> SEQUENCE: 66

Gly Ile Phe Ser Thr Ala Arg Glu Lys Lys
1               5                   10

<210> SEQ ID NO 67
<211> LENGTH: 9
<212> TYPE: PRT
<213> ORGANISM: Homo sapiens

<400> SEQUENCE: 67

Ile Phe Ser Thr Ala Arg Gln Val Phe
1               5

<210> SEQ ID NO 68
<211> LENGTH: 9
<212> TYPE: PRT
<213> ORGANISM: Homo sapiens

<400> SEQUENCE: 68

Ile Phe Ser Thr Ala Ser Val Gln Val
1               5

<210> SEQ ID NO 69
<211> LENGTH: 9
<212> TYPE: PRT
<213> ORGANISM: Homo sapiens

<400> SEQUENCE: 69

Lys Glu Asp Ser Thr Lys Gln Val Phe
1               5

<210> SEQ ID NO 70
<211> LENGTH: 9
<212> TYPE: PRT
<213> ORGANISM: Homo sapiens

<400> SEQUENCE: 70

Lys Thr Gln Asp Ile Ser Ser Glu Ile
1               5

<210> SEQ ID NO 71
<211> LENGTH: 9
<212> TYPE: PRT
<213> ORGANISM: Homo sapiens

<400> SEQUENCE: 71

Met Leu His Tyr Lys Thr Gln Asp Ile
1               5

<210> SEQ ID NO 72
<211> LENGTH: 9
<212> TYPE: PRT
<213> ORGANISM: Homo sapiens

<400> SEQUENCE: 72
```

```
Met Leu His Tyr Lys Thr Gln Glu Ile
1               5

<210> SEQ ID NO 73
<211> LENGTH: 9
<212> TYPE: PRT
<213> ORGANISM: Homo sapiens

<400> SEQUENCE: 73

Asn Thr Cys Gly Ile Phe Ser Thr Ile
1               5

<210> SEQ ID NO 74
<211> LENGTH: 10
<212> TYPE: PRT
<213> ORGANISM: Homo sapiens

<400> SEQUENCE: 74

Gln Glu Ile Glu Asp Ser Thr Lys Gln Val
1               5                   10

<210> SEQ ID NO 75
<211> LENGTH: 11
<212> TYPE: PRT
<213> ORGANISM: Homo sapiens

<400> SEQUENCE: 75

Gln Glu Ile Glu Asp Ser Thr Lys Gln Val Phe
1               5                   10

<210> SEQ ID NO 76
<211> LENGTH: 9
<212> TYPE: PRT
<213> ORGANISM: Homo sapiens

<400> SEQUENCE: 76

Arg Glu Lys Lys Ser Val Gln Val Ser
1               5

<210> SEQ ID NO 77
<211> LENGTH: 9
<212> TYPE: PRT
<213> ORGANISM: Homo sapiens

<400> SEQUENCE: 77

Arg Glu Lys Val Ser Asp Ala Ser Leu
1               5

<210> SEQ ID NO 78
<211> LENGTH: 9
<212> TYPE: PRT
<213> ORGANISM: Homo sapiens

<400> SEQUENCE: 78

Arg Glu Asn Leu Ser Asp Ala Ser Leu
1               5

<210> SEQ ID NO 79
<211> LENGTH: 9
<212> TYPE: PRT
<213> ORGANISM: Homo sapiens

<400> SEQUENCE: 79

Arg Glu Asn Thr Ala Ile Arg Thr Pro
```

-continued

```
1               5

<210> SEQ ID NO 80
<211> LENGTH: 11
<212> TYPE: PRT
<213> ORGANISM: Homo sapiens

<400> SEQUENCE: 80

Ser Arg Phe Ser Glu Ile Glu Asp Ser Thr Lys
1               5                   10

<210> SEQ ID NO 81
<211> LENGTH: 10
<212> TYPE: PRT
<213> ORGANISM: Homo sapiens

<400> SEQUENCE: 81

Ser Thr Ala Arg Glu Asn Leu Ser Arg Phe
1               5                   10

<210> SEQ ID NO 82
<211> LENGTH: 9
<212> TYPE: PRT
<213> ORGANISM: Homo sapiens

<400> SEQUENCE: 82

Ser Thr Ala Arg Glu Asn Thr Ala Ile
1               5

<210> SEQ ID NO 83
<211> LENGTH: 10
<212> TYPE: PRT
<213> ORGANISM: Homo sapiens

<400> SEQUENCE: 83

Ser Thr Ala Arg Glu Asn Thr Ala Ile Arg
1               5                   10

<210> SEQ ID NO 84
<211> LENGTH: 8
<212> TYPE: PRT
<213> ORGANISM: Homo sapiens

<400> SEQUENCE: 84

Thr Ala Arg Glu Lys Lys Ser Val
1               5

<210> SEQ ID NO 85
<211> LENGTH: 11
<212> TYPE: PRT
<213> ORGANISM: Homo sapiens

<400> SEQUENCE: 85

Thr Ala Arg Glu Lys Val Ser Asp Ala Ser Leu
1               5                   10

<210> SEQ ID NO 86
<211> LENGTH: 9
<212> TYPE: PRT
<213> ORGANISM: Homo sapiens

<400> SEQUENCE: 86

Thr Ala Arg Glu Asn Leu Ser Arg Phe
1               5
```

```
<210> SEQ ID NO 87
<211> LENGTH: 8
<212> TYPE: PRT
<213> ORGANISM: Homo sapiens

<400> SEQUENCE: 87

Thr Ala Arg Glu Asn Thr Ala Ile
1               5

<210> SEQ ID NO 88
<211> LENGTH: 9
<212> TYPE: PRT
<213> ORGANISM: Homo sapiens

<400> SEQUENCE: 88

Thr Ala Arg Glu Asn Thr Ala Ile Arg
1               5

<210> SEQ ID NO 89
<211> LENGTH: 9
<212> TYPE: PRT
<213> ORGANISM: Homo sapiens

<400> SEQUENCE: 89

Thr Ala Arg Gln Val Phe Ser Glu Ile
1               5

<210> SEQ ID NO 90
<211> LENGTH: 9
<212> TYPE: PRT
<213> ORGANISM: Homo sapiens

<400> SEQUENCE: 90

Ala Ala Glu Asn Gln Met Thr Ile Leu
1               5

<210> SEQ ID NO 91
<211> LENGTH: 10
<212> TYPE: PRT
<213> ORGANISM: Homo sapiens

<400> SEQUENCE: 91

Ala Ala Glu Asn Gln Met Thr Ile Leu Lys
1               5                   10

<210> SEQ ID NO 92
<211> LENGTH: 9
<212> TYPE: PRT
<213> ORGANISM: Homo sapiens

<400> SEQUENCE: 92

Ala Ala Val Pro Ile Ser Cys Lys Lys
1               5

<210> SEQ ID NO 93
<211> LENGTH: 9
<212> TYPE: PRT
<213> ORGANISM: Homo sapiens

<400> SEQUENCE: 93

Ala Ala Val Pro Ile Ser Cys Lys Arg
1               5

<210> SEQ ID NO 94
```

```
<211> LENGTH: 11
<212> TYPE: PRT
<213> ORGANISM: Homo sapiens

<400> SEQUENCE: 94

Ala Glu Glu Ser Leu His Lys Asn Asn Asn Tyr
1               5                   10

<210> SEQ ID NO 95
<211> LENGTH: 10
<212> TYPE: PRT
<213> ORGANISM: Homo sapiens

<400> SEQUENCE: 95

Ala Glu Lys His Lys Gly Glu Glu His Trp
1               5                   10

<210> SEQ ID NO 96
<211> LENGTH: 8
<212> TYPE: PRT
<213> ORGANISM: Homo sapiens

<400> SEQUENCE: 96

Ala Glu Asn Gln Met Thr Ile Leu
1               5

<210> SEQ ID NO 97
<211> LENGTH: 9
<212> TYPE: PRT
<213> ORGANISM: Homo sapiens

<400> SEQUENCE: 97

Ala Glu Asn Gln Met Thr Ile Leu Lys
1               5

<210> SEQ ID NO 98
<211> LENGTH: 10
<212> TYPE: PRT
<213> ORGANISM: Homo sapiens

<400> SEQUENCE: 98

Ala Glu Asn Gln Met Thr Ile Leu Lys Thr
1               5                   10

<210> SEQ ID NO 99
<211> LENGTH: 9
<212> TYPE: PRT
<213> ORGANISM: Homo sapiens

<400> SEQUENCE: 99

Ala Glu Thr Tyr Asn Ser Trp Lys Val
1               5

<210> SEQ ID NO 100
<211> LENGTH: 10
<212> TYPE: PRT
<213> ORGANISM: Homo sapiens

<400> SEQUENCE: 100

Ala Glu Thr Tyr Asn Ser Trp Lys Val Lys
1               5                   10

<210> SEQ ID NO 101
<211> LENGTH: 8
<212> TYPE: PRT
```

-continued

<213> ORGANISM: Homo sapiens

<400> SEQUENCE: 101

Ala Glu Trp Asn Lys Gln Lys Leu
1               5

<210> SEQ ID NO 102
<211> LENGTH: 9
<212> TYPE: PRT
<213> ORGANISM: Homo sapiens

<400> SEQUENCE: 102

Ala Glu Trp Asn Lys Gln Lys Leu Pro
1               5

<210> SEQ ID NO 103
<211> LENGTH: 8
<212> TYPE: PRT
<213> ORGANISM: Homo sapiens

<400> SEQUENCE: 103

Ala Glu Tyr Glu Pro Asn Leu Phe
1               5

<210> SEQ ID NO 104
<211> LENGTH: 9
<212> TYPE: PRT
<213> ORGANISM: Homo sapiens

<400> SEQUENCE: 104

Ala Glu Tyr Glu Pro Asn Leu Phe Lys
1               5

<210> SEQ ID NO 105
<211> LENGTH: 10
<212> TYPE: PRT
<213> ORGANISM: Homo sapiens

<400> SEQUENCE: 105

Ala Glu Tyr Glu Pro Asn Leu Phe Lys Thr
1               5                   10

<210> SEQ ID NO 106
<211> LENGTH: 9
<212> TYPE: PRT
<213> ORGANISM: Homo sapiens

<400> SEQUENCE: 106

Ala Phe Arg Ile Ala Ser Gly Asn Lys
1               5

<210> SEQ ID NO 107
<211> LENGTH: 10
<212> TYPE: PRT
<213> ORGANISM: Homo sapiens

<400> SEQUENCE: 107

Ala Phe Arg Ile Ala Ser Gly Asn Lys Lys
1               5                   10

<210> SEQ ID NO 108
<211> LENGTH: 9
<212> TYPE: PRT
<213> ORGANISM: Homo sapiens -continued

```
<400> SEQUENCE: 108

Ala His Gly Thr Lys Leu Asn Val Leu
1               5

<210> SEQ ID NO 109
<211> LENGTH: 10
<212> TYPE: PRT
<213> ORGANISM: Homo sapiens

<400> SEQUENCE: 109

Ala Ile Lys Leu Ser Ile Ser Asn Ser Tyr
1               5               10

<210> SEQ ID NO 110
<211> LENGTH: 10
<212> TYPE: PRT
<213> ORGANISM: Homo sapiens

<400> SEQUENCE: 110

Ala Leu Gly Phe Ser Trp Thr Pro Ser Arg
1               5               10

<210> SEQ ID NO 111
<211> LENGTH: 9
<212> TYPE: PRT
<213> ORGANISM: Homo sapiens

<400> SEQUENCE: 111

Ala Leu Leu Leu Lys Lys Leu Leu Lys
1               5

<210> SEQ ID NO 112
<211> LENGTH: 9
<212> TYPE: PRT
<213> ORGANISM: Homo sapiens

<400> SEQUENCE: 112

Ala Leu Ser Ile His Trp Asp Met Lys
1               5

<210> SEQ ID NO 113
<211> LENGTH: 9
<212> TYPE: PRT
<213> ORGANISM: Homo sapiens

<400> SEQUENCE: 113

Ala Pro Gly Ala Leu Cys Pro Ala Leu
1               5

<210> SEQ ID NO 114
<211> LENGTH: 9
<212> TYPE: PRT
<213> ORGANISM: Homo sapiens

<400> SEQUENCE: 114

Ala Pro Lys Lys Asn Arg Leu Thr Thr
1               5

<210> SEQ ID NO 115
<211> LENGTH: 9
<212> TYPE: PRT
<213> ORGANISM: Homo sapiens

<400> SEQUENCE: 115
```

-continued

```
Ala Pro Leu Leu Pro Ser Val Cys Leu
1               5

<210> SEQ ID NO 116
<211> LENGTH: 11
<212> TYPE: PRT
<213> ORGANISM: Homo sapiens

<400> SEQUENCE: 116

Ala Pro Pro Tyr Asn Ser Glu Pro Ala Glu Tyr
1               5                   10

<210> SEQ ID NO 117
<211> LENGTH: 8
<212> TYPE: PRT
<213> ORGANISM: Homo sapiens

<400> SEQUENCE: 117

Ala Gln Ser Pro Arg Lys Leu Tyr
1               5

<210> SEQ ID NO 118
<211> LENGTH: 9
<212> TYPE: PRT
<213> ORGANISM: Homo sapiens

<400> SEQUENCE: 118

Ala Gln Ser Pro Arg Lys Leu Tyr Arg
1               5

<210> SEQ ID NO 119
<211> LENGTH: 9
<212> TYPE: PRT
<213> ORGANISM: Homo sapiens

<400> SEQUENCE: 119

Ala Ser Val Pro Val Lys Thr Gln Ile
1               5

<210> SEQ ID NO 120
<211> LENGTH: 10
<212> TYPE: PRT
<213> ORGANISM: Homo sapiens

<400> SEQUENCE: 120

Ala Ser Val Pro Val Lys Thr Gln Ile Lys
1               5                   10

<210> SEQ ID NO 121
<211> LENGTH: 9
<212> TYPE: PRT
<213> ORGANISM: Homo sapiens

<400> SEQUENCE: 121

Ala Ser Val Thr Asp Ser Glu Asn Lys
1               5

<210> SEQ ID NO 122
<211> LENGTH: 10
<212> TYPE: PRT
<213> ORGANISM: Homo sapiens

<400> SEQUENCE: 122

Ala Ser Val Thr Val Lys Thr Asn Gln Arg
1               5                   10
```

```
<210> SEQ ID NO 123
<211> LENGTH: 9
<212> TYPE: PRT
<213> ORGANISM: Homo sapiens

<400> SEQUENCE: 123

Ala Ser Val Thr Val Lys Thr Gln Ile
1               5

<210> SEQ ID NO 124
<211> LENGTH: 9
<212> TYPE: PRT
<213> ORGANISM: Homo sapiens

<400> SEQUENCE: 124

Ala Ser Val Thr Val Lys Thr Gln Arg
1               5

<210> SEQ ID NO 125
<211> LENGTH: 9
<212> TYPE: PRT
<213> ORGANISM: Homo sapiens

<400> SEQUENCE: 125

Ala Thr Thr Val Pro Leu Gln Thr Ile
1               5

<210> SEQ ID NO 126
<211> LENGTH: 9
<212> TYPE: PRT
<213> ORGANISM: Homo sapiens

<400> SEQUENCE: 126

Ala Thr Tyr His Leu Gln Pro Leu His
1               5

<210> SEQ ID NO 127
<211> LENGTH: 9
<212> TYPE: PRT
<213> ORGANISM: Homo sapiens

<400> SEQUENCE: 127

Ala Thr Tyr His Leu Thr Ser Ala Leu
1               5

<210> SEQ ID NO 128
<211> LENGTH: 10
<212> TYPE: PRT
<213> ORGANISM: Homo sapiens

<400> SEQUENCE: 128

Ala Thr Tyr His Leu Thr Ser Ala Leu Lys
1               5                   10

<210> SEQ ID NO 129
<211> LENGTH: 9
<212> TYPE: PRT
<213> ORGANISM: Homo sapiens

<400> SEQUENCE: 129

Cys Lys Lys Thr Ser Gly Asn Ser Phe
1               5
```

-continued

```
<210> SEQ ID NO 130
<211> LENGTH: 9
<212> TYPE: PRT
<213> ORGANISM: Homo sapiens

<400> SEQUENCE: 130

Cys Lys Tyr Lys His Pro Gly Ser Phe
1               5

<210> SEQ ID NO 131
<211> LENGTH: 8
<212> TYPE: PRT
<213> ORGANISM: Homo sapiens

<400> SEQUENCE: 131

Cys Pro Ala Leu Gly Phe Ser Trp
1               5

<210> SEQ ID NO 132
<211> LENGTH: 8
<212> TYPE: PRT
<213> ORGANISM: Homo sapiens

<400> SEQUENCE: 132

Cys Pro Tyr Leu Ile Val Ile Ile
1               5

<210> SEQ ID NO 133
<211> LENGTH: 9
<212> TYPE: PRT
<213> ORGANISM: Homo sapiens

<400> SEQUENCE: 133

Cys Pro Tyr Leu Ile Val Ile Ile Leu
1               5

<210> SEQ ID NO 134
<211> LENGTH: 9
<212> TYPE: PRT
<213> ORGANISM: Homo sapiens

<400> SEQUENCE: 134

Cys Gln Ser Gly Thr Ala Glu Thr Tyr
1               5

<210> SEQ ID NO 135
<211> LENGTH: 8
<212> TYPE: PRT
<213> ORGANISM: Homo sapiens

<400> SEQUENCE: 135

Asp Ala Leu Ser Ile Cys Arg Ile
1               5

<210> SEQ ID NO 136
<211> LENGTH: 9
<212> TYPE: PRT
<213> ORGANISM: Homo sapiens

<400> SEQUENCE: 136

Asp Ala Asn Ala Tyr Pro Gln Thr Lys
1               5

<210> SEQ ID NO 137
<211> LENGTH: 9
```

<212> TYPE: PRT
<213> ORGANISM: Homo sapiens

<400> SEQUENCE: 137

Asp Glu Cys Ser Thr His Lys Val Phe
1               5

<210> SEQ ID NO 138
<211> LENGTH: 10
<212> TYPE: PRT
<213> ORGANISM: Homo sapiens

<400> SEQUENCE: 138

Asp Glu Cys Ser Thr His Ser Gln Gly Phe
1               5                   10

<210> SEQ ID NO 139
<211> LENGTH: 8
<212> TYPE: PRT
<213> ORGANISM: Homo sapiens

<400> SEQUENCE: 139

Asp Glu Lys Asp Gln Arg Thr Tyr
1               5

<210> SEQ ID NO 140
<211> LENGTH: 11
<212> TYPE: PRT
<213> ORGANISM: Homo sapiens

<400> SEQUENCE: 140

Asp Glu Asn Glu Val Gly Phe Arg Gly Ser Trp
1               5                   10

<210> SEQ ID NO 141
<211> LENGTH: 10
<212> TYPE: PRT
<213> ORGANISM: Homo sapiens

<400> SEQUENCE: 141

Asp Glu Ser Leu Lys Lys Asn Glu Ile Tyr
1               5                   10

<210> SEQ ID NO 142
<211> LENGTH: 9
<212> TYPE: PRT
<213> ORGANISM: Homo sapiens

<400> SEQUENCE: 142

Asp Glu Ser Leu Lys Lys Asn Arg Phe
1               5

<210> SEQ ID NO 143
<211> LENGTH: 9
<212> TYPE: PRT
<213> ORGANISM: Homo sapiens

<400> SEQUENCE: 143

Asp Glu Ser Leu Thr Val Lys Thr Gln
1               5

<210> SEQ ID NO 144
<211> LENGTH: 9
<212> TYPE: PRT
<213> ORGANISM: Homo sapiens -continued

<400> SEQUENCE: 144

Asp Phe Asn Ser Asn His Asn Ile Leu
1               5

<210> SEQ ID NO 145
<211> LENGTH: 9
<212> TYPE: PRT
<213> ORGANISM: Homo sapiens

<400> SEQUENCE: 145

Asp Phe Tyr Lys Thr His Ile Val Tyr
1               5

<210> SEQ ID NO 146
<211> LENGTH: 9
<212> TYPE: PRT
<213> ORGANISM: Homo sapiens

<400> SEQUENCE: 146

Asp Gly Glu Asn Thr Pro Ile Ala Tyr
1               5

<210> SEQ ID NO 147
<211> LENGTH: 10
<212> TYPE: PRT
<213> ORGANISM: Homo sapiens

<400> SEQUENCE: 147

Asp Gly Glu Asn Thr Pro Ile Ala Tyr Phe
1               5                   10

<210> SEQ ID NO 148
<211> LENGTH: 9
<212> TYPE: PRT
<213> ORGANISM: Homo sapiens

<400> SEQUENCE: 148

Asp Gly Lys Ile Pro Leu Leu His Ile
1               5

<210> SEQ ID NO 149
<211> LENGTH: 9
<212> TYPE: PRT
<213> ORGANISM: Homo sapiens

<400> SEQUENCE: 149

Asp Ile Phe Thr Asp Asn Glu Asn Lys
1               5

<210> SEQ ID NO 150
<211> LENGTH: 9
<212> TYPE: PRT
<213> ORGANISM: Homo sapiens

<400> SEQUENCE: 150

Asp Ile Phe Thr Asp Ser Phe Ser Tyr
1               5

<210> SEQ ID NO 151
<211> LENGTH: 10
<212> TYPE: PRT
<213> ORGANISM: Homo sapiens

<400> SEQUENCE: 151

-continued

```
Asp Ile Leu His Asn Ser Leu Glu Asp Tyr
1               5                   10

<210> SEQ ID NO 152
<211> LENGTH: 9
<212> TYPE: PRT
<213> ORGANISM: Homo sapiens

<400> SEQUENCE: 152

Asp Ile Val Thr Glu Ser Val Pro Val
1               5

<210> SEQ ID NO 153
<211> LENGTH: 9
<212> TYPE: PRT
<213> ORGANISM: Homo sapiens

<400> SEQUENCE: 153

Asp Lys Ile Ser Lys Glu Val Val Leu
1               5

<210> SEQ ID NO 154
<211> LENGTH: 10
<212> TYPE: PRT
<213> ORGANISM: Homo sapiens

<400> SEQUENCE: 154

Asp Leu Asn Ala Asp Pro Leu Cys Lys Arg
1               5                   10

<210> SEQ ID NO 155
<211> LENGTH: 9
<212> TYPE: PRT
<213> ORGANISM: Homo sapiens

<400> SEQUENCE: 155

Asp Leu Asn Ala Asp Pro Leu Cys Trp
1               5

<210> SEQ ID NO 156
<211> LENGTH: 9
<212> TYPE: PRT
<213> ORGANISM: Homo sapiens

<400> SEQUENCE: 156

Asp Leu Asn Ala Asp Pro Leu Cys Tyr
1               5

<210> SEQ ID NO 157
<211> LENGTH: 10
<212> TYPE: PRT
<213> ORGANISM: Homo sapiens

<400> SEQUENCE: 157

Asp Leu Asn Ala Asp Pro Leu Cys Tyr Arg
1               5                   10

<210> SEQ ID NO 158
<211> LENGTH: 9
<212> TYPE: PRT
<213> ORGANISM: Homo sapiens

<400> SEQUENCE: 158

Asp Leu Asn Phe Trp Lys Leu Arg Lys
```

```
1               5

<210> SEQ ID NO 159
<211> LENGTH: 9
<212> TYPE: PRT
<213> ORGANISM: Homo sapiens

<400> SEQUENCE: 159

Asp Leu Ser Asp Leu Asn Phe Trp Lys
1               5

<210> SEQ ID NO 160
<211> LENGTH: 10
<212> TYPE: PRT
<213> ORGANISM: Homo sapiens

<400> SEQUENCE: 160

Asp Leu Ser Asp Leu Asn Phe Trp Lys Tyr
1               5                   10

<210> SEQ ID NO 161
<211> LENGTH: 9
<212> TYPE: PRT
<213> ORGANISM: Homo sapiens

<400> SEQUENCE: 161

Asp Met Lys Leu Thr Thr Val Gly Lys
1               5

<210> SEQ ID NO 162
<211> LENGTH: 9
<212> TYPE: PRT
<213> ORGANISM: Homo sapiens

<400> SEQUENCE: 162

Asp Met Arg Phe Ile Ser Leu Thr Lys
1               5

<210> SEQ ID NO 163
<211> LENGTH: 9
<212> TYPE: PRT
<213> ORGANISM: Homo sapiens

<400> SEQUENCE: 163

Asp Pro Leu Cys Trp Arg Lys Glu Trp
1               5

<210> SEQ ID NO 164
<211> LENGTH: 9
<212> TYPE: PRT
<213> ORGANISM: Homo sapiens

<400> SEQUENCE: 164

Asp Pro Leu Cys Tyr Arg Lys Glu Trp
1               5

<210> SEQ ID NO 165
<211> LENGTH: 9
<212> TYPE: PRT
<213> ORGANISM: Homo sapiens

<400> SEQUENCE: 165

Asp Pro Leu Asp Ser Pro Leu Arg Val
1               5
```

```
<210> SEQ ID NO 166
<211> LENGTH: 9
<212> TYPE: PRT
<213> ORGANISM: Homo sapiens

<400> SEQUENCE: 166

Asp Pro Ser Leu Gln Glu Thr Ser Leu
1               5

<210> SEQ ID NO 167
<211> LENGTH: 9
<212> TYPE: PRT
<213> ORGANISM: Homo sapiens

<400> SEQUENCE: 167

Asp Gln Arg Thr Tyr Ser Ile Gly Phe
1               5

<210> SEQ ID NO 168
<211> LENGTH: 11
<212> TYPE: PRT
<213> ORGANISM: Homo sapiens

<400> SEQUENCE: 168

Asp Gln Arg Thr Tyr Ser Ile Gly Phe Ser Tyr
1               5                   10

<210> SEQ ID NO 169
<211> LENGTH: 9
<212> TYPE: PRT
<213> ORGANISM: Homo sapiens

<400> SEQUENCE: 169

Asp Arg Asp Lys Leu Lys Pro Ala Leu
1               5

<210> SEQ ID NO 170
<211> LENGTH: 10
<212> TYPE: PRT
<213> ORGANISM: Homo sapiens

<400> SEQUENCE: 170

Asp Arg Phe Ile Ala Ala Ser His Gly Phe
1               5                   10

<210> SEQ ID NO 171
<211> LENGTH: 9
<212> TYPE: PRT
<213> ORGANISM: Homo sapiens

<400> SEQUENCE: 171

Asp Arg Phe Ile Ala Ser Val Lys Thr
1               5

<210> SEQ ID NO 172
<211> LENGTH: 9
<212> TYPE: PRT
<213> ORGANISM: Homo sapiens

<400> SEQUENCE: 172

Asp Arg Phe Ile Ala Ser Val Pro Val
1               5

<210> SEQ ID NO 173
```

```
<211> LENGTH: 9
<212> TYPE: PRT
<213> ORGANISM: Homo sapiens

<400> SEQUENCE: 173

Asp Arg Phe Ile Ala Ser Val Thr Glu
1               5

<210> SEQ ID NO 174
<211> LENGTH: 10
<212> TYPE: PRT
<213> ORGANISM: Homo sapiens

<400> SEQUENCE: 174

Asp Arg Phe Ile Ala Ser Val Thr Glu Ala
1               5                   10

<210> SEQ ID NO 175
<211> LENGTH: 11
<212> TYPE: PRT
<213> ORGANISM: Homo sapiens

<400> SEQUENCE: 175

Asp Arg Phe Ile Ala Ser Val Thr Glu Ala Ala
1               5                   10

<210> SEQ ID NO 176
<211> LENGTH: 9
<212> TYPE: PRT
<213> ORGANISM: Homo sapiens

<400> SEQUENCE: 176

Asp Arg Phe Ile Ala Ser Val Thr Val
1               5

<210> SEQ ID NO 177
<211> LENGTH: 9
<212> TYPE: PRT
<213> ORGANISM: Homo sapiens

<400> SEQUENCE: 177

Asp Arg Phe Thr Asn Gln Arg Glu Ala
1               5

<210> SEQ ID NO 178
<211> LENGTH: 10
<212> TYPE: PRT
<213> ORGANISM: Homo sapiens

<400> SEQUENCE: 178

Asp Arg Phe Thr Asn Gln Arg Glu Ala Ala
1               5                   10

<210> SEQ ID NO 179
<211> LENGTH: 9
<212> TYPE: PRT
<213> ORGANISM: Homo sapiens

<400> SEQUENCE: 179

Asp Arg Leu Trp Pro Val Asn Gly Leu
1               5

<210> SEQ ID NO 180
<211> LENGTH: 10
<212> TYPE: PRT
```

<213> ORGANISM: Homo sapiens

<400> SEQUENCE: 180

Asp Arg Leu Trp Pro Val Asn Gly Leu Leu
1               5                   10

<210> SEQ ID NO 181
<211> LENGTH: 9
<212> TYPE: PRT
<213> ORGANISM: Homo sapiens

<400> SEQUENCE: 181

Asp Arg Gln Thr Val Lys Thr Gln Ile
1               5

<210> SEQ ID NO 182
<211> LENGTH: 10
<212> TYPE: PRT
<213> ORGANISM: Homo sapiens

<400> SEQUENCE: 182

Asp Ser Glu Asn Thr Ala Ser His Gly Phe
1               5                   10

<210> SEQ ID NO 183
<211> LENGTH: 10
<212> TYPE: PRT
<213> ORGANISM: Homo sapiens

<400> SEQUENCE: 183

Asp Ser Glu Asn Thr Asn Gln Arg Gly Phe
1               5                   10

<210> SEQ ID NO 184
<211> LENGTH: 9
<212> TYPE: PRT
<213> ORGANISM: Homo sapiens

<400> SEQUENCE: 184

Asp Ser Lys Asn Lys Ile Asn Asp Met
1               5

<210> SEQ ID NO 185
<211> LENGTH: 9
<212> TYPE: PRT
<213> ORGANISM: Homo sapiens

<400> SEQUENCE: 185

Asp Ser Asn Val Ala Gln Ser Pro Arg
1               5

<210> SEQ ID NO 186
<211> LENGTH: 9
<212> TYPE: PRT
<213> ORGANISM: Homo sapiens

<400> SEQUENCE: 186

Asp Ser Asn Val Gly Ser Pro Leu Arg
1               5

<210> SEQ ID NO 187
<211> LENGTH: 9
<212> TYPE: PRT
<213> ORGANISM: Homo sapiens

```
<400> SEQUENCE: 187

Asp Ser Gln Gln Val Ser Arg Arg Trp
1               5

<210> SEQ ID NO 188
<211> LENGTH: 9
<212> TYPE: PRT
<213> ORGANISM: Homo sapiens

<400> SEQUENCE: 188

Asp Ser Ser Ala Leu Glu Asp Leu Trp
1               5

<210> SEQ ID NO 189
<211> LENGTH: 9
<212> TYPE: PRT
<213> ORGANISM: Homo sapiens

<400> SEQUENCE: 189

Asp Thr Asp Pro Leu Asp Ser Pro Leu
1               5

<210> SEQ ID NO 190
<211> LENGTH: 9
<212> TYPE: PRT
<213> ORGANISM: Homo sapiens

<400> SEQUENCE: 190

Asp Val Ala Arg Ile His Lys Val Phe
1               5

<210> SEQ ID NO 191
<211> LENGTH: 8
<212> TYPE: PRT
<213> ORGANISM: Homo sapiens

<400> SEQUENCE: 191

Asp Val Leu Ser Asn Leu Val Ile
1               5

<210> SEQ ID NO 192
<211> LENGTH: 9
<212> TYPE: PRT
<213> ORGANISM: Homo sapiens

<400> SEQUENCE: 192

Asp Val Leu Ser Asn Leu Val Met Lys
1               5

<210> SEQ ID NO 193
<211> LENGTH: 10
<212> TYPE: PRT
<213> ORGANISM: Homo sapiens

<400> SEQUENCE: 193

Asp Val Leu Ser Asn Leu Val Met Lys Arg
1               5                   10

<210> SEQ ID NO 194
<211> LENGTH: 8
<212> TYPE: PRT
<213> ORGANISM: Homo sapiens

<400> SEQUENCE: 194
```

-continued

```
Asp Val Pro Trp Ile Thr Leu Ile
1               5

<210> SEQ ID NO 195
<211> LENGTH: 9
<212> TYPE: PRT
<213> ORGANISM: Homo sapiens

<400> SEQUENCE: 195

Glu Ala Leu Asp Asp Ser Glu Asp Met
1               5

<210> SEQ ID NO 196
<211> LENGTH: 9
<212> TYPE: PRT
<213> ORGANISM: Homo sapiens

<400> SEQUENCE: 196

Glu Ala Leu Gly Phe Val Tyr His Leu
1               5

<210> SEQ ID NO 197
<211> LENGTH: 9
<212> TYPE: PRT
<213> ORGANISM: Homo sapiens

<400> SEQUENCE: 197

Glu Asp Ile Leu His Asn Ser Val Phe
1               5

<210> SEQ ID NO 198
<211> LENGTH: 9
<212> TYPE: PRT
<213> ORGANISM: Homo sapiens

<400> SEQUENCE: 198

Glu Asp Leu Ser Asp Leu Asn Phe Trp
1               5

<210> SEQ ID NO 199
<211> LENGTH: 11
<212> TYPE: PRT
<213> ORGANISM: Homo sapiens

<400> SEQUENCE: 199

Glu Asp Leu Ser Asp Leu Asn Phe Trp Lys Tyr
1               5                   10

<210> SEQ ID NO 200
<211> LENGTH: 9
<212> TYPE: PRT
<213> ORGANISM: Homo sapiens

<400> SEQUENCE: 200

Glu Asp Val Pro Trp Ile Thr Leu Ile
1               5

<210> SEQ ID NO 201
<211> LENGTH: 10
<212> TYPE: PRT
<213> ORGANISM: Homo sapiens

<400> SEQUENCE: 201

Glu Glu Gly Gly Lys Ala Leu Glu Asp Phe
1               5                   10
```

```
<210> SEQ ID NO 202
<211> LENGTH: 10
<212> TYPE: PRT
<213> ORGANISM: Homo sapiens

<400> SEQUENCE: 202

Glu Glu His Leu Lys Ala Leu Glu Asp Phe
1               5                   10

<210> SEQ ID NO 203
<211> LENGTH: 9
<212> TYPE: PRT
<213> ORGANISM: Homo sapiens

<400> SEQUENCE: 203

Glu Glu His Ser Met Ser Pro Glu Met
1               5

<210> SEQ ID NO 204
<211> LENGTH: 10
<212> TYPE: PRT
<213> ORGANISM: Homo sapiens

<400> SEQUENCE: 204

Glu Glu His Trp Lys Ala Leu Glu Asp Phe
1               5                   10

<210> SEQ ID NO 205
<211> LENGTH: 9
<212> TYPE: PRT
<213> ORGANISM: Homo sapiens

<400> SEQUENCE: 205

Glu Glu Leu Val Thr Leu His Pro Ala
1               5

<210> SEQ ID NO 206
<211> LENGTH: 9
<212> TYPE: PRT
<213> ORGANISM: Homo sapiens

<400> SEQUENCE: 206

Glu Glu Gln Ser Thr Val Ser Thr Ile
1               5

<210> SEQ ID NO 207
<211> LENGTH: 10
<212> TYPE: PRT
<213> ORGANISM: Homo sapiens

<400> SEQUENCE: 207

Glu Glu Ser Glu Leu Asp Ala Leu Ser Ile
1               5                   10

<210> SEQ ID NO 208
<211> LENGTH: 10
<212> TYPE: PRT
<213> ORGANISM: Homo sapiens

<400> SEQUENCE: 208

Glu Glu Ser Leu His Lys Asn Asn Asn Tyr
1               5                   10
```

-continued

```
<210> SEQ ID NO 209
<211> LENGTH: 9
<212> TYPE: PRT
<213> ORGANISM: Homo sapiens

<400> SEQUENCE: 209

Glu Glu Thr Asp Ile Thr Glu Ser Val
1               5

<210> SEQ ID NO 210
<211> LENGTH: 9
<212> TYPE: PRT
<213> ORGANISM: Homo sapiens

<400> SEQUENCE: 210

Glu Glu Thr Asp Ile Val Thr Glu Ser
1               5

<210> SEQ ID NO 211
<211> LENGTH: 10
<212> TYPE: PRT
<213> ORGANISM: Homo sapiens

<400> SEQUENCE: 211

Glu Glu Thr Asp Ile Val Thr Glu Ser Val
1               5                   10

<210> SEQ ID NO 212
<211> LENGTH: 9
<212> TYPE: PRT
<213> ORGANISM: Homo sapiens

<400> SEQUENCE: 212

Glu Phe Ile Ile Ser Asn Gln Val Ile
1               5

<210> SEQ ID NO 213
<211> LENGTH: 9
<212> TYPE: PRT
<213> ORGANISM: Homo sapiens

<400> SEQUENCE: 213

Glu His Leu Lys Ala Leu Glu Asp Phe
1               5

<210> SEQ ID NO 214
<211> LENGTH: 11
<212> TYPE: PRT
<213> ORGANISM: Homo sapiens

<400> SEQUENCE: 214

Glu His Leu Lys Ala Leu Glu Asp Phe Thr Leu
1               5                   10

<210> SEQ ID NO 215
<211> LENGTH: 9
<212> TYPE: PRT
<213> ORGANISM: Homo sapiens

<400> SEQUENCE: 215

Glu His Trp Lys Ala Leu Glu Asp Phe
1               5

<210> SEQ ID NO 216
<211> LENGTH: 11
```

-continued

```
<212> TYPE: PRT
<213> ORGANISM: Homo sapiens

<400> SEQUENCE: 216

Glu His Trp Lys Ala Leu Glu Asp Phe Thr Leu
1               5                   10

<210> SEQ ID NO 217
<211> LENGTH: 9
<212> TYPE: PRT
<213> ORGANISM: Homo sapiens

<400> SEQUENCE: 217

Glu Ile Lys Lys Lys Ser Thr Thr Lys
1               5

<210> SEQ ID NO 218
<211> LENGTH: 9
<212> TYPE: PRT
<213> ORGANISM: Homo sapiens

<400> SEQUENCE: 218

Glu Lys Asp Gln Arg Thr Tyr Ser Ile
1               5

<210> SEQ ID NO 219
<211> LENGTH: 9
<212> TYPE: PRT
<213> ORGANISM: Homo sapiens

<400> SEQUENCE: 219

Glu Leu Val Thr Leu His Pro Ala Lys
1               5

<210> SEQ ID NO 220
<211> LENGTH: 10
<212> TYPE: PRT
<213> ORGANISM: Homo sapiens

<400> SEQUENCE: 220

Glu Asn Glu Val Gly Phe Arg Gly Ser Trp
1               5                   10

<210> SEQ ID NO 221
<211> LENGTH: 9
<212> TYPE: PRT
<213> ORGANISM: Homo sapiens

<400> SEQUENCE: 221

Glu Asn Phe Glu Glu Gln Ser Thr Val
1               5

<210> SEQ ID NO 222
<211> LENGTH: 9
<212> TYPE: PRT
<213> ORGANISM: Homo sapiens

<400> SEQUENCE: 222

Glu Asn Asn His Ser Ile Ser Thr Arg
1               5

<210> SEQ ID NO 223
<211> LENGTH: 10
<212> TYPE: PRT
<213> ORGANISM: Homo sapiens
```

-continued

<400> SEQUENCE: 223

```
Glu Asn Ser Leu Pro Arg Ile Ser Ser Arg
1               5                   10
```

<210> SEQ ID NO 224
<211> LENGTH: 10
<212> TYPE: PRT
<213> ORGANISM: Homo sapiens

<400> SEQUENCE: 224

```
Glu Asn Thr Ala Ser His Gly Phe Gly Lys
1               5                   10
```

<210> SEQ ID NO 225
<211> LENGTH: 9
<212> TYPE: PRT
<213> ORGANISM: Homo sapiens

<400> SEQUENCE: 225

```
Glu Asn Thr Pro Ile Ala Tyr Phe Phe
1               5
```

<210> SEQ ID NO 226
<211> LENGTH: 9
<212> TYPE: PRT
<213> ORGANISM: Homo sapiens

<400> SEQUENCE: 226

```
Glu Pro Ala Glu Tyr Glu Pro Asn Leu
1               5
```

<210> SEQ ID NO 227
<211> LENGTH: 10
<212> TYPE: PRT
<213> ORGANISM: Homo sapiens

<400> SEQUENCE: 227

```
Glu Pro Ala Glu Tyr Glu Pro Asn Leu Phe
1               5                   10
```

<210> SEQ ID NO 228
<211> LENGTH: 9
<212> TYPE: PRT
<213> ORGANISM: Homo sapiens

<400> SEQUENCE: 228

```
Glu Pro Asn Thr Val Asn Ile Thr Ala
1               5
```

<210> SEQ ID NO 229
<211> LENGTH: 11
<212> TYPE: PRT
<213> ORGANISM: Homo sapiens

<400> SEQUENCE: 229

```
Glu Pro Asn Thr Val Asn Ile Thr Ala Gly Phe
1               5                   10
```

<210> SEQ ID NO 230
<211> LENGTH: 9
<212> TYPE: PRT
<213> ORGANISM: Homo sapiens

<400> SEQUENCE: 230

-continued

```
Glu Pro Gln Ser Gln Leu Val Leu Ala
1               5

<210> SEQ ID NO 231
<211> LENGTH: 11
<212> TYPE: PRT
<213> ORGANISM: Homo sapiens

<400> SEQUENCE: 231

Glu Pro Gln Ser Gln Leu Val Leu Ala Thr Tyr
1               5                   10

<210> SEQ ID NO 232
<211> LENGTH: 9
<212> TYPE: PRT
<213> ORGANISM: Homo sapiens

<400> SEQUENCE: 232

Glu Pro Arg Arg Val Thr Ser Gln Met
1               5

<210> SEQ ID NO 233
<211> LENGTH: 10
<212> TYPE: PRT
<213> ORGANISM: Homo sapiens

<400> SEQUENCE: 233

Glu Gln Glu His Gln Ala Ala Gly Ala Trp
1               5                   10

<210> SEQ ID NO 234
<211> LENGTH: 9
<212> TYPE: PRT
<213> ORGANISM: Homo sapiens

<400> SEQUENCE: 234

Glu Gln Lys Ala Phe Asn His Ser Arg
1               5

<210> SEQ ID NO 235
<211> LENGTH: 9
<212> TYPE: PRT
<213> ORGANISM: Homo sapiens

<400> SEQUENCE: 235

Glu Gln Lys Ala Leu Ser Ile His Trp
1               5

<210> SEQ ID NO 236
<211> LENGTH: 10
<212> TYPE: PRT
<213> ORGANISM: Homo sapiens

<400> SEQUENCE: 236

Glu Arg Asp Glu Lys Asp Gln Arg Thr Tyr
1               5                   10

<210> SEQ ID NO 237
<211> LENGTH: 9
<212> TYPE: PRT
<213> ORGANISM: Homo sapiens

<400> SEQUENCE: 237

Glu Arg Ile Lys Pro Val Gln Thr Val
```

-continued

```
1               5

<210> SEQ ID NO 238
<211> LENGTH: 9
<212> TYPE: PRT
<213> ORGANISM: Homo sapiens

<400> SEQUENCE: 238

Glu Arg Met Ser Leu Ile Ser Ser Leu
1               5

<210> SEQ ID NO 239
<211> LENGTH: 10
<212> TYPE: PRT
<213> ORGANISM: Homo sapiens

<400> SEQUENCE: 239

Glu Arg Met Ser Leu Ile Ser Ser Leu Tyr
1               5                   10

<210> SEQ ID NO 240
<211> LENGTH: 9
<212> TYPE: PRT
<213> ORGANISM: Homo sapiens

<400> SEQUENCE: 240

Glu Arg Val Leu Gln Thr Glu Asp Leu
1               5

<210> SEQ ID NO 241
<211> LENGTH: 9
<212> TYPE: PRT
<213> ORGANISM: Homo sapiens

<400> SEQUENCE: 241

Glu Ser Lys Ser Ile Phe Leu Lys Val
1               5

<210> SEQ ID NO 242
<211> LENGTH: 9
<212> TYPE: PRT
<213> ORGANISM: Homo sapiens

<400> SEQUENCE: 242

Glu Ser Leu His Lys Asn Asn Asn Tyr
1               5

<210> SEQ ID NO 243
<211> LENGTH: 9
<212> TYPE: PRT
<213> ORGANISM: Homo sapiens

<400> SEQUENCE: 243

Glu Ser Leu Lys Lys Asn Glu Ile Tyr
1               5

<210> SEQ ID NO 244
<211> LENGTH: 10
<212> TYPE: PRT
<213> ORGANISM: Homo sapiens

<400> SEQUENCE: 244

Glu Ser Leu Lys Lys Asn Glu Ile Tyr Arg
1               5                   10
```

-continued

<210> SEQ ID NO 245
<211> LENGTH: 10
<212> TYPE: PRT
<213> ORGANISM: Homo sapiens

<400> SEQUENCE: 245

Glu Ser Leu Lys Thr Val Lys Thr Gln Arg
1               5                   10

<210> SEQ ID NO 246
<211> LENGTH: 10
<212> TYPE: PRT
<213> ORGANISM: Homo sapiens

<400> SEQUENCE: 246

Glu Ser Tyr Lys Leu Lys Gly Asn Asn Tyr
1               5                   10

<210> SEQ ID NO 247
<211> LENGTH: 10
<212> TYPE: PRT
<213> ORGANISM: Homo sapiens

<400> SEQUENCE: 247

Glu Thr Asp Ile Thr Glu Ser Val Pro Val
1               5                   10

<210> SEQ ID NO 248
<211> LENGTH: 9
<212> TYPE: PRT
<213> ORGANISM: Homo sapiens

<400> SEQUENCE: 248

Glu Thr Asp Ile Val Thr Glu Ser Val
1               5

<210> SEQ ID NO 249
<211> LENGTH: 9
<212> TYPE: PRT
<213> ORGANISM: Homo sapiens

<400> SEQUENCE: 249

Glu Thr Phe Asn Ala Ser Phe Gln Val
1               5

<210> SEQ ID NO 250
<211> LENGTH: 10
<212> TYPE: PRT
<213> ORGANISM: Homo sapiens

<400> SEQUENCE: 250

Glu Thr Phe Asn Ala Ser Phe Gln Val Ile
1               5                   10

<210> SEQ ID NO 251
<211> LENGTH: 9
<212> TYPE: PRT
<213> ORGANISM: Homo sapiens

<400> SEQUENCE: 251

Glu Thr Asn Glu Gln Thr Ser Lys Arg
1               5

<210> SEQ ID NO 252

<211> LENGTH: 9
<212> TYPE: PRT
<213> ORGANISM: Homo sapiens

<400> SEQUENCE: 252

Glu Thr Tyr Asn Ser Trp Lys Val Lys
1               5

<210> SEQ ID NO 253
<211> LENGTH: 10
<212> TYPE: PRT
<213> ORGANISM: Homo sapiens

<400> SEQUENCE: 253

Glu Val Gly Phe Arg Gly Ser Trp His Lys
1               5                   10

<210> SEQ ID NO 254
<211> LENGTH: 10
<212> TYPE: PRT
<213> ORGANISM: Homo sapiens

<400> SEQUENCE: 254

Glu Val Thr Lys Ser Pro Arg Lys Leu Tyr
1               5                   10

<210> SEQ ID NO 255
<211> LENGTH: 9
<212> TYPE: PRT
<213> ORGANISM: Homo sapiens

<400> SEQUENCE: 255

Glu Val Val Leu Thr Leu Ser Gly Leu
1               5

<210> SEQ ID NO 256
<211> LENGTH: 10
<212> TYPE: PRT
<213> ORGANISM: Homo sapiens

<400> SEQUENCE: 256

Glu Val Val Pro Ser Leu Ala Cys Glu Leu
1               5                   10

<210> SEQ ID NO 257
<211> LENGTH: 9
<212> TYPE: PRT
<213> ORGANISM: Homo sapiens

<400> SEQUENCE: 257

Glu Val Val Pro Val Asn Gly Leu Leu
1               5

<210> SEQ ID NO 258
<211> LENGTH: 10
<212> TYPE: PRT
<213> ORGANISM: Homo sapiens

<400> SEQUENCE: 258

Glu Trp Ser Leu Arg Thr Asn Pro Phe Arg
1               5                   10

<210> SEQ ID NO 259
<211> LENGTH: 9
<212> TYPE: PRT

```
<213> ORGANISM: Homo sapiens

<400> SEQUENCE: 259

Phe Glu Asp Ile Leu His Asn Ser Leu
1               5

<210> SEQ ID NO 260
<211> LENGTH: 9
<212> TYPE: PRT
<213> ORGANISM: Homo sapiens

<400> SEQUENCE: 260

Phe Glu Glu Gln Ser Thr Val Ser Thr
1               5

<210> SEQ ID NO 261
<211> LENGTH: 10
<212> TYPE: PRT
<213> ORGANISM: Homo sapiens

<400> SEQUENCE: 261

Phe Glu Glu Gln Ser Thr Val Ser Thr Ile
1               5                   10

<210> SEQ ID NO 262
<211> LENGTH: 9
<212> TYPE: PRT
<213> ORGANISM: Homo sapiens

<400> SEQUENCE: 262

Phe Glu Phe Thr Gln Phe Arg Lys Leu
1               5

<210> SEQ ID NO 263
<211> LENGTH: 9
<212> TYPE: PRT
<213> ORGANISM: Homo sapiens

<400> SEQUENCE: 263

Phe Glu Lys Lys Ser Pro Arg Lys Leu
1               5

<210> SEQ ID NO 264
<211> LENGTH: 10
<212> TYPE: PRT
<213> ORGANISM: Homo sapiens

<400> SEQUENCE: 264

Phe Glu Lys Lys Ser Pro Arg Lys Leu Tyr
1               5                   10

<210> SEQ ID NO 265
<211> LENGTH: 9
<212> TYPE: PRT
<213> ORGANISM: Homo sapiens

<400> SEQUENCE: 265

Phe Glu Ser Gly Ser Asp Arg Leu Trp
1               5

<210> SEQ ID NO 266
<211> LENGTH: 8
<212> TYPE: PRT
<213> ORGANISM: Homo sapiens
```

```
<400> SEQUENCE: 266

Phe Glu Thr Glu Ala Val Ala Phe
1               5

<210> SEQ ID NO 267
<211> LENGTH: 9
<212> TYPE: PRT
<213> ORGANISM: Homo sapiens

<400> SEQUENCE: 267

Phe Glu Thr Glu Ala Val Ala Phe Met
1               5

<210> SEQ ID NO 268
<211> LENGTH: 9
<212> TYPE: PRT
<213> ORGANISM: Homo sapiens

<400> SEQUENCE: 268

Phe Glu Val Gly Pro Pro Val Gln Val
1               5

<210> SEQ ID NO 269
<211> LENGTH: 8
<212> TYPE: PRT
<213> ORGANISM: Homo sapiens

<400> SEQUENCE: 269

Phe Phe Pro Ser Ser His Leu Leu
1               5

<210> SEQ ID NO 270
<211> LENGTH: 10
<212> TYPE: PRT
<213> ORGANISM: Homo sapiens

<400> SEQUENCE: 270

Phe Phe Pro Ser Ser His Leu Leu Lys Leu
1               5                   10

<210> SEQ ID NO 271
<211> LENGTH: 9
<212> TYPE: PRT
<213> ORGANISM: Homo sapiens

<400> SEQUENCE: 271

Phe Phe Gln Thr Asn Glu Ala Ser Val
1               5

<210> SEQ ID NO 272
<211> LENGTH: 10
<212> TYPE: PRT
<213> ORGANISM: Homo sapiens

<400> SEQUENCE: 272

Phe Ile Ala Ala Ser His Gly Phe Gly Lys
1               5                   10

<210> SEQ ID NO 273
<211> LENGTH: 9
<212> TYPE: PRT
<213> ORGANISM: Homo sapiens

<400> SEQUENCE: 273
```

```
Phe Ile Ala Ser Val Lys Thr Gln Ile
1               5

<210> SEQ ID NO 274
<211> LENGTH: 10
<212> TYPE: PRT
<213> ORGANISM: Homo sapiens

<400> SEQUENCE: 274

Phe Ile Ala Ser Val Lys Thr Gln Ile Lys
1               5                   10

<210> SEQ ID NO 275
<211> LENGTH: 9
<212> TYPE: PRT
<213> ORGANISM: Homo sapiens

<400> SEQUENCE: 275

Phe Ile Ala Ser Val Thr Glu Ala Ala
1               5

<210> SEQ ID NO 276
<211> LENGTH: 9
<212> TYPE: PRT
<213> ORGANISM: Homo sapiens

<400> SEQUENCE: 276

Phe Ile Ala Ser Val Thr Val Lys His
1               5

<210> SEQ ID NO 277
<211> LENGTH: 9
<212> TYPE: PRT
<213> ORGANISM: Homo sapiens

<400> SEQUENCE: 277

Phe Ile Ala Ser Val Thr Val Lys Thr
1               5

<210> SEQ ID NO 278
<211> LENGTH: 9
<212> TYPE: PRT
<213> ORGANISM: Homo sapiens

<400> SEQUENCE: 278

Phe Ile Ile Ser Asn Gln Val Ile Leu
1               5

<210> SEQ ID NO 279
<211> LENGTH: 9
<212> TYPE: PRT
<213> ORGANISM: Homo sapiens

<400> SEQUENCE: 279

Phe Lys Asn Asn Ser Asn Gln Ala Val
1               5

<210> SEQ ID NO 280
<211> LENGTH: 8
<212> TYPE: PRT
<213> ORGANISM: Homo sapiens

<400> SEQUENCE: 280

Phe Leu Gln Arg Arg Thr Lys Ile
1               5
```

-continued

```
<210> SEQ ID NO 281
<211> LENGTH: 9
<212> TYPE: PRT
<213> ORGANISM: Homo sapiens

<400> SEQUENCE: 281

Phe Leu Gln Arg Arg Thr Lys Ile Val
1               5

<210> SEQ ID NO 282
<211> LENGTH: 10
<212> TYPE: PRT
<213> ORGANISM: Homo sapiens

<400> SEQUENCE: 282

Phe Leu Arg Arg Pro Asn Phe Thr Arg Arg
1               5                   10

<210> SEQ ID NO 283
<211> LENGTH: 9
<212> TYPE: PRT
<213> ORGANISM: Homo sapiens

<400> SEQUENCE: 283

Phe Asn His Ser Arg Glu Thr Ser Ile
1               5

<210> SEQ ID NO 284
<211> LENGTH: 10
<212> TYPE: PRT
<213> ORGANISM: Homo sapiens

<400> SEQUENCE: 284

Phe Pro Ile Lys Ser Phe Val Lys Thr Leu
1               5                   10

<210> SEQ ID NO 285
<211> LENGTH: 9
<212> TYPE: PRT
<213> ORGANISM: Homo sapiens

<400> SEQUENCE: 285

Phe Pro Ser Ser His Leu Leu Lys Leu
1               5

<210> SEQ ID NO 286
<211> LENGTH: 9
<212> TYPE: PRT
<213> ORGANISM: Homo sapiens

<400> SEQUENCE: 286

Phe Gln His Leu Leu Phe Gly Ile Tyr
1               5

<210> SEQ ID NO 287
<211> LENGTH: 10
<212> TYPE: PRT
<213> ORGANISM: Homo sapiens

<400> SEQUENCE: 287

Phe Gln Ile Ser Ala His Ser Gly Ser Leu
1               5                   10
```

-continued

```
<210> SEQ ID NO 288
<211> LENGTH: 9
<212> TYPE: PRT
<213> ORGANISM: Homo sapiens

<400> SEQUENCE: 288

Phe Gln Ser Ala Ser His Leu Leu Arg
1               5

<210> SEQ ID NO 289
<211> LENGTH: 8
<212> TYPE: PRT
<213> ORGANISM: Homo sapiens

<400> SEQUENCE: 289

Phe Gln Val Ser Lys Ser Leu Tyr
1               5

<210> SEQ ID NO 290
<211> LENGTH: 8
<212> TYPE: PRT
<213> ORGANISM: Homo sapiens

<400> SEQUENCE: 290

Phe Arg Gly Phe Tyr Ser Ala Leu
1               5

<210> SEQ ID NO 291
<211> LENGTH: 9
<212> TYPE: PRT
<213> ORGANISM: Homo sapiens

<400> SEQUENCE: 291

Phe Arg Ile Ala Gly Cys Tyr Glu Ala
1               5

<210> SEQ ID NO 292
<211> LENGTH: 10
<212> TYPE: PRT
<213> ORGANISM: Homo sapiens

<400> SEQUENCE: 292

Phe Arg Ile Ala Gly Cys Tyr Glu Ala Leu
1               5                   10

<210> SEQ ID NO 293
<211> LENGTH: 9
<212> TYPE: PRT
<213> ORGANISM: Homo sapiens

<400> SEQUENCE: 293

Phe Arg Ile Ala Ser Gly Asn Lys Lys
1               5

<210> SEQ ID NO 294
<211> LENGTH: 11
<212> TYPE: PRT
<213> ORGANISM: Homo sapiens

<400> SEQUENCE: 294

Phe Arg Lys Leu Met Ser Gly Phe Pro Glu Val
1               5                   10

<210> SEQ ID NO 295
<211> LENGTH: 8
```

-continued

```
<212> TYPE: PRT
<213> ORGANISM: Homo sapiens

<400> SEQUENCE: 295

Phe Arg Leu Asn Gly Ala Gln Met
1               5

<210> SEQ ID NO 296
<211> LENGTH: 10
<212> TYPE: PRT
<213> ORGANISM: Homo sapiens

<400> SEQUENCE: 296

Phe Arg Leu Asn Gly Ala Gln Met Glu Lys
1               5                   10

<210> SEQ ID NO 297
<211> LENGTH: 8
<212> TYPE: PRT
<213> ORGANISM: Homo sapiens

<400> SEQUENCE: 297

Phe Arg Ser Lys Gly Ala Gln Met
1               5

<210> SEQ ID NO 298
<211> LENGTH: 8
<212> TYPE: PRT
<213> ORGANISM: Homo sapiens

<400> SEQUENCE: 298

Phe Arg Ser Lys Trp Ala Gln Met
1               5

<210> SEQ ID NO 299
<211> LENGTH: 8
<212> TYPE: PRT
<213> ORGANISM: Homo sapiens

<400> SEQUENCE: 299

Phe Arg Ser Lys Trp Ser Gln Met
1               5

<210> SEQ ID NO 300
<211> LENGTH: 8
<212> TYPE: PRT
<213> ORGANISM: Homo sapiens

<400> SEQUENCE: 300

Phe Ser Asp Asp Leu Asn Leu Ile
1               5

<210> SEQ ID NO 301
<211> LENGTH: 9
<212> TYPE: PRT
<213> ORGANISM: Homo sapiens

<400> SEQUENCE: 301

Phe Ser Asp Asp Leu Asn Leu Ile Leu
1               5

<210> SEQ ID NO 302
<211> LENGTH: 10
<212> TYPE: PRT
<213> ORGANISM: Homo sapiens
```

<400> SEQUENCE: 302

Phe Ser Asp Asp Leu Asn Leu Ile Leu Leu
1               5                   10

<210> SEQ ID NO 303
<211> LENGTH: 8
<212> TYPE: PRT
<213> ORGANISM: Homo sapiens

<400> SEQUENCE: 303

Phe Ser Lys Val Arg Gln Val Phe
1               5

<210> SEQ ID NO 304
<211> LENGTH: 10
<212> TYPE: PRT
<213> ORGANISM: Homo sapiens

<400> SEQUENCE: 304

Phe Thr Asp Asn Glu Asn Lys Ser Lys Ile
1               5                   10

<210> SEQ ID NO 305
<211> LENGTH: 9
<212> TYPE: PRT
<213> ORGANISM: Homo sapiens

<400> SEQUENCE: 305

Phe Thr Asp Ser Phe Ser Tyr Glu Ala
1               5

<210> SEQ ID NO 306
<211> LENGTH: 10
<212> TYPE: PRT
<213> ORGANISM: Homo sapiens

<400> SEQUENCE: 306

Phe Thr Asp Ser Phe Ser Tyr Glu Ala Leu
1               5                   10

<210> SEQ ID NO 307
<211> LENGTH: 9
<212> TYPE: PRT
<213> ORGANISM: Homo sapiens

<400> SEQUENCE: 307

Phe Thr Arg Arg Leu Gln Phe Leu Tyr
1               5

<210> SEQ ID NO 308
<211> LENGTH: 9
<212> TYPE: PRT
<213> ORGANISM: Homo sapiens

<400> SEQUENCE: 308

Phe Val Tyr His Leu Ser Ser Glu Ala
1               5

<210> SEQ ID NO 309
<211> LENGTH: 10
<212> TYPE: PRT
<213> ORGANISM: Homo sapiens

<400> SEQUENCE: 309

-continued

```
Phe Tyr Ser Ala His Gly Thr Glu Ala Leu
1               5                   10

<210> SEQ ID NO 310
<211> LENGTH: 11
<212> TYPE: PRT
<213> ORGANISM: Homo sapiens

<400> SEQUENCE: 310

Phe Tyr Ser Ala His Gly Thr Lys Gln Cys Phe
1               5                   10

<210> SEQ ID NO 311
<211> LENGTH: 9
<212> TYPE: PRT
<213> ORGANISM: Homo sapiens

<400> SEQUENCE: 311

Phe Tyr Ser Ala Leu Gln Lys Ala Val
1               5

<210> SEQ ID NO 312
<211> LENGTH: 9
<212> TYPE: PRT
<213> ORGANISM: Homo sapiens

<400> SEQUENCE: 312

Gly Glu Cys Ser Asn Gln Val Ile Leu
1               5

<210> SEQ ID NO 313
<211> LENGTH: 9
<212> TYPE: PRT
<213> ORGANISM: Homo sapiens

<400> SEQUENCE: 313

Gly Glu Phe Ile Ile Ser Asn Gln Val
1               5

<210> SEQ ID NO 314
<211> LENGTH: 10
<212> TYPE: PRT
<213> ORGANISM: Homo sapiens

<400> SEQUENCE: 314

Gly Glu Phe Ile Ile Ser Asn Gln Val Ile
1               5                   10

<210> SEQ ID NO 315
<211> LENGTH: 11
<212> TYPE: PRT
<213> ORGANISM: Homo sapiens

<400> SEQUENCE: 315

Gly Glu Phe Ile Ile Ser Asn Gln Val Ile Leu
1               5                   10

<210> SEQ ID NO 316
<211> LENGTH: 9
<212> TYPE: PRT
<213> ORGANISM: Homo sapiens

<400> SEQUENCE: 316

Gly Glu Asn Ile Ser Glu Lys Asp Leu
```

-continued

```
1               5

<210> SEQ ID NO 317
<211> LENGTH: 10
<212> TYPE: PRT
<213> ORGANISM: Homo sapiens

<400> SEQUENCE: 317

Gly Glu Asn Ile Ser Glu Lys Asp Leu Leu
1               5                   10

<210> SEQ ID NO 318
<211> LENGTH: 9
<212> TYPE: PRT
<213> ORGANISM: Homo sapiens

<400> SEQUENCE: 318

Gly Glu Asn Thr Pro Ile Ala Glu Lys
1               5

<210> SEQ ID NO 319
<211> LENGTH: 11
<212> TYPE: PRT
<213> ORGANISM: Homo sapiens

<400> SEQUENCE: 319

Gly Glu Asn Thr Pro Ile Ala Glu Lys Asp Leu
1               5                   10

<210> SEQ ID NO 320
<211> LENGTH: 8
<212> TYPE: PRT
<213> ORGANISM: Homo sapiens

<400> SEQUENCE: 320

Gly Glu Asn Thr Pro Ile Ala Tyr
1               5

<210> SEQ ID NO 321
<211> LENGTH: 9
<212> TYPE: PRT
<213> ORGANISM: Homo sapiens

<400> SEQUENCE: 321

Gly Glu Asn Thr Pro Ile Ala Tyr Phe
1               5

<210> SEQ ID NO 322
<211> LENGTH: 10
<212> TYPE: PRT
<213> ORGANISM: Homo sapiens

<400> SEQUENCE: 322

Gly Glu Asn Thr Pro Ile Ala Tyr Phe Phe
1               5                   10

<210> SEQ ID NO 323
<211> LENGTH: 9
<212> TYPE: PRT
<213> ORGANISM: Homo sapiens

<400> SEQUENCE: 323

Gly Glu Asn Thr Pro Ile Ala Tyr Ser
1               5
```

```
<210> SEQ ID NO 324
<211> LENGTH: 9
<212> TYPE: PRT
<213> ORGANISM: Homo sapiens

<400> SEQUENCE: 324

Gly Phe Arg Gly Phe Tyr Ser Ala Leu
1               5

<210> SEQ ID NO 325
<211> LENGTH: 9
<212> TYPE: PRT
<213> ORGANISM: Homo sapiens

<400> SEQUENCE: 325

Gly Ile Ala Pro Leu Leu Pro Ser Val
1               5

<210> SEQ ID NO 326
<211> LENGTH: 11
<212> TYPE: PRT
<213> ORGANISM: Homo sapiens

<400> SEQUENCE: 326

Gly Ile Ser Leu Phe Ser Asp Asp Leu Asn Leu
1               5                   10

<210> SEQ ID NO 327
<211> LENGTH: 9
<212> TYPE: PRT
<213> ORGANISM: Homo sapiens

<400> SEQUENCE: 327

Gly Lys Ala Leu Glu Asp Phe Thr Leu
1               5

<210> SEQ ID NO 328
<211> LENGTH: 10
<212> TYPE: PRT
<213> ORGANISM: Homo sapiens

<400> SEQUENCE: 328

Gly Lys Glu Ser Tyr Lys Gly Asn Asn Tyr
1               5                   10

<210> SEQ ID NO 329
<211> LENGTH: 10
<212> TYPE: PRT
<213> ORGANISM: Homo sapiens

<400> SEQUENCE: 329

Gly Leu Leu Glu Leu Thr Leu Ser Gly Leu
1               5                   10

<210> SEQ ID NO 330
<211> LENGTH: 9
<212> TYPE: PRT
<213> ORGANISM: Homo sapiens

<400> SEQUENCE: 330

Gly Asn Tyr Leu Tyr Glu Thr Thr Ile
1               5

<210> SEQ ID NO 331
```

```
<211> LENGTH: 9
<212> TYPE: PRT
<213> ORGANISM: Homo sapiens

<400> SEQUENCE: 331

Gly Ser Asp Lys Ile Ser Arg Leu Trp
1               5

<210> SEQ ID NO 332
<211> LENGTH: 9
<212> TYPE: PRT
<213> ORGANISM: Homo sapiens

<400> SEQUENCE: 332

Gly Ser Asp Lys Ser Pro Arg Lys Leu
1               5

<210> SEQ ID NO 333
<211> LENGTH: 10
<212> TYPE: PRT
<213> ORGANISM: Homo sapiens

<400> SEQUENCE: 333

Gly Ser Asp Lys Ser Pro Arg Lys Leu Tyr
1               5                   10

<210> SEQ ID NO 334
<211> LENGTH: 11
<212> TYPE: PRT
<213> ORGANISM: Homo sapiens

<400> SEQUENCE: 334

Gly Ser Asp Arg Leu Trp Pro Val Asn Gly Leu
1               5                   10

<210> SEQ ID NO 335
<211> LENGTH: 9
<212> TYPE: PRT
<213> ORGANISM: Homo sapiens

<400> SEQUENCE: 335

Gly Ser Phe Leu Ile Gly Ser Ser Lys
1               5

<210> SEQ ID NO 336
<211> LENGTH: 9
<212> TYPE: PRT
<213> ORGANISM: Homo sapiens

<400> SEQUENCE: 336

Gly Ser Leu Lys Asn Lys Val Gln Lys
1               5

<210> SEQ ID NO 337
<211> LENGTH: 9
<212> TYPE: PRT
<213> ORGANISM: Homo sapiens

<400> SEQUENCE: 337

Gly Ser Gln Leu Gln Lys Ser Thr Phe
1               5

<210> SEQ ID NO 338
<211> LENGTH: 9
<212> TYPE: PRT
```

-continued

```
<213> ORGANISM: Homo sapiens

<400> SEQUENCE: 338

Gly Ser Ser Asn Thr Ser Glu Leu Lys
1               5

<210> SEQ ID NO 339
<211> LENGTH: 9
<212> TYPE: PRT
<213> ORGANISM: Homo sapiens

<400> SEQUENCE: 339

Gly Thr Ala Glu Thr Tyr Asn Ser Trp
1               5

<210> SEQ ID NO 340
<211> LENGTH: 10
<212> TYPE: PRT
<213> ORGANISM: Homo sapiens

<400> SEQUENCE: 340

Gly Thr Ala Glu Thr Tyr Asn Ser Trp Lys
1               5                   10

<210> SEQ ID NO 341
<211> LENGTH: 9
<212> TYPE: PRT
<213> ORGANISM: Homo sapiens

<400> SEQUENCE: 341

Gly Thr Lys Leu Asn Val Lys Leu Phe
1               5

<210> SEQ ID NO 342
<211> LENGTH: 9
<212> TYPE: PRT
<213> ORGANISM: Homo sapiens

<400> SEQUENCE: 342

Gly Thr Lys Leu Asn Val Leu Leu Lys
1               5

<210> SEQ ID NO 343
<211> LENGTH: 9
<212> TYPE: PRT
<213> ORGANISM: Homo sapiens

<400> SEQUENCE: 343

Gly Tyr Leu Arg Gly Ala Lys Lys Leu
1               5

<210> SEQ ID NO 344
<211> LENGTH: 9
<212> TYPE: PRT
<213> ORGANISM: Homo sapiens

<400> SEQUENCE: 344

Gly Tyr Leu Ser Lys Val Phe Ser Lys
1               5

<210> SEQ ID NO 345
<211> LENGTH: 10
<212> TYPE: PRT
<213> ORGANISM: Homo sapiens
```

-continued

```
<400> SEQUENCE: 345

His Glu Val Asn His Ser Gly Lys Gln Ala
1               5                   10

<210> SEQ ID NO 346
<211> LENGTH: 8
<212> TYPE: PRT
<213> ORGANISM: Homo sapiens

<400> SEQUENCE: 346

His Phe Phe Pro Ser Ser His Leu
1               5

<210> SEQ ID NO 347
<211> LENGTH: 9
<212> TYPE: PRT
<213> ORGANISM: Homo sapiens

<400> SEQUENCE: 347

His Phe Phe Pro Ser Ser His Leu Leu
1               5

<210> SEQ ID NO 348
<211> LENGTH: 10
<212> TYPE: PRT
<213> ORGANISM: Homo sapiens

<400> SEQUENCE: 348

His Phe Phe Pro Ser Ser His Leu Leu Lys
1               5                   10

<210> SEQ ID NO 349
<211> LENGTH: 9
<212> TYPE: PRT
<213> ORGANISM: Homo sapiens

<400> SEQUENCE: 349

His His Phe Phe Pro Ser Ser His Leu
1               5

<210> SEQ ID NO 350
<211> LENGTH: 10
<212> TYPE: PRT
<213> ORGANISM: Homo sapiens

<400> SEQUENCE: 350

His His Phe Phe Pro Ser Ser His Leu Leu
1               5                   10

<210> SEQ ID NO 351
<211> LENGTH: 9
<212> TYPE: PRT
<213> ORGANISM: Homo sapiens

<400> SEQUENCE: 351

His Lys Ile Leu Lys Val Ser Gln Leu
1               5

<210> SEQ ID NO 352
<211> LENGTH: 9
<212> TYPE: PRT
<213> ORGANISM: Homo sapiens

<400> SEQUENCE: 352
```

```
His Leu Leu Phe Gly Ile Tyr Leu Leu
1               5

<210> SEQ ID NO 353
<211> LENGTH: 9
<212> TYPE: PRT
<213> ORGANISM: Homo sapiens

<400> SEQUENCE: 353

His Leu Leu Lys Leu Asn Val Arg Lys
1               5

<210> SEQ ID NO 354
<211> LENGTH: 9
<212> TYPE: PRT
<213> ORGANISM: Homo sapiens

<400> SEQUENCE: 354

His Leu Ser Ser Glu Ala Thr Lys Leu
1               5

<210> SEQ ID NO 355
<211> LENGTH: 10
<212> TYPE: PRT
<213> ORGANISM: Homo sapiens

<400> SEQUENCE: 355

His Pro Ala Lys Ile Lys Met Gln Pro Leu
1               5                   10

<210> SEQ ID NO 356
<211> LENGTH: 8
<212> TYPE: PRT
<213> ORGANISM: Homo sapiens

<400> SEQUENCE: 356

His Pro Gly Ser Phe Leu Asp Trp
1               5

<210> SEQ ID NO 357
<211> LENGTH: 9
<212> TYPE: PRT
<213> ORGANISM: Homo sapiens

<400> SEQUENCE: 357

His Pro Gly Ser Phe Leu Asp Trp Phe
1               5

<210> SEQ ID NO 358
<211> LENGTH: 10
<212> TYPE: PRT
<213> ORGANISM: Homo sapiens

<400> SEQUENCE: 358

His Pro Gly Ser Phe Leu Asp Trp Phe Phe
1               5                   10

<210> SEQ ID NO 359
<211> LENGTH: 9
<212> TYPE: PRT
<213> ORGANISM: Homo sapiens

<400> SEQUENCE: 359

His Gln Ala Ala Gly Ala Trp Arg Val
1               5
```

-continued

```
<210> SEQ ID NO 360
<211> LENGTH: 10
<212> TYPE: PRT
<213> ORGANISM: Homo sapiens

<400> SEQUENCE: 360

His Gln Ala Ala Gly Ala Trp Arg Val Trp
1               5                   10

<210> SEQ ID NO 361
<211> LENGTH: 9
<212> TYPE: PRT
<213> ORGANISM: Homo sapiens

<400> SEQUENCE: 361

His Ser Ile Ser Thr Arg Gln Gln Leu
1               5

<210> SEQ ID NO 362
<211> LENGTH: 10
<212> TYPE: PRT
<213> ORGANISM: Homo sapiens

<400> SEQUENCE: 362

His Ser Met Ser Pro Glu Arg Asn Gly Lys
1               5                   10

<210> SEQ ID NO 363
<211> LENGTH: 10
<212> TYPE: PRT
<213> ORGANISM: Homo sapiens

<400> SEQUENCE: 363

His Ser Arg Phe Gln Ser Ala Ser His Leu
1               5                   10

<210> SEQ ID NO 364
<211> LENGTH: 10
<212> TYPE: PRT
<213> ORGANISM: Homo sapiens

<400> SEQUENCE: 364

His Thr His Leu Ala Gln Gly Tyr Leu Arg
1               5                   10

<210> SEQ ID NO 365
<211> LENGTH: 9
<212> TYPE: PRT
<213> ORGANISM: Homo sapiens

<400> SEQUENCE: 365

His Val Met Val Ile Leu Gln Ile Lys
1               5

<210> SEQ ID NO 366
<211> LENGTH: 9
<212> TYPE: PRT
<213> ORGANISM: Homo sapiens

<400> SEQUENCE: 366

His Trp Asp Met Lys Leu Thr Thr Val
1               5
```

-continued

```
<210> SEQ ID NO 367
<211> LENGTH: 9
<212> TYPE: PRT
<213> ORGANISM: Homo sapiens

<400> SEQUENCE: 367

Ile Ala Ala Glu Asn Gln Met Thr Ile
1               5

<210> SEQ ID NO 368
<211> LENGTH: 10
<212> TYPE: PRT
<213> ORGANISM: Homo sapiens

<400> SEQUENCE: 368

Ile Ala Ala Glu Asn Gln Met Thr Ile Leu
1               5                   10

<210> SEQ ID NO 369
<211> LENGTH: 9
<212> TYPE: PRT
<213> ORGANISM: Homo sapiens

<400> SEQUENCE: 369

Ile Ala Ala Ser His Gly Phe Gly Lys
1               5

<210> SEQ ID NO 370
<211> LENGTH: 8
<212> TYPE: PRT
<213> ORGANISM: Homo sapiens

<400> SEQUENCE: 370

Ile Ala Pro Leu Leu Pro Ser Val
1               5

<210> SEQ ID NO 371
<211> LENGTH: 9
<212> TYPE: PRT
<213> ORGANISM: Homo sapiens

<400> SEQUENCE: 371

Ile Ala Tyr Ser Cys Asp Gln Asn Ile
1               5

<210> SEQ ID NO 372
<211> LENGTH: 9
<212> TYPE: PRT
<213> ORGANISM: Homo sapiens

<400> SEQUENCE: 372

Ile Glu Asn His Asn Lys Cys Gln Leu
1               5

<210> SEQ ID NO 373
<211> LENGTH: 8
<212> TYPE: PRT
<213> ORGANISM: Homo sapiens

<400> SEQUENCE: 373

Ile Phe Thr Asp Ser Phe Ser Tyr
1               5

<210> SEQ ID NO 374
<211> LENGTH: 9
```

```
<212> TYPE: PRT
<213> ORGANISM: Homo sapiens

<400> SEQUENCE: 374

Ile His Trp Asp Met Lys Leu Thr Thr
1               5

<210> SEQ ID NO 375
<211> LENGTH: 10
<212> TYPE: PRT
<213> ORGANISM: Homo sapiens

<400> SEQUENCE: 375

Ile His Trp Asp Met Lys Leu Thr Thr Val
1               5                   10

<210> SEQ ID NO 376
<211> LENGTH: 10
<212> TYPE: PRT
<213> ORGANISM: Homo sapiens

<400> SEQUENCE: 376

Ile Ile Ser Asp Ser Ser Ala Leu Glu Lys
1               5                   10

<210> SEQ ID NO 377
<211> LENGTH: 10
<212> TYPE: PRT
<213> ORGANISM: Homo sapiens

<400> SEQUENCE: 377

Ile Ile Ser Asn Gln Val Ile Leu Ala Lys
1               5                   10

<210> SEQ ID NO 378
<211> LENGTH: 9
<212> TYPE: PRT
<213> ORGANISM: Homo sapiens

<400> SEQUENCE: 378

Ile Lys Glu Ala Ala Ser His Gly Phe
1               5

<210> SEQ ID NO 379
<211> LENGTH: 8
<212> TYPE: PRT
<213> ORGANISM: Homo sapiens

<400> SEQUENCE: 379

Ile Lys Glu Lys Leu Gln Val Met
1               5

<210> SEQ ID NO 380
<211> LENGTH: 9
<212> TYPE: PRT
<213> ORGANISM: Homo sapiens

<400> SEQUENCE: 380

Ile Lys Leu Ser Ile Ser Asn Ser Tyr
1               5

<210> SEQ ID NO 381
<211> LENGTH: 9
<212> TYPE: PRT
<213> ORGANISM: Homo sapiens
```

-continued

```
<400> SEQUENCE: 381

Ile Lys Val Ser Pro Tyr Leu Ser Ile
1               5

<210> SEQ ID NO 382
<211> LENGTH: 9
<212> TYPE: PRT
<213> ORGANISM: Homo sapiens

<400> SEQUENCE: 382

Ile Leu Glu Glu Ser Gly Ser Gln Leu
1               5

<210> SEQ ID NO 383
<211> LENGTH: 9
<212> TYPE: PRT
<213> ORGANISM: Homo sapiens

<400> SEQUENCE: 383

Ile Leu His Asn Ser Leu Glu Asp Tyr
1               5

<210> SEQ ID NO 384
<211> LENGTH: 9
<212> TYPE: PRT
<213> ORGANISM: Homo sapiens

<400> SEQUENCE: 384

Ile Leu Lys Met Lys Ile Thr Asn Ile
1               5

<210> SEQ ID NO 385
<211> LENGTH: 10
<212> TYPE: PRT
<213> ORGANISM: Homo sapiens

<400> SEQUENCE: 385

Ile Leu Lys Met Lys Ile Thr Asn Ile Leu
1               5                   10

<210> SEQ ID NO 386
<211> LENGTH: 9
<212> TYPE: PRT
<213> ORGANISM: Homo sapiens

<400> SEQUENCE: 386

Ile Leu Lys Val Ser Gln Leu Val Leu
1               5

<210> SEQ ID NO 387
<211> LENGTH: 9
<212> TYPE: PRT
<213> ORGANISM: Homo sapiens

<400> SEQUENCE: 387

Ile Leu Leu Ala Leu Leu Leu Lys Lys
1               5

<210> SEQ ID NO 388
<211> LENGTH: 9
<212> TYPE: PRT
<213> ORGANISM: Homo sapiens

<400> SEQUENCE: 388
```

-continued

```
Ile Leu Val Leu Val Lys Val Leu Leu
1               5

<210> SEQ ID NO 389
<211> LENGTH: 8
<212> TYPE: PRT
<213> ORGANISM: Homo sapiens

<400> SEQUENCE: 389

Ile Met Asn Ile Pro Met Glu Lys
1               5

<210> SEQ ID NO 390
<211> LENGTH: 9
<212> TYPE: PRT
<213> ORGANISM: Homo sapiens

<400> SEQUENCE: 390

Ile Met Asn Gln Asp Val Cys Ala Leu
1               5

<210> SEQ ID NO 391
<211> LENGTH: 10
<212> TYPE: PRT
<213> ORGANISM: Homo sapiens

<400> SEQUENCE: 391

Ile Met Ser Gly Leu Glu Lys Val Ser Lys
1               5                   10

<210> SEQ ID NO 392
<211> LENGTH: 9
<212> TYPE: PRT
<213> ORGANISM: Homo sapiens

<400> SEQUENCE: 392

Ile Asn Asp Met Arg Phe Ile Ser Leu
1               5

<210> SEQ ID NO 393
<211> LENGTH: 8
<212> TYPE: PRT
<213> ORGANISM: Homo sapiens

<400> SEQUENCE: 393

Ile Pro Leu Ser Leu Leu Gly Ile
1               5

<210> SEQ ID NO 394
<211> LENGTH: 9
<212> TYPE: PRT
<213> ORGANISM: Homo sapiens

<400> SEQUENCE: 394

Ile Pro Leu Ser Leu Leu Gly Ile Ala
1               5

<210> SEQ ID NO 395
<211> LENGTH: 8
<212> TYPE: PRT
<213> ORGANISM: Homo sapiens

<400> SEQUENCE: 395

Ile Pro Val Asn Leu Lys Asn Val
```

-continued

```
1               5

<210> SEQ ID NO 396
<211> LENGTH: 9
<212> TYPE: PRT
<213> ORGANISM: Homo sapiens

<400> SEQUENCE: 396

Ile Arg Glu Ala Ala Ser His Gly Phe
1               5

<210> SEQ ID NO 397
<211> LENGTH: 10
<212> TYPE: PRT
<213> ORGANISM: Homo sapiens

<400> SEQUENCE: 397

Ile Arg Lys Asp His Ile Gly Lys Ser Met
1               5                   10

<210> SEQ ID NO 398
<211> LENGTH: 9
<212> TYPE: PRT
<213> ORGANISM: Homo sapiens

<400> SEQUENCE: 398

Ile Ser Ala His Ser Gly Ser Leu Lys
1               5

<210> SEQ ID NO 399
<211> LENGTH: 10
<212> TYPE: PRT
<213> ORGANISM: Homo sapiens

<400> SEQUENCE: 399

Ile Ser Ala His Ser Gly Ser Leu Lys Lys
1               5                   10

<210> SEQ ID NO 400
<211> LENGTH: 9
<212> TYPE: PRT
<213> ORGANISM: Homo sapiens

<400> SEQUENCE: 400

Ile Ser Asp Ser Ser Ala Leu Glu Lys
1               5

<210> SEQ ID NO 401
<211> LENGTH: 9
<212> TYPE: PRT
<213> ORGANISM: Homo sapiens

<400> SEQUENCE: 401

Ile Ser Lys Glu Val Val Leu Thr Leu
1               5

<210> SEQ ID NO 402
<211> LENGTH: 10
<212> TYPE: PRT
<213> ORGANISM: Homo sapiens

<400> SEQUENCE: 402

Ile Ser Leu Phe Ser Asp Asp Leu Asn Leu
1               5                   10
```

-continued

```
<210> SEQ ID NO 403
<211> LENGTH: 8
<212> TYPE: PRT
<213> ORGANISM: Homo sapiens

<400> SEQUENCE: 403

Ile Ser Leu Gln Ala Phe Leu Trp
1               5

<210> SEQ ID NO 404
<211> LENGTH: 9
<212> TYPE: PRT
<213> ORGANISM: Homo sapiens

<400> SEQUENCE: 404

Ile Ser Leu Thr Lys Thr Thr Ala Val
1               5

<210> SEQ ID NO 405
<211> LENGTH: 9
<212> TYPE: PRT
<213> ORGANISM: Homo sapiens

<400> SEQUENCE: 405

Ile Ser Asn Gln Val Ile Leu Ala Lys
1               5

<210> SEQ ID NO 406
<211> LENGTH: 9
<212> TYPE: PRT
<213> ORGANISM: Homo sapiens

<400> SEQUENCE: 406

Ile Ser Arg Gly Ile Gln Asn Val Lys
1               5

<210> SEQ ID NO 407
<211> LENGTH: 9
<212> TYPE: PRT
<213> ORGANISM: Homo sapiens

<400> SEQUENCE: 407

Ile Ser Arg Gly Lys Asp Lys Leu Lys
1               5

<210> SEQ ID NO 408
<211> LENGTH: 9
<212> TYPE: PRT
<213> ORGANISM: Homo sapiens

<400> SEQUENCE: 408

Ile Ser Arg Ile Ile Gln Asn Val Lys
1               5

<210> SEQ ID NO 409
<211> LENGTH: 10
<212> TYPE: PRT
<213> ORGANISM: Homo sapiens

<400> SEQUENCE: 409

Ile Ser Arg Leu Trp Pro Val Asn Gly Leu
1               5                   10

<210> SEQ ID NO 410
```

```
<211> LENGTH: 9
<212> TYPE: PRT
<213> ORGANISM: Homo sapiens

<400> SEQUENCE: 410

Ile Ser Ser Asn Gln Ala Val Ala Val
1               5

<210> SEQ ID NO 411
<211> LENGTH: 10
<212> TYPE: PRT
<213> ORGANISM: Homo sapiens

<400> SEQUENCE: 411

Ile Ser Ser Arg Gly Thr Val Val Asn Lys
1               5                   10

<210> SEQ ID NO 412
<211> LENGTH: 9
<212> TYPE: PRT
<213> ORGANISM: Homo sapiens

<400> SEQUENCE: 412

Ile Thr Leu Ile Ala Ala Phe Arg Lys
1               5

<210> SEQ ID NO 413
<211> LENGTH: 9
<212> TYPE: PRT
<213> ORGANISM: Homo sapiens

<400> SEQUENCE: 413

Ile Thr Leu Asn Glu Val Asp Glu Tyr
1               5

<210> SEQ ID NO 414
<211> LENGTH: 9
<212> TYPE: PRT
<213> ORGANISM: Homo sapiens

<400> SEQUENCE: 414

Ile Thr Arg Asp Arg Asp Lys Leu Lys
1               5

<210> SEQ ID NO 415
<211> LENGTH: 9
<212> TYPE: PRT
<213> ORGANISM: Homo sapiens

<400> SEQUENCE: 415

Ile Thr Arg Glu Ile Leu Lys Met Lys
1               5

<210> SEQ ID NO 416
<211> LENGTH: 9
<212> TYPE: PRT
<213> ORGANISM: Homo sapiens

<400> SEQUENCE: 416

Ile Val Lys His Lys Ile Leu Lys Val
1               5

<210> SEQ ID NO 417
<211> LENGTH: 9
<212> TYPE: PRT
```

-continued

```
<213> ORGANISM: Homo sapiens

<400> SEQUENCE: 417

Ile Val Lys His Lys Ser Val Pro Val
1               5

<210> SEQ ID NO 418
<211> LENGTH: 9
<212> TYPE: PRT
<213> ORGANISM: Homo sapiens

<400> SEQUENCE: 418

Ile Val Lys Ile Ala Lys Glu Ser Leu
1               5

<210> SEQ ID NO 419
<211> LENGTH: 9
<212> TYPE: PRT
<213> ORGANISM: Homo sapiens

<400> SEQUENCE: 419

Ile Trp Phe Met Phe Leu Gln Arg Arg
1               5

<210> SEQ ID NO 420
<211> LENGTH: 9
<212> TYPE: PRT
<213> ORGANISM: Homo sapiens

<400> SEQUENCE: 420

Ile Trp Lys Lys Ser Gly Asn Ser Phe
1               5

<210> SEQ ID NO 421
<211> LENGTH: 9
<212> TYPE: PRT
<213> ORGANISM: Homo sapiens

<400> SEQUENCE: 421

Ile Trp Lys Asn Ile Arg Glu Phe Ile
1               5

<210> SEQ ID NO 422
<211> LENGTH: 9
<212> TYPE: PRT
<213> ORGANISM: Homo sapiens

<400> SEQUENCE: 422

Ile Trp Lys Asn Ile Arg Asn Ser Phe
1               5

<210> SEQ ID NO 423
<211> LENGTH: 9
<212> TYPE: PRT
<213> ORGANISM: Homo sapiens

<400> SEQUENCE: 423

Ile Trp Lys Asn Ser Gly Asn Ser Phe
1               5

<210> SEQ ID NO 424
<211> LENGTH: 9
<212> TYPE: PRT
<213> ORGANISM: Homo sapiens
```

```
<400> SEQUENCE: 424

Ile Trp Lys Thr Ser Gly Asn Ser Phe
1               5

<210> SEQ ID NO 425
<211> LENGTH: 9
<212> TYPE: PRT
<213> ORGANISM: Homo sapiens

<400> SEQUENCE: 425

Ile Tyr Leu Leu Ser Leu Leu Gly Ile
1               5

<210> SEQ ID NO 426
<211> LENGTH: 9
<212> TYPE: PRT
<213> ORGANISM: Homo sapiens

<400> SEQUENCE: 426

Lys Ala Lys Thr Glu Pro Asn Thr Val
1               5

<210> SEQ ID NO 427
<211> LENGTH: 9
<212> TYPE: PRT
<213> ORGANISM: Homo sapiens

<400> SEQUENCE: 427

Lys Ala Leu Ser Ile His Trp Asp Met
1               5

<210> SEQ ID NO 428
<211> LENGTH: 10
<212> TYPE: PRT
<213> ORGANISM: Homo sapiens

<400> SEQUENCE: 428

Lys Cys Gln Ser Gly Thr Ala Glu Thr Tyr
1               5                   10

<210> SEQ ID NO 429
<211> LENGTH: 10
<212> TYPE: PRT
<213> ORGANISM: Homo sapiens

<400> SEQUENCE: 429

Lys Asp Ile Phe Thr Asp Ser Phe Ser Tyr
1               5                   10

<210> SEQ ID NO 430
<211> LENGTH: 10
<212> TYPE: PRT
<213> ORGANISM: Homo sapiens

<400> SEQUENCE: 430

Lys Asp Gln Arg Thr Tyr Ser Ile Val Lys
1               5                   10

<210> SEQ ID NO 431
<211> LENGTH: 9
<212> TYPE: PRT
<213> ORGANISM: Homo sapiens

<400> SEQUENCE: 431
```

```
Lys Asp Val Leu Ser Asn Leu Val Ile
1               5

<210> SEQ ID NO 432
<211> LENGTH: 10
<212> TYPE: PRT
<213> ORGANISM: Homo sapiens

<400> SEQUENCE: 432

Lys Asp Val Leu Ser Asn Leu Val Met Lys
1               5                   10

<210> SEQ ID NO 433
<211> LENGTH: 8
<212> TYPE: PRT
<213> ORGANISM: Homo sapiens

<400> SEQUENCE: 433

Lys Glu Ala Ala Ser His Gly Phe
1               5

<210> SEQ ID NO 434
<211> LENGTH: 10
<212> TYPE: PRT
<213> ORGANISM: Homo sapiens

<400> SEQUENCE: 434

Lys Glu Ala Ala Ser His Gly Phe Gly Lys
1               5                   10

<210> SEQ ID NO 435
<211> LENGTH: 8
<212> TYPE: PRT
<213> ORGANISM: Homo sapiens

<400> SEQUENCE: 435

Lys Glu Ala Leu Gly Phe Val Tyr
1               5

<210> SEQ ID NO 436
<211> LENGTH: 9
<212> TYPE: PRT
<213> ORGANISM: Homo sapiens

<400> SEQUENCE: 436

Lys Glu Ala Leu Gly Phe Val Tyr His
1               5

<210> SEQ ID NO 437
<211> LENGTH: 10
<212> TYPE: PRT
<213> ORGANISM: Homo sapiens

<400> SEQUENCE: 437

Lys Glu Ala Leu Gly Phe Val Tyr His Leu
1               5                   10

<210> SEQ ID NO 438
<211> LENGTH: 9
<212> TYPE: PRT
<213> ORGANISM: Homo sapiens

<400> SEQUENCE: 438

Lys Glu Asp Leu Ser Asp Leu Asn Phe
1               5
```

-continued

```
<210> SEQ ID NO 439
<211> LENGTH: 10
<212> TYPE: PRT
<213> ORGANISM: Homo sapiens

<400> SEQUENCE: 439

Lys Glu Asp Leu Ser Asp Leu Asn Phe Trp
1               5                   10

<210> SEQ ID NO 440
<211> LENGTH: 10
<212> TYPE: PRT
<213> ORGANISM: Homo sapiens

<400> SEQUENCE: 440

Lys Glu Asp Leu Ser Glu Val Ala Lys Ala
1               5                   10

<210> SEQ ID NO 441
<211> LENGTH: 9
<212> TYPE: PRT
<213> ORGANISM: Homo sapiens

<400> SEQUENCE: 441

Lys Glu Glu Lys Glu Ala Ala Lys Tyr
1               5

<210> SEQ ID NO 442
<211> LENGTH: 9
<212> TYPE: PRT
<213> ORGANISM: Homo sapiens

<400> SEQUENCE: 442

Lys Glu Glu Leu Thr Leu Ser Gly Leu
1               5

<210> SEQ ID NO 443
<211> LENGTH: 9
<212> TYPE: PRT
<213> ORGANISM: Homo sapiens

<400> SEQUENCE: 443

Lys Glu Lys Leu Gln Val Met Asp Leu
1               5

<210> SEQ ID NO 444
<211> LENGTH: 8
<212> TYPE: PRT
<213> ORGANISM: Homo sapiens

<400> SEQUENCE: 444

Lys Glu Met Gly Asn Glu Asn Ile
1               5

<210> SEQ ID NO 445
<211> LENGTH: 9
<212> TYPE: PRT
<213> ORGANISM: Homo sapiens

<400> SEQUENCE: 445

Lys Glu Asn Asn Glu Asn Cys Ser Ile
1               5
```

```
<210> SEQ ID NO 446
<211> LENGTH: 8
<212> TYPE: PRT
<213> ORGANISM: Homo sapiens

<400> SEQUENCE: 446

Lys Glu Gln Gly Leu Thr Ala Ala
1               5

<210> SEQ ID NO 447
<211> LENGTH: 9
<212> TYPE: PRT
<213> ORGANISM: Homo sapiens

<400> SEQUENCE: 447

Lys Glu Gln Gly Leu Thr Ala Ala Val
1               5

<210> SEQ ID NO 448
<211> LENGTH: 10
<212> TYPE: PRT
<213> ORGANISM: Homo sapiens

<400> SEQUENCE: 448

Lys Glu Arg Ile Lys Pro Val Gln Thr Val
1               5                   10

<210> SEQ ID NO 449
<211> LENGTH: 9
<212> TYPE: PRT
<213> ORGANISM: Homo sapiens

<400> SEQUENCE: 449

Lys Glu Arg Met Ser Leu Ile Ser Ser
1               5

<210> SEQ ID NO 450
<211> LENGTH: 10
<212> TYPE: PRT
<213> ORGANISM: Homo sapiens

<400> SEQUENCE: 450

Lys Glu Arg Met Ser Leu Ile Ser Ser Leu
1               5                   10

<210> SEQ ID NO 451
<211> LENGTH: 9
<212> TYPE: PRT
<213> ORGANISM: Homo sapiens

<400> SEQUENCE: 451

Lys Glu Ser Tyr Lys Gly Asn Asn Tyr
1               5

<210> SEQ ID NO 452
<211> LENGTH: 9
<212> TYPE: PRT
<213> ORGANISM: Homo sapiens

<400> SEQUENCE: 452

Lys Glu Thr Asp Pro Asn Phe Lys Lys
1               5

<210> SEQ ID NO 453
<211> LENGTH: 10
```

-continued

```
<212> TYPE: PRT
<213> ORGANISM: Homo sapiens

<400> SEQUENCE: 453

Lys Glu Thr Phe Asn Ala Ser Phe Gln Val
1               5                   10

<210> SEQ ID NO 454
<211> LENGTH: 11
<212> TYPE: PRT
<213> ORGANISM: Homo sapiens

<400> SEQUENCE: 454

Lys Glu Val Val Pro Ser Leu Ala Cys Glu Leu
1               5                   10

<210> SEQ ID NO 455
<211> LENGTH: 9
<212> TYPE: PRT
<213> ORGANISM: Homo sapiens

<400> SEQUENCE: 455

Lys Glu Val Val Pro Val Asn Gly Leu
1               5

<210> SEQ ID NO 456
<211> LENGTH: 10
<212> TYPE: PRT
<213> ORGANISM: Homo sapiens

<400> SEQUENCE: 456

Lys Glu Val Val Pro Val Asn Gly Leu Leu
1               5                   10

<210> SEQ ID NO 457
<211> LENGTH: 9
<212> TYPE: PRT
<213> ORGANISM: Homo sapiens

<400> SEQUENCE: 457

Lys His Val Met Val Ile Leu Gln Ile
1               5

<210> SEQ ID NO 458
<211> LENGTH: 9
<212> TYPE: PRT
<213> ORGANISM: Homo sapiens

<400> SEQUENCE: 458

Lys Ile Lys Glu Arg Ile Lys Pro Val
1               5

<210> SEQ ID NO 459
<211> LENGTH: 8
<212> TYPE: PRT
<213> ORGANISM: Homo sapiens

<400> SEQUENCE: 459

Lys Ile Lys Glu Arg Met Ser Leu
1               5

<210> SEQ ID NO 460
<211> LENGTH: 9
<212> TYPE: PRT
<213> ORGANISM: Homo sapiens
```

-continued

<400> SEQUENCE: 460

Lys Ile Lys Glu Arg Met Ser Leu Ile
1               5

<210> SEQ ID NO 461
<211> LENGTH: 9
<212> TYPE: PRT
<213> ORGANISM: Homo sapiens

<400> SEQUENCE: 461

Lys Ile Leu Lys Val Ser Gln Leu Val
1               5

<210> SEQ ID NO 462
<211> LENGTH: 8
<212> TYPE: PRT
<213> ORGANISM: Homo sapiens

<400> SEQUENCE: 462

Lys Ile Met Ser Gly Leu Glu Lys
1               5

<210> SEQ ID NO 463
<211> LENGTH: 9
<212> TYPE: PRT
<213> ORGANISM: Homo sapiens

<400> SEQUENCE: 463

Lys Ile Met Ser Gly Leu Glu Lys Val
1               5

<210> SEQ ID NO 464
<211> LENGTH: 11
<212> TYPE: PRT
<213> ORGANISM: Homo sapiens

<400> SEQUENCE: 464

Lys Ile Met Ser Gly Leu Glu Lys Val Ser Lys
1               5                   10

<210> SEQ ID NO 465
<211> LENGTH: 9
<212> TYPE: PRT
<213> ORGANISM: Homo sapiens

<400> SEQUENCE: 465

Lys Ile Ser Lys Glu Glu Leu Thr Leu
1               5

<210> SEQ ID NO 466
<211> LENGTH: 9
<212> TYPE: PRT
<213> ORGANISM: Homo sapiens

<400> SEQUENCE: 466

Lys Ile Ser Lys Glu Val Val Pro Val
1               5

<210> SEQ ID NO 467
<211> LENGTH: 11
<212> TYPE: PRT
<213> ORGANISM: Homo sapiens

<400> SEQUENCE: 467

-continued

```
Lys Ile Ser Arg Leu Trp Pro Val Asn Gly Leu
1               5               10

<210> SEQ ID NO 468
<211> LENGTH: 10
<212> TYPE: PRT
<213> ORGANISM: Homo sapiens

<400> SEQUENCE: 468

Lys Ile Thr Arg Glu Ile Leu Lys Met Lys
1               5               10

<210> SEQ ID NO 469
<211> LENGTH: 9
<212> TYPE: PRT
<213> ORGANISM: Homo sapiens

<400> SEQUENCE: 469

Lys Ile Trp Phe Met Phe Leu Gln Arg
1               5

<210> SEQ ID NO 470
<211> LENGTH: 9
<212> TYPE: PRT
<213> ORGANISM: Homo sapiens

<400> SEQUENCE: 470

Lys Lys Ile Lys Glu Arg Met Ser Leu
1               5

<210> SEQ ID NO 471
<211> LENGTH: 9
<212> TYPE: PRT
<213> ORGANISM: Homo sapiens

<400> SEQUENCE: 471

Lys Lys Asn Asp Ser Ile Tyr Arg Phe
1               5

<210> SEQ ID NO 472
<211> LENGTH: 9
<212> TYPE: PRT
<213> ORGANISM: Homo sapiens

<400> SEQUENCE: 472

Lys Lys Val Asp Leu Asn Ala Glu Trp
1               5

<210> SEQ ID NO 473
<211> LENGTH: 9
<212> TYPE: PRT
<213> ORGANISM: Homo sapiens

<400> SEQUENCE: 473

Lys Leu Asp Lys Phe Lys Leu Asp Leu
1               5

<210> SEQ ID NO 474
<211> LENGTH: 9
<212> TYPE: PRT
<213> ORGANISM: Homo sapiens

<400> SEQUENCE: 474

Lys Leu Ile Val Val Leu Ala Val Lys
```

-continued

```
1               5

<210> SEQ ID NO 475
<211> LENGTH: 9
<212> TYPE: PRT
<213> ORGANISM: Homo sapiens

<400> SEQUENCE: 475

Lys Leu Lys Lys His Val Met Val Ile
1               5

<210> SEQ ID NO 476
<211> LENGTH: 8
<212> TYPE: PRT
<213> ORGANISM: Homo sapiens

<400> SEQUENCE: 476

Lys Leu Lys Pro Ala Leu Gly Arg
1               5

<210> SEQ ID NO 477
<211> LENGTH: 10
<212> TYPE: PRT
<213> ORGANISM: Homo sapiens

<400> SEQUENCE: 477

Lys Leu Lys Pro Ala Leu Gly Arg Ser Trp
1               5                   10

<210> SEQ ID NO 478
<211> LENGTH: 9
<212> TYPE: PRT
<213> ORGANISM: Homo sapiens

<400> SEQUENCE: 478

Lys Leu Leu Lys Ile Thr Arg Glu Ile
1               5

<210> SEQ ID NO 479
<211> LENGTH: 9
<212> TYPE: PRT
<213> ORGANISM: Homo sapiens

<400> SEQUENCE: 479

Lys Leu Met Ser Gly Phe Pro Glu Val
1               5

<210> SEQ ID NO 480
<211> LENGTH: 10
<212> TYPE: PRT
<213> ORGANISM: Homo sapiens

<400> SEQUENCE: 480

Lys Leu Met Ser Gly Phe Pro Glu Val Met
1               5                   10

<210> SEQ ID NO 481
<211> LENGTH: 8
<212> TYPE: PRT
<213> ORGANISM: Homo sapiens

<400> SEQUENCE: 481

Lys Leu Met Ser Gly Phe Ser Arg
1               5
```

<210> SEQ ID NO 482
<211> LENGTH: 9
<212> TYPE: PRT
<213> ORGANISM: Homo sapiens

<400> SEQUENCE: 482

Lys Leu Asn Val Leu Leu Lys Gln Lys
1               5

<210> SEQ ID NO 483
<211> LENGTH: 9
<212> TYPE: PRT
<213> ORGANISM: Homo sapiens

<400> SEQUENCE: 483

Lys Leu Gln Val Met Asp Leu Glu Lys
1               5

<210> SEQ ID NO 484
<211> LENGTH: 8
<212> TYPE: PRT
<213> ORGANISM: Homo sapiens

<400> SEQUENCE: 484

Lys Leu Arg Asn Thr Ser Asn Lys
1               5

<210> SEQ ID NO 485
<211> LENGTH: 8
<212> TYPE: PRT
<213> ORGANISM: Homo sapiens

<400> SEQUENCE: 485

Lys Leu Ser Ile Ser Asn Ser Tyr
1               5

<210> SEQ ID NO 486
<211> LENGTH: 10
<212> TYPE: PRT
<213> ORGANISM: Homo sapiens

<400> SEQUENCE: 486

Lys Leu Thr Asn Ala Pro Gly Leu Leu Leu
1               5                   10

<210> SEQ ID NO 487
<211> LENGTH: 11
<212> TYPE: PRT
<213> ORGANISM: Homo sapiens

<400> SEQUENCE: 487

Lys Leu Tyr Arg Leu Trp Pro Val Asn Gly Leu
1               5                   10

<210> SEQ ID NO 488
<211> LENGTH: 9
<212> TYPE: PRT
<213> ORGANISM: Homo sapiens

<400> SEQUENCE: 488

Lys Met Lys Ile Thr Asn Ile Leu Leu
1               5

<210> SEQ ID NO 489

-continued

```
<211> LENGTH: 9
<212> TYPE: PRT
<213> ORGANISM: Homo sapiens

<400> SEQUENCE: 489

Lys Met Gln Pro Leu Asn Cys Pro Tyr
1               5

<210> SEQ ID NO 490
<211> LENGTH: 10
<212> TYPE: PRT
<213> ORGANISM: Homo sapiens

<400> SEQUENCE: 490

Lys Met Gln Pro Leu Asn Cys Pro Tyr Leu
1               5                   10

<210> SEQ ID NO 491
<211> LENGTH: 9
<212> TYPE: PRT
<213> ORGANISM: Homo sapiens

<400> SEQUENCE: 491

Lys Met Ser Lys Thr Ser Ser Lys Val
1               5

<210> SEQ ID NO 492
<211> LENGTH: 10
<212> TYPE: PRT
<213> ORGANISM: Homo sapiens

<400> SEQUENCE: 492

Lys Asn Ile Arg Lys Asp His Ile Gly Lys
1               5                   10

<210> SEQ ID NO 493
<211> LENGTH: 9
<212> TYPE: PRT
<213> ORGANISM: Homo sapiens

<400> SEQUENCE: 493

Lys Asn Lys Met Asp Ile Leu Ser Leu
1               5

<210> SEQ ID NO 494
<211> LENGTH: 9
<212> TYPE: PRT
<213> ORGANISM: Homo sapiens

<400> SEQUENCE: 494

Lys Asn Val Asn Pro Ser Leu Pro Arg
1               5

<210> SEQ ID NO 495
<211> LENGTH: 11
<212> TYPE: PRT
<213> ORGANISM: Homo sapiens

<400> SEQUENCE: 495

Lys Pro Phe Glu Lys Lys Ser Pro Arg Lys Leu
1               5                   10

<210> SEQ ID NO 496
<211> LENGTH: 10
<212> TYPE: PRT
```

-continued

```
<213> ORGANISM: Homo sapiens

<400> SEQUENCE: 496

Lys Pro Phe Glu Ser Gly Ser Asp Arg Leu
1               5                   10

<210> SEQ ID NO 497
<211> LENGTH: 11
<212> TYPE: PRT
<213> ORGANISM: Homo sapiens

<400> SEQUENCE: 497

Lys Pro Phe Glu Ser Gly Ser Asp Arg Leu Trp
1               5                   10

<210> SEQ ID NO 498
<211> LENGTH: 10
<212> TYPE: PRT
<213> ORGANISM: Homo sapiens

<400> SEQUENCE: 498

Lys Gln Asp Phe Asn Ser Asn His Asn Ile
1               5                   10

<210> SEQ ID NO 499
<211> LENGTH: 9
<212> TYPE: PRT
<213> ORGANISM: Homo sapiens

<400> SEQUENCE: 499

Lys Gln Lys Ala Val Lys Leu Phe Ser
1               5

<210> SEQ ID NO 500
<211> LENGTH: 10
<212> TYPE: PRT
<213> ORGANISM: Homo sapiens

<400> SEQUENCE: 500

Lys Arg Ala Ala Ser His Gly Phe Gly Lys
1               5                   10

<210> SEQ ID NO 501
<211> LENGTH: 9
<212> TYPE: PRT
<213> ORGANISM: Homo sapiens

<400> SEQUENCE: 501

Lys Arg Lys Lys Ile Lys Glu Arg Met
1               5

<210> SEQ ID NO 502
<211> LENGTH: 10
<212> TYPE: PRT
<213> ORGANISM: Homo sapiens

<400> SEQUENCE: 502

Lys Arg Leu Leu Gln Ser Asp Pro Ser Leu
1               5                   10

<210> SEQ ID NO 503
<211> LENGTH: 11
<212> TYPE: PRT
<213> ORGANISM: Homo sapiens
```

-continued

---

<400> SEQUENCE: 503

Lys Ser Glu Lys Pro Leu Asn Glu Glu Gln Trp
1               5                   10

<210> SEQ ID NO 504
<211> LENGTH: 8
<212> TYPE: PRT
<213> ORGANISM: Homo sapiens

<400> SEQUENCE: 504

Lys Ser Phe Val Lys Thr Leu Arg
1               5

<210> SEQ ID NO 505
<211> LENGTH: 9
<212> TYPE: PRT
<213> ORGANISM: Homo sapiens

<400> SEQUENCE: 505

Lys Ser Leu Leu Asn Val Asn Lys Arg
1               5

<210> SEQ ID NO 506
<211> LENGTH: 10
<212> TYPE: PRT
<213> ORGANISM: Homo sapiens

<400> SEQUENCE: 506

Lys Ser Leu Leu Asn Val Asn Lys Arg Lys
1               5                   10

<210> SEQ ID NO 507
<211> LENGTH: 9
<212> TYPE: PRT
<213> ORGANISM: Homo sapiens

<400> SEQUENCE: 507

Lys Ser Pro Arg Lys Leu Tyr Arg Leu
1               5

<210> SEQ ID NO 508
<211> LENGTH: 10
<212> TYPE: PRT
<213> ORGANISM: Homo sapiens

<400> SEQUENCE: 508

Lys Ser Pro Arg Lys Leu Tyr Arg Leu Trp
1               5                   10

<210> SEQ ID NO 509
<211> LENGTH: 11
<212> TYPE: PRT
<213> ORGANISM: Homo sapiens

<400> SEQUENCE: 509

Lys Ser Val Pro Val Gly Thr Gly Asn Gln Leu
1               5                   10

<210> SEQ ID NO 510
<211> LENGTH: 9
<212> TYPE: PRT
<213> ORGANISM: Homo sapiens

<400> SEQUENCE: 510

-continued

```
Lys Ser Trp Ile Asp His Ile Gly Lys
1               5

<210> SEQ ID NO 511
<211> LENGTH: 9
<212> TYPE: PRT
<213> ORGANISM: Homo sapiens

<400> SEQUENCE: 511

Lys Ser Trp Ile Arg Asn Ser Cys Lys
1               5

<210> SEQ ID NO 512
<211> LENGTH: 9
<212> TYPE: PRT
<213> ORGANISM: Homo sapiens

<400> SEQUENCE: 512

Lys Ser Trp Ile Trp Lys Asn Ile Lys
1               5

<210> SEQ ID NO 513
<211> LENGTH: 9
<212> TYPE: PRT
<213> ORGANISM: Homo sapiens

<400> SEQUENCE: 513

Lys Ser Trp Ile Trp Lys Asn Ile Arg
1               5

<210> SEQ ID NO 514
<211> LENGTH: 10
<212> TYPE: PRT
<213> ORGANISM: Homo sapiens

<400> SEQUENCE: 514

Lys Ser Trp Ile Trp Lys Asn Ile Arg Lys
1               5                   10

<210> SEQ ID NO 515
<211> LENGTH: 10
<212> TYPE: PRT
<213> ORGANISM: Homo sapiens

<400> SEQUENCE: 515

Lys Ser Trp Ile Trp Lys Asn Ile Ser Lys
1               5                   10

<210> SEQ ID NO 516
<211> LENGTH: 9
<212> TYPE: PRT
<213> ORGANISM: Homo sapiens

<400> SEQUENCE: 516

Lys Ser Trp Ile Trp Asn Ser Phe Lys
1               5

<210> SEQ ID NO 517
<211> LENGTH: 11
<212> TYPE: PRT
<213> ORGANISM: Homo sapiens

<400> SEQUENCE: 517

Lys Thr Glu Cys Phe Thr Glu Ala Leu Gln Lys
1               5                   10
```

-continued

```
<210> SEQ ID NO 518
<211> LENGTH: 9
<212> TYPE: PRT
<213> ORGANISM: Homo sapiens

<400> SEQUENCE: 518

Lys Thr Glu Pro Asn Thr Val Asn Ile
1               5

<210> SEQ ID NO 519
<211> LENGTH: 9
<212> TYPE: PRT
<213> ORGANISM: Homo sapiens

<400> SEQUENCE: 519

Lys Thr Glu Pro Gln Ser Gln Leu Val
1               5

<210> SEQ ID NO 520
<211> LENGTH: 9
<212> TYPE: PRT
<213> ORGANISM: Homo sapiens

<400> SEQUENCE: 520

Lys Thr His Ile Val Tyr His His Phe
1               5

<210> SEQ ID NO 521
<211> LENGTH: 9
<212> TYPE: PRT
<213> ORGANISM: Homo sapiens

<400> SEQUENCE: 521

Lys Thr Gln Asn Gln Arg Glu Ala Ala
1               5

<210> SEQ ID NO 522
<211> LENGTH: 9
<212> TYPE: PRT
<213> ORGANISM: Homo sapiens

<400> SEQUENCE: 522

Lys Thr Ser Lys Ser Gly Lys Arg Arg
1               5

<210> SEQ ID NO 523
<211> LENGTH: 9
<212> TYPE: PRT
<213> ORGANISM: Homo sapiens

<400> SEQUENCE: 523

Lys Thr Ser Leu Lys Gly Asn Asn Tyr
1               5

<210> SEQ ID NO 524
<211> LENGTH: 10
<212> TYPE: PRT
<213> ORGANISM: Homo sapiens

<400> SEQUENCE: 524

Lys Thr Ser Ser Asp Val Glu Leu Thr Lys
1               5                   10
```

-continued

```
<210> SEQ ID NO 525
<211> LENGTH: 9
<212> TYPE: PRT
<213> ORGANISM: Homo sapiens

<400> SEQUENCE: 525

Lys Thr Ser Ser Lys Gly Asn Asn Tyr
1               5

<210> SEQ ID NO 526
<211> LENGTH: 10
<212> TYPE: PRT
<213> ORGANISM: Homo sapiens

<400> SEQUENCE: 526

Lys Thr Ser Ser Lys Val Glu Leu Thr Lys
1               5                   10

<210> SEQ ID NO 527
<211> LENGTH: 9
<212> TYPE: PRT
<213> ORGANISM: Homo sapiens

<400> SEQUENCE: 527

Lys Thr Ser Ser Lys Val Thr Ile Met
1               5

<210> SEQ ID NO 528
<211> LENGTH: 9
<212> TYPE: PRT
<213> ORGANISM: Homo sapiens

<400> SEQUENCE: 528

Lys Thr Ser Ser Lys Val Thr Asn Ile
1               5

<210> SEQ ID NO 529
<211> LENGTH: 11
<212> TYPE: PRT
<213> ORGANISM: Homo sapiens

<400> SEQUENCE: 529

Lys Thr Ser Thr Leu Pro Phe Ile Ser Leu Lys
1               5                   10

<210> SEQ ID NO 530
<211> LENGTH: 9
<212> TYPE: PRT
<213> ORGANISM: Homo sapiens

<400> SEQUENCE: 530

Lys Thr Thr Ala Val Ala Val Thr Phe
1               5

<210> SEQ ID NO 531
<211> LENGTH: 9
<212> TYPE: PRT
<213> ORGANISM: Homo sapiens

<400> SEQUENCE: 531

Lys Thr Thr Pro Ile Lys Gln Gln Leu
1               5

<210> SEQ ID NO 532
<211> LENGTH: 9
```

-continued

<212> TYPE: PRT
<213> ORGANISM: Homo sapiens

<400> SEQUENCE: 532

Lys Thr Val Lys Thr Gln Arg Glu Ala
1               5

<210> SEQ ID NO 533
<211> LENGTH: 11
<212> TYPE: PRT
<213> ORGANISM: Homo sapiens

<400> SEQUENCE: 533

Lys Val Asp Leu Asn Ala Asp Pro Leu Cys Tyr
1               5                   10

<210> SEQ ID NO 534
<211> LENGTH: 8
<212> TYPE: PRT
<213> ORGANISM: Homo sapiens

<400> SEQUENCE: 534

Lys Val Asp Leu Asn Ala Glu Trp
1               5

<210> SEQ ID NO 535
<211> LENGTH: 10
<212> TYPE: PRT
<213> ORGANISM: Homo sapiens

<400> SEQUENCE: 535

Lys Val Asp Leu Asn Ala Glu Trp Asn Lys
1               5                   10

<210> SEQ ID NO 536
<211> LENGTH: 8
<212> TYPE: PRT
<213> ORGANISM: Homo sapiens

<400> SEQUENCE: 536

Lys Val Phe Ser Lys Val Leu Phe
1               5

<210> SEQ ID NO 537
<211> LENGTH: 9
<212> TYPE: PRT
<213> ORGANISM: Homo sapiens

<400> SEQUENCE: 537

Lys Val Phe Ser Lys Val Leu Phe Lys
1               5

<210> SEQ ID NO 538
<211> LENGTH: 10
<212> TYPE: PRT
<213> ORGANISM: Homo sapiens

<400> SEQUENCE: 538

Lys Val Lys Asn Leu Gln Leu Glu Pro Arg
1               5                   10

<210> SEQ ID NO 539
<211> LENGTH: 9
<212> TYPE: PRT
<213> ORGANISM: Homo sapiens -continued

<400> SEQUENCE: 539

Lys Val Asn Asn Ile Pro Leu Ser Leu
1               5

<210> SEQ ID NO 540
<211> LENGTH: 10
<212> TYPE: PRT
<213> ORGANISM: Homo sapiens

<400> SEQUENCE: 540

Lys Val Asn Asn Ile Pro Leu Ser Leu Leu
1               5                   10

<210> SEQ ID NO 541
<211> LENGTH: 9
<212> TYPE: PRT
<213> ORGANISM: Homo sapiens

<400> SEQUENCE: 541

Lys Val Gln Lys Ser Leu Leu Asn Val
1               5

<210> SEQ ID NO 542
<211> LENGTH: 9
<212> TYPE: PRT
<213> ORGANISM: Homo sapiens

<400> SEQUENCE: 542

Lys Val Arg Gln Val Phe Ser Glu Ile
1               5

<210> SEQ ID NO 543
<211> LENGTH: 9
<212> TYPE: PRT
<213> ORGANISM: Homo sapiens

<400> SEQUENCE: 543

Lys Val Ser Lys Arg Gln Ser Gln Lys
1               5

<210> SEQ ID NO 544
<211> LENGTH: 11
<212> TYPE: PRT
<213> ORGANISM: Homo sapiens

<400> SEQUENCE: 544

Lys Val Ser Pro Tyr Leu Ser Ile Ser Thr Arg
1               5                   10

<210> SEQ ID NO 545
<211> LENGTH: 9
<212> TYPE: PRT
<213> ORGANISM: Homo sapiens

<400> SEQUENCE: 545

Lys Val Ser Gln Leu Val Leu Glu Ile
1               5

<210> SEQ ID NO 546
<211> LENGTH: 11
<212> TYPE: PRT
<213> ORGANISM: Homo sapiens

<400> SEQUENCE: 546

```
Lys Val Thr Ile Met Asn Ile Pro Met Glu Lys
1               5               10

<210> SEQ ID NO 547
<211> LENGTH: 9
<212> TYPE: PRT
<213> ORGANISM: Homo sapiens

<400> SEQUENCE: 547

Lys Val Thr Ile Met Asn Leu Met Leu
1               5

<210> SEQ ID NO 548
<211> LENGTH: 9
<212> TYPE: PRT
<213> ORGANISM: Homo sapiens

<400> SEQUENCE: 548

Lys Val Thr Asn Ile Pro Met Glu Lys
1               5

<210> SEQ ID NO 549
<211> LENGTH: 9
<212> TYPE: PRT
<213> ORGANISM: Homo sapiens

<400> SEQUENCE: 549

Lys Trp Ser Pro Asp Gly Glu Asn Ile
1               5

<210> SEQ ID NO 550
<211> LENGTH: 9
<212> TYPE: PRT
<213> ORGANISM: Homo sapiens

<400> SEQUENCE: 550

Lys Tyr Lys His Pro Gly Ser Phe Leu
1               5

<210> SEQ ID NO 551
<211> LENGTH: 10
<212> TYPE: PRT
<213> ORGANISM: Homo sapiens

<400> SEQUENCE: 551

Lys Tyr Lys His Pro Gly Ser Phe Leu Ile
1               5               10

<210> SEQ ID NO 552
<211> LENGTH: 9
<212> TYPE: PRT
<213> ORGANISM: Homo sapiens

<400> SEQUENCE: 552

Leu Ala Lys Thr Ser Thr Leu Pro Phe
1               5

<210> SEQ ID NO 553
<211> LENGTH: 9
<212> TYPE: PRT
<213> ORGANISM: Homo sapiens

<400> SEQUENCE: 553

Leu Asp Asn Asp Asp Val Ala Arg Ile
```

-continued

```
1               5

<210> SEQ ID NO 554
<211> LENGTH: 9
<212> TYPE: PRT
<213> ORGANISM: Homo sapiens

<400> SEQUENCE: 554

Leu Asp Ser Pro Leu Arg Val Glu Val
1               5

<210> SEQ ID NO 555
<211> LENGTH: 9
<212> TYPE: PRT
<213> ORGANISM: Homo sapiens

<400> SEQUENCE: 555

Leu Glu Lys His Gln Gly Ile His Leu
1               5

<210> SEQ ID NO 556
<211> LENGTH: 10
<212> TYPE: PRT
<213> ORGANISM: Homo sapiens

<400> SEQUENCE: 556

Leu Glu Pro Arg Arg Val Thr Ser Gln Met
1               5               10

<210> SEQ ID NO 557
<211> LENGTH: 9
<212> TYPE: PRT
<213> ORGANISM: Homo sapiens

<400> SEQUENCE: 557

Leu Phe Ser Asp Asp Leu Asn Leu Ile
1               5

<210> SEQ ID NO 558
<211> LENGTH: 10
<212> TYPE: PRT
<213> ORGANISM: Homo sapiens

<400> SEQUENCE: 558

Leu Phe Ser Asp Asp Leu Asn Leu Ile Leu
1               5               10

<210> SEQ ID NO 559
<211> LENGTH: 9
<212> TYPE: PRT
<213> ORGANISM: Homo sapiens

<400> SEQUENCE: 559

Leu Gly Phe Ser Trp Thr Pro Ser Arg
1               5

<210> SEQ ID NO 560
<211> LENGTH: 9
<212> TYPE: PRT
<213> ORGANISM: Homo sapiens

<400> SEQUENCE: 560

Leu His Ile Ala Ala Glu Asn Gln Met
1               5
```

-continued

```
<210> SEQ ID NO 561
<211> LENGTH: 9
<212> TYPE: PRT
<213> ORGANISM: Homo sapiens

<400> SEQUENCE: 561

Leu His Asn Ser Val Phe Ala Asp Ile
1               5

<210> SEQ ID NO 562
<211> LENGTH: 9
<212> TYPE: PRT
<213> ORGANISM: Homo sapiens

<400> SEQUENCE: 562

Leu Ile Met Pro Asn Val Val Ser Lys
1               5

<210> SEQ ID NO 563
<211> LENGTH: 9
<212> TYPE: PRT
<213> ORGANISM: Homo sapiens

<400> SEQUENCE: 563

Leu Ile Ser Leu Gln Ala Phe Leu Trp
1               5

<210> SEQ ID NO 564
<211> LENGTH: 9
<212> TYPE: PRT
<213> ORGANISM: Homo sapiens

<400> SEQUENCE: 564

Leu Lys Ala Leu Glu Asp Phe Thr Leu
1               5

<210> SEQ ID NO 565
<211> LENGTH: 9
<212> TYPE: PRT
<213> ORGANISM: Homo sapiens

<400> SEQUENCE: 565

Leu Lys Lys Asn Ala Ser His Gly Phe
1               5

<210> SEQ ID NO 566
<211> LENGTH: 9
<212> TYPE: PRT
<213> ORGANISM: Homo sapiens

<400> SEQUENCE: 566

Leu Lys Lys Asn Glu Ile Tyr Arg Phe
1               5

<210> SEQ ID NO 567
<211> LENGTH: 9
<212> TYPE: PRT
<213> ORGANISM: Homo sapiens

<400> SEQUENCE: 567

Leu Lys Met Lys Ile Thr Asn Ile Leu
1               5

<210> SEQ ID NO 568
```

```
<211> LENGTH: 8
<212> TYPE: PRT
<213> ORGANISM: Homo sapiens

<400> SEQUENCE: 568

Leu Lys Gln Lys Ala Val Lys Leu
1               5

<210> SEQ ID NO 569
<211> LENGTH: 9
<212> TYPE: PRT
<213> ORGANISM: Homo sapiens

<400> SEQUENCE: 569

Leu Lys Gln Lys Ala Val Lys Leu Phe
1               5

<210> SEQ ID NO 570
<211> LENGTH: 9
<212> TYPE: PRT
<213> ORGANISM: Homo sapiens

<400> SEQUENCE: 570

Leu Lys Thr Glu Pro Gln Ser Gln Leu
1               5

<210> SEQ ID NO 571
<211> LENGTH: 8
<212> TYPE: PRT
<213> ORGANISM: Homo sapiens

<400> SEQUENCE: 571

Leu Leu Phe Gly Ile Tyr Leu Leu
1               5

<210> SEQ ID NO 572
<211> LENGTH: 9
<212> TYPE: PRT
<213> ORGANISM: Homo sapiens

<400> SEQUENCE: 572

Leu Leu Lys Ile Thr Arg Glu Ile Leu
1               5

<210> SEQ ID NO 573
<211> LENGTH: 9
<212> TYPE: PRT
<213> ORGANISM: Homo sapiens

<400> SEQUENCE: 573

Leu Leu Lys Leu Asn Val Arg Lys Ile
1               5

<210> SEQ ID NO 574
<211> LENGTH: 9
<212> TYPE: PRT
<213> ORGANISM: Homo sapiens

<400> SEQUENCE: 574

Leu Leu Lys Gln Lys Ala Val Lys Leu
1               5

<210> SEQ ID NO 575
<211> LENGTH: 9
<212> TYPE: PRT
```

<213> ORGANISM: Homo sapiens

<400> SEQUENCE: 575

Leu Leu Leu Lys Lys Leu Leu Lys Ile
1               5

<210> SEQ ID NO 576
<211> LENGTH: 9
<212> TYPE: PRT
<213> ORGANISM: Homo sapiens

<400> SEQUENCE: 576

Leu Leu Leu Ser Val Gln Ile Pro Val
1               5

<210> SEQ ID NO 577
<211> LENGTH: 9
<212> TYPE: PRT
<213> ORGANISM: Homo sapiens

<400> SEQUENCE: 577

Leu Leu Gln Ile Asn Met Asp Phe Tyr
1               5

<210> SEQ ID NO 578
<211> LENGTH: 9
<212> TYPE: PRT
<213> ORGANISM: Homo sapiens

<400> SEQUENCE: 578

Leu Leu Arg Phe Gln Ile Gln Glu Met
1               5

<210> SEQ ID NO 579
<211> LENGTH: 9
<212> TYPE: PRT
<213> ORGANISM: Homo sapiens

<400> SEQUENCE: 579

Leu Leu Ser Glu Ser Pro Val Val Leu
1               5

<210> SEQ ID NO 580
<211> LENGTH: 9
<212> TYPE: PRT
<213> ORGANISM: Homo sapiens

<400> SEQUENCE: 580

Leu Met Ser Gly Phe Pro Glu Val Met
1               5

<210> SEQ ID NO 581
<211> LENGTH: 9
<212> TYPE: PRT
<213> ORGANISM: Homo sapiens

<400> SEQUENCE: 581

Leu Asn Ala Asp Pro Leu Cys Tyr Arg
1               5

<210> SEQ ID NO 582
<211> LENGTH: 9
<212> TYPE: PRT
<213> ORGANISM: Homo sapiens -continued

```
<400> SEQUENCE: 582

Leu Pro Cys Ile Ser Leu Lys Ala Ala
1               5

<210> SEQ ID NO 583
<211> LENGTH: 10
<212> TYPE: PRT
<213> ORGANISM: Homo sapiens

<400> SEQUENCE: 583

Leu Pro Cys Ile Ser Leu Lys Ala Ala Val
1               5                   10

<210> SEQ ID NO 584
<211> LENGTH: 11
<212> TYPE: PRT
<213> ORGANISM: Homo sapiens

<400> SEQUENCE: 584

Leu Pro Asp Ser Gln Gln Val Ser Arg Arg Trp
1               5                   10

<210> SEQ ID NO 585
<211> LENGTH: 8
<212> TYPE: PRT
<213> ORGANISM: Homo sapiens

<400> SEQUENCE: 585

Leu Pro Phe Ile Ser Leu Lys Ala
1               5

<210> SEQ ID NO 586
<211> LENGTH: 9
<212> TYPE: PRT
<213> ORGANISM: Homo sapiens

<400> SEQUENCE: 586

Leu Pro Phe Ile Ser Leu Lys Ala Ala
1               5

<210> SEQ ID NO 587
<211> LENGTH: 10
<212> TYPE: PRT
<213> ORGANISM: Homo sapiens

<400> SEQUENCE: 587

Leu Pro Phe Ile Ser Leu Lys Ala Ala Val
1               5                   10

<210> SEQ ID NO 588
<211> LENGTH: 10
<212> TYPE: PRT
<213> ORGANISM: Homo sapiens

<400> SEQUENCE: 588

Leu Pro Arg Ile Ser Ser Arg Gly Thr Val
1               5                   10

<210> SEQ ID NO 589
<211> LENGTH: 9
<212> TYPE: PRT
<213> ORGANISM: Homo sapiens

<400> SEQUENCE: 589
```

```
Leu Pro Ser Asp Ala Pro Gly Ala Leu
1               5

<210> SEQ ID NO 590
<211> LENGTH: 8
<212> TYPE: PRT
<213> ORGANISM: Homo sapiens

<400> SEQUENCE: 590

Leu Arg Phe Gln Ile Gln Glu Met
1               5

<210> SEQ ID NO 591
<211> LENGTH: 10
<212> TYPE: PRT
<213> ORGANISM: Homo sapiens

<400> SEQUENCE: 591

Leu Arg Phe Gln Ile Gln Glu Met Gln Lys
1               5                   10

<210> SEQ ID NO 592
<211> LENGTH: 9
<212> TYPE: PRT
<213> ORGANISM: Homo sapiens

<400> SEQUENCE: 592

Leu Arg Lys Leu Lys Lys His Val Met
1               5

<210> SEQ ID NO 593
<211> LENGTH: 10
<212> TYPE: PRT
<213> ORGANISM: Homo sapiens

<400> SEQUENCE: 593

Leu Arg Arg Pro Asn Phe Thr Arg Arg Leu
1               5                   10

<210> SEQ ID NO 594
<211> LENGTH: 10
<212> TYPE: PRT
<213> ORGANISM: Homo sapiens

<400> SEQUENCE: 594

Leu Arg Thr Asn Pro Phe Arg Ser Lys Trp
1               5                   10

<210> SEQ ID NO 595
<211> LENGTH: 9
<212> TYPE: PRT
<213> ORGANISM: Homo sapiens

<400> SEQUENCE: 595

Leu Ser Asp Leu Asn Phe Trp Lys Leu
1               5

<210> SEQ ID NO 596
<211> LENGTH: 9
<212> TYPE: PRT
<213> ORGANISM: Homo sapiens

<400> SEQUENCE: 596

Leu Ser Asp Leu Asn Phe Trp Lys Tyr
1               5
```

-continued

<210> SEQ ID NO 597
<211> LENGTH: 9
<212> TYPE: PRT
<213> ORGANISM: Homo sapiens

<400> SEQUENCE: 597

Leu Ser Ile Cys Arg Ile His Ser Arg
1               5

<210> SEQ ID NO 598
<211> LENGTH: 9
<212> TYPE: PRT
<213> ORGANISM: Homo sapiens

<400> SEQUENCE: 598

Leu Ser Ile His Trp Asp Met Lys Leu
1               5

<210> SEQ ID NO 599
<211> LENGTH: 9
<212> TYPE: PRT
<213> ORGANISM: Homo sapiens

<400> SEQUENCE: 599

Leu Ser Leu Leu Gly Ile Ala Pro Leu
1               5

<210> SEQ ID NO 600
<211> LENGTH: 10
<212> TYPE: PRT
<213> ORGANISM: Homo sapiens

<400> SEQUENCE: 600

Leu Ser Gln Phe Gln Gln Asp Asn Ser Trp
1               5                   10

<210> SEQ ID NO 601
<211> LENGTH: 9
<212> TYPE: PRT
<213> ORGANISM: Homo sapiens

<400> SEQUENCE: 601

Leu Ser Val Gln Ile Pro Val Asn Leu
1               5

<210> SEQ ID NO 602
<211> LENGTH: 10
<212> TYPE: PRT
<213> ORGANISM: Homo sapiens

<400> SEQUENCE: 602

Leu Thr Ala Ala Val Pro Ile Ser Cys Lys
1               5                   10

<210> SEQ ID NO 603
<211> LENGTH: 9
<212> TYPE: PRT
<213> ORGANISM: Homo sapiens

<400> SEQUENCE: 603

Leu Thr Lys Thr Thr Ala Val Ala Val
1               5

```
<210> SEQ ID NO 604
<211> LENGTH: 9
<212> TYPE: PRT
<213> ORGANISM: Homo sapiens

<400> SEQUENCE: 604

Leu Thr Lys Thr Thr Pro Ile Thr Lys
1               5

<210> SEQ ID NO 605
<211> LENGTH: 9
<212> TYPE: PRT
<213> ORGANISM: Homo sapiens

<400> SEQUENCE: 605

Leu Thr Asn Ala Pro Gly Leu Leu Leu
1               5

<210> SEQ ID NO 606
<211> LENGTH: 9
<212> TYPE: PRT
<213> ORGANISM: Homo sapiens

<400> SEQUENCE: 606

Leu Thr Asn Gln Ser Pro Tyr Ser Val
1               5

<210> SEQ ID NO 607
<211> LENGTH: 8
<212> TYPE: PRT
<213> ORGANISM: Homo sapiens

<400> SEQUENCE: 607

Leu Val Arg Lys Ile Ser Gln Leu
1               5

<210> SEQ ID NO 608
<211> LENGTH: 9
<212> TYPE: PRT
<213> ORGANISM: Homo sapiens

<400> SEQUENCE: 608

Leu Val Arg Lys Ile Ser Gln Leu Ile
1               5

<210> SEQ ID NO 609
<211> LENGTH: 10
<212> TYPE: PRT
<213> ORGANISM: Homo sapiens

<400> SEQUENCE: 609

Leu Trp Pro Val Asn Gly Leu Leu Glu Leu
1               5                   10

<210> SEQ ID NO 610
<211> LENGTH: 9
<212> TYPE: PRT
<213> ORGANISM: Homo sapiens

<400> SEQUENCE: 610

Leu Tyr Glu Asn Asn Ser Asn Tyr Tyr
1               5

<210> SEQ ID NO 611
<211> LENGTH: 10
```

-continued

<212> TYPE: PRT
<213> ORGANISM: Homo sapiens

<400> SEQUENCE: 611

Leu Tyr Arg Leu Trp Pro Val Asn Gly Leu
1               5                   10

<210> SEQ ID NO 612
<211> LENGTH: 8
<212> TYPE: PRT
<213> ORGANISM: Homo sapiens

<400> SEQUENCE: 612

Met Asp Phe Tyr Lys Thr His Ile
1               5

<210> SEQ ID NO 613
<211> LENGTH: 9
<212> TYPE: PRT
<213> ORGANISM: Homo sapiens

<400> SEQUENCE: 613

Met Asp Phe Tyr Lys Thr His Ile Val
1               5

<210> SEQ ID NO 614
<211> LENGTH: 10
<212> TYPE: PRT
<213> ORGANISM: Homo sapiens

<400> SEQUENCE: 614

Met Asp Phe Tyr Lys Thr His Ile Val Tyr
1               5                   10

<210> SEQ ID NO 615
<211> LENGTH: 9
<212> TYPE: PRT
<213> ORGANISM: Homo sapiens

<400> SEQUENCE: 615

Met Asp Leu Glu Lys His Gln Gly Ile
1               5

<210> SEQ ID NO 616
<211> LENGTH: 9
<212> TYPE: PRT
<213> ORGANISM: Homo sapiens

<400> SEQUENCE: 616

Met Glu Glu Ser Glu Leu Asp Ala Leu
1               5

<210> SEQ ID NO 617
<211> LENGTH: 9
<212> TYPE: PRT
<213> ORGANISM: Homo sapiens

<400> SEQUENCE: 617

Met Phe Lys Ile Glu Asn His Asn Lys
1               5

<210> SEQ ID NO 618
<211> LENGTH: 9
<212> TYPE: PRT
<213> ORGANISM: Homo sapiens

<400> SEQUENCE: 618

Met Phe Leu Gln Arg Arg Thr Lys Ile
1               5

<210> SEQ ID NO 619
<211> LENGTH: 9
<212> TYPE: PRT
<213> ORGANISM: Homo sapiens

<400> SEQUENCE: 619

Met Ile Ser Arg Gly Ile Gln Asn Val
1               5

<210> SEQ ID NO 620
<211> LENGTH: 10
<212> TYPE: PRT
<213> ORGANISM: Homo sapiens

<400> SEQUENCE: 620

Met Ile Ser Arg Gly Ile Gln Asn Val Lys
1               5                   10

<210> SEQ ID NO 621
<211> LENGTH: 9
<212> TYPE: PRT
<213> ORGANISM: Homo sapiens

<400> SEQUENCE: 621

Met Ile Ser Arg Ile Ile Gln Asn Val
1               5

<210> SEQ ID NO 622
<211> LENGTH: 9
<212> TYPE: PRT
<213> ORGANISM: Homo sapiens

<400> SEQUENCE: 622

Met Asn Arg Gln Ala Pro Gly Ser Phe
1               5

<210> SEQ ID NO 623
<211> LENGTH: 9
<212> TYPE: PRT
<213> ORGANISM: Homo sapiens

<400> SEQUENCE: 623

Met Pro Asn Val Val Ser Lys Glu Ala
1               5

<210> SEQ ID NO 624
<211> LENGTH: 10
<212> TYPE: PRT
<213> ORGANISM: Homo sapiens

<400> SEQUENCE: 624

Met Pro Asn Val Val Ser Lys Glu Ala Leu
1               5                   10

<210> SEQ ID NO 625
<211> LENGTH: 9
<212> TYPE: PRT
<213> ORGANISM: Homo sapiens

<400> SEQUENCE: 625

-continued

```
Met Arg Phe Ile Asn Ser Asn Gln Ala
1               5

<210> SEQ ID NO 626
<211> LENGTH: 10
<212> TYPE: PRT
<213> ORGANISM: Homo sapiens

<400> SEQUENCE: 626

Met Arg Phe Ile Asn Ser Asn Gln Ala Val
1               5                   10

<210> SEQ ID NO 627
<211> LENGTH: 9
<212> TYPE: PRT
<213> ORGANISM: Homo sapiens

<400> SEQUENCE: 627

Met Arg Phe Ile Ser Leu Thr Lys Thr
1               5

<210> SEQ ID NO 628
<211> LENGTH: 9
<212> TYPE: PRT
<213> ORGANISM: Homo sapiens

<400> SEQUENCE: 628

Met Arg Phe Ile Ser Ser Asn Gln Ala
1               5

<210> SEQ ID NO 629
<211> LENGTH: 10
<212> TYPE: PRT
<213> ORGANISM: Homo sapiens

<400> SEQUENCE: 629

Met Arg Phe Ile Ser Ser Asn Gln Ala Val
1               5                   10

<210> SEQ ID NO 630
<211> LENGTH: 11
<212> TYPE: PRT
<213> ORGANISM: Homo sapiens

<400> SEQUENCE: 630

Met Ser Lys Thr Ser Ser Lys Gly Asn Asn Tyr
1               5                   10

<210> SEQ ID NO 631
<211> LENGTH: 9
<212> TYPE: PRT
<213> ORGANISM: Homo sapiens

<400> SEQUENCE: 631

Met Ser Leu Ile Ser Ser Leu Tyr Arg
1               5

<210> SEQ ID NO 632
<211> LENGTH: 9
<212> TYPE: PRT
<213> ORGANISM: Homo sapiens

<400> SEQUENCE: 632

Asn Ala Pro Gly Leu Leu Leu Ser Val
```

-continued

```
1               5

<210> SEQ ID NO 633
<211> LENGTH: 8
<212> TYPE: PRT
<213> ORGANISM: Homo sapiens

<400> SEQUENCE: 633

Asn Asp Met Arg Phe Ile Ser Leu
1               5

<210> SEQ ID NO 634
<211> LENGTH: 10
<212> TYPE: PRT
<213> ORGANISM: Homo sapiens

<400> SEQUENCE: 634

Asn Asp Arg Phe Ile Ala Ser Val Pro Val
1               5                   10

<210> SEQ ID NO 635
<211> LENGTH: 10
<212> TYPE: PRT
<213> ORGANISM: Homo sapiens

<400> SEQUENCE: 635

Asn Asp Arg Phe Ile Ala Ser Val Thr Val
1               5                   10

<210> SEQ ID NO 636
<211> LENGTH: 10
<212> TYPE: PRT
<213> ORGANISM: Homo sapiens

<400> SEQUENCE: 636

Asn Glu Gln Lys Ala Leu Ser Ile His Trp
1               5                   10

<210> SEQ ID NO 637
<211> LENGTH: 9
<212> TYPE: PRT
<213> ORGANISM: Homo sapiens

<400> SEQUENCE: 637

Asn Glu Val Gly Phe Arg Gly Ser Trp
1               5

<210> SEQ ID NO 638
<211> LENGTH: 10
<212> TYPE: PRT
<213> ORGANISM: Homo sapiens

<400> SEQUENCE: 638

Asn Phe Glu Asp Ile Leu His Asn Ser Leu
1               5                   10

<210> SEQ ID NO 639
<211> LENGTH: 9
<212> TYPE: PRT
<213> ORGANISM: Homo sapiens

<400> SEQUENCE: 639

Asn Phe Trp Lys Leu Arg Lys Leu Lys
1               5
```

<210> SEQ ID NO 640
<211> LENGTH: 10
<212> TYPE: PRT
<213> ORGANISM: Homo sapiens

<400> SEQUENCE: 640

Asn His Asp Glu Ser Leu Lys Thr Gln Ile
1               5                   10

<210> SEQ ID NO 641
<211> LENGTH: 9
<212> TYPE: PRT
<213> ORGANISM: Homo sapiens

<400> SEQUENCE: 641

Asn His Asp Glu Ser Leu Lys Thr Val
1               5

<210> SEQ ID NO 642
<211> LENGTH: 8
<212> TYPE: PRT
<213> ORGANISM: Homo sapiens

<400> SEQUENCE: 642

Asn His Asp Glu Ser Leu Thr Val
1               5

<210> SEQ ID NO 643
<211> LENGTH: 10
<212> TYPE: PRT
<213> ORGANISM: Homo sapiens

<400> SEQUENCE: 643

Asn His Ile Thr Arg Asp Arg Asp Lys Leu
1               5                   10

<210> SEQ ID NO 644
<211> LENGTH: 10
<212> TYPE: PRT
<213> ORGANISM: Homo sapiens

<400> SEQUENCE: 644

Asn His Asn Ile Leu Gln Lys Ser Thr Phe
1               5                   10

<210> SEQ ID NO 645
<211> LENGTH: 9
<212> TYPE: PRT
<213> ORGANISM: Homo sapiens

<400> SEQUENCE: 645

Asn His Asn Lys Cys Gln Leu Ile Leu
1               5

<210> SEQ ID NO 646
<211> LENGTH: 10
<212> TYPE: PRT
<213> ORGANISM: Homo sapiens

<400> SEQUENCE: 646

Asn His Ser Ile Ser Thr Arg Gln Gln Leu
1               5                   10

<210> SEQ ID NO 647

-continued

```
<211> LENGTH: 8
<212> TYPE: PRT
<213> ORGANISM: Homo sapiens

<400> SEQUENCE: 647

Asn Ile Leu Gln Lys Ser Thr Phe
1               5

<210> SEQ ID NO 648
<211> LENGTH: 9
<212> TYPE: PRT
<213> ORGANISM: Homo sapiens

<400> SEQUENCE: 648

Asn Ile Arg Glu Val Asn Ser Cys Lys
1               5

<210> SEQ ID NO 649
<211> LENGTH: 9
<212> TYPE: PRT
<213> ORGANISM: Homo sapiens

<400> SEQUENCE: 649

Asn Ile Arg Lys Asp His Ile Gly Lys
1               5

<210> SEQ ID NO 650
<211> LENGTH: 9
<212> TYPE: PRT
<213> ORGANISM: Homo sapiens

<400> SEQUENCE: 650

Asn Ile Ser Lys Val Asn Ser Cys Lys
1               5

<210> SEQ ID NO 651
<211> LENGTH: 9
<212> TYPE: PRT
<213> ORGANISM: Homo sapiens

<400> SEQUENCE: 651

Asn Lys Asp His Ile Gly Lys Ser Met
1               5

<210> SEQ ID NO 652
<211> LENGTH: 9
<212> TYPE: PRT
<213> ORGANISM: Homo sapiens

<400> SEQUENCE: 652

Asn Lys Glu Ala Ala Ser His Gly Phe
1               5

<210> SEQ ID NO 653
<211> LENGTH: 8
<212> TYPE: PRT
<213> ORGANISM: Homo sapiens

<400> SEQUENCE: 653

Asn Lys Met Asp Ile Leu Ser Leu
1               5

<210> SEQ ID NO 654
<211> LENGTH: 9
<212> TYPE: PRT
```

<213> ORGANISM: Homo sapiens

<400> SEQUENCE: 654

Asn Lys Gln Lys Leu Pro Cys Ser Leu
1               5

<210> SEQ ID NO 655
<211> LENGTH: 9
<212> TYPE: PRT
<213> ORGANISM: Homo sapiens

<400> SEQUENCE: 655

Asn Leu Lys Asn Val Asn Pro Ser Leu
1               5

<210> SEQ ID NO 656
<211> LENGTH: 9
<212> TYPE: PRT
<213> ORGANISM: Homo sapiens

<400> SEQUENCE: 656

Asn Leu Leu Thr Asn Gln Ser Pro Tyr
1               5

<210> SEQ ID NO 657
<211> LENGTH: 10
<212> TYPE: PRT
<213> ORGANISM: Homo sapiens

<400> SEQUENCE: 657

Asn Leu Pro Ser Asp Ala Pro Gly Ala Leu
1               5                   10

<210> SEQ ID NO 658
<211> LENGTH: 9
<212> TYPE: PRT
<213> ORGANISM: Homo sapiens

<400> SEQUENCE: 658

Asn Met Asp Phe Tyr Lys Thr His Ile
1               5

<210> SEQ ID NO 659
<211> LENGTH: 11
<212> TYPE: PRT
<213> ORGANISM: Homo sapiens

<400> SEQUENCE: 659

Asn Met Asp Phe Tyr Lys Thr His Ile Val Tyr
1               5                   10

<210> SEQ ID NO 660
<211> LENGTH: 9
<212> TYPE: PRT
<213> ORGANISM: Homo sapiens

<400> SEQUENCE: 660

Asn Asn Phe Glu Val Gly Pro Pro Val
1               5

<210> SEQ ID NO 661
<211> LENGTH: 10
<212> TYPE: PRT
<213> ORGANISM: Homo sapiens -continued

```
<400> SEQUENCE: 661

Asn Pro Phe Arg Leu Asn Gly Ala Gln Met
1               5                   10

<210> SEQ ID NO 662
<211> LENGTH: 10
<212> TYPE: PRT
<213> ORGANISM: Homo sapiens

<400> SEQUENCE: 662

Asn Pro Phe Arg Ser Lys Gly Ala Gln Met
1               5                   10

<210> SEQ ID NO 663
<211> LENGTH: 10
<212> TYPE: PRT
<213> ORGANISM: Homo sapiens

<400> SEQUENCE: 663

Asn Pro Phe Arg Ser Lys Trp Ala Gln Met
1               5                   10

<210> SEQ ID NO 664
<211> LENGTH: 8
<212> TYPE: PRT
<213> ORGANISM: Homo sapiens

<400> SEQUENCE: 664

Asn Gln Ala His Leu Ile Val Leu
1               5

<210> SEQ ID NO 665
<211> LENGTH: 9
<212> TYPE: PRT
<213> ORGANISM: Homo sapiens

<400> SEQUENCE: 665

Asn Gln Arg Ser His Gly Phe Gly Lys
1               5

<210> SEQ ID NO 666
<211> LENGTH: 9
<212> TYPE: PRT
<213> ORGANISM: Homo sapiens

<400> SEQUENCE: 666

Asn Gln Arg Thr Ala Ser His Gly Phe
1               5

<210> SEQ ID NO 667
<211> LENGTH: 9
<212> TYPE: PRT
<213> ORGANISM: Homo sapiens

<400> SEQUENCE: 667

Asn Arg Glu Ala Ala Ser His Gly Phe
1               5

<210> SEQ ID NO 668
<211> LENGTH: 8
<212> TYPE: PRT
<213> ORGANISM: Homo sapiens

<400> SEQUENCE: 668
```

-continued

Asn Arg Asn Glu Gln Lys Ala Leu
1               5

<210> SEQ ID NO 669
<211> LENGTH: 9
<212> TYPE: PRT
<213> ORGANISM: Homo sapiens

<400> SEQUENCE: 669

Asn Arg Gln Val Lys Asp Met Thr Ala
1               5

<210> SEQ ID NO 670
<211> LENGTH: 9
<212> TYPE: PRT
<213> ORGANISM: Homo sapiens

<400> SEQUENCE: 670

Asn Ser Leu Pro Arg Ile Ser Ser Arg
1               5

<210> SEQ ID NO 671
<211> LENGTH: 9
<212> TYPE: PRT
<213> ORGANISM: Homo sapiens

<400> SEQUENCE: 671

Asn Ser Asn His Asn Ile Leu Gln Lys
1               5

<210> SEQ ID NO 672
<211> LENGTH: 9
<212> TYPE: PRT
<213> ORGANISM: Homo sapiens

<400> SEQUENCE: 672

Asn Thr Ala Ser His Gly Phe Gly Lys
1               5

<210> SEQ ID NO 673
<211> LENGTH: 9
<212> TYPE: PRT
<213> ORGANISM: Homo sapiens

<400> SEQUENCE: 673

Asn Thr Ile Lys Glu Ala Ala Ser His
1               5

<210> SEQ ID NO 674
<211> LENGTH: 9
<212> TYPE: PRT
<213> ORGANISM: Homo sapiens

<400> SEQUENCE: 674

Asn Thr Lys Arg Ser Cys Lys Ser Trp
1               5

<210> SEQ ID NO 675
<211> LENGTH: 9
<212> TYPE: PRT
<213> ORGANISM: Homo sapiens

<400> SEQUENCE: 675

Asn Thr Asn Gln Arg Gly Phe Gly Lys
1               5

```
<210> SEQ ID NO 676
<211> LENGTH: 9
<212> TYPE: PRT
<213> ORGANISM: Homo sapiens

<400> SEQUENCE: 676

Asn Thr Asn Gln Arg Ser Cys Lys Tyr
1               5

<210> SEQ ID NO 677
<211> LENGTH: 9
<212> TYPE: PRT
<213> ORGANISM: Homo sapiens

<400> SEQUENCE: 677

Asn Thr Asn Gln Arg Ser His Gly Phe
1               5

<210> SEQ ID NO 678
<211> LENGTH: 9
<212> TYPE: PRT
<213> ORGANISM: Homo sapiens

<400> SEQUENCE: 678

Asn Thr Asn Ser Ser Ile Gln Lys Val
1               5

<210> SEQ ID NO 679
<211> LENGTH: 9
<212> TYPE: PRT
<213> ORGANISM: Homo sapiens

<400> SEQUENCE: 679

Asn Thr Val Asn Ile Thr Ala Gly Phe
1               5

<210> SEQ ID NO 680
<211> LENGTH: 10
<212> TYPE: PRT
<213> ORGANISM: Homo sapiens

<400> SEQUENCE: 680

Asn Val Ala Asn Gln Lys Pro Phe Glu Lys
1               5                   10

<210> SEQ ID NO 681
<211> LENGTH: 9
<212> TYPE: PRT
<213> ORGANISM: Homo sapiens

<400> SEQUENCE: 681

Asn Val Ala Asn Gln Lys Pro Leu Arg
1               5

<210> SEQ ID NO 682
<211> LENGTH: 10
<212> TYPE: PRT
<213> ORGANISM: Homo sapiens

<400> SEQUENCE: 682

Asn Val Ala Gln Ser Pro Arg Lys Leu Tyr
1               5                   10
```

```
<210> SEQ ID NO 683
<211> LENGTH: 11
<212> TYPE: PRT
<213> ORGANISM: Homo sapiens

<400> SEQUENCE: 683

Asn Val Ala Gln Ser Pro Arg Lys Leu Tyr Arg
1               5                   10

<210> SEQ ID NO 684
<211> LENGTH: 9
<212> TYPE: PRT
<213> ORGANISM: Homo sapiens

<400> SEQUENCE: 684

Asn Val Glu Lys Glu Thr Ala Lys Arg
1               5

<210> SEQ ID NO 685
<211> LENGTH: 10
<212> TYPE: PRT
<213> ORGANISM: Homo sapiens

<400> SEQUENCE: 685

Asn Val Gly Ser Pro Leu Arg Val Glu Val
1               5                   10

<210> SEQ ID NO 686
<211> LENGTH: 9
<212> TYPE: PRT
<213> ORGANISM: Homo sapiens

<400> SEQUENCE: 686

Asn Val Leu Leu Lys Gln Lys Ala Val
1               5

<210> SEQ ID NO 687
<211> LENGTH: 8
<212> TYPE: PRT
<213> ORGANISM: Homo sapiens

<400> SEQUENCE: 687

Asn Val Asn Lys Arg Lys Lys Ile
1               5

<210> SEQ ID NO 688
<211> LENGTH: 9
<212> TYPE: PRT
<213> ORGANISM: Homo sapiens

<400> SEQUENCE: 688

Asn Val Gln His Ser Leu Pro Thr Leu
1               5

<210> SEQ ID NO 689
<211> LENGTH: 8
<212> TYPE: PRT
<213> ORGANISM: Homo sapiens

<400> SEQUENCE: 689

Asn Val Val Ser Lys Glu Ala Leu
1               5

<210> SEQ ID NO 690
<211> LENGTH: 10
```

```
<212> TYPE: PRT
<213> ORGANISM: Homo sapiens

<400> SEQUENCE: 690

Asn Val Val Ser Lys Glu Ala Leu Gly Phe
1               5                   10

<210> SEQ ID NO 691
<211> LENGTH: 10
<212> TYPE: PRT
<213> ORGANISM: Homo sapiens

<400> SEQUENCE: 691

Asn Tyr Phe Glu Thr Glu Ala Val Ala Phe
1               5                   10

<210> SEQ ID NO 692
<211> LENGTH: 10
<212> TYPE: PRT
<213> ORGANISM: Homo sapiens

<400> SEQUENCE: 692

Asn Tyr Leu Tyr Glu Asn Asn Ser Asn Tyr
1               5                   10

<210> SEQ ID NO 693
<211> LENGTH: 9
<212> TYPE: PRT
<213> ORGANISM: Homo sapiens

<400> SEQUENCE: 693

Pro Ala Lys Ile Lys Met Gln Pro Leu
1               5

<210> SEQ ID NO 694
<211> LENGTH: 8
<212> TYPE: PRT
<213> ORGANISM: Homo sapiens

<400> SEQUENCE: 694

Pro Met Glu Lys Ile Pro Leu Leu
1               5

<210> SEQ ID NO 695
<211> LENGTH: 9
<212> TYPE: PRT
<213> ORGANISM: Homo sapiens

<400> SEQUENCE: 695

Pro Trp Ile Thr Leu Ile Ala Ala Phe
1               5

<210> SEQ ID NO 696
<211> LENGTH: 10
<212> TYPE: PRT
<213> ORGANISM: Homo sapiens

<400> SEQUENCE: 696

Pro Tyr Ser Val Val Asn Ser Ser Ala Phe
1               5                   10

<210> SEQ ID NO 697
<211> LENGTH: 9
<212> TYPE: PRT
<213> ORGANISM: Homo sapiens
```

-continued

```
<400> SEQUENCE: 697

Gln Ala Ala Gly Ala Trp Arg Val Trp
1               5

<210> SEQ ID NO 698
<211> LENGTH: 9
<212> TYPE: PRT
<213> ORGANISM: Homo sapiens

<400> SEQUENCE: 698

Gln Ala Phe Leu Trp Leu Val Arg Lys
1               5

<210> SEQ ID NO 699
<211> LENGTH: 9
<212> TYPE: PRT
<213> ORGANISM: Homo sapiens

<400> SEQUENCE: 699

Gln Asp Phe Asn Ser Asn His Asn Ile
1               5

<210> SEQ ID NO 700
<211> LENGTH: 9
<212> TYPE: PRT
<213> ORGANISM: Homo sapiens

<400> SEQUENCE: 700

Gln Glu His Gln Ala Ala Gly Ala Trp
1               5

<210> SEQ ID NO 701
<211> LENGTH: 9
<212> TYPE: PRT
<213> ORGANISM: Homo sapiens

<400> SEQUENCE: 701

Gln Phe Gln Gln Asp Asn Ser Trp Tyr
1               5

<210> SEQ ID NO 702
<211> LENGTH: 9
<212> TYPE: PRT
<213> ORGANISM: Homo sapiens

<400> SEQUENCE: 702

Gln Gly Tyr Leu Arg Gly Ala Lys Lys
1               5

<210> SEQ ID NO 703
<211> LENGTH: 9
<212> TYPE: PRT
<213> ORGANISM: Homo sapiens

<400> SEQUENCE: 703

Gln His Leu Leu Phe Gly Ile Tyr Leu
1               5

<210> SEQ ID NO 704
<211> LENGTH: 10
<212> TYPE: PRT
<213> ORGANISM: Homo sapiens

<400> SEQUENCE: 704
```

-continued

```
Gln His Leu Leu Phe Gly Ile Tyr Leu Leu
1               5                   10

<210> SEQ ID NO 705
<211> LENGTH: 9
<212> TYPE: PRT
<213> ORGANISM: Homo sapiens

<400> SEQUENCE: 705

Gln Ile Lys Glu Asp Leu Ser Ala Phe
1               5

<210> SEQ ID NO 706
<211> LENGTH: 9
<212> TYPE: PRT
<213> ORGANISM: Homo sapiens

<400> SEQUENCE: 706

Gln Ile Lys Glu Asp Leu Ser Glu Val
1               5

<210> SEQ ID NO 707
<211> LENGTH: 8
<212> TYPE: PRT
<213> ORGANISM: Homo sapiens

<400> SEQUENCE: 707

Gln Ile Lys Glu Lys Leu Gln Val
1               5

<210> SEQ ID NO 708
<211> LENGTH: 9
<212> TYPE: PRT
<213> ORGANISM: Homo sapiens

<400> SEQUENCE: 708

Gln Ile Lys Glu Lys Leu Gln Val Met
1               5

<210> SEQ ID NO 709
<211> LENGTH: 9
<212> TYPE: PRT
<213> ORGANISM: Homo sapiens

<400> SEQUENCE: 709

Gln Leu Glu Pro Arg Arg Val Asn Lys
1               5

<210> SEQ ID NO 710
<211> LENGTH: 10
<212> TYPE: PRT
<213> ORGANISM: Homo sapiens

<400> SEQUENCE: 710

Gln Leu Ile Met Pro Asn Val Val Ser Lys
1               5                   10

<210> SEQ ID NO 711
<211> LENGTH: 9
<212> TYPE: PRT
<213> ORGANISM: Homo sapiens

<400> SEQUENCE: 711

Gln Leu Ile Ser Leu Gln Ala Phe Leu
```

-continued

```
1               5

<210> SEQ ID NO 712
<211> LENGTH: 9
<212> TYPE: PRT
<213> ORGANISM: Homo sapiens

<400> SEQUENCE: 712

Gln Leu Lys Lys Ile Trp Phe Met Phe
1               5

<210> SEQ ID NO 713
<211> LENGTH: 9
<212> TYPE: PRT
<213> ORGANISM: Homo sapiens

<400> SEQUENCE: 713

Gln Leu Gln Lys Ser Thr Phe Glu Val
1               5

<210> SEQ ID NO 714
<211> LENGTH: 9
<212> TYPE: PRT
<213> ORGANISM: Homo sapiens

<400> SEQUENCE: 714

Gln Leu Val Leu Ala Thr Tyr His Leu
1               5

<210> SEQ ID NO 715
<211> LENGTH: 10
<212> TYPE: PRT
<213> ORGANISM: Homo sapiens

<400> SEQUENCE: 715

Gln Met Asn Arg Gln Ala Pro Gly Ser Phe
1               5                   10

<210> SEQ ID NO 716
<211> LENGTH: 9
<212> TYPE: PRT
<213> ORGANISM: Homo sapiens

<400> SEQUENCE: 716

Gln Asn Met Trp Arg Pro Asn Lys Arg
1               5

<210> SEQ ID NO 717
<211> LENGTH: 9
<212> TYPE: PRT
<213> ORGANISM: Homo sapiens

<400> SEQUENCE: 717

Gln Pro Leu Asn Cys Pro Pro Ala Phe
1               5

<210> SEQ ID NO 718
<211> LENGTH: 9
<212> TYPE: PRT
<213> ORGANISM: Homo sapiens

<400> SEQUENCE: 718

Gln Pro Leu Asn Cys Pro Tyr Leu Ile
1               5
```

-continued

```
<210> SEQ ID NO 719
<211> LENGTH: 10
<212> TYPE: PRT
<213> ORGANISM: Homo sapiens

<400> SEQUENCE: 719

Gln Arg Thr Ala Ser His Gly Phe Gly Lys
1               5                   10

<210> SEQ ID NO 720
<211> LENGTH: 10
<212> TYPE: PRT
<213> ORGANISM: Homo sapiens

<400> SEQUENCE: 720

Gln Arg Thr Tyr Ser Ile Gly Phe Ser Tyr
1               5                   10

<210> SEQ ID NO 721
<211> LENGTH: 9
<212> TYPE: PRT
<213> ORGANISM: Homo sapiens

<400> SEQUENCE: 721

Gln Arg Thr Tyr Ser Ile Val Lys Ile
1               5

<210> SEQ ID NO 722
<211> LENGTH: 9
<212> TYPE: PRT
<213> ORGANISM: Homo sapiens

<400> SEQUENCE: 722

Gln Ser Ala Ser His Leu Leu Arg Phe
1               5

<210> SEQ ID NO 723
<211> LENGTH: 11
<212> TYPE: PRT
<213> ORGANISM: Homo sapiens

<400> SEQUENCE: 723

Gln Ser Gly Thr Ala Glu Thr Tyr Asn Ser Trp
1               5                   10

<210> SEQ ID NO 724
<211> LENGTH: 10
<212> TYPE: PRT
<213> ORGANISM: Homo sapiens

<400> SEQUENCE: 724

Gln Ser Pro Arg Lys Leu Tyr Arg Leu Trp
1               5                   10

<210> SEQ ID NO 725
<211> LENGTH: 9
<212> TYPE: PRT
<213> ORGANISM: Homo sapiens

<400> SEQUENCE: 725

Gln Ser Gln Leu Val Leu Ala Thr Tyr
1               5

<210> SEQ ID NO 726
```

-continued

```
<211> LENGTH: 9
<212> TYPE: PRT
<213> ORGANISM: Homo sapiens

<400> SEQUENCE: 726

Gln Ser Thr Val Ser Thr Ile Ser Arg
1               5

<210> SEQ ID NO 727
<211> LENGTH: 10
<212> TYPE: PRT
<213> ORGANISM: Homo sapiens

<400> SEQUENCE: 727

Gln Thr Glu Gln Ala Ser Val Asn Thr Val
1               5                   10

<210> SEQ ID NO 728
<211> LENGTH: 10
<212> TYPE: PRT
<213> ORGANISM: Homo sapiens

<400> SEQUENCE: 728

Gln Thr Glu Ser Lys Ser Ile Phe Leu Lys
1               5                   10

<210> SEQ ID NO 729
<211> LENGTH: 10
<212> TYPE: PRT
<213> ORGANISM: Homo sapiens

<400> SEQUENCE: 729

Gln Thr Glu Ser Gln Asn Ile Lys Lys Tyr
1               5                   10

<210> SEQ ID NO 730
<211> LENGTH: 9
<212> TYPE: PRT
<213> ORGANISM: Homo sapiens

<400> SEQUENCE: 730

Gln Val Lys Asp Met Thr Ala Ile Leu
1               5

<210> SEQ ID NO 731
<211> LENGTH: 9
<212> TYPE: PRT
<213> ORGANISM: Homo sapiens

<400> SEQUENCE: 731

Arg Ala Ala Ser His Gly Phe Gly Lys
1               5

<210> SEQ ID NO 732
<211> LENGTH: 9
<212> TYPE: PRT
<213> ORGANISM: Homo sapiens

<400> SEQUENCE: 732

Arg Ala Gln Met Glu Lys Ile Pro Leu
1               5

<210> SEQ ID NO 733
<211> LENGTH: 10
<212> TYPE: PRT
```

```
<213> ORGANISM: Homo sapiens

<400> SEQUENCE: 733

Arg Ala Gln Met Glu Lys Ile Pro Leu Leu
1               5                   10

<210> SEQ ID NO 734
<211> LENGTH: 8
<212> TYPE: PRT
<213> ORGANISM: Homo sapiens

<400> SEQUENCE: 734

Arg Glu Ile Leu Lys Met Lys Ile
1               5

<210> SEQ ID NO 735
<211> LENGTH: 9
<212> TYPE: PRT
<213> ORGANISM: Homo sapiens

<400> SEQUENCE: 735

Arg Glu Ile Leu Lys Met Lys Ile Thr
1               5

<210> SEQ ID NO 736
<211> LENGTH: 8
<212> TYPE: PRT
<213> ORGANISM: Homo sapiens

<400> SEQUENCE: 736

Arg Glu Gln Glu His Gln Ala Ala
1               5

<210> SEQ ID NO 737
<211> LENGTH: 9
<212> TYPE: PRT
<213> ORGANISM: Homo sapiens

<400> SEQUENCE: 737

Arg Glu Gln Glu His Gln Ala Ala Gly
1               5

<210> SEQ ID NO 738
<211> LENGTH: 10
<212> TYPE: PRT
<213> ORGANISM: Homo sapiens

<400> SEQUENCE: 738

Arg Glu Gln Glu His Gln Ala Ala Gly Ala
1               5                   10

<210> SEQ ID NO 739
<211> LENGTH: 11
<212> TYPE: PRT
<213> ORGANISM: Homo sapiens

<400> SEQUENCE: 739

Arg Glu Gln Glu His Gln Ala Ala Gly Ala Trp
1               5                   10

<210> SEQ ID NO 740
<211> LENGTH: 9
<212> TYPE: PRT
<213> ORGANISM: Homo sapiens
```

<400> SEQUENCE: 740

Arg Glu Tyr Ser Cys Lys Asp His Ile
1               5

<210> SEQ ID NO 741
<211> LENGTH: 9
<212> TYPE: PRT
<213> ORGANISM: Homo sapiens

<400> SEQUENCE: 741

Arg Phe Ile Ala Ala Ser His Gly Phe
1               5

<210> SEQ ID NO 742
<211> LENGTH: 9
<212> TYPE: PRT
<213> ORGANISM: Homo sapiens

<400> SEQUENCE: 742

Arg Phe Ile Ala Ser Val Pro Val Lys
1               5

<210> SEQ ID NO 743
<211> LENGTH: 9
<212> TYPE: PRT
<213> ORGANISM: Homo sapiens

<400> SEQUENCE: 743

Arg Phe Ile Ala Ser Val Thr Glu Ala
1               5

<210> SEQ ID NO 744
<211> LENGTH: 9
<212> TYPE: PRT
<213> ORGANISM: Homo sapiens

<400> SEQUENCE: 744

Arg Phe Ile Ala Ser Val Thr Val Lys
1               5

<210> SEQ ID NO 745
<211> LENGTH: 9
<212> TYPE: PRT
<213> ORGANISM: Homo sapiens

<400> SEQUENCE: 745

Arg Phe Ile Asn Ser Asn Gln Ala Val
1               5

<210> SEQ ID NO 746
<211> LENGTH: 9
<212> TYPE: PRT
<213> ORGANISM: Homo sapiens

<400> SEQUENCE: 746

Arg Phe Ile Ser Ser Asn Gln Ala Val
1               5

<210> SEQ ID NO 747
<211> LENGTH: 9
<212> TYPE: PRT
<213> ORGANISM: Homo sapiens

<400> SEQUENCE: 747

```
Arg Phe Lys Asn Asn Ser Asn Gln Ala
1               5

<210> SEQ ID NO 748
<211> LENGTH: 9
<212> TYPE: PRT
<213> ORGANISM: Homo sapiens

<400> SEQUENCE: 748

Arg Phe Gln Ile Gln Glu Met Gln Lys
1               5

<210> SEQ ID NO 749
<211> LENGTH: 10
<212> TYPE: PRT
<213> ORGANISM: Homo sapiens

<400> SEQUENCE: 749

Arg Phe Gln Ile Gln Glu Met Gln Lys Arg
1               5                   10

<210> SEQ ID NO 750
<211> LENGTH: 9
<212> TYPE: PRT
<213> ORGANISM: Homo sapiens

<400> SEQUENCE: 750

Arg Phe Gln Ser Ala Ser His Leu Leu
1               5

<210> SEQ ID NO 751
<211> LENGTH: 10
<212> TYPE: PRT
<213> ORGANISM: Homo sapiens

<400> SEQUENCE: 751

Arg Phe Gln Ser Ala Ser His Leu Leu Arg
1               5                   10

<210> SEQ ID NO 752
<211> LENGTH: 11
<212> TYPE: PRT
<213> ORGANISM: Homo sapiens

<400> SEQUENCE: 752

Arg Phe Gln Ser Ala Ser His Leu Leu Arg Phe
1               5                   10

<210> SEQ ID NO 753
<211> LENGTH: 9
<212> TYPE: PRT
<213> ORGANISM: Homo sapiens

<400> SEQUENCE: 753

Arg Gly Phe Tyr Ser Ala Leu Gln Lys
1               5

<210> SEQ ID NO 754
<211> LENGTH: 9
<212> TYPE: PRT
<213> ORGANISM: Homo sapiens

<400> SEQUENCE: 754

Arg Gly Lys Glu Ser Tyr Lys Leu Lys
1               5
```

```
<210> SEQ ID NO 755
<211> LENGTH: 10
<212> TYPE: PRT
<213> ORGANISM: Homo sapiens

<400> SEQUENCE: 755

Arg Gly Lys Glu Ser Tyr Lys Met Ser Lys
1               5               10

<210> SEQ ID NO 756
<211> LENGTH: 10
<212> TYPE: PRT
<213> ORGANISM: Homo sapiens

<400> SEQUENCE: 756

Arg Ile Ala Ser Gly Asn Lys Lys Val Lys
1               5               10

<210> SEQ ID NO 757
<211> LENGTH: 9
<212> TYPE: PRT
<213> ORGANISM: Homo sapiens

<400> SEQUENCE: 757

Arg Ile His Ser Arg Phe Gln Ser Ala
1               5

<210> SEQ ID NO 758
<211> LENGTH: 9
<212> TYPE: PRT
<213> ORGANISM: Homo sapiens

<400> SEQUENCE: 758

Arg Ile Ile Gln Asn Val Lys Asp Lys
1               5

<210> SEQ ID NO 759
<211> LENGTH: 9
<212> TYPE: PRT
<213> ORGANISM: Homo sapiens

<400> SEQUENCE: 759

Arg Ile Lys Pro Val Gln Thr Val Asn
1               5

<210> SEQ ID NO 760
<211> LENGTH: 10
<212> TYPE: PRT
<213> ORGANISM: Homo sapiens

<400> SEQUENCE: 760

Arg Ile Lys Pro Val Gln Thr Val Asn Ile
1               5               10

<210> SEQ ID NO 761
<211> LENGTH: 9
<212> TYPE: PRT
<213> ORGANISM: Homo sapiens

<400> SEQUENCE: 761

Arg Ile Ser Ser Arg Gly Thr Val Val
1               5
```

-continued

```
<210> SEQ ID NO 762
<211> LENGTH: 11
<212> TYPE: PRT
<213> ORGANISM: Homo sapiens

<400> SEQUENCE: 762

Arg Ile Ser Ser Arg Gly Thr Val Val Asn Lys
1               5                   10

<210> SEQ ID NO 763
<211> LENGTH: 9
<212> TYPE: PRT
<213> ORGANISM: Homo sapiens

<400> SEQUENCE: 763

Arg Lys Asp His Ile Gly Lys Ser Met
1               5

<210> SEQ ID NO 764
<211> LENGTH: 10
<212> TYPE: PRT
<213> ORGANISM: Homo sapiens

<400> SEQUENCE: 764

Arg Lys Glu Glu Lys Glu Ala Ala Lys Tyr
1               5                   10

<210> SEQ ID NO 765
<211> LENGTH: 10
<212> TYPE: PRT
<213> ORGANISM: Homo sapiens

<400> SEQUENCE: 765

Arg Lys Leu Met Ser Gly Phe Pro Glu Val
1               5                   10

<210> SEQ ID NO 766
<211> LENGTH: 9
<212> TYPE: PRT
<213> ORGANISM: Homo sapiens

<400> SEQUENCE: 766

Arg Lys Asn Gln Glu Glu Gln Ser Met
1               5

<210> SEQ ID NO 767
<211> LENGTH: 9
<212> TYPE: PRT
<213> ORGANISM: Homo sapiens

<400> SEQUENCE: 767

Arg Leu Leu Gln Ser Asp Pro Ser Leu
1               5

<210> SEQ ID NO 768
<211> LENGTH: 9
<212> TYPE: PRT
<213> ORGANISM: Homo sapiens

<400> SEQUENCE: 768

Arg Leu Asn Gly Ala Gln Met Glu Lys
1               5

<210> SEQ ID NO 769
<211> LENGTH: 8
```

-continued

```
<212> TYPE: PRT
<213> ORGANISM: Homo sapiens

<400> SEQUENCE: 769

Arg Leu Trp Pro Val Asn Gly Leu
1               5

<210> SEQ ID NO 770
<211> LENGTH: 9
<212> TYPE: PRT
<213> ORGANISM: Homo sapiens

<400> SEQUENCE: 770

Arg Leu Trp Pro Val Asn Gly Leu Leu
1               5

<210> SEQ ID NO 771
<211> LENGTH: 11
<212> TYPE: PRT
<213> ORGANISM: Homo sapiens

<400> SEQUENCE: 771

Arg Leu Trp Pro Val Asn Gly Leu Leu Glu Leu
1               5                   10

<210> SEQ ID NO 772
<211> LENGTH: 9
<212> TYPE: PRT
<213> ORGANISM: Homo sapiens

<400> SEQUENCE: 772

Arg Met Ser Leu Ile Ser Ser Leu Tyr
1               5

<210> SEQ ID NO 773
<211> LENGTH: 10
<212> TYPE: PRT
<213> ORGANISM: Homo sapiens

<400> SEQUENCE: 773

Arg Met Ser Leu Ile Ser Ser Leu Tyr Arg
1               5                   10

<210> SEQ ID NO 774
<211> LENGTH: 9
<212> TYPE: PRT
<213> ORGANISM: Homo sapiens

<400> SEQUENCE: 774

Arg Asn Gln Ala His Leu Ile Val Leu
1               5

<210> SEQ ID NO 775
<211> LENGTH: 8
<212> TYPE: PRT
<213> ORGANISM: Homo sapiens

<400> SEQUENCE: 775

Arg Pro Asn Phe Thr Arg Arg Leu
1               5

<210> SEQ ID NO 776
<211> LENGTH: 10
<212> TYPE: PRT
<213> ORGANISM: Homo sapiens
```

-continued

<400> SEQUENCE: 776

Arg Pro Asn Phe Thr Arg Arg Leu Gln Phe
1               5                   10

<210> SEQ ID NO 777
<211> LENGTH: 9
<212> TYPE: PRT
<213> ORGANISM: Homo sapiens

<400> SEQUENCE: 777

Arg Gln Ala Pro Gly Ser Phe Thr Lys
1               5

<210> SEQ ID NO 778
<211> LENGTH: 9
<212> TYPE: PRT
<213> ORGANISM: Homo sapiens

<400> SEQUENCE: 778

Arg Gln Leu Ile Ser Leu Gln Ala Phe
1               5

<210> SEQ ID NO 779
<211> LENGTH: 10
<212> TYPE: PRT
<213> ORGANISM: Homo sapiens

<400> SEQUENCE: 779

Arg Gln Leu Ile Ser Leu Gln Ala Phe Leu
1               5                   10

<210> SEQ ID NO 780
<211> LENGTH: 9
<212> TYPE: PRT
<213> ORGANISM: Homo sapiens

<400> SEQUENCE: 780

Arg Gln Gln Leu Val Leu Gly Thr Lys
1               5

<210> SEQ ID NO 781
<211> LENGTH: 9
<212> TYPE: PRT
<213> ORGANISM: Homo sapiens

<400> SEQUENCE: 781

Arg Gln Thr Glu Ser Lys Ser Ile Phe
1               5

<210> SEQ ID NO 782
<211> LENGTH: 10
<212> TYPE: PRT
<213> ORGANISM: Homo sapiens

<400> SEQUENCE: 782

Arg Gln Thr Glu Ser Lys Ser Ile Phe Leu
1               5                   10

<210> SEQ ID NO 783
<211> LENGTH: 11
<212> TYPE: PRT
<213> ORGANISM: Homo sapiens

<400> SEQUENCE: 783

-continued

```
Arg Gln Thr Glu Ser Gln Asn Ile Lys Lys Tyr
1                5                  10

<210> SEQ ID NO 784
<211> LENGTH: 9
<212> TYPE: PRT
<213> ORGANISM: Homo sapiens

<400> SEQUENCE: 784

Arg Gln Val Lys Asp Met Thr Ala Ile
1                5

<210> SEQ ID NO 785
<211> LENGTH: 10
<212> TYPE: PRT
<213> ORGANISM: Homo sapiens

<400> SEQUENCE: 785

Arg Gln Val Lys Asp Met Thr Ala Ile Leu
1                5                  10

<210> SEQ ID NO 786
<211> LENGTH: 9
<212> TYPE: PRT
<213> ORGANISM: Homo sapiens

<400> SEQUENCE: 786

Arg Arg Leu Gln Phe Leu Tyr Arg Leu
1                5

<210> SEQ ID NO 787
<211> LENGTH: 9
<212> TYPE: PRT
<213> ORGANISM: Homo sapiens

<400> SEQUENCE: 787

Arg Arg Pro Asn Phe Thr Arg Arg Leu
1                5

<210> SEQ ID NO 788
<211> LENGTH: 11
<212> TYPE: PRT
<213> ORGANISM: Homo sapiens

<400> SEQUENCE: 788

Arg Arg Pro Asn Phe Thr Arg Arg Leu Gln Phe
1                5                  10

<210> SEQ ID NO 789
<211> LENGTH: 9
<212> TYPE: PRT
<213> ORGANISM: Homo sapiens

<400> SEQUENCE: 789

Arg Arg Val Thr Ser Gln Met Asn Arg
1                5

<210> SEQ ID NO 790
<211> LENGTH: 9
<212> TYPE: PRT
<213> ORGANISM: Homo sapiens

<400> SEQUENCE: 790

Arg Ser Cys Lys Ser Trp Asn Ser Phe
```

-continued

```
1               5

<210> SEQ ID NO 791
<211> LENGTH: 10
<212> TYPE: PRT
<213> ORGANISM: Homo sapiens

<400> SEQUENCE: 791

Arg Ser Cys Lys Ser Trp Asn Ser Phe Lys
1               5                   10

<210> SEQ ID NO 792
<211> LENGTH: 9
<212> TYPE: PRT
<213> ORGANISM: Homo sapiens

<400> SEQUENCE: 792

Arg Ser Cys Lys Tyr Gly Phe Gly Lys
1               5

<210> SEQ ID NO 793
<211> LENGTH: 9
<212> TYPE: PRT
<213> ORGANISM: Homo sapiens

<400> SEQUENCE: 793

Arg Ser His Gly Phe Gly Lys Thr Ser
1               5

<210> SEQ ID NO 794
<211> LENGTH: 9
<212> TYPE: PRT
<213> ORGANISM: Homo sapiens

<400> SEQUENCE: 794

Arg Ser Lys Gly Ala Gln Met Glu Lys
1               5

<210> SEQ ID NO 795
<211> LENGTH: 9
<212> TYPE: PRT
<213> ORGANISM: Homo sapiens

<400> SEQUENCE: 795

Arg Ser Lys Trp Ala Gln Met Glu Lys
1               5

<210> SEQ ID NO 796
<211> LENGTH: 9
<212> TYPE: PRT
<213> ORGANISM: Homo sapiens

<400> SEQUENCE: 796

Arg Ser Lys Trp Ser Pro Asp Gly Lys
1               5

<210> SEQ ID NO 797
<211> LENGTH: 9
<212> TYPE: PRT
<213> ORGANISM: Homo sapiens

<400> SEQUENCE: 797

Arg Ser Lys Trp Ser Pro Met Glu Lys
1               5
```

-continued

<210> SEQ ID NO 798
<211> LENGTH: 9
<212> TYPE: PRT
<213> ORGANISM: Homo sapiens

<400> SEQUENCE: 798

Arg Ser Lys Trp Ser Gln Met Glu Lys
1               5

<210> SEQ ID NO 799
<211> LENGTH: 9
<212> TYPE: PRT
<213> ORGANISM: Homo sapiens

<400> SEQUENCE: 799

Arg Thr Ala Ser His Gly Phe Gly Lys
1               5

<210> SEQ ID NO 800
<211> LENGTH: 9
<212> TYPE: PRT
<213> ORGANISM: Homo sapiens

<400> SEQUENCE: 800

Arg Thr Asn Pro Phe Arg Leu Asn Gly
1               5

<210> SEQ ID NO 801
<211> LENGTH: 10
<212> TYPE: PRT
<213> ORGANISM: Homo sapiens

<400> SEQUENCE: 801

Arg Thr Asn Pro Phe Arg Leu Asn Gly Ala
1               5                   10

<210> SEQ ID NO 802
<211> LENGTH: 8
<212> TYPE: PRT
<213> ORGANISM: Homo sapiens

<400> SEQUENCE: 802

Arg Thr Asn Pro Phe Arg Ser Lys
1               5

<210> SEQ ID NO 803
<211> LENGTH: 9
<212> TYPE: PRT
<213> ORGANISM: Homo sapiens

<400> SEQUENCE: 803

Arg Thr Asn Pro Phe Arg Ser Lys Gly
1               5

<210> SEQ ID NO 804
<211> LENGTH: 10
<212> TYPE: PRT
<213> ORGANISM: Homo sapiens

<400> SEQUENCE: 804

Arg Thr Asn Pro Phe Arg Ser Lys Gly Ala
1               5                   10

<210> SEQ ID NO 805

-continued

```
<211> LENGTH: 9
<212> TYPE: PRT
<213> ORGANISM: Homo sapiens

<400> SEQUENCE: 805

Arg Thr Asn Pro Phe Arg Ser Lys Trp
1               5

<210> SEQ ID NO 806
<211> LENGTH: 10
<212> TYPE: PRT
<213> ORGANISM: Homo sapiens

<400> SEQUENCE: 806

Arg Thr Asn Pro Phe Arg Ser Lys Trp Ala
1               5                   10

<210> SEQ ID NO 807
<211> LENGTH: 9
<212> TYPE: PRT
<213> ORGANISM: Homo sapiens

<400> SEQUENCE: 807

Arg Thr Gln Glu Asn Leu Leu Ser Leu
1               5

<210> SEQ ID NO 808
<211> LENGTH: 10
<212> TYPE: PRT
<213> ORGANISM: Homo sapiens

<400> SEQUENCE: 808

Arg Thr Gln Glu Asn Leu Leu Ser Leu Lys
1               5                   10

<210> SEQ ID NO 809
<211> LENGTH: 9
<212> TYPE: PRT
<213> ORGANISM: Homo sapiens

<400> SEQUENCE: 809

Arg Thr Tyr Ser Ile Gly Phe Ser Tyr
1               5

<210> SEQ ID NO 810
<211> LENGTH: 10
<212> TYPE: PRT
<213> ORGANISM: Homo sapiens

<400> SEQUENCE: 810

Arg Thr Tyr Ser Ile Gly Phe Ser Tyr Ser
1               5                   10

<210> SEQ ID NO 811
<211> LENGTH: 8
<212> TYPE: PRT
<213> ORGANISM: Homo sapiens

<400> SEQUENCE: 811

Arg Thr Tyr Ser Ile Val Lys Ile
1               5

<210> SEQ ID NO 812
<211> LENGTH: 9
<212> TYPE: PRT
```

<213> ORGANISM: Homo sapiens

<400> SEQUENCE: 812

Arg Thr Tyr Ser Ile Val Lys Ile Ala
1               5

<210> SEQ ID NO 813
<211> LENGTH: 10
<212> TYPE: PRT
<213> ORGANISM: Homo sapiens

<400> SEQUENCE: 813

Arg Thr Tyr Ser Ile Val Lys Ile Ala Lys
1               5                   10

<210> SEQ ID NO 814
<211> LENGTH: 9
<212> TYPE: PRT
<213> ORGANISM: Homo sapiens

<400> SEQUENCE: 814

Arg Val Glu Val Thr Lys Ser Pro Arg
1               5

<210> SEQ ID NO 815
<211> LENGTH: 10
<212> TYPE: PRT
<213> ORGANISM: Homo sapiens

<400> SEQUENCE: 815

Arg Val Glu Val Thr Lys Ser Pro Arg Lys
1               5                   10

<210> SEQ ID NO 816
<211> LENGTH: 9
<212> TYPE: PRT
<213> ORGANISM: Homo sapiens

<400> SEQUENCE: 816

Arg Val His Ser Lys Ser Val Glu Lys
1               5

<210> SEQ ID NO 817
<211> LENGTH: 11
<212> TYPE: PRT
<213> ORGANISM: Homo sapiens

<400> SEQUENCE: 817

Arg Val Asn Lys Pro Asn Glu Gln Thr Ser Lys
1               5                   10

<210> SEQ ID NO 818
<211> LENGTH: 9
<212> TYPE: PRT
<213> ORGANISM: Homo sapiens

<400> SEQUENCE: 818

Ser Ala Phe Met Glu Asp Asp Glu Leu
1               5

<210> SEQ ID NO 819
<211> LENGTH: 9
<212> TYPE: PRT
<213> ORGANISM: Homo sapiens -continued

```
<400> SEQUENCE: 819

Ser Ala His Gly Thr Lys Gln Cys Phe
1               5

<210> SEQ ID NO 820
<211> LENGTH: 10
<212> TYPE: PRT
<213> ORGANISM: Homo sapiens

<400> SEQUENCE: 820

Ser Ala His Ser Gly Ser Leu Lys Asn Lys
1               5                   10

<210> SEQ ID NO 821
<211> LENGTH: 8
<212> TYPE: PRT
<213> ORGANISM: Homo sapiens

<400> SEQUENCE: 821

Ser Ala Leu Glu Lys Ala Val Leu
1               5

<210> SEQ ID NO 822
<211> LENGTH: 9
<212> TYPE: PRT
<213> ORGANISM: Homo sapiens

<400> SEQUENCE: 822

Ser Ala Leu Gln Lys Ala Val Lys Leu
1               5

<210> SEQ ID NO 823
<211> LENGTH: 9
<212> TYPE: PRT
<213> ORGANISM: Homo sapiens

<400> SEQUENCE: 823

Ser Asp Asp Glu Glu Arg Asn Gly Leu
1               5

<210> SEQ ID NO 824
<211> LENGTH: 9
<212> TYPE: PRT
<213> ORGANISM: Homo sapiens

<400> SEQUENCE: 824

Ser Asp Asp Leu Asn Leu Ile Leu Leu
1               5

<210> SEQ ID NO 825
<211> LENGTH: 8
<212> TYPE: PRT
<213> ORGANISM: Homo sapiens

<400> SEQUENCE: 825

Ser Asp Leu Asn Phe Trp Lys Leu
1               5

<210> SEQ ID NO 826
<211> LENGTH: 8
<212> TYPE: PRT
<213> ORGANISM: Homo sapiens

<400> SEQUENCE: 826
```

Ser Asp Leu Asn Phe Trp Lys Tyr
1                   5

<210> SEQ ID NO 827
<211> LENGTH: 10
<212> TYPE: PRT
<213> ORGANISM: Homo sapiens

<400> SEQUENCE: 827

Ser Asp Pro Ser Leu Gln Glu Thr Ser Leu
1                   5                   10

<210> SEQ ID NO 828
<211> LENGTH: 10
<212> TYPE: PRT
<213> ORGANISM: Homo sapiens

<400> SEQUENCE: 828

Ser Asp Arg Leu Trp Pro Val Asn Gly Leu
1                   5                   10

<210> SEQ ID NO 829
<211> LENGTH: 10
<212> TYPE: PRT
<213> ORGANISM: Homo sapiens

<400> SEQUENCE: 829

Ser Asp Ser Ser Ala Leu Glu Asp Leu Trp
1                   5                   10

<210> SEQ ID NO 830
<211> LENGTH: 9
<212> TYPE: PRT
<213> ORGANISM: Homo sapiens

<400> SEQUENCE: 830

Ser Glu Ala Thr Lys Leu Asp Ser Leu
1                   5

<210> SEQ ID NO 831
<211> LENGTH: 10
<212> TYPE: PRT
<213> ORGANISM: Homo sapiens

<400> SEQUENCE: 831

Ser Glu Ala Thr Lys Leu Asp Ser Leu Leu
1                   5                   10

<210> SEQ ID NO 832
<211> LENGTH: 10
<212> TYPE: PRT
<213> ORGANISM: Homo sapiens

<400> SEQUENCE: 832

Ser Glu Asp Ile Leu His Asn Ser Leu Val
1                   5                   10

<210> SEQ ID NO 833
<211> LENGTH: 9
<212> TYPE: PRT
<213> ORGANISM: Homo sapiens

<400> SEQUENCE: 833

Ser Glu Asp Ile Leu His Asn Ser Val
1                   5

-continued

```
<210> SEQ ID NO 834
<211> LENGTH: 10
<212> TYPE: PRT
<213> ORGANISM: Homo sapiens

<400> SEQUENCE: 834

Ser Glu Asp Ile Leu His Asn Ser Val Phe
1               5                   10

<210> SEQ ID NO 835
<211> LENGTH: 10
<212> TYPE: PRT
<213> ORGANISM: Homo sapiens

<400> SEQUENCE: 835

Ser Glu Phe Gly Arg Leu Asp Cys Lys Tyr
1               5                   10

<210> SEQ ID NO 836
<211> LENGTH: 10
<212> TYPE: PRT
<213> ORGANISM: Homo sapiens

<400> SEQUENCE: 836

Ser Glu Lys Pro Leu Asn Glu Glu Gln Trp
1               5                   10

<210> SEQ ID NO 837
<211> LENGTH: 8
<212> TYPE: PRT
<213> ORGANISM: Homo sapiens

<400> SEQUENCE: 837

Ser Glu Leu Asp Ala Leu Ser Ile
1               5

<210> SEQ ID NO 838
<211> LENGTH: 9
<212> TYPE: PRT
<213> ORGANISM: Homo sapiens

<400> SEQUENCE: 838

Ser Glu Leu Asp Ala Leu Ser Ile Cys
1               5

<210> SEQ ID NO 839
<211> LENGTH: 11
<212> TYPE: PRT
<213> ORGANISM: Homo sapiens

<400> SEQUENCE: 839

Ser Glu Asn Lys Glu Ala Ala Ser His Gly Phe
1               5                   10

<210> SEQ ID NO 840
<211> LENGTH: 9
<212> TYPE: PRT
<213> ORGANISM: Homo sapiens

<400> SEQUENCE: 840

Ser Glu Asn Asn His Ser Ile Ser Thr
1               5
```

-continued

```
<210> SEQ ID NO 841
<211> LENGTH: 11
<212> TYPE: PRT
<213> ORGANISM: Homo sapiens

<400> SEQUENCE: 841

Ser Glu Asn Arg Glu Ala Ala Ser His Gly Phe
1               5                   10

<210> SEQ ID NO 842
<211> LENGTH: 9
<212> TYPE: PRT
<213> ORGANISM: Homo sapiens

<400> SEQUENCE: 842

Ser Glu Asn Thr Ala Ser His Gly Phe
1               5

<210> SEQ ID NO 843
<211> LENGTH: 11
<212> TYPE: PRT
<213> ORGANISM: Homo sapiens

<400> SEQUENCE: 843

Ser Glu Asn Thr Ala Ser His Gly Phe Gly Lys
1               5                   10

<210> SEQ ID NO 844
<211> LENGTH: 8
<212> TYPE: PRT
<213> ORGANISM: Homo sapiens

<400> SEQUENCE: 844

Ser Glu Asn Thr Ile Lys Glu Ala
1               5

<210> SEQ ID NO 845
<211> LENGTH: 9
<212> TYPE: PRT
<213> ORGANISM: Homo sapiens

<400> SEQUENCE: 845

Ser Glu Asn Thr Ile Lys Glu Ala Ala
1               5

<210> SEQ ID NO 846
<211> LENGTH: 11
<212> TYPE: PRT
<213> ORGANISM: Homo sapiens

<400> SEQUENCE: 846

Ser Glu Asn Thr Lys Arg Ser Cys Lys Ser Trp
1               5                   10

<210> SEQ ID NO 847
<211> LENGTH: 10
<212> TYPE: PRT
<213> ORGANISM: Homo sapiens

<400> SEQUENCE: 847

Ser Glu Asn Thr Lys Arg Ser His Gly Phe
1               5                   10

<210> SEQ ID NO 848
<211> LENGTH: 8
```

-continued

```
<212> TYPE: PRT
<213> ORGANISM: Homo sapiens

<400> SEQUENCE: 848

Ser Glu Asn Thr Asn His Gly Phe
1               5

<210> SEQ ID NO 849
<211> LENGTH: 9
<212> TYPE: PRT
<213> ORGANISM: Homo sapiens

<400> SEQUENCE: 849

Ser Glu Asn Thr Asn Lys Glu Ala Ala
1               5

<210> SEQ ID NO 850
<211> LENGTH: 9
<212> TYPE: PRT
<213> ORGANISM: Homo sapiens

<400> SEQUENCE: 850

Ser Glu Asn Thr Asn Gln Arg Gly Phe
1               5

<210> SEQ ID NO 851
<211> LENGTH: 11
<212> TYPE: PRT
<213> ORGANISM: Homo sapiens

<400> SEQUENCE: 851

Ser Glu Asn Thr Asn Gln Arg Ser Cys Lys Tyr
1               5                   10

<210> SEQ ID NO 852
<211> LENGTH: 11
<212> TYPE: PRT
<213> ORGANISM: Homo sapiens

<400> SEQUENCE: 852

Ser Glu Asn Thr Asn Gln Arg Ser His Gly Phe
1               5                   10

<210> SEQ ID NO 853
<211> LENGTH: 9
<212> TYPE: PRT
<213> ORGANISM: Homo sapiens

<400> SEQUENCE: 853

Ser Glu Asn Thr Asn Gln Arg Thr Ala
1               5

<210> SEQ ID NO 854
<211> LENGTH: 9
<212> TYPE: PRT
<213> ORGANISM: Homo sapiens

<400> SEQUENCE: 854

Ser Glu Thr Gln Ile Lys Glu Ala Ala
1               5

<210> SEQ ID NO 855
<211> LENGTH: 9
<212> TYPE: PRT
<213> ORGANISM: Homo sapiens
```

-continued

<400> SEQUENCE: 855

Ser Glu Val Ala Lys Ala Gln Glu Ala
1               5

<210> SEQ ID NO 856
<211> LENGTH: 9
<212> TYPE: PRT
<213> ORGANISM: Homo sapiens

<400> SEQUENCE: 856

Ser Phe Asp Thr Thr Glu His Cys Val
1               5

<210> SEQ ID NO 857
<211> LENGTH: 9
<212> TYPE: PRT
<213> ORGANISM: Homo sapiens

<400> SEQUENCE: 857

Ser Phe Gln Val Ser Lys Ser Leu Tyr
1               5

<210> SEQ ID NO 858
<211> LENGTH: 9
<212> TYPE: PRT
<213> ORGANISM: Homo sapiens

<400> SEQUENCE: 858

Ser Phe Ser Lys Val Arg Gln Val Phe
1               5

<210> SEQ ID NO 859
<211> LENGTH: 9
<212> TYPE: PRT
<213> ORGANISM: Homo sapiens

<400> SEQUENCE: 859

Ser Gly Phe Ser Arg Ser Asp Glu Leu
1               5

<210> SEQ ID NO 860
<211> LENGTH: 9
<212> TYPE: PRT
<213> ORGANISM: Homo sapiens

<400> SEQUENCE: 860

Ser Gly Lys Arg Arg Gly Glu Pro Leu
1               5

<210> SEQ ID NO 861
<211> LENGTH: 9
<212> TYPE: PRT
<213> ORGANISM: Homo sapiens

<400> SEQUENCE: 861

Ser Gly Ser Asp Lys Ile Ser Arg Leu
1               5

<210> SEQ ID NO 862
<211> LENGTH: 10
<212> TYPE: PRT
<213> ORGANISM: Homo sapiens

<400> SEQUENCE: 862

-continued

```
Ser Gly Ser Asp Lys Ile Ser Arg Leu Trp
1               5                   10

<210> SEQ ID NO 863
<211> LENGTH: 10
<212> TYPE: PRT
<213> ORGANISM: Homo sapiens

<400> SEQUENCE: 863

Ser Gly Thr Ala Glu Thr Tyr Asn Ser Trp
1               5                   10

<210> SEQ ID NO 864
<211> LENGTH: 10
<212> TYPE: PRT
<213> ORGANISM: Homo sapiens

<400> SEQUENCE: 864

Ser His Leu Leu Lys Leu Asn Val Arg Lys
1               5                   10

<210> SEQ ID NO 865
<211> LENGTH: 8
<212> TYPE: PRT
<213> ORGANISM: Homo sapiens

<400> SEQUENCE: 865

Ser Ile Ser Thr Arg Gln Gln Leu
1               5

<210> SEQ ID NO 866
<211> LENGTH: 9
<212> TYPE: PRT
<213> ORGANISM: Homo sapiens

<400> SEQUENCE: 866

Ser Ile Ser Thr Arg Gln Thr Thr Val
1               5

<210> SEQ ID NO 867
<211> LENGTH: 9
<212> TYPE: PRT
<213> ORGANISM: Homo sapiens

<400> SEQUENCE: 867

Ser Lys Glu Ala Leu Gly Phe Val Tyr
1               5

<210> SEQ ID NO 868
<211> LENGTH: 10
<212> TYPE: PRT
<213> ORGANISM: Homo sapiens

<400> SEQUENCE: 868

Ser Lys Glu Val Val Pro Val Asn Gly Leu
1               5                   10

<210> SEQ ID NO 869
<211> LENGTH: 10
<212> TYPE: PRT
<213> ORGANISM: Homo sapiens

<400> SEQUENCE: 869

Ser Lys Thr Ser Leu Lys Gly Asn Asn Tyr
```

```
1               5                    10

<210> SEQ ID NO 870
<211> LENGTH: 9
<212> TYPE: PRT
<213> ORGANISM: Homo sapiens

<400> SEQUENCE: 870

Ser Lys Thr Ser Ser Asp Val Glu Leu
1               5

<210> SEQ ID NO 871
<211> LENGTH: 10
<212> TYPE: PRT
<213> ORGANISM: Homo sapiens

<400> SEQUENCE: 871

Ser Lys Thr Ser Ser Lys Gly Asn Asn Tyr
1               5                    10

<210> SEQ ID NO 872
<211> LENGTH: 9
<212> TYPE: PRT
<213> ORGANISM: Homo sapiens

<400> SEQUENCE: 872

Ser Lys Thr Ser Ser Lys Val Glu Leu
1               5

<210> SEQ ID NO 873
<211> LENGTH: 9
<212> TYPE: PRT
<213> ORGANISM: Homo sapiens

<400> SEQUENCE: 873

Ser Lys Val Phe Ser Lys Val Leu Phe
1               5

<210> SEQ ID NO 874
<211> LENGTH: 10
<212> TYPE: PRT
<213> ORGANISM: Homo sapiens

<400> SEQUENCE: 874

Ser Lys Val Phe Ser Lys Val Leu Phe Lys
1               5                    10

<210> SEQ ID NO 875
<211> LENGTH: 10
<212> TYPE: PRT
<213> ORGANISM: Homo sapiens

<400> SEQUENCE: 875

Ser Lys Val Thr Asn Ile Pro Met Glu Lys
1               5                    10

<210> SEQ ID NO 876
<211> LENGTH: 9
<212> TYPE: PRT
<213> ORGANISM: Homo sapiens

<400> SEQUENCE: 876

Ser Lys Trp Ser Pro Met Glu Lys Ile
1               5
```

-continued

```
<210> SEQ ID NO 877
<211> LENGTH: 9
<212> TYPE: PRT
<213> ORGANISM: Homo sapiens

<400> SEQUENCE: 877

Ser Leu Asp Asp Ser Glu Asp Ile Leu
1               5

<210> SEQ ID NO 878
<211> LENGTH: 10
<212> TYPE: PRT
<213> ORGANISM: Homo sapiens

<400> SEQUENCE: 878

Ser Leu Asp Asn Asp Asp Val Ala Arg Ile
1               5                   10

<210> SEQ ID NO 879
<211> LENGTH: 9
<212> TYPE: PRT
<213> ORGANISM: Homo sapiens

<400> SEQUENCE: 879

Ser Leu Asp Asn Thr Asn Ser Ser Ile
1               5

<210> SEQ ID NO 880
<211> LENGTH: 9
<212> TYPE: PRT
<213> ORGANISM: Homo sapiens

<400> SEQUENCE: 880

Ser Leu Phe Ser Asp Asp Leu Asn Leu
1               5

<210> SEQ ID NO 881
<211> LENGTH: 10
<212> TYPE: PRT
<213> ORGANISM: Homo sapiens

<400> SEQUENCE: 881

Ser Leu Phe Ser Asp Asp Leu Asn Leu Ile
1               5                   10

<210> SEQ ID NO 882
<211> LENGTH: 11
<212> TYPE: PRT
<213> ORGANISM: Homo sapiens

<400> SEQUENCE: 882

Ser Leu Phe Ser Asp Asp Leu Asn Leu Ile Leu
1               5                   10

<210> SEQ ID NO 883
<211> LENGTH: 10
<212> TYPE: PRT
<213> ORGANISM: Homo sapiens

<400> SEQUENCE: 883

Ser Leu Lys Lys Asn Ala Ser His Gly Phe
1               5                   10

<210> SEQ ID NO 884
```

```
<211> LENGTH: 9
<212> TYPE: PRT
<213> ORGANISM: Homo sapiens

<400> SEQUENCE: 884

Ser Leu Lys Lys Asn Asp Ser Ile Tyr
1               5

<210> SEQ ID NO 885
<211> LENGTH: 10
<212> TYPE: PRT
<213> ORGANISM: Homo sapiens

<400> SEQUENCE: 885

Ser Leu Lys Lys Asn Asp Ser Ile Tyr Arg
1               5                   10

<210> SEQ ID NO 886
<211> LENGTH: 9
<212> TYPE: PRT
<213> ORGANISM: Homo sapiens

<400> SEQUENCE: 886

Ser Leu Lys Lys Asn Glu Ile Tyr Arg
1               5

<210> SEQ ID NO 887
<211> LENGTH: 10
<212> TYPE: PRT
<213> ORGANISM: Homo sapiens

<400> SEQUENCE: 887

Ser Leu Lys Asn Lys Val Gln Lys Ser Leu
1               5                   10

<210> SEQ ID NO 888
<211> LENGTH: 9
<212> TYPE: PRT
<213> ORGANISM: Homo sapiens

<400> SEQUENCE: 888

Ser Leu Lys Thr Val Lys Thr Gln Arg
1               5

<210> SEQ ID NO 889
<211> LENGTH: 9
<212> TYPE: PRT
<213> ORGANISM: Homo sapiens

<400> SEQUENCE: 889

Ser Leu Leu Gly Ile Ala Pro Leu Leu
1               5

<210> SEQ ID NO 890
<211> LENGTH: 9
<212> TYPE: PRT
<213> ORGANISM: Homo sapiens

<400> SEQUENCE: 890

Ser Leu Leu Asn Val Asn Lys Arg Lys
1               5

<210> SEQ ID NO 891
<211> LENGTH: 10
<212> TYPE: PRT
```

<213> ORGANISM: Homo sapiens

<400> SEQUENCE: 891

Ser Leu Leu Asn Val Asn Lys Arg Lys Lys
1               5               10

<210> SEQ ID NO 892
<211> LENGTH: 9
<212> TYPE: PRT
<213> ORGANISM: Homo sapiens

<400> SEQUENCE: 892

Ser Leu Leu Gln Ile Asn Met Asp Phe
1               5

<210> SEQ ID NO 893
<211> LENGTH: 10
<212> TYPE: PRT
<213> ORGANISM: Homo sapiens

<400> SEQUENCE: 893

Ser Leu Leu Gln Ile Asn Met Asp Phe Tyr
1               5               10

<210> SEQ ID NO 894
<211> LENGTH: 9
<212> TYPE: PRT
<213> ORGANISM: Homo sapiens

<400> SEQUENCE: 894

Ser Leu Gln Ala Phe Leu Trp Leu Val
1               5

<210> SEQ ID NO 895
<211> LENGTH: 9
<212> TYPE: PRT
<213> ORGANISM: Homo sapiens

<400> SEQUENCE: 895

Ser Leu Arg Thr Asn Pro Phe Arg Leu
1               5

<210> SEQ ID NO 896
<211> LENGTH: 10
<212> TYPE: PRT
<213> ORGANISM: Homo sapiens

<400> SEQUENCE: 896

Ser Leu Arg Thr Asn Pro Phe Arg Ser Lys
1               5               10

<210> SEQ ID NO 897
<211> LENGTH: 11
<212> TYPE: PRT
<213> ORGANISM: Homo sapiens

<400> SEQUENCE: 897

Ser Leu Arg Thr Asn Pro Phe Arg Ser Lys Trp
1               5               10

<210> SEQ ID NO 898
<211> LENGTH: 9
<212> TYPE: PRT
<213> ORGANISM: Homo sapiens

```
<400> SEQUENCE: 898

Ser Leu Thr Lys Thr Thr Pro Ile Lys
1               5

<210> SEQ ID NO 899
<211> LENGTH: 10
<212> TYPE: PRT
<213> ORGANISM: Homo sapiens

<400> SEQUENCE: 899

Ser Leu Thr Lys Thr Thr Pro Ile Thr Lys
1               5               10

<210> SEQ ID NO 900
<211> LENGTH: 9
<212> TYPE: PRT
<213> ORGANISM: Homo sapiens

<400> SEQUENCE: 900

Ser Leu Thr Val Lys Thr Gln Ile Lys
1               5

<210> SEQ ID NO 901
<211> LENGTH: 10
<212> TYPE: PRT
<213> ORGANISM: Homo sapiens

<400> SEQUENCE: 901

Ser Leu Val Cys Ser Thr His Ser His Lys
1               5               10

<210> SEQ ID NO 902
<211> LENGTH: 9
<212> TYPE: PRT
<213> ORGANISM: Homo sapiens

<400> SEQUENCE: 902

Ser Leu Tyr Arg Gln Leu Ile Ser Leu
1               5

<210> SEQ ID NO 903
<211> LENGTH: 10
<212> TYPE: PRT
<213> ORGANISM: Homo sapiens

<400> SEQUENCE: 903

Ser Met Phe Lys Ile Glu Asn His Asn Lys
1               5               10

<210> SEQ ID NO 904
<211> LENGTH: 9
<212> TYPE: PRT
<213> ORGANISM: Homo sapiens

<400> SEQUENCE: 904

Ser Met Ser Pro Glu Arg Asn Gly Lys
1               5

<210> SEQ ID NO 905
<211> LENGTH: 9
<212> TYPE: PRT
<213> ORGANISM: Homo sapiens

<400> SEQUENCE: 905
```

-continued

Ser Asn His Asp Glu Ser Leu Thr Val
1               5

<210> SEQ ID NO 906
<211> LENGTH: 11
<212> TYPE: PRT
<213> ORGANISM: Homo sapiens

<400> SEQUENCE: 906

Ser Asn Leu Pro Ser Asp Ala Pro Gly Ala Leu
1               5                   10

<210> SEQ ID NO 907
<211> LENGTH: 9
<212> TYPE: PRT
<213> ORGANISM: Homo sapiens

<400> SEQUENCE: 907

Ser Asn Leu Val Met Ile Ser Arg Ile
1               5

<210> SEQ ID NO 908
<211> LENGTH: 9
<212> TYPE: PRT
<213> ORGANISM: Homo sapiens

<400> SEQUENCE: 908

Ser Pro Asp Gly Glu Lys Asp Leu Leu
1               5

<210> SEQ ID NO 909
<211> LENGTH: 9
<212> TYPE: PRT
<213> ORGANISM: Homo sapiens

<400> SEQUENCE: 909

Ser Pro Asp Gly Glu Asn Thr Pro Ile
1               5

<210> SEQ ID NO 910
<211> LENGTH: 11
<212> TYPE: PRT
<213> ORGANISM: Homo sapiens

<400> SEQUENCE: 910

Ser Pro Asp Gly Glu Asn Thr Pro Ile Ala Tyr
1               5                   10

<210> SEQ ID NO 911
<211> LENGTH: 8
<212> TYPE: PRT
<213> ORGANISM: Homo sapiens

<400> SEQUENCE: 911

Ser Pro Asp Gly Lys Ile Pro Leu
1               5

<210> SEQ ID NO 912
<211> LENGTH: 9
<212> TYPE: PRT
<213> ORGANISM: Homo sapiens

<400> SEQUENCE: 912

Ser Pro Asp Gly Lys Ile Pro Leu Leu
1               5

```
<210> SEQ ID NO 913
<211> LENGTH: 9
<212> TYPE: PRT
<213> ORGANISM: Homo sapiens

<400> SEQUENCE: 913

Ser Pro Glu Met Gly Asn Glu Asn Ile
1               5

<210> SEQ ID NO 914
<211> LENGTH: 9
<212> TYPE: PRT
<213> ORGANISM: Homo sapiens

<400> SEQUENCE: 914

Ser Pro Lys Glu Thr Asp Pro Asn Phe
1               5

<210> SEQ ID NO 915
<211> LENGTH: 8
<212> TYPE: PRT
<213> ORGANISM: Homo sapiens

<400> SEQUENCE: 915

Ser Pro Met Glu Lys Ile Pro Leu
1               5

<210> SEQ ID NO 916
<211> LENGTH: 9
<212> TYPE: PRT
<213> ORGANISM: Homo sapiens

<400> SEQUENCE: 916

Ser Pro Met Glu Lys Ile Pro Leu Leu
1               5

<210> SEQ ID NO 917
<211> LENGTH: 11
<212> TYPE: PRT
<213> ORGANISM: Homo sapiens

<400> SEQUENCE: 917

Ser Pro Met Glu Lys Ile Pro Leu Leu His Ile
1               5                   10

<210> SEQ ID NO 918
<211> LENGTH: 8
<212> TYPE: PRT
<213> ORGANISM: Homo sapiens

<400> SEQUENCE: 918

Ser Pro Arg Lys Leu Tyr Arg Leu
1               5

<210> SEQ ID NO 919
<211> LENGTH: 9
<212> TYPE: PRT
<213> ORGANISM: Homo sapiens

<400> SEQUENCE: 919

Ser Pro Arg Lys Leu Tyr Arg Leu Trp
1               5
```

```
<210> SEQ ID NO 920
<211> LENGTH: 9
<212> TYPE: PRT
<213> ORGANISM: Homo sapiens

<400> SEQUENCE: 920

Ser Pro Val Ala Ser Ser Phe Gln Val
1               5

<210> SEQ ID NO 921
<211> LENGTH: 8
<212> TYPE: PRT
<213> ORGANISM: Homo sapiens

<400> SEQUENCE: 921

Ser Pro Tyr Leu Ser Ile Ser Thr
1               5

<210> SEQ ID NO 922
<211> LENGTH: 9
<212> TYPE: PRT
<213> ORGANISM: Homo sapiens

<400> SEQUENCE: 922

Ser Pro Tyr Leu Ser Ile Ser Thr Arg
1               5

<210> SEQ ID NO 923
<211> LENGTH: 9
<212> TYPE: PRT
<213> ORGANISM: Homo sapiens

<400> SEQUENCE: 923

Ser Pro Tyr Ser Val Val Asn Ser Ser
1               5

<210> SEQ ID NO 924
<211> LENGTH: 10
<212> TYPE: PRT
<213> ORGANISM: Homo sapiens

<400> SEQUENCE: 924

Ser Pro Tyr Ser Val Val Asn Ser Ser Ala
1               5                   10

<210> SEQ ID NO 925
<211> LENGTH: 11
<212> TYPE: PRT
<213> ORGANISM: Homo sapiens

<400> SEQUENCE: 925

Ser Pro Tyr Ser Val Val Asn Ser Ser Ala Phe
1               5                   10

<210> SEQ ID NO 926
<211> LENGTH: 9
<212> TYPE: PRT
<213> ORGANISM: Homo sapiens

<400> SEQUENCE: 926

Ser Gln Phe Gln Gln Asp Asn Ser Trp
1               5

<210> SEQ ID NO 927
<211> LENGTH: 10
```

```
<212> TYPE: PRT
<213> ORGANISM: Homo sapiens

<400> SEQUENCE: 927

Ser Gln Phe Gln Gln Asp Asn Ser Trp Tyr
1               5                   10

<210> SEQ ID NO 928
<211> LENGTH: 8
<212> TYPE: PRT
<213> ORGANISM: Homo sapiens

<400> SEQUENCE: 928

Ser Gln Leu Ile Met Pro Asn Val
1               5

<210> SEQ ID NO 929
<211> LENGTH: 9
<212> TYPE: PRT
<213> ORGANISM: Homo sapiens

<400> SEQUENCE: 929

Ser Gln Leu Ile Met Pro Asn Val Val
1               5

<210> SEQ ID NO 930
<211> LENGTH: 11
<212> TYPE: PRT
<213> ORGANISM: Homo sapiens

<400> SEQUENCE: 930

Ser Gln Leu Ile Met Pro Asn Val Val Ser Lys
1               5                   10

<210> SEQ ID NO 931
<211> LENGTH: 8
<212> TYPE: PRT
<213> ORGANISM: Homo sapiens

<400> SEQUENCE: 931

Ser Gln Leu Gln Lys Ser Thr Phe
1               5

<210> SEQ ID NO 932
<211> LENGTH: 8
<212> TYPE: PRT
<213> ORGANISM: Homo sapiens

<400> SEQUENCE: 932

Ser Gln Leu Val Leu Ala Thr Tyr
1               5

<210> SEQ ID NO 933
<211> LENGTH: 8
<212> TYPE: PRT
<213> ORGANISM: Homo sapiens

<400> SEQUENCE: 933

Ser Gln Met Glu Lys Ile Pro Leu
1               5

<210> SEQ ID NO 934
<211> LENGTH: 9
<212> TYPE: PRT
<213> ORGANISM: Homo sapiens
```

-continued

<400> SEQUENCE: 934

Ser Gln Met Glu Lys Ile Pro Leu Leu
1               5

<210> SEQ ID NO 935
<211> LENGTH: 11
<212> TYPE: PRT
<213> ORGANISM: Homo sapiens

<400> SEQUENCE: 935

Ser Gln Met Asn Arg Gln Ala Pro Gly Ser Phe
1               5                   10

<210> SEQ ID NO 936
<211> LENGTH: 8
<212> TYPE: PRT
<213> ORGANISM: Homo sapiens

<400> SEQUENCE: 936

Ser Gln Asn Ile Lys Lys Tyr Leu
1               5

<210> SEQ ID NO 937
<211> LENGTH: 9
<212> TYPE: PRT
<213> ORGANISM: Homo sapiens

<400> SEQUENCE: 937

Ser Gln Asn Ile Lys Lys Tyr Leu Phe
1               5

<210> SEQ ID NO 938
<211> LENGTH: 11
<212> TYPE: PRT
<213> ORGANISM: Homo sapiens

<400> SEQUENCE: 938

Ser Arg Ala Gln Met Glu Lys Ile Pro Leu Leu
1               5                   10

<210> SEQ ID NO 939
<211> LENGTH: 9
<212> TYPE: PRT
<213> ORGANISM: Homo sapiens

<400> SEQUENCE: 939

Ser Arg Phe Gln Ser Ala Ser His Leu
1               5

<210> SEQ ID NO 940
<211> LENGTH: 10
<212> TYPE: PRT
<213> ORGANISM: Homo sapiens

<400> SEQUENCE: 940

Ser Arg Phe Gln Ser Ala Ser His Leu Leu
1               5                   10

<210> SEQ ID NO 941
<211> LENGTH: 11
<212> TYPE: PRT
<213> ORGANISM: Homo sapiens

<400> SEQUENCE: 941

```
Ser Arg Phe Gln Ser Ala Ser His Leu Leu Arg
1               5                   10

<210> SEQ ID NO 942
<211> LENGTH: 9
<212> TYPE: PRT
<213> ORGANISM: Homo sapiens

<400> SEQUENCE: 942

Ser Arg Gly Lys Glu Ser Tyr Lys Leu
1               5

<210> SEQ ID NO 943
<211> LENGTH: 9
<212> TYPE: PRT
<213> ORGANISM: Homo sapiens

<400> SEQUENCE: 943

Ser Arg Leu Trp Pro Val Asn Gly Leu
1               5

<210> SEQ ID NO 944
<211> LENGTH: 10
<212> TYPE: PRT
<213> ORGANISM: Homo sapiens

<400> SEQUENCE: 944

Ser Arg Leu Trp Pro Val Asn Gly Leu Leu
1               5                   10

<210> SEQ ID NO 945
<211> LENGTH: 9
<212> TYPE: PRT
<213> ORGANISM: Homo sapiens

<400> SEQUENCE: 945

Ser Arg Asn Gln Ala His Leu Ile Val
1               5

<210> SEQ ID NO 946
<211> LENGTH: 10
<212> TYPE: PRT
<213> ORGANISM: Homo sapiens

<400> SEQUENCE: 946

Ser Arg Asn Gln Ala His Leu Ile Val Leu
1               5                   10

<210> SEQ ID NO 947
<211> LENGTH: 8
<212> TYPE: PRT
<213> ORGANISM: Homo sapiens

<400> SEQUENCE: 947

Ser Ser Ala Leu Glu Asp Leu Trp
1               5

<210> SEQ ID NO 948
<211> LENGTH: 9
<212> TYPE: PRT
<213> ORGANISM: Homo sapiens

<400> SEQUENCE: 948

Ser Ser Phe Gln Val Ser Lys Ser Leu
```

-continued

```
1               5

<210> SEQ ID NO 949
<211> LENGTH: 10
<212> TYPE: PRT
<213> ORGANISM: Homo sapiens

<400> SEQUENCE: 949

Ser Ser Phe Gln Val Ser Lys Ser Leu Tyr
1               5                   10

<210> SEQ ID NO 950
<211> LENGTH: 9
<212> TYPE: PRT
<213> ORGANISM: Homo sapiens

<400> SEQUENCE: 950

Ser Ser Gly Leu Tyr Ile Phe Arg Lys
1               5

<210> SEQ ID NO 951
<211> LENGTH: 9
<212> TYPE: PRT
<213> ORGANISM: Homo sapiens

<400> SEQUENCE: 951

Ser Ser Lys Val Thr Ile Met Asn Ile
1               5

<210> SEQ ID NO 952
<211> LENGTH: 9
<212> TYPE: PRT
<213> ORGANISM: Homo sapiens

<400> SEQUENCE: 952

Ser Ser Lys Val Thr Ile Met Asn Leu
1               5

<210> SEQ ID NO 953
<211> LENGTH: 9
<212> TYPE: PRT
<213> ORGANISM: Homo sapiens

<400> SEQUENCE: 953

Ser Ser Lys Val Thr Asn Ile Pro Met
1               5

<210> SEQ ID NO 954
<211> LENGTH: 11
<212> TYPE: PRT
<213> ORGANISM: Homo sapiens

<400> SEQUENCE: 954

Ser Ser Lys Val Thr Asn Ile Pro Met Glu Lys
1               5                   10

<210> SEQ ID NO 955
<211> LENGTH: 10
<212> TYPE: PRT
<213> ORGANISM: Homo sapiens

<400> SEQUENCE: 955

Ser Ser Asn Gln Ala Val Ala Val Thr Phe
1               5                   10
```

<210> SEQ ID NO 956
<211> LENGTH: 9
<212> TYPE: PRT
<213> ORGANISM: Homo sapiens

<400> SEQUENCE: 956

Ser Ser Arg Gly Thr Val Val Asn Lys
1               5

<210> SEQ ID NO 957
<211> LENGTH: 10
<212> TYPE: PRT
<213> ORGANISM: Homo sapiens

<400> SEQUENCE: 957

Ser Ser Arg Gly Thr Val Val Asn Lys Arg
1               5                   10

<210> SEQ ID NO 958
<211> LENGTH: 9
<212> TYPE: PRT
<213> ORGANISM: Homo sapiens

<400> SEQUENCE: 958

Ser Thr Leu Pro Cys Ile Ser Leu Lys
1               5

<210> SEQ ID NO 959
<211> LENGTH: 9
<212> TYPE: PRT
<213> ORGANISM: Homo sapiens

<400> SEQUENCE: 959

Ser Thr Leu Pro Phe Ile Ser Leu Lys
1               5

<210> SEQ ID NO 960
<211> LENGTH: 8
<212> TYPE: PRT
<213> ORGANISM: Homo sapiens

<400> SEQUENCE: 960

Ser Thr Arg Gln Gln Leu Val Leu
1               5

<210> SEQ ID NO 961
<211> LENGTH: 9
<212> TYPE: PRT
<213> ORGANISM: Homo sapiens

<400> SEQUENCE: 961

Ser Thr Arg Gln Thr Thr Val Gly Ile
1               5

<210> SEQ ID NO 962
<211> LENGTH: 10
<212> TYPE: PRT
<213> ORGANISM: Homo sapiens

<400> SEQUENCE: 962

Ser Thr Arg Gln Thr Thr Val Gly Ile Arg
1               5                   10

<210> SEQ ID NO 963

```
<211> LENGTH: 9
<212> TYPE: PRT
<213> ORGANISM: Homo sapiens

<400> SEQUENCE: 963

Ser Thr Val Ala Thr Glu Cys Leu Arg
1               5

<210> SEQ ID NO 964
<211> LENGTH: 11
<212> TYPE: PRT
<213> ORGANISM: Homo sapiens

<400> SEQUENCE: 964

Ser Thr Tyr Ser Lys Asp Ser Glu Asn Ala Lys
1               5                   10

<210> SEQ ID NO 965
<211> LENGTH: 9
<212> TYPE: PRT
<213> ORGANISM: Homo sapiens

<400> SEQUENCE: 965

Ser Val Asn Thr Val Ser Ala His Leu
1               5

<210> SEQ ID NO 966
<211> LENGTH: 9
<212> TYPE: PRT
<213> ORGANISM: Homo sapiens

<400> SEQUENCE: 966

Ser Val Gln Ile Pro Val Asn Leu Lys
1               5

<210> SEQ ID NO 967
<211> LENGTH: 10
<212> TYPE: PRT
<213> ORGANISM: Homo sapiens

<400> SEQUENCE: 967

Ser Val Thr Asp Ser Glu Asn Thr Ile Lys
1               5                   10

<210> SEQ ID NO 968
<211> LENGTH: 9
<212> TYPE: PRT
<213> ORGANISM: Homo sapiens

<400> SEQUENCE: 968

Ser Val Thr Asp Ser Glu Asn Thr Lys
1               5

<210> SEQ ID NO 969
<211> LENGTH: 10
<212> TYPE: PRT
<213> ORGANISM: Homo sapiens

<400> SEQUENCE: 969

Ser Val Thr Asp Ser Glu Asn Thr Lys Arg
1               5                   10

<210> SEQ ID NO 970
<211> LENGTH: 10
<212> TYPE: PRT
```

-continued

<213> ORGANISM: Homo sapiens

<400> SEQUENCE: 970

Ser Val Thr Asp Ser Glu Asn Thr Asn Lys
1               5                   10

<210> SEQ ID NO 971
<211> LENGTH: 10
<212> TYPE: PRT
<213> ORGANISM: Homo sapiens

<400> SEQUENCE: 971

Ser Val Thr Asp Ser Glu Thr Gln Ile Lys
1               5                   10

<210> SEQ ID NO 972
<211> LENGTH: 10
<212> TYPE: PRT
<213> ORGANISM: Homo sapiens

<400> SEQUENCE: 972

Ser Val Thr Glu Ala Ala Ser His Gly Phe
1               5                   10

<210> SEQ ID NO 973
<211> LENGTH: 10
<212> TYPE: PRT
<213> ORGANISM: Homo sapiens

<400> SEQUENCE: 973

Ser Val Thr Val Lys His Thr Asn Gln Arg
1               5                   10

<210> SEQ ID NO 974
<211> LENGTH: 9
<212> TYPE: PRT
<213> ORGANISM: Homo sapiens

<400> SEQUENCE: 974

Ser Val Thr Val Lys Thr Asn Gln Arg
1               5

<210> SEQ ID NO 975
<211> LENGTH: 9
<212> TYPE: PRT
<213> ORGANISM: Homo sapiens

<400> SEQUENCE: 975

Ser Val Thr Val Lys Thr Gln Ile Lys
1               5

<210> SEQ ID NO 976
<211> LENGTH: 9
<212> TYPE: PRT
<213> ORGANISM: Homo sapiens

<400> SEQUENCE: 976

Ser Val Thr Val Lys Thr Gln Ile Arg
1               5

<210> SEQ ID NO 977
<211> LENGTH: 10
<212> TYPE: PRT
<213> ORGANISM: Homo sapiens

```
<400> SEQUENCE: 977

Ser Val Thr Val Lys Thr Gln Asn Gln Arg
1               5                   10

<210> SEQ ID NO 978
<211> LENGTH: 10
<212> TYPE: PRT
<213> ORGANISM: Homo sapiens

<400> SEQUENCE: 978

Ser Trp Ile Asp His Ile Gly Lys Ser Met
1               5                   10

<210> SEQ ID NO 979
<211> LENGTH: 11
<212> TYPE: PRT
<213> ORGANISM: Homo sapiens

<400> SEQUENCE: 979

Ser Trp Ile Trp Lys Lys Ser Gly Asn Ser Phe
1               5                   10

<210> SEQ ID NO 980
<211> LENGTH: 9
<212> TYPE: PRT
<213> ORGANISM: Homo sapiens

<400> SEQUENCE: 980

Ser Trp Ile Trp Lys Asn Ile Lys Val
1               5

<210> SEQ ID NO 981
<211> LENGTH: 10
<212> TYPE: PRT
<213> ORGANISM: Homo sapiens

<400> SEQUENCE: 981

Ser Trp Ile Trp Lys Asn Ile Arg Glu Phe
1               5                   10

<210> SEQ ID NO 982
<211> LENGTH: 9
<212> TYPE: PRT
<213> ORGANISM: Homo sapiens

<400> SEQUENCE: 982

Ser Trp Ile Trp Lys Asn Ile Arg Lys
1               5

<210> SEQ ID NO 983
<211> LENGTH: 11
<212> TYPE: PRT
<213> ORGANISM: Homo sapiens

<400> SEQUENCE: 983

Ser Trp Ile Trp Lys Asn Ile Arg Asn Ser Phe
1               5                   10

<210> SEQ ID NO 984
<211> LENGTH: 9
<212> TYPE: PRT
<213> ORGANISM: Homo sapiens

<400> SEQUENCE: 984
```

```
Ser Trp Ile Trp Lys Asn Ile Ser Lys
1               5

<210> SEQ ID NO 985
<211> LENGTH: 11
<212> TYPE: PRT
<213> ORGANISM: Homo sapiens

<400> SEQUENCE: 985

Ser Trp Ile Trp Lys Asn Ser Gly Asn Ser Phe
1               5                   10

<210> SEQ ID NO 986
<211> LENGTH: 11
<212> TYPE: PRT
<213> ORGANISM: Homo sapiens

<400> SEQUENCE: 986

Ser Trp Ile Trp Lys Thr Ser Gly Asn Ser Phe
1               5                   10

<210> SEQ ID NO 987
<211> LENGTH: 9
<212> TYPE: PRT
<213> ORGANISM: Homo sapiens

<400> SEQUENCE: 987

Ser Trp Ile Trp Asn Ser Phe Lys Val
1               5

<210> SEQ ID NO 988
<211> LENGTH: 9
<212> TYPE: PRT
<213> ORGANISM: Homo sapiens

<400> SEQUENCE: 988

Ser Trp Lys Val Lys Asn Leu Gln Leu
1               5

<210> SEQ ID NO 989
<211> LENGTH: 9
<212> TYPE: PRT
<213> ORGANISM: Homo sapiens

<400> SEQUENCE: 989

Ser Tyr Lys Leu Lys Gly Asn Asn Tyr
1               5

<210> SEQ ID NO 990
<211> LENGTH: 9
<212> TYPE: PRT
<213> ORGANISM: Homo sapiens

<400> SEQUENCE: 990

Ser Tyr Lys Met Ser Lys Asp Lys Leu
1               5

<210> SEQ ID NO 991
<211> LENGTH: 9
<212> TYPE: PRT
<213> ORGANISM: Homo sapiens

<400> SEQUENCE: 991

Ser Tyr Lys Met Ser Lys Thr Ser Leu
1               5
```

-continued

```
<210> SEQ ID NO 992
<211> LENGTH: 9
<212> TYPE: PRT
<213> ORGANISM: Homo sapiens

<400> SEQUENCE: 992

Thr Ala Ala Val Pro Ile Ser Cys Lys
1               5

<210> SEQ ID NO 993
<211> LENGTH: 10
<212> TYPE: PRT
<213> ORGANISM: Homo sapiens

<400> SEQUENCE: 993

Thr Ala Ala Val Pro Ile Ser Cys Lys Lys
1               5                   10

<210> SEQ ID NO 994
<211> LENGTH: 10
<212> TYPE: PRT
<213> ORGANISM: Homo sapiens

<400> SEQUENCE: 994

Thr Ala Ala Val Pro Ile Ser Cys Lys Arg
1               5                   10

<210> SEQ ID NO 995
<211> LENGTH: 8
<212> TYPE: PRT
<213> ORGANISM: Homo sapiens

<400> SEQUENCE: 995

Thr Ala Lys Arg Ser Cys Asn Leu
1               5

<210> SEQ ID NO 996
<211> LENGTH: 9
<212> TYPE: PRT
<213> ORGANISM: Homo sapiens

<400> SEQUENCE: 996

Thr Ala Val Ala Val Thr Phe Thr Lys
1               5

<210> SEQ ID NO 997
<211> LENGTH: 9
<212> TYPE: PRT
<213> ORGANISM: Homo sapiens

<400> SEQUENCE: 997

Thr Asp Ile Val Lys His Lys Ser Val
1               5

<210> SEQ ID NO 998
<211> LENGTH: 10
<212> TYPE: PRT
<213> ORGANISM: Homo sapiens

<400> SEQUENCE: 998

Thr Asp Pro Leu Asp Ser Pro Leu Arg Val
1               5                   10
```

-continued

```
<210> SEQ ID NO 999
<211> LENGTH: 11
<212> TYPE: PRT
<213> ORGANISM: Homo sapiens

<400> SEQUENCE: 999

Thr Asp Ser Glu Asn Thr Ala Ser His Gly Phe
1               5                   10

<210> SEQ ID NO 1000
<211> LENGTH: 11
<212> TYPE: PRT
<213> ORGANISM: Homo sapiens

<400> SEQUENCE: 1000

Thr Asp Ser Glu Asn Thr Asn Gln Arg Gly Phe
1               5                   10

<210> SEQ ID NO 1001
<211> LENGTH: 9
<212> TYPE: PRT
<213> ORGANISM: Homo sapiens

<400> SEQUENCE: 1001

Thr Asp Ser Phe Ser Tyr Glu Ala Leu
1               5

<210> SEQ ID NO 1002
<211> LENGTH: 8
<212> TYPE: PRT
<213> ORGANISM: Homo sapiens

<400> SEQUENCE: 1002

Thr Glu Ala Ala Ser His Gly Phe
1               5

<210> SEQ ID NO 1003
<211> LENGTH: 10
<212> TYPE: PRT
<213> ORGANISM: Homo sapiens

<400> SEQUENCE: 1003

Thr Glu Asp Val Pro Trp Ile Thr Leu Ile
1               5                   10

<210> SEQ ID NO 1004
<211> LENGTH: 9
<212> TYPE: PRT
<213> ORGANISM: Homo sapiens

<400> SEQUENCE: 1004

Thr Glu His Cys Val Asn Ser Glu Met
1               5

<210> SEQ ID NO 1005
<211> LENGTH: 11
<212> TYPE: PRT
<213> ORGANISM: Homo sapiens

<400> SEQUENCE: 1005

Thr Glu Lys Lys Val Asp Leu Asn Ala Glu Trp
1               5                   10

<210> SEQ ID NO 1006
<211> LENGTH: 10
```

-continued

```
<212> TYPE: PRT
<213> ORGANISM: Homo sapiens

<400> SEQUENCE: 1006

Thr Glu Pro Asn Thr Val Asn Ile Thr Ala
1               5                   10

<210> SEQ ID NO 1007
<211> LENGTH: 9
<212> TYPE: PRT
<213> ORGANISM: Homo sapiens

<400> SEQUENCE: 1007

Thr Glu Pro Gln Ser Gln Leu Val Leu
1               5

<210> SEQ ID NO 1008
<211> LENGTH: 10
<212> TYPE: PRT
<213> ORGANISM: Homo sapiens

<400> SEQUENCE: 1008

Thr Glu Pro Gln Ser Gln Leu Val Leu Ala
1               5                   10

<210> SEQ ID NO 1009
<211> LENGTH: 9
<212> TYPE: PRT
<213> ORGANISM: Homo sapiens

<400> SEQUENCE: 1009

Thr Glu Gln Ala Ser Val Asn Thr Val
1               5

<210> SEQ ID NO 1010
<211> LENGTH: 11
<212> TYPE: PRT
<213> ORGANISM: Homo sapiens

<400> SEQUENCE: 1010

Thr Glu Gln Ala Ser Val Asn Thr Val Ser Ala
1               5                   10

<210> SEQ ID NO 1011
<211> LENGTH: 8
<212> TYPE: PRT
<213> ORGANISM: Homo sapiens

<400> SEQUENCE: 1011

Thr Glu Ser Lys Ser Ile Phe Leu
1               5

<210> SEQ ID NO 1012
<211> LENGTH: 9
<212> TYPE: PRT
<213> ORGANISM: Homo sapiens

<400> SEQUENCE: 1012

Thr Glu Ser Gln Asn Ile Lys Lys Tyr
1               5

<210> SEQ ID NO 1013
<211> LENGTH: 10
<212> TYPE: PRT
<213> ORGANISM: Homo sapiens
```

<400> SEQUENCE: 1013

Thr Glu Ser Gln Asn Ile Lys Lys Tyr Leu
1               5                   10

<210> SEQ ID NO 1014
<211> LENGTH: 11
<212> TYPE: PRT
<213> ORGANISM: Homo sapiens

<400> SEQUENCE: 1014

Thr Glu Ser Gln Asn Ile Lys Lys Tyr Leu Phe
1               5                   10

<210> SEQ ID NO 1015
<211> LENGTH: 11
<212> TYPE: PRT
<213> ORGANISM: Homo sapiens

<400> SEQUENCE: 1015

Thr Phe Leu Arg Arg Pro Asn Phe Thr Arg Arg
1               5                   10

<210> SEQ ID NO 1016
<211> LENGTH: 9
<212> TYPE: PRT
<213> ORGANISM: Homo sapiens

<400> SEQUENCE: 1016

Thr Phe Asn Ala Ser Phe Gln Val Ile
1               5

<210> SEQ ID NO 1017
<211> LENGTH: 10
<212> TYPE: PRT
<213> ORGANISM: Homo sapiens

<400> SEQUENCE: 1017

Thr Gly Glu Phe Ile Ile Ser Asn Gln Val
1               5                   10

<210> SEQ ID NO 1018
<211> LENGTH: 9
<212> TYPE: PRT
<213> ORGANISM: Homo sapiens

<400> SEQUENCE: 1018

Thr His Ile Val Tyr His His Phe Phe
1               5

<210> SEQ ID NO 1019
<211> LENGTH: 8
<212> TYPE: PRT
<213> ORGANISM: Homo sapiens

<400> SEQUENCE: 1019

Thr His Leu Ala Gln Gly Tyr Leu
1               5

<210> SEQ ID NO 1020
<211> LENGTH: 9
<212> TYPE: PRT
<213> ORGANISM: Homo sapiens

<400> SEQUENCE: 1020

```
Thr His Leu Ala Gln Gly Tyr Leu Arg
1               5

<210> SEQ ID NO 1021
<211> LENGTH: 10
<212> TYPE: PRT
<213> ORGANISM: Homo sapiens

<400> SEQUENCE: 1021

Thr Ile Lys Glu Ala Ala Ser His Gly Phe
1               5                   10

<210> SEQ ID NO 1022
<211> LENGTH: 9
<212> TYPE: PRT
<213> ORGANISM: Homo sapiens

<400> SEQUENCE: 1022

Thr Ile Met Asn Ile Pro Met Glu Lys
1               5

<210> SEQ ID NO 1023
<211> LENGTH: 9
<212> TYPE: PRT
<213> ORGANISM: Homo sapiens

<400> SEQUENCE: 1023

Thr Ile Met Asn Leu Met Asn Asn Tyr
1               5

<210> SEQ ID NO 1024
<211> LENGTH: 9
<212> TYPE: PRT
<213> ORGANISM: Homo sapiens

<400> SEQUENCE: 1024

Thr Lys Leu Asp Ser Leu Leu Gln Ile
1               5

<210> SEQ ID NO 1025
<211> LENGTH: 9
<212> TYPE: PRT
<213> ORGANISM: Homo sapiens

<400> SEQUENCE: 1025

Thr Lys Leu Asn Val Leu Leu Lys Leu
1               5

<210> SEQ ID NO 1026
<211> LENGTH: 9
<212> TYPE: PRT
<213> ORGANISM: Homo sapiens

<400> SEQUENCE: 1026

Thr Lys Arg Ala Ala Ser His Gly Phe
1               5

<210> SEQ ID NO 1027
<211> LENGTH: 9
<212> TYPE: PRT
<213> ORGANISM: Homo sapiens

<400> SEQUENCE: 1027

Thr Leu His Pro Ala Lys Ile Lys Met
```

-continued

```
1                5

<210> SEQ ID NO 1028
<211> LENGTH: 9
<212> TYPE: PRT
<213> ORGANISM: Homo sapiens

<400> SEQUENCE: 1028

Thr Leu Ile Ala Ala Phe Arg Lys Leu
1                5

<210> SEQ ID NO 1029
<211> LENGTH: 10
<212> TYPE: PRT
<213> ORGANISM: Homo sapiens

<400> SEQUENCE: 1029

Thr Leu Pro Phe Ile Ser Leu Lys Ala Ala
1                5                    10

<210> SEQ ID NO 1030
<211> LENGTH: 10
<212> TYPE: PRT
<213> ORGANISM: Homo sapiens

<400> SEQUENCE: 1030

Thr Leu Arg Asn Ile Gln Cys His Leu Lys
1                5                    10

<210> SEQ ID NO 1031
<211> LENGTH: 9
<212> TYPE: PRT
<213> ORGANISM: Homo sapiens

<400> SEQUENCE: 1031

Thr Asn Ile Leu Leu Ala Ala Ser Arg
1                5

<210> SEQ ID NO 1032
<211> LENGTH: 10
<212> TYPE: PRT
<213> ORGANISM: Homo sapiens

<400> SEQUENCE: 1032

Thr Asn Gln Arg Thr Ala Ser His Gly Phe
1                5                    10

<210> SEQ ID NO 1033
<211> LENGTH: 9
<212> TYPE: PRT
<213> ORGANISM: Homo sapiens

<400> SEQUENCE: 1033

Thr Pro Ile Ala Cys Asp Gln Asn Ile
1                5

<210> SEQ ID NO 1034
<211> LENGTH: 9
<212> TYPE: PRT
<213> ORGANISM: Homo sapiens

<400> SEQUENCE: 1034

Thr Pro Ile Ala Glu Lys Asp Leu Leu
1                5
```

-continued

<210> SEQ ID NO 1035
<211> LENGTH: 8
<212> TYPE: PRT
<213> ORGANISM: Homo sapiens

<400> SEQUENCE: 1035

Thr Pro Ile Ala Tyr Phe Phe Met
1               5

<210> SEQ ID NO 1036
<211> LENGTH: 8
<212> TYPE: PRT
<213> ORGANISM: Homo sapiens

<400> SEQUENCE: 1036

Thr Gln Phe Arg Lys Leu His Ile
1               5

<210> SEQ ID NO 1037
<211> LENGTH: 10
<212> TYPE: PRT
<213> ORGANISM: Homo sapiens

<400> SEQUENCE: 1037

Thr Gln Ile Lys Glu Asp Leu Ser Ala Phe
1               5                   10

<210> SEQ ID NO 1038
<211> LENGTH: 10
<212> TYPE: PRT
<213> ORGANISM: Homo sapiens

<400> SEQUENCE: 1038

Thr Gln Ile Lys Glu Asp Leu Ser Glu Val
1               5                   10

<210> SEQ ID NO 1039
<211> LENGTH: 9
<212> TYPE: PRT
<213> ORGANISM: Homo sapiens

<400> SEQUENCE: 1039

Thr Gln Ile Lys Glu Lys Leu Gln Val
1               5

<210> SEQ ID NO 1040
<211> LENGTH: 10
<212> TYPE: PRT
<213> ORGANISM: Homo sapiens

<400> SEQUENCE: 1040

Thr Gln Arg Glu Ala Ala Ser His Gly Phe
1               5                   10

<210> SEQ ID NO 1041
<211> LENGTH: 9
<212> TYPE: PRT
<213> ORGANISM: Homo sapiens

<400> SEQUENCE: 1041

Thr Arg Asp Arg Asp Ser Ser Asn Leu
1               5

<210> SEQ ID NO 1042

```
<211> LENGTH: 9
<212> TYPE: PRT
<213> ORGANISM: Homo sapiens

<400> SEQUENCE: 1042

Thr Arg Glu Ile Leu Lys Met Lys Ile
1               5

<210> SEQ ID NO 1043
<211> LENGTH: 10
<212> TYPE: PRT
<213> ORGANISM: Homo sapiens

<400> SEQUENCE: 1043

Thr Arg Arg Leu Gln Phe Leu Tyr Arg Leu
1               5               10

<210> SEQ ID NO 1044
<211> LENGTH: 9
<212> TYPE: PRT
<213> ORGANISM: Homo sapiens

<400> SEQUENCE: 1044

Thr Ser Phe Ser Lys Val Arg Gln Val
1               5

<210> SEQ ID NO 1045
<211> LENGTH: 10
<212> TYPE: PRT
<213> ORGANISM: Homo sapiens

<400> SEQUENCE: 1045

Thr Ser Phe Ser Lys Val Arg Gln Val Phe
1               5               10

<210> SEQ ID NO 1046
<211> LENGTH: 9
<212> TYPE: PRT
<213> ORGANISM: Homo sapiens

<400> SEQUENCE: 1046

Thr Ser Ser Asp Val Glu Leu Thr Lys
1               5

<210> SEQ ID NO 1047
<211> LENGTH: 10
<212> TYPE: PRT
<213> ORGANISM: Homo sapiens

<400> SEQUENCE: 1047

Thr Ser Ser Gly Leu Tyr Ile Phe Arg Lys
1               5               10

<210> SEQ ID NO 1048
<211> LENGTH: 9
<212> TYPE: PRT
<213> ORGANISM: Homo sapiens

<400> SEQUENCE: 1048

Thr Ser Ser Lys Val Glu Leu Thr Lys
1               5

<210> SEQ ID NO 1049
<211> LENGTH: 10
<212> TYPE: PRT
```

<213> ORGANISM: Homo sapiens

<400> SEQUENCE: 1049

Thr Ser Thr Leu Pro Cys Ile Ser Leu Lys
1               5                   10

<210> SEQ ID NO 1050
<211> LENGTH: 9
<212> TYPE: PRT
<213> ORGANISM: Homo sapiens

<400> SEQUENCE: 1050

Thr Ser Thr Leu Pro Phe Ile Ser Leu
1               5

<210> SEQ ID NO 1051
<211> LENGTH: 10
<212> TYPE: PRT
<213> ORGANISM: Homo sapiens

<400> SEQUENCE: 1051

Thr Ser Thr Leu Pro Phe Ile Ser Leu Lys
1               5                   10

<210> SEQ ID NO 1052
<211> LENGTH: 10
<212> TYPE: PRT
<213> ORGANISM: Homo sapiens

<400> SEQUENCE: 1052

Thr Thr Ala Val Ala Val Thr Phe Thr Lys
1               5                   10

<210> SEQ ID NO 1053
<211> LENGTH: 9
<212> TYPE: PRT
<213> ORGANISM: Homo sapiens

<400> SEQUENCE: 1053

Thr Thr Asp Ser Gly Ser Ser Gln His
1               5

<210> SEQ ID NO 1054
<211> LENGTH: 10
<212> TYPE: PRT
<213> ORGANISM: Homo sapiens

<400> SEQUENCE: 1054

Thr Thr Val Gly Ile Arg Asn Gln Ser Val
1               5                   10

<210> SEQ ID NO 1055
<211> LENGTH: 9
<212> TYPE: PRT
<213> ORGANISM: Homo sapiens

<400> SEQUENCE: 1055

Thr Thr Val Pro Leu Gln Thr Ile Arg
1               5

<210> SEQ ID NO 1056
<211> LENGTH: 9
<212> TYPE: PRT
<213> ORGANISM: Homo sapiens

<400> SEQUENCE: 1056

Thr Val Gly Ile Arg Asn Gln Ser Val
1               5

<210> SEQ ID NO 1057
<211> LENGTH: 9
<212> TYPE: PRT
<213> ORGANISM: Homo sapiens

<400> SEQUENCE: 1057

Thr Val Lys Thr Gln Ile Lys Glu Lys
1               5

<210> SEQ ID NO 1058
<211> LENGTH: 8
<212> TYPE: PRT
<213> ORGANISM: Homo sapiens

<400> SEQUENCE: 1058

Thr Tyr His Leu Thr Ser Ala Leu
1               5

<210> SEQ ID NO 1059
<211> LENGTH: 8
<212> TYPE: PRT
<213> ORGANISM: Homo sapiens

<400> SEQUENCE: 1059

Thr Tyr Ser Ile Gly Phe Ser Tyr
1               5

<210> SEQ ID NO 1060
<211> LENGTH: 9
<212> TYPE: PRT
<213> ORGANISM: Homo sapiens

<400> SEQUENCE: 1060

Thr Tyr Ser Ile Val Lys Ile Ala Lys
1               5

<210> SEQ ID NO 1061
<211> LENGTH: 9
<212> TYPE: PRT
<213> ORGANISM: Homo sapiens

<400> SEQUENCE: 1061

Val Ala Phe Met Glu Asp Asp Glu Leu
1               5

<210> SEQ ID NO 1062
<211> LENGTH: 9
<212> TYPE: PRT
<213> ORGANISM: Homo sapiens

<400> SEQUENCE: 1062

Val Ala Asn Gln Lys Pro Phe Glu Lys
1               5

<210> SEQ ID NO 1063
<211> LENGTH: 9
<212> TYPE: PRT
<213> ORGANISM: Homo sapiens

<400> SEQUENCE: 1063

-continued

```
Val Ala Asn Gln Lys Pro Leu Arg Val
1               5

<210> SEQ ID NO 1064
<211> LENGTH: 9
<212> TYPE: PRT
<213> ORGANISM: Homo sapiens

<400> SEQUENCE: 1064

Val Ala Gln Ser Pro Arg Lys Leu Tyr
1               5

<210> SEQ ID NO 1065
<211> LENGTH: 10
<212> TYPE: PRT
<213> ORGANISM: Homo sapiens

<400> SEQUENCE: 1065

Val Ala Gln Ser Pro Arg Lys Leu Tyr Arg
1               5                   10

<210> SEQ ID NO 1066
<211> LENGTH: 8
<212> TYPE: PRT
<213> ORGANISM: Homo sapiens

<400> SEQUENCE: 1066

Val Ala Arg Ile His Lys Val Phe
1               5

<210> SEQ ID NO 1067
<211> LENGTH: 9
<212> TYPE: PRT
<213> ORGANISM: Homo sapiens

<400> SEQUENCE: 1067

Val Ala Arg Ile His Lys Val Phe Ala
1               5

<210> SEQ ID NO 1068
<211> LENGTH: 9
<212> TYPE: PRT
<213> ORGANISM: Homo sapiens

<400> SEQUENCE: 1068

Val Ala Ser Ser Phe Gln Val Ser Lys
1               5

<210> SEQ ID NO 1069
<211> LENGTH: 10
<212> TYPE: PRT
<213> ORGANISM: Homo sapiens

<400> SEQUENCE: 1069

Val Asp Leu Asn Ala Asp Pro Leu Cys Tyr
1               5                   10

<210> SEQ ID NO 1070
<211> LENGTH: 8
<212> TYPE: PRT
<213> ORGANISM: Homo sapiens

<400> SEQUENCE: 1070

Val Glu Glu Leu Val Glu Ala Leu
1               5
```

-continued

```
<210> SEQ ID NO 1071
<211> LENGTH: 9
<212> TYPE: PRT
<213> ORGANISM: Homo sapiens

<400> SEQUENCE: 1071

Val Glu Lys Ala Ser Leu Pro Asn Leu
1               5

<210> SEQ ID NO 1072
<211> LENGTH: 10
<212> TYPE: PRT
<213> ORGANISM: Homo sapiens

<400> SEQUENCE: 1072

Val Glu Val Thr Lys Ser Pro Arg Lys Leu
1               5                   10

<210> SEQ ID NO 1073
<211> LENGTH: 11
<212> TYPE: PRT
<213> ORGANISM: Homo sapiens

<400> SEQUENCE: 1073

Val Glu Val Thr Lys Ser Pro Arg Lys Leu Tyr
1               5                   10

<210> SEQ ID NO 1074
<211> LENGTH: 9
<212> TYPE: PRT
<213> ORGANISM: Homo sapiens

<400> SEQUENCE: 1074

Val Gly Phe Arg Gly Ser Trp His Lys
1               5

<210> SEQ ID NO 1075
<211> LENGTH: 9
<212> TYPE: PRT
<213> ORGANISM: Homo sapiens

<400> SEQUENCE: 1075

Val Leu Leu Phe Tyr Asn Val His Met
1               5

<210> SEQ ID NO 1076
<211> LENGTH: 9
<212> TYPE: PRT
<213> ORGANISM: Homo sapiens

<400> SEQUENCE: 1076

Val Leu Leu Lys Gln Lys Ala Val Lys
1               5

<210> SEQ ID NO 1077
<211> LENGTH: 9
<212> TYPE: PRT
<213> ORGANISM: Homo sapiens

<400> SEQUENCE: 1077

Val Leu Asn Cys Lys Leu Ile Val Val
1               5
```

-continued

```
<210> SEQ ID NO 1078
<211> LENGTH: 10
<212> TYPE: PRT
<213> ORGANISM: Homo sapiens

<400> SEQUENCE: 1078

Val Leu Ser Asn Leu Val Ile Gln Asn Val
1               5                   10

<210> SEQ ID NO 1079
<211> LENGTH: 9
<212> TYPE: PRT
<213> ORGANISM: Homo sapiens

<400> SEQUENCE: 1079

Val Leu Ser Asn Leu Val Met Lys Arg
1               5

<210> SEQ ID NO 1080
<211> LENGTH: 9
<212> TYPE: PRT
<213> ORGANISM: Homo sapiens

<400> SEQUENCE: 1080

Val Leu Val Lys Val Leu Leu Phe Tyr
1               5

<210> SEQ ID NO 1081
<211> LENGTH: 10
<212> TYPE: PRT
<213> ORGANISM: Homo sapiens

<400> SEQUENCE: 1081

Val Met Ile Ser Arg Gly Ile Gln Asn Val
1               5                   10

<210> SEQ ID NO 1082
<211> LENGTH: 10
<212> TYPE: PRT
<213> ORGANISM: Homo sapiens

<400> SEQUENCE: 1082

Val Met Ile Ser Arg Ile Ile Gln Asn Val
1               5                   10

<210> SEQ ID NO 1083
<211> LENGTH: 9
<212> TYPE: PRT
<213> ORGANISM: Homo sapiens

<400> SEQUENCE: 1083

Val Met Lys Arg Ile Ile Gln Asn Val
1               5

<210> SEQ ID NO 1084
<211> LENGTH: 10
<212> TYPE: PRT
<213> ORGANISM: Homo sapiens

<400> SEQUENCE: 1084

Val Pro Ser Leu Ala Cys Glu Leu Thr Leu
1               5                   10

<210> SEQ ID NO 1085
<211> LENGTH: 10
```

<212> TYPE: PRT
<213> ORGANISM: Homo sapiens

<400> SEQUENCE: 1085

Val Pro Val Lys Thr Gln Ile Lys Glu Ala
1               5                   10

<210> SEQ ID NO 1086
<211> LENGTH: 9
<212> TYPE: PRT
<213> ORGANISM: Homo sapiens

<400> SEQUENCE: 1086

Val Pro Val Asn Gly Leu Leu Glu Leu
1               5

<210> SEQ ID NO 1087
<211> LENGTH: 11
<212> TYPE: PRT
<213> ORGANISM: Homo sapiens

<400> SEQUENCE: 1087

Val Pro Val Asn Gly Leu Leu Glu Leu Thr Leu
1               5                   10

<210> SEQ ID NO 1088
<211> LENGTH: 8
<212> TYPE: PRT
<213> ORGANISM: Homo sapiens

<400> SEQUENCE: 1088

Val Pro Trp Ile Thr Leu Ile Ala
1               5

<210> SEQ ID NO 1089
<211> LENGTH: 9
<212> TYPE: PRT
<213> ORGANISM: Homo sapiens

<400> SEQUENCE: 1089

Val Pro Trp Ile Thr Leu Ile Ala Ala
1               5

<210> SEQ ID NO 1090
<211> LENGTH: 9
<212> TYPE: PRT
<213> ORGANISM: Homo sapiens

<400> SEQUENCE: 1090

Val Pro Trp Ile Thr Leu Asn Glu Val
1               5

<210> SEQ ID NO 1091
<211> LENGTH: 8
<212> TYPE: PRT
<213> ORGANISM: Homo sapiens

<400> SEQUENCE: 1091

Val Gln His Ser Leu Pro Thr Leu
1               5

<210> SEQ ID NO 1092
<211> LENGTH: 10
<212> TYPE: PRT
<213> ORGANISM: Homo sapiens -continued

```
<400> SEQUENCE: 1092

Val Gln Ile Pro Val Asn Leu Lys Asn Val
1               5                   10

<210> SEQ ID NO 1093
<211> LENGTH: 9
<212> TYPE: PRT
<213> ORGANISM: Homo sapiens

<400> SEQUENCE: 1093

Val Arg Lys Ile Ser Gln Leu Ile Met
1               5

<210> SEQ ID NO 1094
<211> LENGTH: 10
<212> TYPE: PRT
<213> ORGANISM: Homo sapiens

<400> SEQUENCE: 1094

Val Ser Lys Glu Ala Leu Gly Phe Val Tyr
1               5                   10

<210> SEQ ID NO 1095
<211> LENGTH: 9
<212> TYPE: PRT
<213> ORGANISM: Homo sapiens

<400> SEQUENCE: 1095

Val Ser Arg Asn Gln Ala His Leu Ile
1               5

<210> SEQ ID NO 1096
<211> LENGTH: 10
<212> TYPE: PRT
<213> ORGANISM: Homo sapiens

<400> SEQUENCE: 1096

Val Thr Asp Ser Glu Asn Thr His Gly Phe
1               5                   10

<210> SEQ ID NO 1097
<211> LENGTH: 9
<212> TYPE: PRT
<213> ORGANISM: Homo sapiens

<400> SEQUENCE: 1097

Val Thr Asp Ser Glu Asn Thr Ile Lys
1               5

<210> SEQ ID NO 1098
<211> LENGTH: 9
<212> TYPE: PRT
<213> ORGANISM: Homo sapiens

<400> SEQUENCE: 1098

Val Thr Asp Ser Glu Asn Thr Asn His
1               5

<210> SEQ ID NO 1099
<211> LENGTH: 11
<212> TYPE: PRT
<213> ORGANISM: Homo sapiens

<400> SEQUENCE: 1099
```

-continued

```
Val Thr Asp Ser Glu Asn Thr Asn His Gly Phe
1               5                   10

<210> SEQ ID NO 1100
<211> LENGTH: 9
<212> TYPE: PRT
<213> ORGANISM: Homo sapiens

<400> SEQUENCE: 1100

Val Thr Asp Ser Glu Asn Thr Asn Lys
1               5

<210> SEQ ID NO 1101
<211> LENGTH: 9
<212> TYPE: PRT
<213> ORGANISM: Homo sapiens

<400> SEQUENCE: 1101

Val Thr Glu Ala Ala Ser His Gly Phe
1               5

<210> SEQ ID NO 1102
<211> LENGTH: 10
<212> TYPE: PRT
<213> ORGANISM: Homo sapiens

<400> SEQUENCE: 1102

Val Thr Ile Met Asn Ile Pro Met Glu Lys
1               5                   10

<210> SEQ ID NO 1103
<211> LENGTH: 10
<212> TYPE: PRT
<213> ORGANISM: Homo sapiens

<400> SEQUENCE: 1103

Val Thr Ile Met Asn Leu Met Asn Asn Tyr
1               5                   10

<210> SEQ ID NO 1104
<211> LENGTH: 9
<212> TYPE: PRT
<213> ORGANISM: Homo sapiens

<400> SEQUENCE: 1104

Val Thr Lys Ser Pro Arg Lys Leu Tyr
1               5

<210> SEQ ID NO 1105
<211> LENGTH: 10
<212> TYPE: PRT
<213> ORGANISM: Homo sapiens

<400> SEQUENCE: 1105

Val Thr Lys Ser Pro Arg Lys Leu Tyr Arg
1               5                   10

<210> SEQ ID NO 1106
<211> LENGTH: 9
<212> TYPE: PRT
<213> ORGANISM: Homo sapiens

<400> SEQUENCE: 1106

Val Thr Leu His Pro Ala Lys Ile Lys
```

-continued

```
1               5

<210> SEQ ID NO 1107
<211> LENGTH: 9
<212> TYPE: PRT
<213> ORGANISM: Homo sapiens

<400> SEQUENCE: 1107

Val Thr Val Lys His Thr Asn Gln Arg
1               5

<210> SEQ ID NO 1108
<211> LENGTH: 9
<212> TYPE: PRT
<213> ORGANISM: Homo sapiens

<400> SEQUENCE: 1108

Val Thr Val Lys Thr Gln Asn Gln Arg
1               5

<210> SEQ ID NO 1109
<211> LENGTH: 9
<212> TYPE: PRT
<213> ORGANISM: Homo sapiens

<400> SEQUENCE: 1109

Val Val Pro Ser Leu Ala Cys Glu Leu
1               5

<210> SEQ ID NO 1110
<211> LENGTH: 10
<212> TYPE: PRT
<213> ORGANISM: Homo sapiens

<400> SEQUENCE: 1110

Val Val Pro Val Asn Gly Leu Leu Glu Leu
1               5                   10

<210> SEQ ID NO 1111
<211> LENGTH: 9
<212> TYPE: PRT
<213> ORGANISM: Homo sapiens

<400> SEQUENCE: 1111

Val Val Ser Lys Glu Ala Leu Gly Phe
1               5

<210> SEQ ID NO 1112
<211> LENGTH: 10
<212> TYPE: PRT
<213> ORGANISM: Homo sapiens

<400> SEQUENCE: 1112

Trp Ala Gln Met Glu Lys Ile Pro Leu Leu
1               5                   10

<210> SEQ ID NO 1113
<211> LENGTH: 9
<212> TYPE: PRT
<213> ORGANISM: Homo sapiens

<400> SEQUENCE: 1113

Trp Ile Asp His Ile Gly Lys Ser Met
1               5
```

<210> SEQ ID NO 1114
<211> LENGTH: 9
<212> TYPE: PRT
<213> ORGANISM: Homo sapiens

<400> SEQUENCE: 1114

Trp Ile Thr Leu Ile Ala Ala Phe Arg
1               5

<210> SEQ ID NO 1115
<211> LENGTH: 10
<212> TYPE: PRT
<213> ORGANISM: Homo sapiens

<400> SEQUENCE: 1115

Trp Ile Thr Leu Asn Glu Val Asp Glu Tyr
1               5                   10

<210> SEQ ID NO 1116
<211> LENGTH: 9
<212> TYPE: PRT
<213> ORGANISM: Homo sapiens

<400> SEQUENCE: 1116

Trp Ile Trp Lys Asn Ile Arg Glu Phe
1               5

<210> SEQ ID NO 1117
<211> LENGTH: 9
<212> TYPE: PRT
<213> ORGANISM: Homo sapiens

<400> SEQUENCE: 1117

Trp Ile Trp Lys Asn Ile Arg Glu Val
1               5

<210> SEQ ID NO 1118
<211> LENGTH: 9
<212> TYPE: PRT
<213> ORGANISM: Homo sapiens

<400> SEQUENCE: 1118

Trp Ile Trp Lys Asn Ile Arg Glu Tyr
1               5

<210> SEQ ID NO 1119
<211> LENGTH: 9
<212> TYPE: PRT
<213> ORGANISM: Homo sapiens

<400> SEQUENCE: 1119

Trp Ile Trp Lys Asn Ile Ser Lys Val
1               5

<210> SEQ ID NO 1120
<211> LENGTH: 9
<212> TYPE: PRT
<213> ORGANISM: Homo sapiens

<400> SEQUENCE: 1120

Trp Lys Ala Leu Glu Asp Phe Thr Leu
1               5

<210> SEQ ID NO 1121

```
<211> LENGTH: 9
<212> TYPE: PRT
<213> ORGANISM: Homo sapiens

<400> SEQUENCE: 1121

Trp Leu Val Arg Lys Ile Ser Gln Leu
1               5

<210> SEQ ID NO 1122
<211> LENGTH: 10
<212> TYPE: PRT
<213> ORGANISM: Homo sapiens

<400> SEQUENCE: 1122

Trp Pro Asn Leu Pro Asp Ser Gln Gln Val
1               5                   10

<210> SEQ ID NO 1123
<211> LENGTH: 9
<212> TYPE: PRT
<213> ORGANISM: Homo sapiens

<400> SEQUENCE: 1123

Trp Pro Val Asn Gly Leu Leu Glu Leu
1               5

<210> SEQ ID NO 1124
<211> LENGTH: 11
<212> TYPE: PRT
<213> ORGANISM: Homo sapiens

<400> SEQUENCE: 1124

Trp Pro Val Asn Gly Leu Leu Glu Leu Thr Leu
1               5                   10

<210> SEQ ID NO 1125
<211> LENGTH: 9
<212> TYPE: PRT
<213> ORGANISM: Homo sapiens

<400> SEQUENCE: 1125

Trp Ser Pro Asp Gly Lys Ile Pro Leu
1               5

<210> SEQ ID NO 1126
<211> LENGTH: 10
<212> TYPE: PRT
<213> ORGANISM: Homo sapiens

<400> SEQUENCE: 1126

Trp Ser Pro Asp Gly Lys Ile Pro Leu Leu
1               5                   10

<210> SEQ ID NO 1127
<211> LENGTH: 10
<212> TYPE: PRT
<213> ORGANISM: Homo sapiens

<400> SEQUENCE: 1127

Trp Ser Pro Met Glu Lys Ile Pro Leu Leu
1               5                   10

<210> SEQ ID NO 1128
<211> LENGTH: 10
<212> TYPE: PRT
```

-continued

<213> ORGANISM: Homo sapiens

<400> SEQUENCE: 1128

Trp Ser Gln Met Glu Lys Ile Pro Leu Leu
1               5                   10

<210> SEQ ID NO 1129
<211> LENGTH: 10
<212> TYPE: PRT
<213> ORGANISM: Homo sapiens

<400> SEQUENCE: 1129

Tyr Glu Glu Thr Asp Ile Thr Glu Ser Val
1               5                   10

<210> SEQ ID NO 1130
<211> LENGTH: 8
<212> TYPE: PRT
<213> ORGANISM: Homo sapiens

<400> SEQUENCE: 1130

Tyr Glu Asn Asn Ser Asn Tyr Tyr
1               5

<210> SEQ ID NO 1131
<211> LENGTH: 9
<212> TYPE: PRT
<213> ORGANISM: Homo sapiens

<400> SEQUENCE: 1131

Tyr Glu Asn Asn Ser Asn Tyr Tyr Ser
1               5

<210> SEQ ID NO 1132
<211> LENGTH: 9
<212> TYPE: PRT
<213> ORGANISM: Homo sapiens

<400> SEQUENCE: 1132

Tyr Phe Glu Thr Glu Ala Val Ala Phe
1               5

<210> SEQ ID NO 1133
<211> LENGTH: 10
<212> TYPE: PRT
<213> ORGANISM: Homo sapiens

<400> SEQUENCE: 1133

Tyr Phe Glu Thr Glu Ala Val Ala Phe Met
1               5                   10

<210> SEQ ID NO 1134
<211> LENGTH: 9
<212> TYPE: PRT
<213> ORGANISM: Homo sapiens

<400> SEQUENCE: 1134

Tyr His His Phe Phe Pro Ser Ser His
1               5

<210> SEQ ID NO 1135
<211> LENGTH: 10
<212> TYPE: PRT
<213> ORGANISM: Homo sapiens -continued

<400> SEQUENCE: 1135

Tyr His His Phe Phe Pro Ser Ser His Leu
1               5                   10

<210> SEQ ID NO 1136
<211> LENGTH: 11
<212> TYPE: PRT
<213> ORGANISM: Homo sapiens

<400> SEQUENCE: 1136

Tyr His His Phe Phe Pro Ser Ser His Leu Leu
1               5                   10

<210> SEQ ID NO 1137
<211> LENGTH: 10
<212> TYPE: PRT
<213> ORGANISM: Homo sapiens

<400> SEQUENCE: 1137

Tyr His Leu Ser Ser Glu Ala Thr Lys Leu
1               5                   10

<210> SEQ ID NO 1138
<211> LENGTH: 9
<212> TYPE: PRT
<213> ORGANISM: Homo sapiens

<400> SEQUENCE: 1138

Tyr His Leu Thr Ser Ala Leu Lys Val
1               5

<210> SEQ ID NO 1139
<211> LENGTH: 9
<212> TYPE: PRT
<213> ORGANISM: Homo sapiens

<400> SEQUENCE: 1139

Tyr Ile Phe Arg Asn Glu Arg Lys Lys
1               5

<210> SEQ ID NO 1140
<211> LENGTH: 9
<212> TYPE: PRT
<213> ORGANISM: Homo sapiens

<400> SEQUENCE: 1140

Tyr Lys His Pro Gly Ser Phe Leu Ile
1               5

<210> SEQ ID NO 1141
<211> LENGTH: 8
<212> TYPE: PRT
<213> ORGANISM: Homo sapiens

<400> SEQUENCE: 1141

Tyr Lys Met Ser Lys Thr Ser Leu
1               5

<210> SEQ ID NO 1142
<211> LENGTH: 8
<212> TYPE: PRT
<213> ORGANISM: Homo sapiens

<400> SEQUENCE: 1142

```
Tyr Leu Arg Gly Ala Lys Lys Leu
1               5

<210> SEQ ID NO 1143
<211> LENGTH: 9
<212> TYPE: PRT
<213> ORGANISM: Homo sapiens

<400> SEQUENCE: 1143

Tyr Leu Ser Lys Val Phe Ser Lys Val
1               5

<210> SEQ ID NO 1144
<211> LENGTH: 9
<212> TYPE: PRT
<213> ORGANISM: Homo sapiens

<400> SEQUENCE: 1144

Tyr Leu Tyr Glu Asn Asn Ser Asn Tyr
1               5

<210> SEQ ID NO 1145
<211> LENGTH: 10
<212> TYPE: PRT
<213> ORGANISM: Homo sapiens

<400> SEQUENCE: 1145

Tyr Leu Tyr Glu Asn Asn Ser Asn Tyr Tyr
1               5                   10

<210> SEQ ID NO 1146
<211> LENGTH: 8
<212> TYPE: PRT
<213> ORGANISM: Homo sapiens

<400> SEQUENCE: 1146

Tyr Leu Tyr Glu Thr Thr Ile Ala
1               5

<210> SEQ ID NO 1147
<211> LENGTH: 9
<212> TYPE: PRT
<213> ORGANISM: Homo sapiens

<400> SEQUENCE: 1147

Tyr Leu Tyr Glu Thr Thr Ile Ala Glu
1               5

<210> SEQ ID NO 1148
<211> LENGTH: 10
<212> TYPE: PRT
<213> ORGANISM: Homo sapiens

<400> SEQUENCE: 1148

Tyr Arg Lys Glu Trp Asn Lys Gln Lys Leu
1               5                   10

<210> SEQ ID NO 1149
<211> LENGTH: 9
<212> TYPE: PRT
<213> ORGANISM: Homo sapiens

<400> SEQUENCE: 1149

Tyr Arg Leu Trp Pro Val Asn Gly Leu
1               5
```

-continued

```
<210> SEQ ID NO 1150
<211> LENGTH: 10
<212> TYPE: PRT
<213> ORGANISM: Homo sapiens

<400> SEQUENCE: 1150

Tyr Arg Leu Trp Pro Val Asn Gly Leu Leu
1               5                   10

<210> SEQ ID NO 1151
<211> LENGTH: 9
<212> TYPE: PRT
<213> ORGANISM: Homo sapiens

<400> SEQUENCE: 1151

Tyr Arg Gln Leu Ile Ser Leu Gln Ala
1               5

<210> SEQ ID NO 1152
<211> LENGTH: 10
<212> TYPE: PRT
<213> ORGANISM: Homo sapiens

<400> SEQUENCE: 1152

Tyr Arg Gln Leu Ile Ser Leu Gln Ala Phe
1               5                   10

<210> SEQ ID NO 1153
<211> LENGTH: 9
<212> TYPE: PRT
<213> ORGANISM: Homo sapiens

<400> SEQUENCE: 1153

Tyr Ser Ala His Gly Thr Glu Ala Leu
1               5

<210> SEQ ID NO 1154
<211> LENGTH: 9
<212> TYPE: PRT
<213> ORGANISM: Homo sapiens

<400> SEQUENCE: 1154

Tyr Ser Lys Asp Ser Glu Asn Ala Lys
1               5

<210> SEQ ID NO 1155
<211> LENGTH: 9
<212> TYPE: PRT
<213> ORGANISM: Homo sapiens

<400> SEQUENCE: 1155

Tyr Ser Val Val Asn Ser Ser Ala Phe
1               5

<210> SEQ ID NO 1156
<211> LENGTH: 10
<212> TYPE: PRT
<213> ORGANISM: Homo sapiens

<400> SEQUENCE: 1156

Tyr Thr Asn Gln Ser Pro Tyr Ser Val Val
1               5                   10
```

```
<210> SEQ ID NO 1157
<211> LENGTH: 12
<212> TYPE: PRT
<213> ORGANISM: Homo sapiens

<400> SEQUENCE: 1157

Ser His Leu Ser Gly Val Asp Gln Gly Thr Cys Leu
1               5                   10

<210> SEQ ID NO 1158
<211> LENGTH: 9
<212> TYPE: PRT
<213> ORGANISM: Homo sapiens

<400> SEQUENCE: 1158

Asn Ala Met Gln Lys Ile Leu Val Ser
1               5

<210> SEQ ID NO 1159
<211> LENGTH: 11
<212> TYPE: PRT
<213> ORGANISM: Homo sapiens

<400> SEQUENCE: 1159

Asn Ala Met Gln Lys Ile Leu Val Ser His Leu
1               5                   10

<210> SEQ ID NO 1160
<211> LENGTH: 9
<212> TYPE: PRT
<213> ORGANISM: Homo sapiens

<400> SEQUENCE: 1160

Ala Met Gln Lys Ile Leu Val Ser His
1               5

<210> SEQ ID NO 1161
<211> LENGTH: 10
<212> TYPE: PRT
<213> ORGANISM: Homo sapiens

<400> SEQUENCE: 1161

Ala Met Gln Lys Ile Leu Val Ser His Leu
1               5                   10

<210> SEQ ID NO 1162
<211> LENGTH: 8
<212> TYPE: PRT
<213> ORGANISM: Homo sapiens

<400> SEQUENCE: 1162

Met Gln Lys Ile Leu Val Ser His
1               5

<210> SEQ ID NO 1163
<211> LENGTH: 11
<212> TYPE: PRT
<213> ORGANISM: Homo sapiens

<400> SEQUENCE: 1163

Leu Ser Gly Val Asp Gln Gly Thr Cys Leu His
1               5                   10

<210> SEQ ID NO 1164
<211> LENGTH: 10
```

-continued

```
<212> TYPE: PRT
<213> ORGANISM: Homo sapiens

<400> SEQUENCE: 1164

Ser Gly Val Asp Gln Gly Thr Cys Leu His
1               5                   10

<210> SEQ ID NO 1165
<211> LENGTH: 9
<212> TYPE: PRT
<213> ORGANISM: Homo sapiens

<400> SEQUENCE: 1165

Gly Val Asp Gln Gly Thr Cys Leu His
1               5

<210> SEQ ID NO 1166
<211> LENGTH: 10
<212> TYPE: PRT
<213> ORGANISM: Homo sapiens

<400> SEQUENCE: 1166

Ala Arg Glu Ser Pro Gly Gln Lys Asp Leu
1               5                   10

<210> SEQ ID NO 1167
<211> LENGTH: 9
<212> TYPE: PRT
<213> ORGANISM: Homo sapiens

<400> SEQUENCE: 1167

Gly Pro Lys Arg Ala Arg Glu Ser Pro
1               5

<210> SEQ ID NO 1168
<211> LENGTH: 11
<212> TYPE: PRT
<213> ORGANISM: Homo sapiens

<400> SEQUENCE: 1168

Arg Ala Arg Glu Ser Pro Gly Gln Lys Asp Leu
1               5                   10

<210> SEQ ID NO 1169
<211> LENGTH: 11
<212> TYPE: PRT
<213> ORGANISM: Homo sapiens

<400> SEQUENCE: 1169

Gly Gln Lys Asp Leu Gln Gly Ala Arg Asn Leu
1               5                   10

<210> SEQ ID NO 1170
<211> LENGTH: 12
<212> TYPE: PRT
<213> ORGANISM: Homo sapiens

<400> SEQUENCE: 1170

Lys Asp Leu Gln Gly Ala Arg Asn Leu Leu Leu Trp
1               5                   10

<210> SEQ ID NO 1171
<211> LENGTH: 9
<212> TYPE: PRT
<213> ORGANISM: Homo sapiens
```

<400> SEQUENCE: 1171

Asp Leu Gln Gly Ala Arg Asn Leu Leu
1               5

<210> SEQ ID NO 1172
<211> LENGTH: 10
<212> TYPE: PRT
<213> ORGANISM: Homo sapiens

<400> SEQUENCE: 1172

Leu Gln Gly Ala Arg Asn Leu Leu Leu Trp
1               5                   10

<210> SEQ ID NO 1173
<211> LENGTH: 11
<212> TYPE: PRT
<213> ORGANISM: Homo sapiens

<400> SEQUENCE: 1173

Gln Gly Ala Arg Asn Leu Leu Leu Trp Ala Leu
1               5                   10

<210> SEQ ID NO 1174
<211> LENGTH: 10
<212> TYPE: PRT
<213> ORGANISM: Homo sapiens

<400> SEQUENCE: 1174

Ala Arg Asn Leu Leu Leu Trp Ala Leu His
1               5                   10

<210> SEQ ID NO 1175
<211> LENGTH: 12
<212> TYPE: PRT
<213> ORGANISM: Homo sapiens

<400> SEQUENCE: 1175

Ala Arg Asn Leu Leu Leu Trp Ala Leu His Gln His
1               5                   10

<210> SEQ ID NO 1176
<211> LENGTH: 9
<212> TYPE: PRT
<213> ORGANISM: Homo sapiens

<400> SEQUENCE: 1176

Leu Leu Trp Ala Leu His Gln His Ala
1               5

<210> SEQ ID NO 1177
<211> LENGTH: 10
<212> TYPE: PRT
<213> ORGANISM: Homo sapiens

<400> SEQUENCE: 1177

His Gln His Ala His Arg Ser Thr Gly Met
1               5                   10

<210> SEQ ID NO 1178
<211> LENGTH: 12
<212> TYPE: PRT
<213> ORGANISM: Homo sapiens

<400> SEQUENCE: 1178

```
His Arg Ser Thr Gly Met Asp Gly Thr Ala Val Trp
1               5               10

<210> SEQ ID NO 1179
<211> LENGTH: 12
<212> TYPE: PRT
<213> ORGANISM: Homo sapiens

<400> SEQUENCE: 1179

Arg Ser Thr Gly Met Asp Gly Thr Ala Val Trp Cys
1               5               10

<210> SEQ ID NO 1180
<211> LENGTH: 11
<212> TYPE: PRT
<213> ORGANISM: Homo sapiens

<400> SEQUENCE: 1180

Ser Thr Gly Met Asp Gly Thr Ala Val Trp Cys
1               5               10

<210> SEQ ID NO 1181
<211> LENGTH: 8
<212> TYPE: PRT
<213> ORGANISM: Homo sapiens

<400> SEQUENCE: 1181

Gly Ala Phe Ile Ile His Pro Trp
1               5

<210> SEQ ID NO 1182
<211> LENGTH: 12
<212> TYPE: PRT
<213> ORGANISM: Homo sapiens

<400> SEQUENCE: 1182

His Arg Cys Pro Pro Asn Cys Gly Cys Ala Ala Arg
1               5               10

<210> SEQ ID NO 1183
<211> LENGTH: 11
<212> TYPE: PRT
<213> ORGANISM: Homo sapiens

<400> SEQUENCE: 1183

Cys Ala Ala Arg Cys Leu Asp Arg Gly Gln Trp
1               5               10

<210> SEQ ID NO 1184
<211> LENGTH: 9
<212> TYPE: PRT
<213> ORGANISM: Homo sapiens

<400> SEQUENCE: 1184

Ala Arg Cys Leu Asp Arg Gly Gln Trp
1               5

<210> SEQ ID NO 1185
<211> LENGTH: 8
<212> TYPE: PRT
<213> ORGANISM: Homo sapiens

<400> SEQUENCE: 1185

Arg Cys Leu Asp Arg Gly Gln Trp
```

-continued

```
1               5

<210> SEQ ID NO 1186
<211> LENGTH: 9
<212> TYPE: PRT
<213> ORGANISM: Homo sapiens

<400> SEQUENCE: 1186

Arg Gly Gln Trp Leu Pro Cys Asn Trp
1               5

<210> SEQ ID NO 1187
<211> LENGTH: 11
<212> TYPE: PRT
<213> ORGANISM: Homo sapiens

<400> SEQUENCE: 1187

Lys Ser Met Ile Leu Lys Ser Glu Glu Met Trp
1               5                   10

<210> SEQ ID NO 1188
<211> LENGTH: 9
<212> TYPE: PRT
<213> ORGANISM: Homo sapiens

<400> SEQUENCE: 1188

Ser Met Ile Leu Lys Ser Glu Glu Met
1               5

<210> SEQ ID NO 1189
<211> LENGTH: 10
<212> TYPE: PRT
<213> ORGANISM: Homo sapiens

<400> SEQUENCE: 1189

Ser Met Ile Leu Lys Ser Glu Glu Met Trp
1               5                   10

<210> SEQ ID NO 1190
<211> LENGTH: 9
<212> TYPE: PRT
<213> ORGANISM: Homo sapiens

<400> SEQUENCE: 1190

Met Ile Leu Lys Ser Glu Glu Met Trp
1               5

<210> SEQ ID NO 1191
<211> LENGTH: 9
<212> TYPE: PRT
<213> ORGANISM: Homo sapiens

<400> SEQUENCE: 1191

Gln Glu Asn Pro Gln Asp Arg Lys Ile
1               5

<210> SEQ ID NO 1192
<211> LENGTH: 8
<212> TYPE: PRT
<213> ORGANISM: Homo sapiens

<400> SEQUENCE: 1192

Met Ile Leu Lys Ser Glu Glu Met
1               5
```

-continued

```
<210> SEQ ID NO 1193
<211> LENGTH: 8
<212> TYPE: PRT
<213> ORGANISM: Homo sapiens

<400> SEQUENCE: 1193

Ile Leu Lys Ser Glu Glu Met Trp
1               5

<210> SEQ ID NO 1194
<211> LENGTH: 10
<212> TYPE: PRT
<213> ORGANISM: Homo sapiens

<400> SEQUENCE: 1194

Ile Leu Lys Ser Glu Glu Met Trp Ser Met
1               5                   10

<210> SEQ ID NO 1195
<211> LENGTH: 9
<212> TYPE: PRT
<213> ORGANISM: Homo sapiens

<400> SEQUENCE: 1195

Leu Lys Ser Glu Glu Met Trp Ser Met
1               5

<210> SEQ ID NO 1196
<211> LENGTH: 11
<212> TYPE: PRT
<213> ORGANISM: Homo sapiens

<400> SEQUENCE: 1196

Glu Met Trp Ser Met Glu Glu Thr Thr Lys Val
1               5                   10

<210> SEQ ID NO 1197
<211> LENGTH: 9
<212> TYPE: PRT
<213> ORGANISM: Homo sapiens

<400> SEQUENCE: 1197

Trp Ser Met Glu Glu Thr Thr Lys Val
1               5

<210> SEQ ID NO 1198
<211> LENGTH: 11
<212> TYPE: PRT
<213> ORGANISM: Homo sapiens

<400> SEQUENCE: 1198

Ser Glu Gln Glu Asn Pro Gln Asp Arg Lys Ile
1               5                   10

<210> SEQ ID NO 1199
<211> LENGTH: 12
<212> TYPE: PRT
<213> ORGANISM: Homo sapiens

<400> SEQUENCE: 1199

Ser Glu Gln Glu Asn Pro Gln Asp Arg Lys Ile Phe
1               5                   10

<210> SEQ ID NO 1200
```

```
<211> LENGTH: 10
<212> TYPE: PRT
<213> ORGANISM: Homo sapiens

<400> SEQUENCE: 1200

Gln Glu Asn Pro Gln Asp Arg Lys Ile Phe
1               5                   10

<210> SEQ ID NO 1201
<211> LENGTH: 8
<212> TYPE: PRT
<213> ORGANISM: Homo sapiens

<400> SEQUENCE: 1201

Asn Pro Gln Asp Arg Lys Ile Phe
1               5

<210> SEQ ID NO 1202
<211> LENGTH: 11
<212> TYPE: PRT
<213> ORGANISM: Homo sapiens

<400> SEQUENCE: 1202

Asn Pro Gln Asp Arg Lys Ile Phe Arg Gly Leu
1               5                   10

<210> SEQ ID NO 1203
<211> LENGTH: 11
<212> TYPE: PRT
<213> ORGANISM: Homo sapiens

<400> SEQUENCE: 1203

Phe Ser Thr Ala Arg Glu Asn Leu Ser Arg Tyr
1               5                   10

<210> SEQ ID NO 1204
<211> LENGTH: 10
<212> TYPE: PRT
<213> ORGANISM: Homo sapiens

<400> SEQUENCE: 1204

Leu His Tyr Lys Thr Gln Asp Lys Cys Phe
1               5                   10

<210> SEQ ID NO 1205
<211> LENGTH: 11
<212> TYPE: PRT
<213> ORGANISM: Homo sapiens

<400> SEQUENCE: 1205

Leu His Tyr Lys Thr Gln Asp Lys Cys Phe Leu
1               5                   10

<210> SEQ ID NO 1206
<211> LENGTH: 11
<212> TYPE: PRT
<213> ORGANISM: Homo sapiens

<400> SEQUENCE: 1206

Ser Thr Ala Arg Glu Asn Leu Ser Arg Tyr Gln
1               5                   10

<210> SEQ ID NO 1207
<211> LENGTH: 11
<212> TYPE: PRT
```

<213> ORGANISM: Homo sapiens

<400> SEQUENCE: 1207

Ala Arg Glu Asn Leu Ser Arg Tyr Gln Met Leu
1               5                   10

<210> SEQ ID NO 1208
<211> LENGTH: 8
<212> TYPE: PRT
<213> ORGANISM: Homo sapiens

<400> SEQUENCE: 1208

Glu Asn Leu Ser Arg Tyr Gln Met
1               5

<210> SEQ ID NO 1209
<211> LENGTH: 11
<212> TYPE: PRT
<213> ORGANISM: Homo sapiens

<400> SEQUENCE: 1209

Asn Leu Ser Arg Tyr Gln Met Leu His Tyr Lys
1               5                   10

<210> SEQ ID NO 1210
<211> LENGTH: 10
<212> TYPE: PRT
<213> ORGANISM: Homo sapiens

<400> SEQUENCE: 1210

Leu Ser Arg Tyr Gln Met Leu His Tyr Lys
1               5                   10

<210> SEQ ID NO 1211
<211> LENGTH: 10
<212> TYPE: PRT
<213> ORGANISM: Homo sapiens

<400> SEQUENCE: 1211

Ser Arg Tyr Gln Met Leu His Tyr Lys Thr
1               5                   10

<210> SEQ ID NO 1212
<211> LENGTH: 11
<212> TYPE: PRT
<213> ORGANISM: Homo sapiens

<400> SEQUENCE: 1212

Ser Arg Tyr Gln Met Leu His Tyr Lys Thr Gln
1               5                   10

<210> SEQ ID NO 1213
<211> LENGTH: 10
<212> TYPE: PRT
<213> ORGANISM: Homo sapiens

<400> SEQUENCE: 1213

Gln Met Leu His Tyr Lys Thr Gln Asp Lys
1               5                   10

<210> SEQ ID NO 1214
<211> LENGTH: 9
<212> TYPE: PRT
<213> ORGANISM: Homo sapiens -continued

<400> SEQUENCE: 1214

Met Leu His Tyr Lys Thr Gln Asp Lys
1               5

<210> SEQ ID NO 1215
<211> LENGTH: 9
<212> TYPE: PRT
<213> ORGANISM: Homo sapiens

<400> SEQUENCE: 1215

Leu His Tyr Lys Thr Gln Asp Lys Cys
1               5

<210> SEQ ID NO 1216
<211> LENGTH: 9
<212> TYPE: PRT
<213> ORGANISM: Homo sapiens

<400> SEQUENCE: 1216

His Tyr Lys Thr Gln Asp Lys Cys Phe
1               5

<210> SEQ ID NO 1217
<211> LENGTH: 9
<212> TYPE: PRT
<213> ORGANISM: Homo sapiens

<400> SEQUENCE: 1217

Tyr Lys Thr Gln Asp Lys Cys Phe Leu
1               5

<210> SEQ ID NO 1218
<211> LENGTH: 9
<212> TYPE: PRT
<213> ORGANISM: Homo sapiens

<400> SEQUENCE: 1218

His Ser Lys Gly Lys Ser Val Gln Val
1               5

<210> SEQ ID NO 1219
<211> LENGTH: 15
<212> TYPE: DNA
<213> ORGANISM: Homo sapiens

<400> SEQUENCE: 1219
tagagtgtcc catct                                                    15

<210> SEQ ID NO 1220
<211> LENGTH: 11
<212> TYPE: DNA
<213> ORGANISM: Homo sapiens

<400> SEQUENCE: 1220
ttttctgaaa t                                                        11

<210> SEQ ID NO 1221
<211> LENGTH: 16
<212> TYPE: DNA
<213> ORGANISM: Homo sapiens

<400> SEQUENCE: 1221
gcaagtggaa aatctg                                                   16

<210> SEQ ID NO 1222
<211> LENGTH: 14
<212> TYPE: DNA
<213> ORGANISM: Homo sapiens

<400> SEQUENCE: 1222
caagtgtttt ctga                                                                                              14

<210> SEQ ID NO 1223
<211> LENGTH: 26
<212> TYPE: PRT
<213> ORGANISM: Homo sapiens

<400> SEQUENCE: 1223

Asn Val Ile Asn Ala Met Gln Lys Ile Leu Val Ser His Leu Ser Gly
1               5                   10                  15

Val Asp Gln Gly Thr Cys Leu His Lys Val
            20                  25

<210> SEQ ID NO 1224
<211> LENGTH: 36
<212> TYPE: PRT
<213> ORGANISM: Homo sapiens

<400> SEQUENCE: 1224

Lys Ser Met Ile Leu Lys Ser Glu Glu Met Trp Ser Met Glu Glu Thr
1               5                   10                  15

Thr Lys Val Gln Ser Glu Gln Glu Asn Pro Gln Asp Arg Lys Ile Phe
            20                  25                  30

Arg Gly Leu Glu
        35

<210> SEQ ID NO 1225
<211> LENGTH: 83
<212> TYPE: PRT
<213> ORGANISM: Homo sapiens

<400> SEQUENCE: 1225

His Gln Gly Pro Lys Arg Ala Arg Glu Ser Pro Gly Gln Lys Asp Leu
1               5                   10                  15

Gln Gly Ala Arg Asn Leu Leu Leu Trp Ala Leu His Gln His Ala His
            20                  25                  30

Arg Ser Thr Gly Met Asp Gly Thr Ala Val Trp Cys Phe Cys Gly Glu
        35                  40                  45

Gly Ala Phe Ile Ile His Pro Trp His Arg Cys Pro Pro Asn Cys Gly
    50                  55                  60

Cys Ala Ala Arg Cys Leu Asp Arg Gly Gln Trp Leu Pro Cys Asn Trp
65                  70                  75                  80

Ala Asp Val

<210> SEQ ID NO 1226
<211> LENGTH: 13
<212> TYPE: PRT
<213> ORGANISM: Homo sapiens

<400> SEQUENCE: 1226

His Ser Lys Gly Lys Ser Val Gln Val Ser Asp Ala Ser
1               5                   10

<210> SEQ ID NO 1227

```
<211> LENGTH: 31
<212> TYPE: PRT
<213> ORGANISM: Homo sapiens

<400> SEQUENCE: 1227

Ala Asn Thr Cys Gly Ile Phe Ser Thr Ala Arg Glu Asn Leu Ser Arg
1               5                   10                  15

Tyr Gln Met Leu His Tyr Lys Thr Gln Asp Lys Cys Phe Leu Lys
            20                  25                  30

<210> SEQ ID NO 1228
<211> LENGTH: 45
<212> TYPE: DNA
<213> ORGANISM: Homo sapiens

<400> SEQUENCE: 1228
cctgcagaag aatctgaaca taaaaacaac aattacgaac caaac                        45

<210> SEQ ID NO 1229
<211> LENGTH: 45
<212> TYPE: DNA
<213> ORGANISM: Homo sapiens

<400> SEQUENCE: 1229
cctgcagaat aatctgaaca taaaaacaac aattacgaac caaac                        45

<210> SEQ ID NO 1230
<211> LENGTH: 21
<212> TYPE: DNA
<213> ORGANISM: Homo sapiens

<400> SEQUENCE: 1230
cctgcagaat acgaaccaaa c                                                  21

<210> SEQ ID NO 1231
<211> LENGTH: 55
<212> TYPE: PRT
<213> ORGANISM: Homo sapiens

<400> SEQUENCE: 1231

Phe Ser Thr Ala Ser Gly Lys Ser Val Gln Val Ser Asp Ala Ser Leu
1               5                   10                  15

Gln Asn Ala Arg Gln Val Phe Ser Glu Ile Glu Asp Ser Thr Lys Gln
            20                  25                  30

Val Phe Ser Lys Val Leu Phe Lys Ser Asn Glu His Ser Asp Gln Leu
        35                  40                  45

Thr Arg Glu Glu Asn Thr Ala
    50                  55

<210> SEQ ID NO 1232
<211> LENGTH: 26
<212> TYPE: PRT
<213> ORGANISM: Homo sapiens
<220> FEATURE:
<221> NAME/KEY: misc_feature
<222> LOCATION: (26)..(26)
<223> OTHER INFORMATION: Xaa can be any naturally occurring amino acid

<400> SEQUENCE: 1232

Phe Ser Thr Ala Arg Glu Asn Leu Ser Arg Tyr Gln Met Leu His Tyr
1               5                   10                  15

Lys Thr Gln Asp Lys Cys Phe Leu Lys Xaa
            20                  25
```

```
<210> SEQ ID NO 1233
<211> LENGTH: 52
<212> TYPE: PRT
<213> ORGANISM: Homo sapiens

<400> SEQUENCE: 1233

Phe Ser Thr Ala Arg Glu Asn Leu Ser Arg Tyr Gln Met Leu His Tyr
1               5                   10                  15

Lys Thr Gln Asp Lys Cys Lys Glu Asp Ser Thr Lys Gln Val Phe Ser
            20                  25                  30

Lys Val Leu Phe Lys Ser Asn Glu His Ser Asp Gln Leu Thr Arg Glu
        35                  40                  45

Glu Asn Thr Ala
    50

<210> SEQ ID NO 1234
<211> LENGTH: 54
<212> TYPE: PRT
<213> ORGANISM: Homo sapiens

<400> SEQUENCE: 1234

Phe Ser Thr Ala Arg Glu Asn Leu Ser Arg Tyr Gln Met Leu His Tyr
1               5                   10                  15

Lys Thr Gln Asp Ile Ser Ser Glu Ile Glu Asp Ser Thr Lys Gln Val
            20                  25                  30

Phe Ser Lys Val Leu Phe Lys Ser Asn Glu His Ser Asp Gln Leu Thr
        35                  40                  45

Arg Glu Glu Asn Thr Ala
    50

<210> SEQ ID NO 1235
<211> LENGTH: 50
<212> TYPE: PRT
<213> ORGANISM: Homo sapiens

<400> SEQUENCE: 1235

Phe Ser Thr Ala Arg Glu Asn Leu Ser Arg Tyr Gln Met Leu His Tyr
1               5                   10                  15

Lys Thr Gln Glu Ile Glu Asp Ser Thr Lys Gln Val Phe Ser Lys Val
            20                  25                  30

Leu Phe Lys Ser Asn Glu His Ser Asp Gln Leu Thr Arg Glu Glu Asn
        35                  40                  45

Thr Ala
    50

<210> SEQ ID NO 1236
<211> LENGTH: 43
<212> TYPE: PRT
<213> ORGANISM: Homo sapiens

<400> SEQUENCE: 1236

Phe Ser Thr Ala Arg Glu Asn Leu Ser Arg Phe Ser Glu Ile Glu Asp
1               5                   10                  15

Ser Thr Lys Gln Val Phe Ser Lys Val Leu Phe Lys Ser Asn Glu His
            20                  25                  30

Ser Asp Gln Leu Thr Arg Glu Glu Asn Thr Ala
        35                  40
```

```
<210> SEQ ID NO 1237
<211> LENGTH: 52
<212> TYPE: PRT
<213> ORGANISM: Homo sapiens

<400> SEQUENCE: 1237

Phe Ser Thr Ala Arg Glu Asn Leu Ser Asp Ala Ser Leu Gln Asn Ala
1               5                   10                  15

Arg Gln Val Phe Ser Glu Ile Glu Asp Ser Thr Lys Gln Val Phe Ser
            20                  25                  30

Lys Val Leu Phe Lys Ser Asn Glu His Ser Asp Gln Leu Thr Arg Glu
        35                  40                  45

Glu Asn Thr Ala
    50

<210> SEQ ID NO 1238
<211> LENGTH: 9
<212> TYPE: PRT
<213> ORGANISM: Homo sapiens

<400> SEQUENCE: 1238

Phe Ser Thr Ala Arg Glu Asn Thr Ala
1               5

<210> SEQ ID NO 1239
<211> LENGTH: 52
<212> TYPE: PRT
<213> ORGANISM: Homo sapiens

<400> SEQUENCE: 1239

Phe Ser Thr Ala Arg Glu Lys Val Ser Asp Ala Ser Leu Gln Asn Ala
1               5                   10                  15

Arg Gln Val Phe Ser Glu Ile Glu Asp Ser Thr Lys Gln Val Phe Ser
            20                  25                  30

Lys Val Leu Phe Lys Ser Asn Glu His Ser Asp Gln Leu Thr Arg Glu
        35                  40                  45

Glu Asn Thr Ala
    50

<210> SEQ ID NO 1240
<211> LENGTH: 56
<212> TYPE: PRT
<213> ORGANISM: Homo sapiens

<400> SEQUENCE: 1240

Phe Ser Thr Ala Arg Glu Lys Lys Ser Val Gln Val Ser Asp Ala Ser
1               5                   10                  15

Leu Gln Asn Ala Arg Gln Val Phe Ser Glu Ile Glu Asp Ser Thr Lys
            20                  25                  30

Gln Val Phe Ser Lys Val Leu Phe Lys Ser Asn Glu His Ser Asp Gln
        35                  40                  45

Leu Thr Arg Glu Glu Asn Thr Ala
    50                  55

<210> SEQ ID NO 1241
<211> LENGTH: 40
<212> TYPE: PRT
<213> ORGANISM: Homo sapiens

<400> SEQUENCE: 1241

Phe Ser Thr Ala Arg Gln Val Phe Ser Glu Ile Glu Asp Ser Thr Lys
```

-continued

```
1               5               10              15

Gln Val Phe Ser Lys Val Leu Phe Lys Ser Asn Glu His Ser Asp Gln
            20              25              30

Leu Thr Arg Glu Glu Asn Thr Ala
        35              40

<210> SEQ ID NO 1242
<211> LENGTH: 52
<212> TYPE: PRT
<213> ORGANISM: Homo sapiens

<400> SEQUENCE: 1242

Phe Ser Thr Ala Ser Val Gln Val Ser Asp Ala Ser Leu Gln Asn Ala
1               5               10              15

Arg Gln Val Phe Ser Glu Ile Glu Asp Ser Thr Lys Gln Val Phe Ser
            20              25              30

Lys Val Leu Phe Lys Ser Asn Glu His Ser Asp Gln Leu Thr Arg Glu
        35              40              45

Glu Asn Thr Ala
    50

<210> SEQ ID NO 1243
<211> LENGTH: 4
<212> TYPE: PRT
<213> ORGANISM: Homo sapiens

<400> SEQUENCE: 1243

Arg Glu Asn Leu
1

<210> SEQ ID NO 1244
<211> LENGTH: 5
<212> TYPE: PRT
<213> ORGANISM: Homo sapiens

<400> SEQUENCE: 1244

Arg Glu Asn Leu Ser
1               5

<210> SEQ ID NO 1245
<211> LENGTH: 6
<212> TYPE: PRT
<213> ORGANISM: Homo sapiens

<400> SEQUENCE: 1245

Arg Glu Asn Leu Ser Arg
1               5

<210> SEQ ID NO 1246
<211> LENGTH: 7
<212> TYPE: PRT
<213> ORGANISM: Homo sapiens

<400> SEQUENCE: 1246

Arg Glu Asn Leu Ser Arg Tyr
1               5

<210> SEQ ID NO 1247
<211> LENGTH: 15
<212> TYPE: PRT
<213> ORGANISM: Homo sapiens
```

-continued

<400> SEQUENCE: 1247

```
Arg Glu Asn Leu Ser Arg Tyr Gln Met Leu His Tyr Lys Thr Gln
1               5               10              15
```

ANTI-CANCER VACCINES AND RELATED THERAPY

This application is the § 371 U.S. National Stage of International Application No. PCT/EP2021/061184, filed Apr. 28, 2021, which was published in English under PCT Article 21(2), which in turn claims priority from GB 2006254.3 filed 28 Apr. 2020, the contents and elements of which are herein incorporated by reference for all purposes. This application contains a sequence listing as part of the description. The sequences set forth in the sequence listing form part of the present description just as if each of the amino acid sequences and nucleotide sequences of the sequence listing had been individually set forth in the main body of the description. The Sequence Listing is submitted as an ST.25 (.txt) file in the form of the file named 6947-109208-01 ST25, which was created on Oct. 27, 2022, and is 197,695 bytes, which is incorporated by reference herein.

FIELD OF THE INVENTION

The present invention relates to products and methods for the treatment of certain cancers. In particular, vaccine-based therapy for the prevention or treatment of drug resistant cancers is disclosed.

BACKGROUND TO THE INVENTION

Defects in genes that control homologous recombination (HR) DNA repair, such as BRCA1, BRCA2, RAD51C, RAD51D and PALB2, are common in cancer and are enriched in high grade serous ovarian cancers (HGSOC (Cancer Genome Atlas Research, 2011)), triple-negative breast cancer (TNBC (Cancer Genome Atlas, 2012; Staaf et al., 2019)) castrate resistant metastatic prostate cancer (Grasso et al., 2012) and pancreatic cancer (Bailey et al., 2016; Holter et al., 2015; Waddell et al., 2015). Following the pre-clinical identification of synthetic lethality between BRCA1/2-mutation and poly ADP ribose polymerase (PARP) PARP inhibitors (PARPi) (Lord and Ashworth, 2016, 2017), a number of clinical trials demonstrated that PARPi, as well as platinum, are effective in patients with either germ-line or somatic HR gene mutations, leading to the approval of four different PARPi for the treatment of HR-defective breast or ovarian cancers, and the increased use of platinum in a similar clinical context (Alsop et al., 2012; Lord and Ashworth, 2017; Tutt, 2018; Tutt et al., 2018).

Platinum salts and PARPi are now widely used to treat cancers with mutations in HR genes, including BRCA1 and BRCA2 (Alsop et al. 2012; Lord and Ashworth 2017; Tutt et al. 2018). Resistance to these agents frequently emerges, especially in the advanced disease setting and, in cases where the original pathogenic BRCA1/2 mutation causes a frameshift, is often via secondary, or reversion, mutations that restore the native reading frame of the mutated gene (Edwards et al. 2008; Sakai et al. 2008; Lin et al. 2019).

There remains an unmet need for therapies that prevent or treat drug resistant cancers, including the growing population of PARPi or platinum salt resistant cancers caused by reversion mutations. The present invention addresses these and other needs, and provides related advantages as described herein.

BRIEF DESCRIPTION OF THE INVENTION

Broadly, the present invention relates to cancer treatment. The present inventors have surprisingly found that homologous recombination (HR) deficient cancers that acquire PARP inhibitor resistance or platinum resistance by development of reversion mutations in genes that encode (HR) DNA repair proteins, such as BRCA1, BRCA2, PALB2, CDK12, RAD51B, RAD51C and RAD51D, frequently encode neoantigen sequence by virtue of regions of out-of-frame amino acid sequence. MHC presentation predictor tools indicate that the neoantigen sequence is capable of eliciting an immune response that opens the door to novel and effective immunotherapy for the cancer. In particular, anti-cancer vaccines based on the neoantigen encoded by the reversion mutation (or encoded by the primary mutation and stabilised by the reversion mutation) and/or engineered T cells that recognise the neoantigen may be used to treat the cancer, including by preventing or reversing acquisition of PARP inhibitor resistance or platinum resistance.

Accordingly, in a first aspect of the invention, there is provided an anti-cancer vaccine comprising: (i) at least one peptide comprising the amino acid sequence of a neoantigen encoded by a mutant HR DNA repair gene selected from the group: BRCA1, BRCA2, PALB2, CDK12, RAD51B, RAD51C and RAD51D, wherein said mutant gene comprises a reversion mutation; and/or (ii) at least one polynucleotide encoding the at least one peptide of (i).

In some embodiments the neoantigen is encoded by a portion of the mutant gene comprising the reversion mutation.

In some embodiments the neoantigen is encoded by a portion of the mutant gene comprising a primary mutation (e.g. a truncation mutation). Expression of the neoantigen sequence may be stabilised by the presence of a reversion mutation in the gene. Neoantigen sequence encoded by primary mutations that are stabilised by a reversion mutation are considered particularly attractive targets for vaccine use because such neoantigen sequences are more likely to reoccur between patients with the same or similar primary mutations, thereby offering potentially greater therapeutic utility across a range of patients (e.g. patients having the same primary mutation, but different reversion mutations).

In some embodiments the neoantigen may be associated with a common founder mutation and comprise a peptide of 8-12 amino acids derived from the following sequences, including at least some of the underlined sequence (the out-of-frame sequence) and potentially including some additional flanking sequence:

BRCA1:c.185delAG [aka 68_69delAG]—these names may be used interchangeably.

```
Downstream:
                                    (SEQ ID NO: 1223)
         NVINAMQKILVSHLSGVDQGTCLHKV.
```

Note that there is no upstream sequence for this mutation due to the stop codon position.

BRCA1:c.5382insC [aka 5266insC or dupC].

```
Upstream:
                                    (SEQ ID NO: 1224)
KSMILKSEEMWSMEETTKVQSEQENPQDRKIFRGLE.

Downstream:
                                    (SEQ ID NO: 1225)
HQGPKRARESPGQKDLQGARNLLLWALHQHAHRSTGMDGTAVWCFCGEGA

FIIHPWHRCPPNCGCAARCLDRGQWLPCNWADV.
```

BRCA2:c.6174delT [aka 5946delT].

```
Upstream:
                              (SEQ ID NO: 1226)
HSKGKSVQVSDAS.

Downstream:
                              (SEQ ID NO: 1227)
ANTCGIFSTARENLSRYQMLHYKTQDKCFLK
```

In some embodiments the neoantigen comprises or consists of an amino acid sequence set forth in any one of SEQ ID Nos: 1-1218, 1223-1227, and/or 1231-1247.

In some embodiments the neoantigen comprises or consists of an amino acid sequence set forth in any one of SEQ ID Nos: 1-89.

In some embodiments the neoantigen comprises or consists of an amino acid sequence selected from the group consisting of: the peptide sequences set forth in Table 5 and Table 6.

In some embodiments the neoantigen comprises or consists of an amino acid sequence selected from the group consisting of the peptide sequences set forth in Table 5. These neoantigen sequence, being encoded by primary mutations (and stabilised by reversion mutations) are considered particularly attractive targets for vaccine use because such neoantigen sequences are more likely to reoccur between patients with the same or similar primary mutations, thereby offering potentially greater therapeutic utility across a range of patients (e.g. patients having the same primary mutation, but different reversion mutations). The primary mutations may be common founder mutations. However, it is also contemplated that the primary mutation may be a less common primary mutation.

Using the NetMHCpan 4.0 algorithm (Jurtz et al., 2017), the neoantigen sequences (see, e.g., those set forth in Tables 5 and 6) were predicted to be presented by the MHC in a significant proportion of individuals (in some cases at least 75% of individuals taking into account the population frequencies of different HLA types) making them particularly preferred for vaccine therapy. However, in some embodiments the vaccine may form part of a personalized medicine strategy, wherein the neoantigen sequence is determined by sequencing a mutant HR DNA repair gene selected from the group: BRCA1, BRCA2, PALB2, CDK12, RAD51B, RAD51C and RAD51D from a tumour sample, or from circulating tumour DNA, from a subject and then tailoring the vaccine to that same subject by employing a neoantigen sequence found to be present in the tumour of the subject. In such cases, it is the predicted or actual degree of MHC presentation by the HLA allotype of the subject concerned that is relevant rather than a population-level degree of MHC presentation.

In some embodiments the neoantigen comprises the amino acid sequence: RENLSRYQMLHYKTQ (SEQ ID NO: 1247). Peptides derived from this neoantigen sequence (potentially also including some of the 5' flanking wild type BRCA2 sequence), which is encoded by patients with observed reversion mutations, were found to have a high immunogenicity as measured by best predicted rank among possible neoantigens. In particular embodiments, the neoantigen peptide may comprise, for example, 1, 2, 3, 4 or more amino acids encoded by 5' flanking wild-type BRCA2 sequence (see FIGS. 4B and 4C) (e.g. A, TA, STA, etc. may form additional sequence N-terminal of the amino acid sequence of SEQ ID NO: 1247. Peptides derived from the neoantigen of SEQ ID NO: 1247 have strong binding affinity predicted for many HLA alleles, indicating that they are likely to be presented to the immune system. This neoantigen is encoded by out-of-frame protein sequence following the BRCA2:c.5946delT founder mutation and may be of use in treating cancers associated with this mutation.

In some embodiments the vaccine comprises a DNA or RNA sequence encoding said neoantigen. The DNA or RNA may be single-stranded or double-stranded. The RNA sequence may be mRNA. In some cases the DNA or RNA sequence is provided in the form of a vector, such as a viral vector. In particular, the vaccine may comprise an oncolytic virus. Examples of oncolytic viruses include: viruses based on herpes simplex virus-1 (HSV-1), such as Talimogene laherparepvec; an oncolytic adenovirus; and an oncolytic adeno-associated virus (AAV).

In some embodiments the vaccine is in the form of a plurality of dendritic cells (DCs) that have been pulsed with the at least one peptide comprising the neoantigen. The DCs are capable of presenting the neoantigen to one or more T cells when administered to a subject. The DCs may be cultured ex vivo, optionally expanded and/or matured prior to being contacted with the neoantigen peptide(s). Injection of the DCs may then stimulate T cells in vivo and thereby facilitate the development of an immune response against the tumour.

The neoantigen is typically an MHC class I restricted peptide. Such MHC I binding peptides are typically 8-13 amino acids in length. However, MHC class II restricted peptides (typically longer, such as 15-24 amino acids in length) are also specifically contemplated herein.

The neoantigen may have a sequence that is predicted to be presented by at least 10%, 25%, 50% or at least 75% of the HLA-A, HLA-B and/or HLA-C allotypes of the 1000 Genomes dataset as disclosed by Gourraud et al., 2014, PLoS ONE, Vol. 9, e97282.

The neoantigen may have a sequence that is predicted to be presented by MHC class I by an MHC class I predictor. The skilled person will be aware of a number of algorithms that are widely used to predict whether a peptide sequence will be displayed by MHC class I. These include: NNAlign-2.0, NetMHC, NetMHCpan and NetMHCpan-4.0. Preferably the neoantigen sequence is predicted to be displayed by MHC class I by NetMHCpan-4.0 (Jurtz et al., (2017) J. Immunol., Vol. 199, pp. 3360-3368). NetMHCpan-4.0 is a neural network that was trained on binding affinity and eluted ligand data leveraging the information from both data types. Large-scale benchmarking has shown that NetMHC-pan-4.0 demonstrates enhanced predicted performance compared with other methods when it comes to identification of naturally processed ligands, cancer neoantigens and T cell epitopes. In some cases the neoantigen has a sequence that exhibits a best rank (BR) score of 0.5 or less using the NetMHCpan-4.0 neural network predictor.

In some the vaccine comprises 2, 3, 4, 5, 6, 7, 8, 9, 10 or more different neoantigens and/or polynucleotide encoding the different neoantigens (for example the neoantigen sequences set forth in SEQ ID Nos: 1-1218, 1228-1247, Table 5 and Table 6). In some cases the plurality of different neoantigens may be different neoantigens that are encoded by different HR DNA repair gene mutations (e.g. a gene selected from the group: BRCA1, BRCA2, PALB2, CDK12, RAD51B, RAD51C and RAD51D, wherein said gene comprises a reversion mutation). In some cases, the plurality of different neoantigens may combine at least one neoantigen that is encoded by a BRCA1, BRCA2, PALB2, CDK12, RAD51B, RAD51C or RAD51D reversion mutations together with a neoantigen encoded by a different gene. Combining two or more (such as several, e.g. 3, 4, 5, 6, 7, 8, 9, 10 or more) neoantigens in a single vaccine ("multiepitope vaccination") may be employed to increase the efficacy of the vaccine, including by combating the problems of epitope loss by malignant cells and/or an immune-suppressive tumour microenvironment.

In some cases the anti-cancer vaccine of the invention further comprises at least one adjuvant. In some cases the adjuvant may be a toll-like receptor (TLR) agonist, such as an agonist of TLR3 (e.g. polyinosinic-polycytidylic acid), TLR4 (monophos-phoryl lipid A), TLR7 (imiquimod), TLR8 (resiquimod) and TLR9 (CpG oligodeoxynucleotide). In some cases the adjuvant may comprise a monoclonal antibody that targets the neoantigen to DCs (e.g. anti-DEC205. In some cases the vaccine may be delivered in the form of or in conjunction with a nanoparticle, such as a nanoparticle that targets the neoantigen to antigen presenting cells.

In a second aspect the present invention provides an engineered T cell that recognises a neoantigen encoded by a mutant HR DNA repair gene selected from the group: BRCA1, BRCA2, PALB2, CDK12, RAD51B, RAD51C and RAD51D. The reversion mutation and/or neoantigen may be as defined in connection with the first aspect of the invention. In particular, the neoantigen may have an amino acid sequence set forth in any one of SEQ ID Nos: 1-1218, such as for example, any one of SEQ ID Nos: 1-89. In particular, the neoantigen may have an amino acid sequence as set forth for a peptide of Table 5 or Table 6. In some cases the engineered T cell is selected from: a chimeric antigen receptor T cell (CAR-T), an engineered T cell receptor (TCR) T cell and a neoantigen-reactive T cell (NAR-T).

In a third aspect the present invention provides the anti-cancer vaccine of the first aspect of the invention or the engineered T cell of the second aspect of the invention for use in medicine.

In a fourth aspect the present invention provides the anti-cancer vaccine of the first aspect of the invention or the engineered T cell of the second aspect of the invention for use in a method of treatment of a proliferative disorder in a mammalian subject.

In some embodiments the proliferative disorder is a cancer that exhibits a homologous recombination (HR) defect. In particular, a mutation in one or more of BRCA1, BRCA2, CDK12, RAD51B, RAD51C, RAD51D and PALB2. In some cases, the mutation may be a truncation mutation.

In some embodiments the proliferative disorder is a cancer, such as a solid tumour. The proliferative disorder may, in some embodiments, be selected from: high grade serous ovarian cancer (HGSOC), triple-negative breast cancer (TNBC), castrate resistant metastatic prostate cancer and pancreatic cancer.

In some embodiments the method of treatment comprises the inhibition or prevention of development of, or reduction or reversal of tumour resistance to PARP inhibitor therapy and/or platinum therapy.

In some embodiments the subject has a mutation in the BRCA1 gene, BRCA2 gene, PALB2 gene, CDK12 gene, RAD51B gene, RAD51C gene and/or RAD51D gene. In particular, the mutation may be a somatic mutation. A subject having a germ line mutation (usually heterozygous) in the BRCA1 gene, BRCA2 gene, PALB2 gene, CDK12 gene, RAD51B gene, RAD51C gene and/or RAD51D gene, may potentially have central immune tolerance to the out-of-frame sequence associated with that mutation. This sequence would theoretically be shared with the primary tumor (e.g. in cases of somatic BRCA mutation) or with heterozygous normal cells in the body in carriers of BRCA germ line mutations, and thus may have previously been exposed to the immune system during development of central tolerance. Additionally, it is possible that stimulation of an immune response against reversions using a vaccine might result in development of auto-immunity in BRCA carriers in cases where the neoantigen sequence is shared between reversion and pathogenic mutations. For these reasons, in some embodiments the subject may have a somatic mutation in the BRCA1 gene, BRCA2 gene, PALB2 gene, CDK12 gene, RAD51B gene, RAD51C gene and/or RAD51D gene without having that mutation in his or her germ line (i.e. a non-carrier). In other words, a non-carrier subject may in some cases be preferred for vaccine therapy of the present invention owing to the non-carrier subject being less likely to have central tolerance for the out-of-frame sequence and/or less likely to develop possible auto-immune complications.

In some embodiments the BRCA1 mutation, BRCA2 mutation, PALB2 mutation, CDK12 mutation, RAD51B mutation, RAD51C mutation and/or RAD51D mutation is a reversion mutation, optionally wherein the reversion mutation is as set forth in Table 5 or Table 6.

In some embodiments the method of treatment comprises a step of determining whether said BRCA1 mutation, said BRCA2 mutation, said PALB2 mutation, said CDK12 mutation, said RAD51B mutation, RAD51C mutation and/or said RAD51D mutation is present in a tumour of the subject. This may involve analysis (e.g. sequencing) of a DNA or RNA containing sample (e.g. a ctDNA sample) obtained from the subject or if a tumour sample (e.g. biopsy sample) obtained from the subject.

In some embodiments the tumour is determined have a BRCA1 mutation, BRCA2 mutation, PALB2 mutation, CDK12 mutation, RAD51B mutation, RAD51C mutation and/or RAD51D mutation comprising a reversion mutation that encodes and/or causes the mutant gene to express a gene product comprising a neoantigen amino acid sequence. In particular, the neoantigen amino acid sequence may be as defined in accordance with the first aspect of the invention (e.g. a neoantigen peptide as set forth in Table 5 or Table 6).

In some embodiments the subject is undergoing or is a candidate to undergo therapy with a PARP inhibitor and/or a platinum-based chemotherapeutic.

In some embodiments the method of treatment is a combination therapy that further comprises treatment with an immune checkpoint inhibitor.

In some embodiments the method of treatment is a combination therapy that further comprises treatment with radiotherapy and/or chemotherapy.

In some embodiments the method of treatment is a combination therapy that comprises treatment with both said anti-cancer vaccine and said engineered T cell.

In some embodiments the method of treatment further comprises a step of HLA typing the subject and matching the neoantigen to the HLA allotype of the subject.

In some cases matching the neoantigen to the HLA allotype of the subject comprises a step of predicting MHC class I presentation of the neoantigen sequence by the subject. This may involve use of a computational tool, such as NetMHCpan-4 described in further detail herein.

In a fifth aspect the present invention provides a method for treatment of a proliferative disorder in a mammalian subject in need thereof, comprising administering a therapeutically effective amount of an anti-cancer vaccine of the first aspect of the invention or an engineered T cell of the second aspect of the invention to the subject.

In a sixth aspect, the present invention provide use of an anti-cancer vaccine of the first aspect of the invention or an engineered T cell of the second aspect of the invention in the preparation of a medicament for use in a method of the fifth aspect of the invention.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

FIG. 2—Directionality, hot and cold spots for reversion mutations. A. Scatter plots showing orientation (5'/upstream or 3'/downstream) of all reversions relative to original pathogenic mutation in BRCA1 (left) or BRCA2 (right). The start and end positions of each reversion mutation (i.e. the start and end of deleted regions) are joined by lines; insertions are not shown. All positions are shown in CDS coordinates. In a few cases deletions extend beyond the plot boundaries, denoted by lines without a terminating point. For the majority of pathogenic mutations, reversion mutations do not have a directional bias and are seen both upstream and downstream of the pathogenic mutation. However, for some pathogenic mutations, e.g. BRCA2 c.5946delT and BRCA2:c7355delA, second site reversions are biased to the DNA sequence downstream of the pathogenic mutation. There is some evidence of a hotspot for reversion mutations at BRCA2 position c.750-775 (highlighted in grey) and for a desert at the BRCA2 C-terminus (highlighted in blue). Colours of points and lines denote different studies. B. Conservation of amino acid sequence in BRCA1 (left) and BRCA2 (right) mapped onto CDS position for BRCA1 and BRCA2, defined by conservation scores (see materials and methods) determined by the alignment of 11 mammalian species. Notable peaks of conservation in BRCA2 are seen in the BRC region and the C-terminal OB and TR2 domains. C. Histogram illustrating the frequency of pathogenic mutations in the reversion dataset annotated by CDS position in BRCA1 or BRCA2. Pathogenic mutations are shown in 40-bp bins. Two regions of BRCA2 are highlighted; the candidate reversion hotspot at c.750-775 (grey) and C-terminal region (blue). D. Histogram illustrating the frequency of pathogenic mutations in BRCA1 or BRCA2 in TCGA studies covering breast, ovarian, pancreatic and prostate cancer, plotted as in (C). The distribution of reverting mutations in BRCA1 (shown in (C)) was not significantly different from the distribution of BRCA1 mutations in the TCGA dataset (p=0.21, two-sided Kolmogorov-Smirnov test). The frequency of reversions 3' to CDS position 7500 of BRCA2 was significantly lower than expected frequency based on TCGA mutation data (p=0.003, permutation test). E. Domain structure of BRCA1 and BRCA2 proteins annotated by CDS position. F. Bar chart illustrating the frequency of different pathogenic mutation types in the reversion (lower) and compared to frequency in TCGA data (upper).

FIG. 3—Microhomology usage in reversion mutations. A. Example of a reversion mutation in BRCA2 associated with microhomology (patient 201 from Cruz et al.). The pathogenic G>T substitution mutation (BRCA2 c.145G>T) introduces a premature stop codon (TAA) as shown. The reversion mutation (c.145_168de124) is an in-frame deletion removing the mutated codon (shown in two different alignments). The existence of microhomology at this deletion is illustrated by the ambiguous alignment of the two nucleotides (TA) flanking it—these could be aligned equally well at either end as illustrated. B. Bar chart of reversion events classified by type. Reversions occurring via deletion are more frequent in BRCA2 than in BRCA1. C. Within deletion mutations, the use of microhomology occurs at a similar frequency in BRCA1 and BRCA2. Reversion mutations are plotted as in (B) for deletions only. D. Breakdown of microhomology use at deletions by primary tumour site and gene. E. Deletion sizes are generally larger in BRCA2 reversions (p=0.0036, Wilcoxon rank sum test) with evidence of microhomology use. Total length of deleted sequence is shown for each reversion event, broken down by gene and presence of microhomology. The y-axis is truncated; seven mutations with deletions>140 bp are not shown. F. BRCA2 reversions use longer lengths of microhomology compared to BRCA1. Frequency distribution of length of microhomology used in BRCA1 (red, left—mode 1 bp) compared with BRCA2 (blue, right—mode 2 bp) plotted for all secondary deletions.

FIG. 4—Prediction of HLA-mediated antigen presentation of reversion peptides. A. Percentage of individuals predicted to present at least one neopeptide from out-of-frame sequence associated with the listed pathogenic deletion mutations. This sequence will be shared with reversion mutations to some extent depending on the position of the reversion relative to the pathogenic mutation. Common founder mutations are highlighted. B. Predicted amino acid sequences from BRCA2:c.5946delT [c.6174delT] reversion events showing retention of out-of-frame sequence in many reversion alleles. The predicted protein sequence for each reversion observed for BRCA2:c.5946delT is shown compared to the wild-type (top) and predicted truncated c.5946delT protein sequence (second row). Sequences deriving from translation of out-of-frame coding sequence are shown in the yellow box. Amino acids are shaded based on their alignment to the wild type sequence. C. Computational prediction of HLA (HLA-A, HLA-B, HLA-C) presentation of out-of-frame protein sequences from BRCA2 c.5946delT downstream reversions. Presentation likelihood calculated using NetMHCpan 4.0. The table shows the proportion of individuals in a set of 1,261 from the 1000 genomes project that have an HLA type predicted to present (% rank<0.5) at least one neopeptide (length 8 to 11) associated with the indicated out-of-frame sequence (note that such neopeptides can include one or more WT amino acids upstream of the out-of-frame sequence). D. Percentage of individuals predicted to present at least one neopeptide for reverted protein sequences from all published cases of reversion mutations that encode neopeptides.

FIG. 7—Reversion mutations often occur at a distance from the original mutation, leading to out-of-frame protein sequence. A. Schematic illustrating reversion distance being defined as the minimum distance between the pathogenic and reversion mutation. If the reversion mutation encompasses the pathogenic mutation, the reversion distance will be zero. B. Cumulative frequency distribution of reversion distance (in CDS coordinates) using data from all 231 reversion events.

Figure 1:
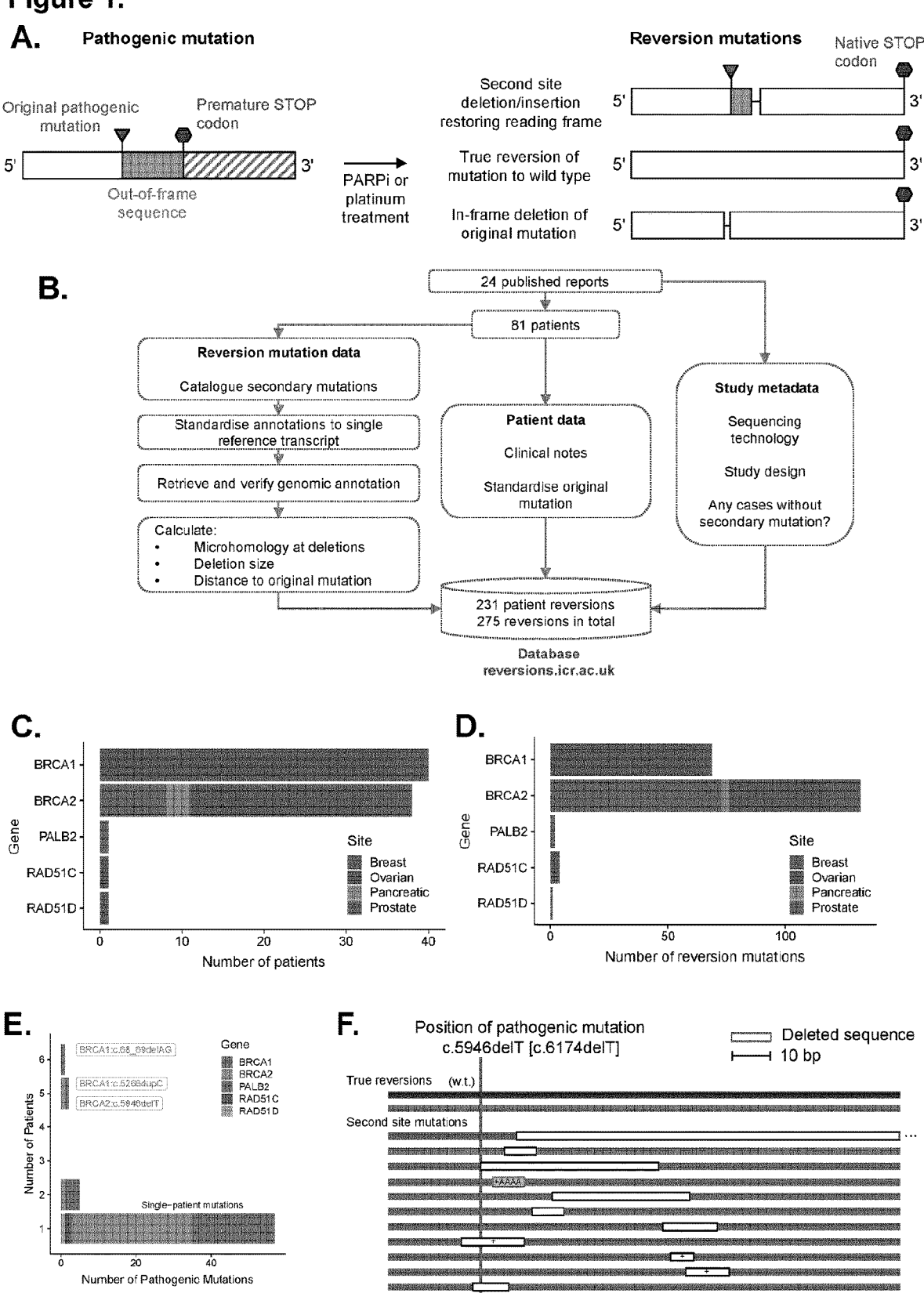
FIG. 1—Collation, annotation and standardisation of HR gene reversion mutations. A. Common architectures of HR gene reversion mutations associated with platinum or PARPi resistance. B. Workflow schematic illustrating the collation, annotation and standardisation of HR gene reversion mutations. C. Bar chart illustrating the primary tumour site in 81 patients with HR gene reversions described in the dataset. Patients are stratified by HR gene and by primary tumour site (see colour key). D. Bar chart illustrating 231 reversion mutations in the dataset, stratified by HR gene and by primary tumour site. E. Bar chart illustrating that the majority of reversion mutations in the dataset arise from patients with different pathogenic mutations. Most patients (80%) had unique pathogenic mutations (annotated as "single-patient" mutations). Reversion cases from multiple patients with common Ashkenazi founder mutations, such as BRCA2:c.6174delT (c.5946delT in standardised nomenclature) and BRCA1:c.185delAG (c.68_69delAG), were also identified. F. Example of unique reversion events observed for multiple patients with a common founder mutation, BRCA2:c.6174delT (c.5496delT), represented on the BRCA2 coding sequence (CDS). Two true reversions to wild-type DNA sequence were observed in two different patients. Second site reversion mutations in other patients are also shown, colored by patient.

Table 1—Studies describing HR-gene reversion mutations in patients collated for this analysis. Some studies not listed in the table reported mutations in cell lines and PDX (Dréan et al., 2017; Ikeda et al., 2003; Sakai et al., 2009; Ter Brugge et al., 2016; Wang et al., 2016). These are included in the database but not the analysis described in this paper.

Table 2—List of cases in collected studies for which reversions were assessed but not identified.

Table 3—NetMHCpan predictions for neopeptides unique to revertant sequences (FIG. 4D).

Table 4—Studies from cBioPortal used for analysis of pathogenic mutations.

Table 5—Selected primary mutations encoding neopeptides. The peptide sequence of each neoantigen is shown together with the number of individuals presenting the peptide sequence, the primary mutations encoding the peptide sequence and the number of primary mutations that encode the peptide sequence.

Table 6—Selected reversion mutations encoding neopeptides. The peptide sequence of each neoantigen is shown together with the number of individuals presenting the peptide sequence, the reversion mutations encoding the peptide sequence and the number of reversion mutations that encode the peptide sequence.

Table 7—Presentation scores of specified reversion mutations. "HLA presentation likelihood" shows the percentage of 1000 genomes individuals.

Table 8—Predicted binding capacity of the predicted mutations.

DETAILED DESCRIPTION OF THE INVENTION

In describing the present invention, the following terms will be employed, and are intended to be defined as indicated below.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

BRCA1

BRCA1 DNA repair associated or BRCA1 gene encodes a nuclear phosphoprotein that plays a role in maintaining genomic stability, and it also acts as a tumour suppressor. The human BRCA1 gene has the NCBI Gene ID: 672. The genomic sequence of BRCA1 is disclosed at NCBI Reference sequence NC_000017.11>NC_000017.11:c43125364-43044295 *Homo sapiens* chromosome 17, GRCh38.p13 Primary Assembly. LOCUS NC_000017 81070 bp DNA linear CON 2 Mar. 2020 DEFINITION *Homo sapiens* chromosome 17, GRCh38.p13 Primary Assembly. ACCESSION NC_000017 REGION: complement (43044295 . . . 43125364) VERSION NC_000017.11. The entire contents of which are incorporated herein by reference. The transcript for BRCA1 is disclosed at NM_007294.3;

BRCA2

BRCA2 DNA repair associated or BRCA2 gene encodes a DNA repair protein. The BRCA2 gene has the NCBI Gene ID: 675. The genomic sequence of BRCA2 is disclosed at NCBI Reference sequence >NC_000013.11:32315508-32400268 *Homo sapiens* chromosome 13, GRCh38.p13 Primary Assembly. LOCUS NC_000013 84761 bp DNA linear CON 2 Mar. 2020 DEFINITION *Homo sapiens* chromosome 13, GRCh38.p13 Primary Assembly. ACCESSION NC_000013 REGION: 32315508.32400268. VERSION NC_000013.11. The entire contents of which are incorporated herein by reference. The transcript for BRCA2 is disclosed at NM_000059.3

PALB2

Partner and localizer of BRCA2 (PALB2) is protein which in humans is encoded by the PALB2 gene. The PALB2 gene has the NCBI Gene ID: 79728. The genomic sequence of PALB2 is disclosed at NCBI reference sequence NG_007406 38196 bp DNA linear PRI 3 Jan. 2020 DEFINITION *Homo sapiens* partner and localizer of BRCA2 (PALB2), RefSeqGene (LRG_308) on chromosome 16 ACCESSION NG_007406 REGION: 5001 . . . 43196 VERSION NG_007406.1. The entire contents of which are incorporated herein by reference. The transcript for PALB2 is disclosed at NM_024675.4.

CDK12

CDK12 cyclin-dependent kinase 12 (CDK12) is a protein which in humans is encoded by the CDK12 gene. The CDK12 gene has the NCBI Gene ID: 51755. Reversion mutations in the CDK12 gene have been described in Fu et al AACR Meeting 2021, Proceedings of the 112th Annual Meeting of the American Association for Cancer Research; 2021 Apr. 10-15. Philadelphia (Pa.): AACR; 2021. Abstract 25 in session MS.CL01.01—Biomarkers (incorporated herein by reference).

RAD51B

RAD51 paralog B is encoded by the RAD51B gene having the NCBI Gene ID: 5890. Reversion mutations in the RAD51B gene have been described in L'heureux et al. Clin Cancer Res 2020 DOI: 10.1158/1078-0432.CCR-19-4121 (incorporated herein by reference).

RAD51C

RAD51 paralog C (RAD51C) is protein which in humans is encoded by the RAD51C gene. The RAD51C gene has the NCBI Gene ID: 5889. The genomic sequence of RAD51C is disclosed at NCBI reference sequence NG_023199 41770 bp DNA linear PRI 5 Aug. 2019 DEFINITION *Homo sapiens* RAD51 paralog C (RAD51C), RefSegGene (LRG_314) on chromosome 17. ACCESSION NG_023199 REGION: 4972 . . . 46741 VERSION NG_023199.1. The entire contents of which are incorporated herein by reference. The transcript for RAD51C is disclosed at NM_002876.3.

RAD51D

RAD51 paralog D (RAD51D) is protein which in humans is encoded by the RAD51D gene. The RAD51D gene has the NCBI Gene ID: 5892. The genomic sequence of RAD51D is disclosed at NCBI reference sequence NG_031858 20078 bp DNA linear PRI 4 Aug. 2019 DEFINITION *Homo sapiens* RAD51 paralog D (RAD51D), RefSegGene (LRG_516) on chromosome 17. ACCESSION NG_031858 REGION: 5001 . . . 25078 VERSION NG_031858.1. The entire contents of which are incorporated herein by reference. The transcript for RAD51D is disclosed at NM_001142571.2

Sample and Mutation Detection

A sample or "test sample" as used herein may be a cell or tissue sample (e.g. a biopsy), a biological fluid, an extract (e.g. a protein or DNA extract obtained from the subject). In particular, the sample may be a tumour sample. The sample may be one which has been freshly obtained from the subject or may be one which has been processed and/or stored prior to making a determination (e.g. frozen, fixed or subjected to one or more purification, enrichment or extractions steps). When the mutation (e.g. a BRCA1, BRCA2, PALB2, CDK12, RAD51B, RAD51C or RAD51D mutation, whether heterozygous or homozygous) is a germline mutation it may be convenient to use a non-tumour sample (e.g. a cheek swab, blood sample, hair sample or similar DNA-containing sample) to determine the presence or absence of a mutation. When the mutation (e.g. a BRCA1, BRCA2, PALB2, CDK12, RAD51B, RAD51C or RAD51D mutation) is a somatic mutation, for example a mutation that has triggered and/or developed with the cancer, the sample will generally be obtained directly from the tumour, obtained from circulating cancer cells and/or circulating tumour DNA (ctDNA). Techniques for enriching a blood or plasma sample for circulating tumour DNA (e.g. based on fragment size) have been described. Moreover, sequencing techniques for identifying cancer-associated mutations in ctDNA have been described (e.g. based on digital PCR, targeted deep sequencing, nested real-time PCR, and the like). Mutation detection may, for example, comprise sequence alignment between the BRCA1, BRCA2, PALB2, CDK12, RAD51B, RAD51C or RAD51D gene sequence determined for the tumour and the corresponding reference gene sequence, followed by a step of variant calling in which sequence differences (including substitutions, insertions or deletions) are identified. Optionally the corresponding amino acid sequence of the polypeptide encoded by the mutant BRCA1, BRCA2, PALB2, CDK12, RAD51B, RAD51C or RAD51D gene may be derived and used to determine the presence of and/or identity of a neoantigen sequence in the tumour of the subject.

Thus, tumour sequencing, including ctDNA sequencing, may be employed for vaccine selection and/or cell therapy selection, including personalised vaccine and/or persona-lised cell therapy. Mutation detection based on ctDNA has the advantage of being non-invasive ("liquid biopsy"). In some cases a blood sample may be a source of tumour DNA in the form of plasma-derived ctDNA and a source of germ line DNA, e.g., in the form of buffy coat (comprising leukocytes and platelets). The germ line DNA sequence may be compared with the ctDNA sequence to identify somatic mutations in HR DNA repair genes, such as BRCA1, BRCA2, PALB2, CDK12, RAD51B, RAD51C and RAD51D. Additionally or alternatively, ctDNA-derived sequence reads may be aligned to a wild-type reference sequence to identify mutations in one or more of said HR DNA repair genes. In some cases, a subject may be a carrier of a mutation in in one or more of said HR DNA repair genes, e.g. having a germ line mutation in one or more of the BRCA1, BRCA2, PALB2, CDK12, RAD51B, RAD51C and RAD51D genes. The tumour cells of such a carrier subject may comprise the same germ line mutation(s) and/or dif-ferent or additional mutations. In some cases, the subject may be a non-carrier of a mutation in in one or more of said HR DNA repair genes, i.e. having a somatic mutation, but not having germ line mutation in one or more of the BRCA1, BRCA2, PALB2, CDK12, RAD51B, RAD51C and RAD51D genes.

Chimeric Antigen Receptors

Chimeric Antigen Receptors (CARs) are recombinant receptor molecules which provide both antigen-binding and T cell activating functions. CAR structure and engineering is reviewed, for example, in Dotti et al., Immunol Rev (2014) 257(1), which is hereby incorporated by reference in its entirety.

CARs comprise an antigen-binding domain linked to a transmembrane domain and a signalling domain. An optional hinge domain may provide separation between the antigen-binding domain and transmembrane domain, and may act as a flexible linker.

The antigen-binding domain of a CAR may be based on the antigen-binding region of an antibody which is specific for the antigen to which the CAR is targeted. For example, the antigen-binding domain of a CAR may comprise amino acid sequences for the complementarity-determining regions (CDRs) of an antibody which binds specifically to the target protein. The antigen-binding domain of a CAR may com-prise or consist of the light chain and heavy chain variable region amino acid sequences of an antibody which binds specifically to the target protein. The antigen-binding domain may be p7rovided as a single chain variable frag-ment (scFv) comprising the sequences of the light chain and heavy chain variable region amino acid sequences of an antibody. Antigen-binding domains of CARs may target antigen based on other protein:protein interaction, such as ligand:receptor binding; for example an IL-13Rα2-targeted CAR has been developed using an antigen-binding domain based on IL-13 (see e.g. Kahlon et al. 2004 Cancer Res 64(24): 9160-9166).

The transmembrane domain is provided between the antigen-binding domain and the signalling domain of the CAR. The transmembrane domain provides for anchoring the CAR to the cell membrane of a cell expressing a CAR, with the antigen-binding domain in the extracellular space, and signalling domain inside the cell. Transmembrane domains of CARs may be derived from transmembrane region sequences for CD3-ζ, CD4, CD8 or CD28.

The signalling domain allows for activation of the T cell. The CAR signalling domains may comprise the amino acid sequence of the intracellular domain of CD3-ζ, which pro-vides immunoreceptor tyrosine-based activation motifs (ITAMs) for phosphorylation and activation of the CAR-expressing T cell. Signalling domains comprising sequences of other ITAM-containing proteins have also been employed in CARs, such as domains comprising the ITAM containing region of FcγRI (Haynes et al., 2001 J Immunol 166(1):182-187). CARs comprising a signalling domain derived from the intracellular domain of CD3-ζ are often referred to as first generation CARs.

Signalling domains of CARs may also comprise co-stimulatory sequences derived from the signalling domains of co-stimulatory molecules, to facilitate activation of CAR-expressing T cells upon binding to the target protein. Suit-able co-stimulatory molecules include CD28, OX40, 4-1BB, ICOS and CD27. CARs having a signalling domain includ-ing additional co-stimulatory sequences are often referred to as second generation CARs.

In some cases CARs are engineered to provide for costimulation of different intracellular signalling pathways. For example, signalling associated with CD28 co-stimula-tion preferentially activates the phosphatidylinositol 3-ki-nase (P13K) pathway, whereas the 4-1BB-mediated signal-ling is through TNF receptor associated factor (TRAF) adaptor proteins. Signalling domains of CARs therefore sometimes contain co-stimulatory sequences derived from signalling domains of more than one co-stimulatory mol-ecule. CARs comprising a signalling domain with multiple co-stimulatory sequences are often referred to as third generation CARs.

An optional hinge region may provide separation between the antigen-binding domain and the transmembrane domain, and may act as a flexible linker. Hinge regions may be flexible domains allowing the binding moiety to orient in different directions. Hinge regions may be derived from IgG1 or the $CH_2CH_3$ region of immunoglobulin.

Neoantigen Reactive T Cells (NAR-T)

A neoantigen is a newly formed antigen that has not been previously presented to the immune system. The neoantigen is tumour-specific, which arises as a consequence of a mutation within a cancer cell and is therefore not expressed by healthy (i.e. non-tumour) cells.

The neoantigen may be caused by any non-silent mutation which alters a protein expressed by a cancer cell compared to the non-mutated protein expressed by a wild-type, healthy cell. For example, the mutated protein may be a transloca-tion or fusion.

A "mutation" refers to a difference in a nucleotide sequence (e.g. DNA or RNA) in a tumour cell compared to a healthy cell from the same individual. The difference in the nucleotide sequence can result in the expression of a protein which is not expressed by a healthy cell from the same individual. For example, the mutation may be a single nucleotide variant (SNV), multiple nucleotide variants, a deletion mutation, an insertion mutation, a translocation, a missense mutation or a splice site mutation resulting in a change in the amino acid sequence (coding mutation).

The human leukocyte antigen (HLA) system is a gene complex encoding the major histocompatibility complex (MHC) proteins in humans. A neoantigen may be processed to generate distinct peptides which can be recognised by T cells when presented in the context of MHC molecules. A neoantigen presented as such may represent a target for therapeutic or prophylactic intervention in the treatment or prevention of cancer in a subject.

An intervention may comprise an active immunotherapy approach, such as administering an immunogenic composition or vaccine comprising a neoantigen to a subject. Alternatively, a passive immunotherapy approach may be taken, for example adoptive T cell transfer or B cell transfer, wherein a T and/or B cells which recognise a neoantigen are isolated from tumours, or other bodily tissues (including but not limited to lymph node, blood or ascites), expanded ex vivo or in vitro and readministered to a subject.

T cells may be expanded by ex vivo culture in conditions which are known to provide mitogenic stimuli for T cells. By way of example, the T cells may be cultured with cytokines such as IL-2 or with mitogenic antibodies such as anti-CD3 and/or CD28. The T cells may be co-cultured with antigen-presenting cells (APCs), which may have been irradiated. The APCs may be dendritic cells or B cells. The dendritic cells may have been pulsed with peptides containing the identified neoantigen as single stimulants or as pools of stimulating neoantigen peptides. Expansion of T cells may be performed using methods which are known in the art, including for example the use of artificial antigen presenting cells (aAPCs), which provide additional co-stimulatory signals, and autologous PBMCs which present appropriate peptides. Autologous PBMCs may be pulsed with peptides containing neoantigens as single stimulants, or alternatively as pools of stimulating neoantigens.

Engineered T Cell

The cell may be a eukaryotic cell, e.g. a mammalian cell. The mammal may be a human, or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

In some embodiments, the cell may be from, or may have been obtained from, a human subject.

The cell may be a CD4$^+$ T cell or a CD8$^+$ T cell. In some embodiments, the cell is a target protein-reactive CAR-T cell. In embodiments herein, a "target protein-reactive" CAR-T cell is a cell which displays certain functional properties of a T cell in response to the target protein for which the antigen-binding domain of the CAR is specific, e.g. expressed at the surface of a cell. In some embodiments, the properties are functional properties associated with effector T cells, e.g. cytotoxic T cells.

In some embodiments, the engineered T cell may display one or more of the following properties: cytotoxicity to a cell comprising or expressing the target protein; proliferation, increased IFNγ expression, increased CD107a expression, increased IL-2 expression, increased TNFα expression, increased perforin expression, increased granzyme B expression, increased granulysin expression, and/or increased FAS ligand (FASL) expression in response to the target protein, or a cell comprising or expressing the target protein. In some embodiments, the engineered T cell expresses an engineered T cell receptor. For example, the engineered T cell may express a cancer-specific T cell receptor, such as the NY-ESO-1 T cell receptor. In embodiments, the engineered T cell does not express an endogenous T cell receptor. In embodiments, the engineered T cell does not express the immune checkpoint molecule programmed cell death protein 1 (PD-1). In embodiments, the engineered T cell has been engineered to remove the endogenous T cell receptor and/or the immune checkpoint molecule programmed cell death protein 1 (PD-1).

The present invention also provides a method for producing an engineered T cell according to the present invention. In some embodiments, the methods are performed in vitro.

In some embodiments, the engineered T cell further comprises an introduced T cell receptor (e.g. a chimeric antigen receptor) that specifically recognises the neoantigen that is encoded by the BRCA1, BRCA2, PALB2, CDK12, RAD51B, RAD51C or RAD51D reversion mutation and which is expressed on or in proximity to a tumour (e.g. tumour stroma). The present invention also provides methods of introducing an isolated nucleic acid or vector encoding the T cell receptor into the T cell. In some embodiments the isolated nucleic acid or vector is comprised in a viral vector, or the vector is a viral vector. In some embodiments, the method comprises introducing a nucleic acid or vector according to the invention by electroporation.

Compositions

The present invention also provides compositions comprising a vaccine or cell according to the invention.

Vaccines and engineered T cells according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating a vaccine or engineered T cell as described herein; and/or mixing with a pharmaceutically acceptable carrier, adjuvant, excipient or diluent.

Uses of and Methods of Using the Vaccines, Cells and Compositions

The vaccines and engineered T cells and pharmaceutical compositions according to the present invention find use in therapeutic and prophylactic methods. In particular, in the manufacture of a medicament for treating or preventing a disease or disorder.

The present invention also provides a method of treating or preventing a disease or disorder, comprising administering to a subject a therapeutically or prophylactically effective amount of a vaccine or an engineered T cell or pharmaceutical composition according to the present invention.

Administration

Administration of a vaccine or engineered T cell or composition according to the invention is preferably in a "therapeutically effective" or "prophylactically effective" amount, this being sufficient to show benefit to the subject. The actual amount administered, and rate and time-course of administration, will depend on the nature and severity of the disease or disorder. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The vaccines and engineered T cells, compositions and other therapeutic agents, medicaments and pharmaceutical compositions according to aspects of the present invention may be formulated for administration by a number of routes, including but not limited to, parenteral, intravenous, intraarterial, intramuscular, subcutaneous, intradermal, intratu- moural and oral. The vaccine peptides, nucleic acids, vec- tors, cells, composition and other therapeutic agents and therapeutic agents may be formulated in fluid or solid form. Fluid formulations may be formulated for administration by injection to a selected region of the human or animal body, or by infusion to the blood. Administration may be by injection or infusion to the blood, e.g. intravenous or intra- arterial administration.

Administration may be alone or in combination with other treatments, either simultaneously or sequentially dependent upon the condition to be treated.

In some embodiments, treatment with a vaccine or engi- neered T cell or composition of the present invention may be accompanied by other therapeutic or prophylactic interven- tion, e.g. chemotherapy, immunotherapy (including immune checkpoint inhibitor therapy), radiotherapy, surgery, and/or hormone therapy.

In some embodiments the other therapeutic or prophylac- tic intervention may comprise a PARP inhibitor (e.g. one or more of Olaparib, Rucaparib, Niraparib, Talazoparib, Veli- parib, BGB-290 (Pamiparib), CEP 9722 and E7016), an ATR (ataxia-telangiectasia and Rad3 related) inhibitor (e.g. one or more of NU6027, NVP-BEZ235, VE-821, VE-822, AZ20, and AZD6738—see Weber and Ryan, *Pharmacology & Therapeutics,* 2015, Vol. 149, pp. 124-138, incorporated herein by reference), an ATM (ataxia-telangiectasia mutated) inhibitor (e.g. one or more of CP-466722, KU-55933, KU-60019 and KU-559403—see Weber and Ryan, *Pharmacology & Therapeutics,* 2015, Vol. 149, pp. 124-138, incorporated herein by reference), a DNA-depen- dent protein kinase (DNA-PK) inhibitor (e.g. one or more of LY294002, NU7441, KU-0060648—see Mohiuddin and Kang, *Front. Oncol.,* 2019, Vol. 9, 635, doi: 10.3389/ fonc.2019.00635) and/or a DNA polymerase theta (DNA POLQ) inhibitor (e.g. a heterocyclic substituted urea as disclosed in WO2020/030925, incorporated herein by ref- erence and/or a thiazoleurea as disclosed in WO2020/ 030924, incorporated herein by reference).

Simultaneous administration refers to administration of the vaccine, engineered T cell or composition and therapeu- tic agent together, for example as a pharmaceutical compo- sition containing both agents (combined preparation), or immediately after each other and optionally via the same route of administration, e.g. to the same artery, vein or other blood vessel. Sequential administration refers to adminis- tration of one therapeutic agent followed after a given time interval by separate administration of the other agent. It is not required that the two agents are administered by the same route, although this is the case in some embodiments. The time interval may be any time interval.

Chemotherapy and radiotherapy respectively refer to treatment of a cancer with a drug or with ionising radiation (e.g. radiotherapy using X-rays or γ-rays).

The drug may be a chemical entity, e.g. small molecule pharmaceutical, antibiotic, DNA intercalator, protein inhibi- tor (e.g. kinase inhibitor), or a biological agent, e.g. anti- body, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injec- tion, oral, subcutaneous, intradermal or intratumoural.

The chemotherapy may be administered according to a treatment regime. The treatment regime may be a pre- determined timetable, plan, scheme or schedule of chemo- therapy administration which may be prepared by a physi- cian or medical practitioner and may be tailored to suit the patient requiring treatment.

The treatment regime may indicate one or more of: the type of chemotherapy to administer to the patient; the dose of each drug or radiation; the time interval between admin- istrations; the length of each treatment; the number and nature of any treatment holidays, if any etc. For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosf- amide; purine or pyrimidine anti-metabolites such as aza- thiopurine or mercaptopurine; alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camp- tothecins irinotecan and topotecan, or the type II topoi- somerase inhibitors amsacrine, etoposide, etoposide phos- phate, teniposide; antitumour antibiotics (e.g. anthracyline antibiotics) such as dactinomycin, doxorubicin (Adriamy- cin™), epirubicin, bleomycin, rapamycin; antibody based agents, such as anti-PD-1 antibodies, anti-PD-L1 antibodies, anti-TIM-3 antibodies, anti-CTLA-4, anti-4-1BB, anti- GITR, anti-CD27, anti-BLTA, anti-OX43, anti-VEGF, anti- TNFα, anti-IL-2, antiGpIIb/IIIa, anti-CD-52, anti-CD20, anti-RSV, anti-HER2/neu(erbB2), anti-TNF receptor, anti- EGFR antibodies, monoclonal antibodies or antibody frag- ments, examples include: cetuximab, panitumumab, inflix- imab, basiliximab, bevacizumab (Avastin®), abciximab, daclizumab, gemtuzumab, alemtuzumab, rituximab (Mabthera®), palivizumab, trastuzumab, etanercept, adali- mumab, nimotuzumab; EGFR inhibitors such as erlotinib, cetuximab and gefitinib; anti-angiogenic agents such as bevacizumab (Avastin®); cancer vaccines such as Sipuleu- cel-T (Provenge®).

Further chemotherapeutic drugs may be selected from: a PARP inhibitor (e.g. one or more of Olaparib, Rucaparib, Niraparib, Talazoparib, Veliparib, BGB-290 (Pamiparib), CEP 9722 and E7016), an ATR (ataxia-telangiectasia and Rad3 related) inhibitor (e.g. one or more of NU6027, NVP-BEZ235, VE-821, VE-822, AZ20, and AZD6738— see Weber and Ryan, *Pharmacology & Therapeutics,* 2015, Vol. 149, pp. 124-138, incorporated herein by reference), an ATM (ataxia-telangiectasia mutated) inhibitor (e.g. one or more of CP-466722, KU-55933, KU-60019 and KU-559403—see Weber and Ryan, *Pharmacology & Thera- peutics,* 2015, Vol. 149, pp. 124-138, incorporated herein by reference), a DNA-dependent protein kinase (DNA-PK) inhibitor (e.g. one or more of LY294002, NU7441, KU-0060648—see Mohiuddin and Kang, Front. Oncol., 2019, Vol. 9, 635, doi: 10.3389/fonc.2019.00635) and/or a DNA polymerase theta (DNA POLQ) inhibitor (e.g. a het- erocyclic substituted urea as disclosed in WO2020/030925, incorporated herein by reference and/or a thiazoleurea as disclosed in WO2020/030924, incorporated herein by reference).

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femora®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleeve™, Gliadel® Wafer, Goserelin, Granulocyte—Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin—2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Immune Checkpoint Inhibitor

Immune checkpoint inhibitors include inhibitors of PD-1 (e.g. Nivolumab, Pembrolizumab and BGB-A317), inhibitors of PD-L1 (e.g. atezolizumab, avelumab and durvalumab) and inhibitors of CTLA-4 (e.g. ipilimumab). As described herein, treatment with immune checkpoint inhibitor therapy is expected to be particularly beneficial for cancers that have one or more mutant HR DNA repair genes (e.g. BRCA1, BRCA2, PALB2, CDK12, RAD51B, RAD51C or RAD51D) comprising reversion mutations that result in neoantigen sequence capable of eliciting an immune response. In particular, combination therapy with a vaccine or engineered T cell of the present invention with immune checkpoint inhibitor therapy is expected to combat immune escape by the tumour and render the anti-cancer therapy more effective.

Cancer

In some embodiments, the disease or disorder to be treated or prevented in accordance with the present invention is a cancer.

The cancer may be any unwanted cell proliferation (or any disease manifesting itself by unwanted cell proliferation), neoplasm or tumour or increased risk of or predisposition to the unwanted cell proliferation, neoplasm or tumour. The cancer may be benign or malignant and may be primary or secondary (metastatic). A neoplasm or tumour may be any abnormal growth or proliferation of cells and may be located in any tissue. Examples of tissues include the adrenal gland, adrenal medulla, anus, appendix, bladder, blood, bone, bone marrow, bowel, brain, breast, cecum, central nervous system (including or excluding the brain) cerebellum, cervix, colon, duodenum, endometrium, epithelial cells (e.g. renal epithelia), eye, germ cells, gallbladder, oesophagus, glial cells, head and neck, heart, ileum, jejunum, kidney, lacrimal glad, larynx, liver, lung, lymph, lymph node, lymphoblast, maxilla, mediastinum, mesentery, myometrium, mouth, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Without wishing to be bound by theory, it is believed that immune dysfunction may enable the progression of any type of cancer since most cancers exist in the context of the host's immune system. Indeed, most cancers are at least initially recognised and attacked by the immune system, and eventually able to progress through tumour-mediated immuno-suppression and tumour evasion mechanisms. Examples of cancer to treat may be selected from bladder cancer, gastric cancer, oesophageal cancer, breast cancer, colorectal cancer, cervical cancer, ovarian cancer, endometrial cancer, kidney cancer (renal cell), lung cancer (small cell, non-small cell and mesothelioma), brain cancer (gliomas, astrocytomas, glioblastomas), melanoma, lymphoma, small bowel cancers (duodenal and jejunal), leukemia, pancreatic cancer, hepatobiliary tumours, germ cell cancers, prostate cancer, head and neck cancers, thyroid cancer and sarcomas. The present invention is likely to be particularly useful in the context of treatment of cancers including high grade serous ovarian cancer (HGSOC), triple-negative breast cancer (TNBC), castrate resistant metastatic prostate cancer and pancreatic cancer.

Further, the present invention is likely to be particularly useful in the context of treatment of cancers that have a high neoantigen load. A cancer may be predicted to have high neoantigen load if it has high tumour mutational burden, which can be quantified by measuring the somatic mutation prevalence (number of somatic mutations per megabase of tumour genome) for a sample or plurality of samples. Somatic mutation prevalence for various cancer types have been quantified in Alexandrov et al. (Nature volume 500, pages 415-421(2013)). Cancer types that have high tumour mutational burden may include those with a median numbers of somatic mutations per megabase of at least 1, at least 5, or at least 10. For example, melanomas and squamous lung cancers are typically considered to have high mutational burden.

The present invention is likely to be particularly useful for the treatment of a tumour that has acquired or is predicted to be likely to acquire or show resistance to PARP inhibitor therapy or platinum therapy. Examples of PARP inhibitor therapy include: Olaparib, Rucaparib, Niraparib, Talazoparib, Veliparib, BGB-290 (Pamiparib), CEP 9722 and E7016. Platinum-based chemotherapeutic agents include: cisplatin, carboplatin, oxaliplatin, nedaplatin, triplatin tetranitrate, phenanthriplatin, picoplatin, and satraplatin.

Tumours to be treated may be nervous or non-nervous system tumours. Nervous system tumours may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumours may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer (e.g. small cell), colon cancer, ovarian cancer, pancreatic cancer, thymic carcinoma, NSCLC, haematologic cancer and sarcoma.

Adoptive Transfer

In embodiments of the present invention, a method of treatment or prophylaxis may comprise adoptive transfer of immune cells, particularly T cells. Adoptive T cell transfer generally refers to a process by which T cells are obtained from a subject, typically by drawing a blood sample from which T cells are isolated. The T cells are then typically treated or altered in some way, optionally expanded, and then administered either to the same subject or to a different subject. The treatment is typically aimed at providing a T cell population with certain desired characteristics to a subject, or increasing the frequency of T cells with such characteristics in that subject. Adoptive transfer of CAR-T cells is described, for example, in Kalos and June 2013, Immunity 39(1): 49-60, which is hereby incorporated by reference in its entirety.

In the present invention, adoptive transfer is performed with the aim of introducing, or increasing the frequency of, target protein-reactive T cells in a subject, in particular target protein-reactive CD8$^+$ T cells.

In some embodiments, the subject from which the T cell is isolated is the subject administered with the modified T cell (i.e., adoptive transfer is of autologous T cells). In some embodiments, the subject from which the T cell is isolated is a different subject to the subject to which the modified T cell is administered (i.e., adoptive transfer is of allogenic T cells).

The at least one T cell modified according to the present invention can be modified according to methods well known to the skilled person. The modification may comprise nucleic acid transfer for permanent or transient expression of the transferred nucleic acid.

In some embodiments the method may comprise one or more of the following steps: taking a blood sample from a subject; isolating and/or expanding at least one T cell from the blood sample; culturing the at least one T cell in in vitro or ex vivo cell culture; engineering the at least one T cell to insert a modified T cell receptor or CAR, or a nucleic acid, or vector encoding the modified T cell receptor or CAR; expanding the at least one engineered T cell, collecting the at least one engineered T cell; mixing the engineered T cell with an adjuvant, diluent, or carrier; administering the engineered T cell to a subject.

In embodiments according to the present invention the subject is preferably a human subject. In some embodiments, the subject to be treated according to a therapeutic or prophylactic method of the invention herein is a subject having, or at risk of developing, a cancer, e.g. a cancer having a BRCA1, BRCA2, PALB2, CDK12, RAD51B, RAD51C or RAD51D reversion mutation giving rise to expression of the neoantigen.

In some embodiments, the method additionally comprise therapeutic or prophylactic intervention for the treatment or prevention of a disease or disorder, e.g. chemotherapy, immunotherapy, radiotherapy, surgery, vaccination and/or hormone therapy. In some embodiments, the method additionally comprises therapeutic or prophylactic intervention, for the treatment or prevention of a cancer.

T Cell Therapy

T cell therapy can include adoptive T cell therapy, tumour-infiltrating lymphocyte (TIL) immunotherapy, autologous cell therapy, engineered autologous cell therapy (eACT), and allogeneic T cell transplantation.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumours. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in US2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumour cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumour antigen linked to an intracellular signalling part comprising a costimulatory domain and an activating domain. The costimulatory domain can be derived from, e.g., CD28, and the activating domain can be derived from, e.g., CD3-zeta (FIG. 1). In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. Example CAR+ T cell therapies and constructs are described in US2013/0287748, US2014/0227237, US2014/0099309, and US2014/0050708, and these references are incorporated by reference in their entirety.

Subjects

The subject to be treated according to the invention may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, may be suspected of having such a disease or condition, or may be at risk from developing such a disease or condition. In particular, the subject may have an HR deficient cancer. The subject may be undergoing or be a candidate for PARP inhibitor therapy or platinum-based therapy. The subject may have wild-type germ-line BRCA1, BRCA2, PALB2, CDK12, RAD51B, RAD51C or RAD51D gene sequence. Alternatively, the subject may be homozygous or heterozygous for a mutation in his or her germ-line gene sequence of BRCA1, BRCA2, PALB2, CDK12, RAD51B, RAD51C or RAD51D (i.e. be a BRCA1, BRCA2, PALB2, CDK12, RAD51B, RAD51C and/or RAD51D mutation carrier). The subject may have a somatic mutation in BRCA1, BRCA2, PALB2, CDK12, RAD51B, RAD51C and/or RAD51D identified in the tumour sample, or in circulating tumour DNA (ctDNA).

The following is presented by way of example and is not to be construed as a limitation to the scope of the claims.

EXAMPLES

Materials and Methods
Collation, Annotation and Standardisation of Reversion Mutations Studies for this analysis were collated by searching the PubMed database for BRCA1, BRCA2, RAD51C, RAD51D or PALB2 and "Secondary Mutation" or "Reversion". These studies, or others referenced in these papers, describing mutations in cell lines, patients or PDX models were included. In addition, some cases of reversions discovered as part of a phase I clinical trial that included patients that had progressed on PARP inhibitor or platinum treatment (Yap et al. Cancer Discov. 2020 October; 10(10):1528-1543. doi: 10.1158/2159-8290.CD-20-0163) were included.

To aid with the overall analysis, a single transcript was used to annotate all the mutations for a gene. Where sequence information was available in the original publication this was used to annotate the mutation, otherwise the reported annotations were checked for correspondence with the reference transcript chosen for each gene. The original annotation in the publication is provided for cross-referencing purposes, along with patient or case identifiers where used in the published paper. If no case/patient identifiers were used in the original publication, these were constructed for the purposes of this analysis based on the study and sequentially-numbered reversion events. In the database both forms of annotation for the original mutation, the secondary mutations and the chromosomal location (where available) were listed. Where a chromosomal location was not annotated in the original report, this was back-calculated from the CDS annotation using the Ensembl Variant Effect Predictor (VEP, (McLaren et al., 2016)).

Once the original and secondary mutations are mapped for each case, the distance between the mutations was calculated, noting evidence of microhomology use. The distance between the original mutation and the secondary reversion was measured as the shortest distance, specifically the bases between the last base of one mutation and the first base of the other. Where the secondary reversions are deletions that span the original mutation, the distance was recorded as zero. Mutations with evidence of microhomology use have also been annotated (FIG. 3A), requiring at least one base pair homology. Microhomology is not reported for complex mutations such as insertion-deletions.

The transcripts used for codified annotations were: BRCA1, NM_007294.3; BRCA2, NM_000059.3; RAD51C, NM_058216.2; RAD51D, NM_002878.3 and PALB2, NM_024675_3. Genomic coordinates (hg38) were retrieved using the HGVS CDS annotation on the transcripts above via the Ensembl VEP (Yates et al., 2016). In annotations of the original pathogenic mutation deletions in repetitive regions were aligned to the 3' end of the deletion, and small insertion were aligned as duplications where appropriate, in order to ensure compatibility with annotations in the BRCA exchange database. Reversion mutation alleles were annotated relative to the reference sequence, including the original pathogenic mutation where this was retained. Secondary deletions that encompassed or were immediately adjacent to the pathogenic mutation (or an alternative valid annotation of the pathogenic mutation) were annotated as a single deletion relative to the reference sequence.

The database recorded reversion mutations on a "per-event" basis, an event being a single observation of a reversion mutation in a patient with a pathogenic mutation in an HR gene. Where individual patients possessed multiple, distinct, reversions (as seen in 29 (36%) of patients described in the database), each reversion was recorded as a different event. In addition, clinical information was recorded, including, where available, information pertaining to cancer type, stage and treatment history (FIG. 1B).

Mutation Data from Tumour Sequencing Studies

BRCA1 and BRCA2 mutation data were retrieved from cBioPortal from the studies listed in Table 4. These studies were chosen to approximately reflect the composition of histologies in the revertant dataset. Mutations were filtered to remove benign variants, but variants of unknown significance were retained.

Conservation Analysis

Multiple sequence alignments of BRCA1 and BRCA2 orthologues across 11 mammalian species were downloaded from EGGNOG (Powell et al., 2014) and visualised using JalView. Sequences with large gaps relative to the human protein were removed and a consensus score generated (Livingstone and Barton, 1993).

HLA-Presentation Score Predictions

Given a gene and a mutational event (primary or reversion), an in-house python script was used to generate all peptides associated with the mutation(s). For primary events, the set A of all non-WT peptides associated with the primary mutation was generated (FIG. 4C); for reversions the set B of all non-WT peptides associated to the reversion that are not in A was generated (FIG. 4D. The Best Rank (BR) HLA-presentation score of the mutation was then calculated with respect to each HLA allotype in a list of 195 HLA-A/-B allotypes total found among 1,261 individuals in 1000 Genomes (Gourraud et al., 2014). The BR was defined by predicting the eluted ligand likelihood percentile rank for each peptide associated to the mutation using the program NetMHCpan-4.0 (Jurtz et al., 2017) and taking the minimum elution rank among all peptides (Marty et al., 2017), excluding those with a wild-type NetMHC predicted Icore (Punta et al., 2019). An individual's best rank (IBR) for a mutation m was defined as the minimum BR of the mutation across all HLA allotypes of the individual. The percentage of individuals in 1000 Genomes for which $IBR<0.5$ were also calculated.

Data Availability

All data used in this study, along with updated analysis including any cases reported in future, are available to download from reversions.icr.ac.uk.

Example 1—Collation, Review and Codification of Cases of HR-Gene Reversion Mutation In order to collate all of the available data on HR-gene reversions associated with PARPi or platinum resistance (FIG. 1A), the literature was searched (see Materials and Methods) up until 1 Nov. 2019, identifying 24 publications which, when combined with some unpublished observations (Yap, T A et al.), described 231 reversion mutation events from a total of 81 patients (Table 1). The majority of patient-derived reversion mutations were in BRCA1 (n=91, 39%) or BRCA2 (n=133, 58%). Relevant studies identifying reversion mutations in tumour cell lines and patient-derived xenografts (PDX) were also included. The number of cases of PARPi or platinum resistance that are not explained by reversion mutations was difficult to determine, as there will be many unreported cases where a reversion is not detected, not investigated or cannot be ruled out. Across all the studies collated, a total of 111 patients with recurrent or platinum/PARPi resistant cancer where the presence of reversion mutations was assessed but not detected were identified (Table 2).

Differences in nomenclature and annotation exist between publications. This often arises from the use of historical mutation nomenclature for BRCA1/2, and/or the varied use of either transcript-based or coding sequence (CDS)-based numbering across different studies. In addition, the nucleotide-based annotation of microhomologies at reversion deletions lacks a standard definition. Given this, all published reversion mutations were reannotated and codified, both in terms of nucleotide change and microhomology use (see Materials and Methods and FIG. 1B). In addition, the clinical information provided for all reported cases was reviewed. All of this information was collated as a singular, freely accessible, database (http://reversions.icr.ac.uk).

In terms of disease subtype, the largest number of revertant cases were from patients with ovarian cancer (131 reversion events from 58 patients; FIG. 1C, D). Rather than reflecting a greater propensity for ovarian cancers to exhibit reversion mutations, the number of ovarian cancers in the collated dataset might reflect the longer period over which PARPi and platinum treatments have been in routine use in this disease. The 81 patients collected in this study possessed 65 different pathogenic HR-gene mutations, the vast majority being in BRCA1 (41 patients with 28 mutations), or BRCA2 (39 patients with 34 mutations) with one case each for PALB2, RAD51C and RAD51D (FIG. 1C). For the majority (78%) of patients, the pathogenic HR gene mutation was a confirmed germline mutation. Two patients (Lin 2018 SubjectID_63 and Carneiro 2018 Patient 1 in the database) had two different pathogenic alleles with reversions in each.

Example 2—Reversion Mutations are Frequently Unique Events

Figure 5:
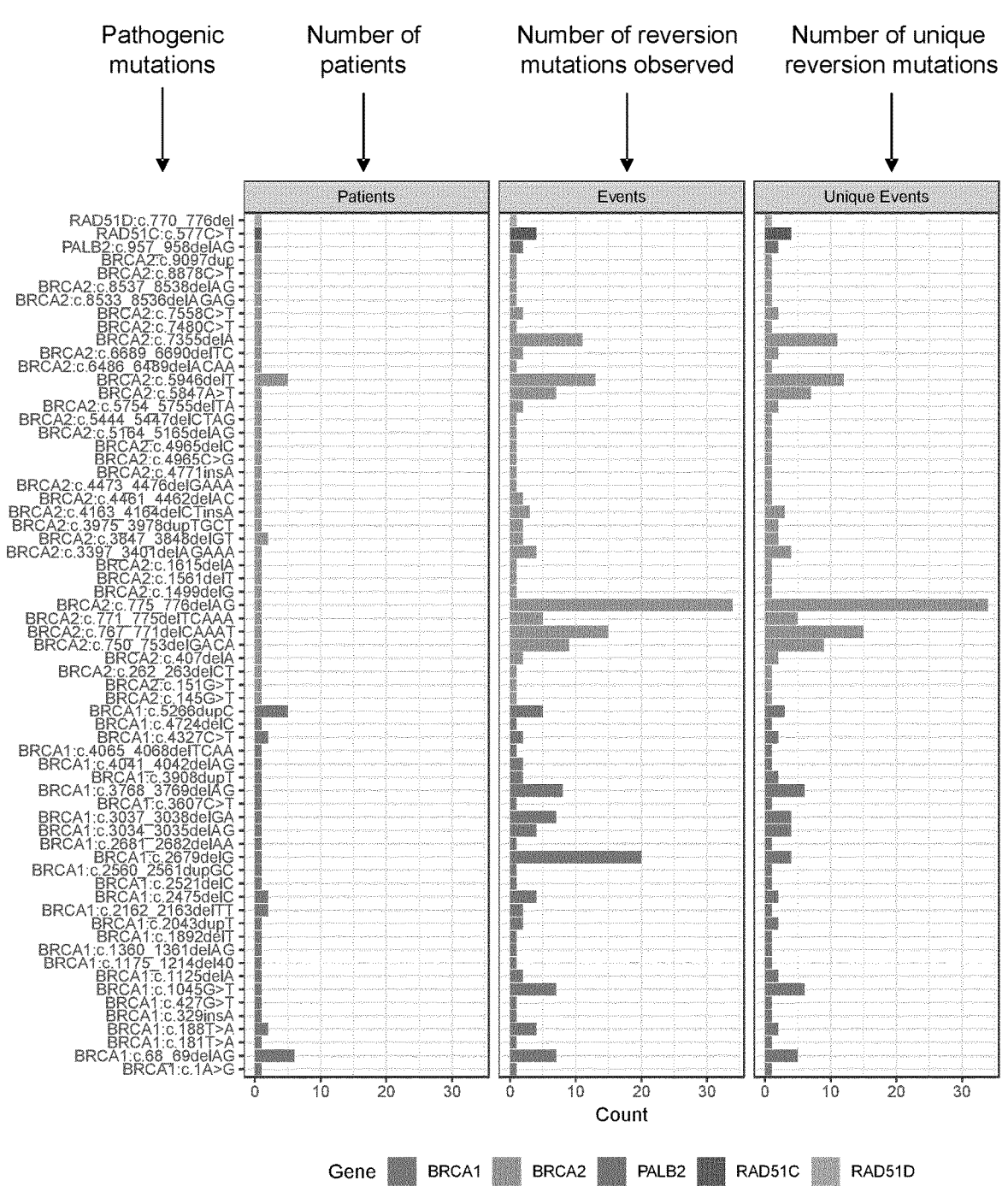
FIG. 5—Most reversion mutations are unique. Bar graph describing the number of reversion mutations associated with each pathogenic HR-gene mutation described in the dataset. Most pathogenic mutations in the dataset are observed in a single patient (left panel). In general, reversion mutations were unique for a given pathogenic mutation.
Figure 6:
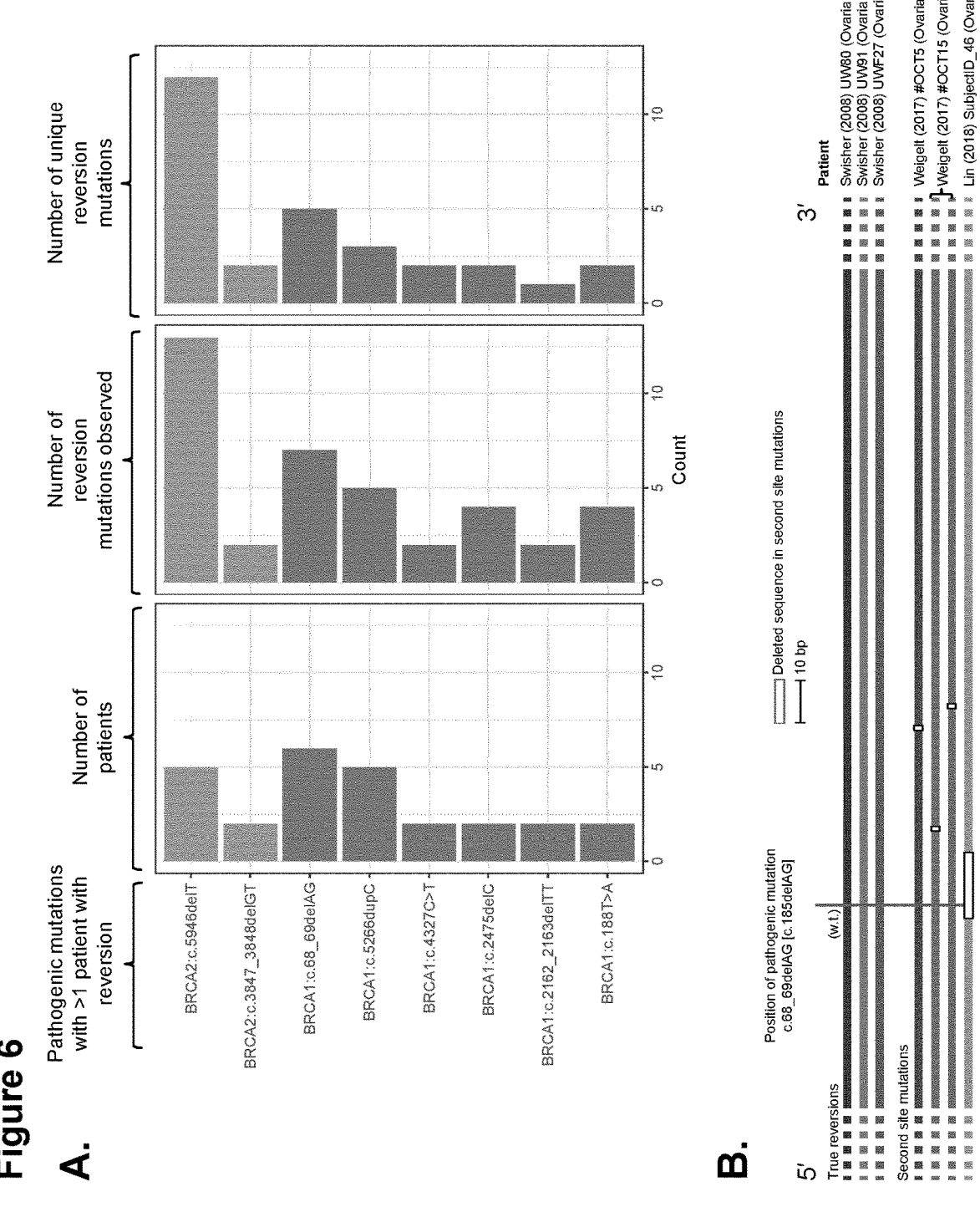
FIG. 6—A. Number of reversion mutations for pathogenic mutations represented by multiple patients, plotted as in FIG. 5. B. Example of unique reversion events observed for a common founder mutation BRCA1:c.185delAG (c.68_68delAG), represented on the BRCA1 CDS. Three true reversions to wild-type sequence were observed in two different patients. Second site reversion mutations are also shown, colored by patient.

Amongst the 81 patients data was collated from, most (65/81, 80%) had unique pathogenic mutations (FIG. 1E, annotated as "single-patient mutations" and FIG. 5). There were eight pathogenic mutations represented by multiple patients in the dataset, including common founder mutations such as BRCA2:c.6174delT (c.5946delT in the codified annotation, five patients in the dataset) and BRCA1: c.185delAG (c.68_69delAG, six patients in the dataset; FIG. 1E, FIG. 6A). Even where patients had the same founder pathogenic mutation, the DNA sequences of the reversion mutations that emerged in these patients were all unique, with the exception of true reversions to wild-type, suggesting that there is not a strong propensity for any particular reversion mutation to arise from a particular pathogenic mutation (FIG. 1E, FIG. 5). True wild-type reversions were observed for the BRCA1:c.68_69delAG (n=3) and BRCA2: c.5946delT (n=2) pathogenic mutations (FIG. 1F, FIG. 6B). This could be an intrinsic characteristic of these mutations or a consequence of how these true reversions were identified (Sanger sequencing and haplotype phasing (Norquist et al., 2011; Swisher et al., 2008)). Detection of these true reversions requires relatively long DNA reads to enable these to be phased accurately with a nearby variant.

For each of these common founder mutations, the inventors noted that the reversions that emerged in these patients were generally localised to the 3' flanking sequence of the original pathogenic mutation (transcriptionally downstream, FIG. 1F, FIG. 6B). Several other sites in both BRCA1 and BRCA2 exhibited a predominant directionality in the deletion reversions that were associated with them (e.g. BRCA2: c.7355delA, FIG. 2A, B). However, other pathogenic mutations in BRCA1 or BRCA2 had reversion deletions that occurred on either side of the pathogenic mutation, suggesting that this was not a universal property, but specific to certain pathogenic mutations.

Without being bound by theory, one possible explanation for the directionality of some reversion mutations is that there is critical amino acid sequence encoded by the DNA upstream of the pathogenic mutation that cannot be disrupted if a productive reversion allele is to be formed. However, the inventors did not find any evidence for particular evolutionary conservation of the amino acid residues immediately upstream of the pathogenic mutation, as assessed by Conservation Score (see Materials and Methods, FIG. 2B). Another possible consideration is the position of out-of-frame stop codons relative to the pathogenic mutation, which constrains where productive reversions can occur.

Example 3—Reversion Mutations in BRCA2 Exhibit Position Dependence

Although the reversion events that emerged in patients with the same founder pathogenic mutations tended to be unique, it was assessed whether the propensity of a pathogenic mutant allele to acquire reversion mutations might depend on its position in either BRCA1 or BRCA2. To do this, the CDS positions and distribution of pathogenic BRCA-gene mutations known to revert (i.e. those in the reversion dataset) were compared to the CDS positions and distribution of likely pathogenic BRCA-gene mutations in TCGA cancer resequencing studies covering ovarian, prostate and breast cancers—the predominant tumour types in our reversion dataset. In the case of BRCA1 mutations, the pathogenic mutations in the reversion dataset were distributed fairly evenly throughout the BRCA1 coding sequence, suggesting that reversion mutation is a possible resistance mechanism for pathogenic mutations at most positions (FIG. 2C) and their distribution was not significantly different from the distribution of BRCA1 mutations in the TCGA dataset (FIG. 2D, p=0.21, two-sided Kolmogorov-Smirnov test).

In contrast to BRCA1, the distribution of BRCA2 reversion mutation positions was less evenly distributed (FIG. 2A). Despite pathogenic truncating mutations in the C-terminal region of BRCA2 being relatively common in large-scale tumour sequencing studies (31% of the pathogenic mutations in the TGCA dataset occurring 3' to CDS position 7500, FIG. 2D), reversions of pathogenic mutations in this region were rare (FIG. 2C; p=0.003, permutation test). All but one of the reversions in this "desert" region were true reversions to wild-type, or missense mutations rather than deletions. This region of BRCA2 encodes the oligonucleotide/oligosaccharide binding (OB) folds, the nuclear localisation signal (NLS) and TR2 domains known to be required for HR activity (Esashi et al., 2007). Without wishing to be bound by theory, the inventors believe that this distortion in the reversion distribution might suggest that pathogenic mutations in the C-terminal coding sequence of BRCA2 are less able to be productively reverted by second site mutations, particularly deletions, possibly because the surrounding sequence is critical for HR function. This theory was consistent with the known importance of the C terminus for HR function (Esashi et al., 2007) and the high degree of amino acid sequence conservation in this region (FIG. 2B).

In contrast to the reversion "desert" at the C-terminus of BRCA2, the inventors noted a large number of reversion mutations in the N-terminal c.750-775 region (61 reversions in total from four patients in four separate studies, FIG. 2A). These reversions were identified by ctDNA sequencing, which might be more effective in identifying more reversion events per patient than, for example, the bulk sequencing of tumour cells from a solid tumour biopsy (Quigley et al., 2017). However, these mutations originated from four different patients, and this region of BRCA2 did not show a high frequency of pathogenic mutations in the TCGA dataset (FIG. 2D). Without being bound by theory, the inventors theorised that BRCA2 mutations in this region might show a greater propensity to acquire reversions and/or better tolerate the local disruption of the coding sequence in the reverted BRCA2 allele. Consistent with this theory, compared to the C-terminus of BRCA2, the c.750-775 region is not a highly-conserved region of the protein (FIG. 2B).

Example 4—Reversion of Pathogenic Missense Mutations is Rare

Multiple types of known pathogenic BRCA1 and BRCA2 mutation exist, including frameshift or nonsense mutations, as well as well-characterised missense and splice site mutations (Cline et al., 2018; Futreal et al., 1994; Lancaster et al., 1996; Landrum et al., 2017). The inventors therefore investigated whether the propensity of a BRCA-gene mutation to acquire reversion mutations might depend on the nature of the pathogenic mutation. Of the 65 pathogenic mutations in the reversion dataset, 40 were present in the BRCA Exchange database of reported mutations (Cline et al., 2018). All of these 40 mutations were classified as pathogenic by the ENIGMA (Spurdle et al., 2011) or ClinVar (Landrum et al., 2017) criteria. All remaining mutations (n=25) without an entry in the BRCA Exchange database were frameshift or nonsense mutations and therefore would be predicted as pathogenic.

Interestingly, very few missense pathogenic mutations in the set of reported reversions were noted. For example, in the TCGA tumour resequencing datasets used previously, 8.6% (8/93) of the known or likely pathogenic BRCA1/2 mutations were missense variants; conversely in the reversion dataset, only a single patient with a missense mutation (BRCA1:p.C61S missense mutation, known to be pathogenic) was present (FIG. 2F). A revertant patient with a BRCA1 p.M1I pathogenic mutation, which would, in its non-reverted state, result in loss of the translation start site was also noted. In each of these cases, the reversion seen was a true reversion to wild-type. Moreover, there were no splice-site pathogenic mutations among the reversion cases. A similar observation had been previously made in an analysis of the ARIEL2 clinical trial assessing the efficacy of the PARPi, rucaparib, in relapsed, platinum-sensitive high-grade ovarian carcinomas; out of a cohort of 112 patients, four had BRCA-gene missense mutations and ten possessed splice-site mutations. No reversions were found in any of these 14 patients, five of which were platinum resistant or refractory at the start of the study (Lin et al., 2019). One explanation for this relative paucity of reversions from tumours with pathogenic missense BRCA-gene mutations could be that missense variants affect individual amino acid residues that are critical for BRCA1/2 function; such mutations may thus be less likely to revert productively by deletion, since this would also render the "reverted" protein non-functional.

Example 5—Microhomology Use in Reversions is Frequent but not Universal

When BRCA2 reversion mutations were originally identified in cultured tumour cell lines, each of the deletion-mediated second site reversion events was characterised by the presence of DNA sequence microhomology at the ends of deleted regions (Edwards et al., 2008; Sakai et al., 2009; Sakai et al., 2008). Without being bound by theory, the inventors theorised that DNA repair processes that exploit regions of microhomology to repair DSBs could be responsible for the reversion events. From a mechanistic perspective, the loss of homologous recombination is known to cause increased use of MMEJ (Yun and Hiom, 2009), suggesting that the microhomology-characterised reversions could even be a downstream effect of the loss of HR (Edwards et al., 2008). In subsequent reports of HR-gene reversion in patients, microhomology was also a frequent feature of reversions mediated by deletion, an observation that extended beyond BRCA1 or BRCA2 reversion, to reversion events in PALB2, RAD51C and RAD51D (Barber et al., 2013; Edwards et al., 2008; Goodall et al., 2017; Kondrashova et al., 2017; Norquist et al., 2011; Patch et al., 2015; Quigley et al., 2017; Sakai et al., 2008; Swisher et al., 2008). Therefore, to better understand the aetiology of reversion mutations, the use of microhomology was assessed for the reversion events in the dataset. Such events can be recognised via their ambiguous alignments to the reference sequence, as the bases immediately adjacent to the deletion can be aligned equally well at either side of the deletion (FIG. 3A, alignment 1 and 2). Surprisingly, when all of the reported reversion events were systematically assessed, the use of microhomology mediated deletions was clearly not universal. Only 51% (106 of 205 with sequence information) of the reversion cases across the whole dataset were deletions that had evidence of microhomology. In cases of BRCA1 reversion, only 45% showed evidence of microhomology use; for BRCA2 reversions, only 56% showed microhomology use (FIG. 3B).

Overall, 66% of the BRCA1 reversions were mediated by deletions compared to 85% for BRCA2 (categories "deletion" and "microhomology deletion" in FIG. 3B). Therefore, the inventors theorised that BRCA1 mutant cells may use a wider range of pathways of DNA repair that lead to substitution or true wild-type reversions compared to BRCA2, where most events are deletion-mediated (FIG. 3B). When considering only reversions mediated by deletion, the fraction for which microhomology was present was similar between BRCA1 (67%) and BRCA2 (66%), but still approximately one third of deletions in each case did not exhibit microhomology (FIG. 3C). This suggested that DNA repair or mutagenic processes that do not utilise regions of DNA microhomology could also play a major role in the formation of reversion deletion mutations in patients.

There may also be primary tumour site differences in the use of microhomology. Microhomology use was rarely observed in breast cancer reversion cases in the dataset compared with reversions in ovarian or prostate cancers (FIG. 3D); however, the numbers in these subgroups are small and based on limited numbers of studies.

Example 6—Characteristics of Reversion Mutations Indicate Strong Selective Pressure for Close to Full-Length Proteins BRCA2 reversion mutations identified in cell line models were often large intragenic deletions (>50 kb in some cases) that removed large segments of the coding sequence despite restoring the open reading frame of the gene and leading to expression of the C-terminal NLS and OB/TR2 domains (Edwards et al., 2008). This might suggest that much of the BRCA2 coding sequence, with the exception of the C-terminus, is dispensable for tolerance of PARPi or platinum, at least in cultured cells. For BRCA1, cell line-based studies suggest that much of the protein coded for by exon 11 (1142 amino acids, 60% of the coding sequence) is dispensable for therapy resistance (Wang et al., 2016). However, and in contrast to the observations in pre-clinical models (Edwards et al., 2008), the intragenic deletions seen in clinical reversion cases ranged from 1 to 1168 base pairs (in cDNA coordinates), with most deletions being <50 bp (FIG. 3E) and contained within a single exon. Therefore, while cells in culture appeared able to tolerate, for example, the loss of thousands of bases and multiple exons of BRCA2 coding sequence, this does not appear to be recapitulated clinically. This may reflect a greater requirement or fitness advantage for tumour cells with near-full length BRCA1 or BRCA2 proteins. It should be noted here that some NGS technologies or variant calling pipelines may not be optimised to detect large intragenic deletions or fusion events.

Interestingly, deletion size was generally larger in reversion mutations that displayed evidence of microhomology use, an observation that appeared to be limited to reversion mutations occurring in BRCA2-mutant tumours (BRCA1, p=0.60; BRCA2, p=0.0036; Wilcoxon rank sum test, FIG. 3E) perhaps reflecting a greater extent of end resection and microhomology search in BRCA2 mutant tumours than in BRCA1 mutant tumours. One reason for the increased deletion size in BRCA2 reversion mutations with microhomology could be that longer regions of microhomology are required for DNA end joining in this context. Longer regions of microhomology would be expected to occur less frequently, resulting in increased DNA resection length during microhomology searching. Consistent with this hypothesis, BRCA2 reversion mutations did indeed exhibit longer regions of microhomology on average, peaking at 2-3 nt, when compared with BRCA1 reversion events (which predominantly utilised 1 bp of microhomology on each side of the reversion deletion, FIG. 3F). A general consensus of opinion is that whilst canonical NHEJ exploits either no DNA sequence microhomology or very short regions (1-3 bp) to repair DNA, MMEJ and SSA exploit somewhat longer regions (2-20 bp and >15 bp, respectively (Bhargava et al., 2016; Sinha et al., 2016)). Taken at face value, this might therefore suggest that differences in DNA repair pathway usage could explain the differences in microhomology length associated with BRCA1 vs. BRCA2 reversion deletions. Understanding the common mutational outcomes can be used to predict likely reversion mutations for a given pathogenic mutation and thus refine designs of potential vaccines for prophylaxis.

Example 7—Proximity of Reversion Mutations to Original Truncating Mutation Suggests that Many Revertant Proteins Will Constitute Neoantigens Compensatory frameshift reversions that do not restore the same codon as the original mutation (i.e. second site reversions) will introduce out-of-frame stretches of novel amino acid sequence in the revertant protein that are not encoded by the wild-type allele and may not be stably expressed from the pathogenic allele. Overall, 50% of reversions occurred at a distance of at least 6 bp from the pathogenic mutation, ranging up to 86 bp (FIG. 7). Thus, most revertant proteins will contain some out-of-frame sequence of 2-30 amino acids, or at least a novel breakpoint amino acid junction. These amino acid sequences may not have previously been visible to the host immune system and could constitute neoantigens. The inventors theorised that this could provide an opportunity to therapeutically target tumour cells expressing these candidate neoantigens, using approaches such as CAR-T cell therapies that target tumour cells expressing these neoantigens, immune checkpoint inhibitors or anticancer vaccines.

Figure 8:
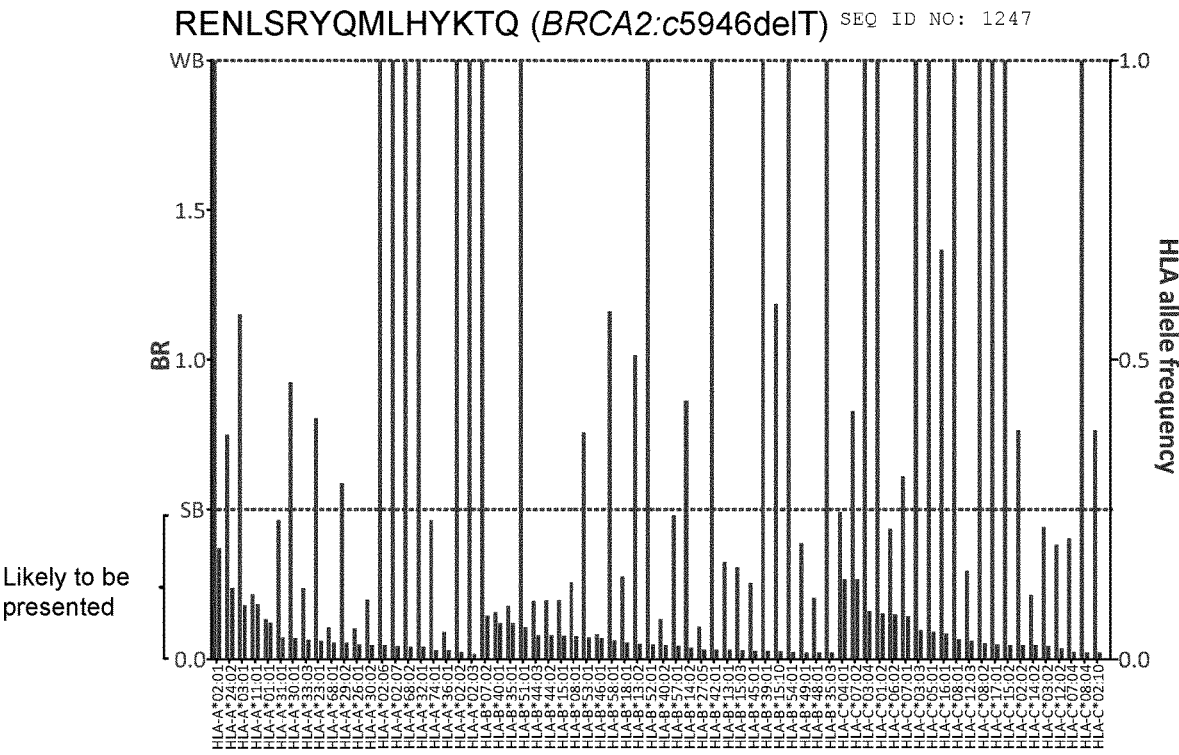
FIG. 8—HLA presentation profile for the BRCA2 RENLSRYQMLHYKTQ (SEQ ID NO: 1247) neo-peptides (most likely peptides to be immunogenic). BR—Best predicted rank among possible neopeptides. WB—weak binding threshold, SB—strong binding threshold. Peptides derived from the sequence shown have a strong binding affinity predicted for many HLA alleles, indicating that they are likely to be presented to the immune system.

To assess this possibility, the inventors assessed how frequently reverted alleles contained out-of-frame amino acid sequences and whether peptides containing these out of frame sequences were likely to be presented by antigen-presenting HLA complexes. In the case of BRCA2: c.5946delT reversions, these contained out-of-frame peptide sequence ranging from 3-15 amino acids (FIG. 4A). Using the NetMHCpan 4.0 algorithm (Jurtz et al., 2017), the likelihood of antigen presentation of these peptides across a range of HLA allotypes was calculated. Peptides containing seven amino acids or longer (representing 3/10 revertant alleles analysed for this mutation) of the out-of-frame sequence following the c.5946delT mutation were predicted to be presented by the MHC in at least 75% of individuals (taking into account the population frequencies of different HLA types, see Materials and Methods) making them likely tumour antigens (FIG. 4B, FIG. 8). Similar frequencies of predicted neoantigen presentation frequency were calculated for the out-of-frame sequence following other pathogenic deletion mutations in the dataset, including other common founder mutations such as BRCA1:c.68_69delAG (66%, FIG. 4C). This out-of-frame sequence will be shared to some extent between reversions in patients with the same pathogenic mutation. Many of the actual neopeptides retained in the reverted alleles also had high predicted likelihoods of HLA presentation (FIG. 4D, Table 3). Without being bound by theory, the inventors believe that tumours with some revertant alleles may be targetable with immunotherapies that either relieve immune suppression or those that exploit the introduction of specific T cell clones that recognise specific neoepitopes. For some pathogenic mutations it may be possible to vaccinate against the peptides predicted to be expressed in revertant alleles prior to the commencement of PARPi or platinum therapy, as a route to delay or even prevent the emergence of therapy-resistant disease.

TABLE 3

| Gene | Pathogenic Mutation | Reverted allele | % individuals predicted to present at least one neopeptide | Annotation |
|---|---|---|---|---|
| BRCA1 | c.68_69delAG | c.68_69delAG; 85delG | 81 | BRCA1:c.68_69delAG; 85delG |
| BRCA1 | c.68_69delAG | c.68_69delAG; 113delA | 66 | BRCA1:c.68_69delAG; 113delA |
| BRCA1 | c.68_69delAG | c.68_69delAG; 108delC | 66 | BRCA1:c.68_69delAG; 108delC |
| BRCA1 | c.68_69delAG | c.65_79delTAGAGTGTCCCATCT [SEQ ID NO: 1219] | 7 | BRCA1:c.65_79delTAGAGT GTCCCATCT [SEQ ID NO: 1219] |
| BRCA1 | c.5266dupC | c.5272delA | 64 | BRCA1: c.5266dupC; 5272delA |
| BRCA1 | c.5266dupC | c.5266dupC; 5276_5277 dupAG | 54 | BRCA1: c.5266dupC; 5276_5277 dupAG |
| BRCA2 | c.5946delT | c.5946delT; 5994_5999del AGTGTTinsTATC | 98 | BRCA2: c.5946delT; 5994_5999delAGTGTTinsTATC |
| BRCA2 | c.5946delT | c.5946delT; 5992_6005del CAAGTGTTTTCTGA [SEQ ID NO: 1222] | 97 | BRCA2: c.5946delT; 5992_6005delCAAGTGTT TTCTGA [SEQ ID NO: 1222] |
| BRCA2 | c.5946delT | c.5946delT; 5998_6008del TTTTCTGAAAT [SEQ ID NO: 1220] insCAA | 96 | BRCA2: c.5946delT; 5998_6008delTTTTCTGA AAT [SEQ ID NO: 1220] insCAA |

TABLE 3-continued

| Gene | Patho-genic Mutation | Reverted allele | % indi-viduals pre-dicted to present at least one neo-peptide | Annotation |
|---|---|---|---|---|
| BRCA2 | c.5946delT | c.5946delT; 5964_5998 del35 | 84 | BRCA2: c.5946delT; 5964_5998del35 |
| BRCA2 | c.5946delT | c.5946_5990 del45 | 75 | BRCA2: c.5946_5990del45 |
| BRCA2 | c.5946delT | c.5946delT; 5959_5966del CAGGTATC | 69 | BRCA2: c.5946delT; 5959_5966delCAGGTATC |
| BRCA2 | c.5946delT | c.5946delT; 5952_5959del ATCTGTCC | 69 | BRCA2: c.5946delT; 5952_5959delATCTGTCC |
| BRCA2 | c.5946delT | c.5946delT; 5949_5952 dupAAAA | 59 | BRCA2: c.5946delT; 5949_5952dupAAAA |
| BRCA2 | c.5946delT | c.5946delT; 5954_6090de l137 | 29 | BRCA2: c.5946delT; 5954_6090del137 |
| BRCA2 | c.5946delT | c.5944_5952 delAGTGGAAAA | 25 | BRCA2: c.5944_5952delAGTGGAAAA |
| BRCA2 | c.5946delT | c.5941_5956 delGCAAGTG GAAAATCTG [SEQ ID NO: 1221] insA | 4 | BRCA2: c.5941_5956delGCAAGTGGA AAATCTG [SEQ ID NO: 1221] insA |

TABLE 4

Studies from cBioPortal used for analysis of pathogenic mutations
Study

Ovarian Serous Cystadenocarcinoma (TCGA, Provisional)
Breast Cancer (METABRIC, Nature 2012 & Nat Commun 2016)
Breast Invasive Carcinoma (TCGA, Cell 2015)
Breast Invasive Carcinoma (Sanger, Nature 2012)
Breast Cancer (MSK, Cancer Cell 2018)
The Metastatic Breast Cancer Project (Provisional, October 2018)
Breast Cancer (MSKCC, 2019)

TABLE 4-continued

Studies from cBioPortal used for analysis of pathogenic mutations
Study

Metastatic Prostate Adenocarcinoma (SU2C/PCF Dream Team, PNAS 2019)
Pancreatic Adenocarcinoma (QCMG, Nature 2016)
Breast Invasive Carcinoma (Broad, Nature 2012)
Breast Invasive Carcinoma (British Columbia, Nature 2012)
Metastatic Breast Cancer (INSERM, PLoS Med 2016)
Prostate Adenocarcinoma (MSKCC/DFCI, Nature Genetics 2018)
Pancreatic Adenocarcinoma (TCGA, Provisional)

TABLE 5

Selected Primary Neopeptides Retained in Observed Reversion Mutations

| SEQ ID NO: | Neo-peptide | Indivi-duals pre-senting | Mutations | Num-ber of muta-tions |
|---|---|---|---|---|
| 1 | ILVSHLSGV | 577 | ['c.68_69delAG\|c.65_79delTAGAGTGTCCCATCT [SEQ ID NO: 1219]', 'c.68_69delAG\|c.85delG', 'c.68_69delAG\|c.113delA', 'c.68_69delAG\|c.108delC'] | 4 |

TABLE 5-continued

Selected Primary Neopeptides Retained in Observed Reversion Mutations

| SEQ ID NO: | Neo-peptide | Individuals pre-senting | Mutations | Number of muta-tions |
|---|---|---|---|---|
| 2 | GVDQGTCLHK | 230 | ['c.68_69delAG\|c.65_79delTAGAGTGTCCCATCT [SEQ ID NO: 1219]', 'c.68_69delAG\|c.85delG', 'c.68_69delAG\|c.113delA', 'c.68_69delAG\|c.108delC'] | 4 |
| 3 | NAMQKILV | 222 | ['c.68_69delAG\|c.65_79delTAGAGTGTCCCATCT [SEQ ID NO: 1219]', 'c.68_69delAG\|c.85delG', 'c.68_69delAG\|c.113delA', 'c.68_69delAG\|c.108delC'] | 4 |
| 4 | MQKILVSHL | 28 | ['.68_69delAG\|c.65_79delTAGAGTGTCCCATCT [SEQ ID NO: 1219]', 'c.68_69delAG\|c.85delG', 'c.68_69delAG\|c.113delA', 'c.68_69delAG\|c.108delC'] | 4 |
| 5 | KILVSHLSGV | 26 | ['c.68_69delAG\|c.65_79delTAGAGTGTCCCATCT [SEQ ID NO: 1219]', 'c.68_69delAG\|c.85delG', 'c.68_69delAG\|c.113delA', 'c.68_69delAG\|c.108delC'] | 4 |
| 6 | ARNLLLWAL | 731 | ['c.5266dupC\|c.5276_5277dupAG', 'c.5266dupC\|c.5272delA'] | 2 |
| 7 | RESPGQKDL | 411 | ['c.5266dupC\|c.5276_5277dupAG', 'c.5266dupC\|c.5272delA'] | 2 |
| 8 | STGMDGTAVW | 280 | ['c.5266dupC\|c.5276_5277dupAG', 'c.5266dupC\|c.5272delA'] | 2 |
| 9 | TGMDGTAVW | 250 | ['c.5266dupC\|c.5276_5277dupAG', 'c.5266dupC\|c.5272delA'] | 2 |
| 10 | AFIIHPWHR | 217 | ['c.5266dupC\|c.5276_5277dupAG', 'c.5266dupC\|c.5272delA'] | 2 |
| 11 | GEGAFIIHPW | 195 | ['c.5266dupC\|c.5276_5277dupAG', 'c.5266dupC\|c.5272delA'] | 2 |
| 12 | RSTGMDGTAVW | 194 | ['c.5266dupC\|c.5276_5277dupAG', 'c.5266dupC\|c.5272delA'] | 2 |
| 13 | QGARNLLLW | 178 | ['c.5266dupC\|c.5276_5277dupAG', 'c.5266dupC\|c.5272delA'] | 2 |
| 14 | QHAHRSTGM | 119 | ['c.5266dupC\|c.5276_5277dupAG', 'c.5266dupC\|c.5272delA'] | 2 |
| 15 | GAFIIHPWHR | 109 | ['c.5266dupC\|c.5276_5277dupAG', 'c.5266dupC\|c.5272delA'] | 2 |
| 16 | FIIHPWHR | 97 | ['c.5266dupC\|c.5276_5277dupAG', 'c.5266dupC\|c.5272delA'] | 2 |
| 17 | WALHQHAHR | 97 | ['c.5266dupC\|c.5276_5277dupAG', 'c.5266dupC\|c.5272delA'] | 2 |
| 18 | HAHRSTGM | 94 | ['c.5266dupC\|c.5276_5277dupAG', 'c.5266dupC\|c.5272delA'] | 2 |
| 19 | KRARESPGQK | 86 | ['c.5266dupC\|c.5276_5277dupAG', 'c.5266dupC\|c.5272delA'] | 2 |
| 20 | RARESPGQK | 86 | ['c.5266dupC\|c.5276_5277dupAG', 'c.5266dupC\|c.5272delA'] | 2 |
| 21 | EGAFIIHPW | 83 | ['c.5266dupC\|c.5276_5277dupAG', 'c.5266dupC\|c.5272delA'] | 2 |

TABLE 5-continued

Selected Primary Neopeptides Retained in Observed Reversion Mutations

| SEQ ID NO: | Neo-peptide | Individuals presenting | Mutations | Number of mutations |
|---|---|---|---|---|
| 22 | AARCLDRGQW | 56 | ['c.5266dupC\|c.5276_5277dupAG', 'c.5266dupC\|c.5272delA'] | 2 |
| 23 | GARNLLLW | 56 | ['c.5266dupC\|c.5276_5277dupAG', 'c.5266dupC\|c.5272delA'] | 2 |
| 24 | ARCLDRGQWL | 43 | ['c.5266dupC\|c.5276_5277dupAG', 'c.5266dupC\|c.5272delA'] | 2 |
| 25 | GEGAFIIHP | 32 | ['c.5266dupC\|c.5276_5277dupAG', 'c.5266dupC\|c.5272delA'] | 2 |
| 26 | EGAFIIHPWHR | 18 | ['c.5266dupC\|c.5276_5277dupAG', 'c.5266dupC\|c.5272delA'] | 2 |
| 27 | KDLQGARNL | 15 | ['c.5266dupC\|c.5276_5277dupAG', 'c.5266dupC\|c.5272delA'] | 2 |
| 28 | GARNLLLWAL | 1 | ['c.5266dupC\|c.5276_5277dupAG', 'c.5266dupC\|c.5272delA'] | 2 |
| 29 | LQGARNLLL | 1 | ['c.5266dupC\|c.5276_5277dupAG', 'c.5266dupC\|c.5272delA'] | 2 |
| 30 | TARENLSRY | 672 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 31 | RENLSRYQM | 630 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 32 | KTQDKCFLK | 604 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |

TABLE 5-continued

Selected Primary Neopeptides Retained in Observed Reversion Mutations

| SEQ ID NO: | Neo- peptide | Indivi- duals pre- senting | Mutations | Num- ber of muta- tions |
|---|---|---|---|---|
| 33 | STARENLSR | 507 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 34 | IFSTARENL | 416 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 35 | STARENLSRY | 384 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 36 | SRYQMLHY | 199 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 37 | NTCGIFSTAR | 162 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', | 11 |

TABLE 5-continued

Selected Primary Neopeptides Retained in Observed Reversion Mutations

| SEQ ID NO: | Neo- peptide | Indivi- duals pre- senting | Mutations | Num- ber of muta- tions |
|---|---|---|---|---|
| | | | 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | |
| 38 | ARENLSRYQM | 100 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 39 | LSRYQMLHY | 99 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 40 | ENLSRYQML | 94 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 41 | NLSRYQML | 94 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |

TABLE 5-continued

Selected Primary Neopeptides Retained in Observed Reversion Mutations

| SEQ ID NO: | Neo-peptide | Individuals pre-senting | Mutations | Number of muta-tions |
|---|---|---|---|---|
| 42 | FSTARENLSR | 67 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 43 | SRYQMLHYK | 48 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 44 | RENLSRYQML | 14 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |
| 45 | NLSRYQMLHY | 6 | ['c.5946delT\|c.5998_6008delTTTTCTGAAAT [SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5941_5956 delGCAAGTGGAAAATCTG [SEQ ID NO: 1221]insA', 'c.5946delT\|c.5944_5952delAGTGGAAAA', 'c.5946delT\|c.5952_5959delATCTGTCC', 'c.5946delT\|c.5992_6005 delCAAGTGTTTTCTGA[SEQ ID NO: 1222]', 'c.5946delT\|c.5964_5998del35'] | 11 |

TABLE 6

| SEQ ID NO: | Neo-peptide | Individuals pre-senting | Mutations | Number of mu-tions |
|---|---|---|---|---|
| 4 | MQKILVSHL | 28 | ['c.68_69delAG\|c.85delG', 'c.68_69delAG\|c.113delA', 'c.68_69delAG\|c.108delC'] | 3 |
| 3 | NAMQKILV | 222 | ['c.68_69delAG\|c.85delG', 'c.68_69delAG\|c.113delA', 'c.68_69delAG\|c.108delC'] | 3 |
| 1 | ILVSHLSGV | 577 | ['c.68_69delAG\|c.113delA', 'c.68_69delAG\|c.108delC'] | 2 |
| 5 | KILVSHLSGV | 26 | ['c.68_69delAG\|c.113delA', 'c.68_69delAG\|c.108delC'] | 2 |
| 2 | GVDQGTCLHK | 230 | ['c.68_69delAG\|c.113delA'] | 1 |
| 46 | GVDQGTCLTK | 230 | ['c.68_69delAG\|c.108delC'] | 1 |
| 47 | ILVSHLSEL | 838 | ['c.68_69delAG\|c.85delG'] | 1 |
| 48 | NAMQKICL | 94 | ['c.68_69delAG\|c.65_79delTAGAGTGTCCCATCT[SEQ ID NO: 1219]' | 1 |
| 49 | SELIKEPVSTK | 215 | ['c.68_69delAG\|c.85delG'] | 1 |
| 50 | ARESPGQKEI | 103 | ['c.5266dupC\|c.5276_5277dupAG'] | 1 |
| 51 | ARESPGRKIF | 200 | ['c.5266dupC\|c.5272delA'] | 1 |
| 52 | ESPGRKIFR | 97 | ['c.5266dupC\|c.5272delA'] | 1 |
| 53 | GQKEIFRGL | 82 | ['c.5266dupC\|c.5276_5277dupAG'] | 1 |
| 54 | GRKIFRGLEI | 5 | ['c.5266dupC\|c.5272delA'] | 1 |
| 55 | KEIFRGLEI | 639 | ['c.5266dupC\|c.5276_5277dupAG'] | 1 |
| 19 | KRARESPGQK | 86 | ['c.5266dupC\|c.5276_5277dupAG'] | 1 |
| 20 | RARESPGQK | 86 | ['c.5266dupC\|c.5276_5277dupAG'] | 1 |
| 56 | RARESPGRK | 86 | ['c.5266dupC\|c.5272delA'] | 1 |
| 57 | RESPGQKEI | 589 | ['c.5266dupC\|c.5276_5277dupAG'] | 1 |
| 58 | RESPGQKEIF | 336 | ['c.5266dupC\|c.5276_5277dupAG'] | 1 |
| 59 | RESPGRKI | 26 | ['c.5266dupC\|c.5272delA'] | 1 |
| 60 | RESPGRKIF | 558 | ['c.5266dupC\|c.5272delA'] | 1 |
| 61 | SPGRKIFRGL | 217 | ['c.5266dupC\|c.5272delA'] | 1 |
| 37 | NTCGIFSTAR | 162 | ['c.5946delT\|c.5998_6008delTTTTCTGAAAT[SEQ ID NO: 1220]insCAA', 'c.5946delT\|c.5949_5952dupAAAA', 'c.5946delT\|c.5994_5999delAGTGTTinsTATC', 'c.5946delT\|c.5946_5990del45', 'c.5946delT\|c.5954_6090del137', 'c.5946delT\|c.5959_5966delCAGGTATC', 'c.5946delT\|c.5952_5959delATCTGTCC', 'c.5946delT\|c.5992_6005delCAAGTGTTTTCTGA[SEQ ID NO: 1222]', 'c.5946delT\|c.5964_5998del35'] | 9 |
| 34 | IFSTARENL | 416 | ['c.5946delT\|c.5998_6008delTTTTCTGAAAT[SEQ ID NO: 1220]insCAA', 'c.5946delT\|c.5994_5999delAGTGTTinsTATC', 'c.5946delT\|c.5959_5966delCAGGTATC', 'c.5946delT\|c.5992_6005delCAAGTGTTTTCTGA[SEQ ID NO: 1222]', 'c.5946delT\|c.5964_5998del35'] | 5 |

TABLE 6-continued

| | | Selected Reversion Mutations Encoding Neopeptides | | Num- |
|---|---|---|---|---|
| SEQ | Indiv-<br>duals | | | ber<br>of |
| ID Neo- | pre- | | | mu- |
| NO: peptide | senting | Mutations | | tions |
| 42 FSTARENLSR | 67 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID: 1222]',<br>'c.5946delT\|c.5964_5998del35'] | | 4 |
| 33 STARENLSR | 507 | ['c.5946delT\|c.5998_6008delTTTTCTGAAAT<br>[SEQ ID: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]',<br>'c.5946delT\|c.5964_5998del35'] | | 4 |
| 38 ARENLSRYQM | 100 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 40 ENLSRYQML | 94 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 39 LSRYQMLHY | 99 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 41 NLSRYQML | 94 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 45 NLSRYQMLHY | 6 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 31 RENLSRYQM | 630 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 44 RENLSRYQML | 14 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 36 SRYQMLHY | 199 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |
| 43 SRYQMLHYK | 48 | ['c.5946delT\|c.5998_6008delTTTTCTGAAAT<br>[SEQ ID NO: 1220]insCAA',<br>'c.5946delT\|c.5994_5999delAGTGTTinsTATC',<br>'c.5946delT\|c.5992_6005delCAAGTGTTTTCTGA<br>[SEQ ID NO: 1222]'] | | 3 |

TABLE 6-continued

| | | | Number |
|---|---|---|---|
| SEQ ID NO: | Neo-peptide | Individuals pre-senting | Mutations | of mutations |

| SEQ ID NO: | Neo-peptide | Individuals pre-senting | Mutations | Number of mutations |
|---|---|---|---|---|
| 35 | STARENLSRY | 384 | ['c.5946delT\|c.5998_6008delTTTTCTGAAAT [SEQ ID NO: 1220]insCAA', 'c.5946delT\|c.5994_5999delAGTGTTinsTATC', 'c.5946delT\|c.5992_6005delCAAGTGTTTTCTGA [SEQ ID NO: 1222]'] | 3 |
| 30 | TARENLSRY | 672 | ['c.5946delT\|c.5998_6008delTTTTCTGAAAT [SEQ ID NO: 1220]insCAA', 'c.5946delT\|c.5994_5999delAGTGTTinsTATC', 'c.5946delT\|c.5992_6005delCAAGTGTTTTCTGA [SEQ ID NO: 1222]'] | 3 |
| 62 | GIFSTAREK | 550 | ['c.5946delT\|c.5949_5952dupAAAA', 'c.5946delT\|c.5952_5959delATCTGTCC'] | 2 |
| 63 | AREKVSDASL | 2 | ['c.5946delT\|c.5952_5959delATCTGTCC'] | 1 |
| 64 | ARENLSDASL | 189 | ['c.5946delT\|c.5959_5966delCAGGTATC'] | 1 |
| 65 | ENLSRFSEI | 94 | ['c.5946delT\|c.5964_5998del35'] | 1 |
| 66 | GIFSTAREKK | 216 | ['c.5946delT\|c.5949_5952dupAAAA'] | 1 |
| 67 | IFSTARQVF | 802 | ['c.5946delT\|c.5946_5990del45'] | 1 |
| 68 | IFSTASVQV | 312 | ['c.5946delT\|c.5944_5952delAGTGGAAAA'] | 1 |
| 69 | KEDSTKQVF | 596 | ['c.5946delT\|c.5998_6008delTTTTCTGAAAT [SEQ ID NO: 1220]insCAA'] | 1 |
| 70 | KTQDISSEI | 600 | ['c.5946delT\|c.5994_5999delAGTGTTinsTATC'] | 1 |
| 71 | MLHYKTQDI | 94 | ['c.5946delT\|c.5994_5999delAGTGTTinsTATC'] | 1 |
| 72 | MLHYKTQEI | 192 | ['c.5946delT\|c.5992_6005delCAAGTGTTTTCTGA [SEQ ID NO: 1222]'] | 1 |
| 73 | NTCGIFSTI | 54 | ['c.5946delT\|c.5941_5956delGCAAGTGGAAAATCTG [SEQ ID NO: 1221]GinsA'] | 1 |
| 74 | QEIEDSTKQV | 262 | ['c.5946delT\|c.5992_6005delCAAGTGTTTTCTGA [SEQ ID NO: 1222]'] | 1 |
| 75 | QEIEDSTKQVF | 255 | ['c.5946delT\|c.5992_6005delCAAGTGTTTTCTGA [SEQ ID NO: 1222]'] | 1 |
| 76 | REKKSVQVS | 18 | ['c.5946delT\|c.5949_5952dupAAAA'] | 1 |
| 77 | REKVSDASL | 318 | ['c.5946deIT\|c.5952_5959delATCTGTCC'] | 1 |
| 78 | RENLSDASL | 552 | ['c.5946deIT\|c.5959_5966delCAGGTATC'] | 1 |
| 79 | RENTAIRTP | 76 | ['c.5946delT\|c.5954_6090del137'] | 1 |
| 80 | SRFSEIEDSTK | 43 | ['c.5946delT\|c.5964_5998del35'] | 1 |
| 81 | STARENLSRF | 179 | ['c.5946delT\|c.5964_5998del35'] | 1 |
| 82 | STARENTAI | 52 | ['c.5946delT\|c.5954_6090del137'] | 1 |
| 83 | STARENTAIR | 77 | ['c.5946delT\|c.5954_6090del137'] | 1 |
| 84 | TAREKKSV | 94 | ['c.5946delT\|c.5949_5952dupAAAA'] | 1 |
| 85 | TAREKVSDASL | 94 | ['c.5946deIT\|c.5952_5959delATCTGTCC'] | 1 |
| 86 | TARENLSRF | 665 | ['c.5946delT\|c.5964_5998del35'] | 1 |
| 87 | TARENTAI | 94 | ['c.5946delT\|c.5954_6090del137'] | 1 |

TABLE 6-continued

Selected Reversion Mutations Encoding Neopeptides

| SEQ ID NO: | Neo-peptide | Individuals presenting | Mutations | Number of mutations |
|---|---|---|---|---|
| 88 | TARENTAIR | 170 | ['c.5946delT\|c.5954_6090del137'] | 1 |
| 89 | TARQVFSEI | 240 | ['c.5946delT\|c.5946_5990del45'] | 1 |

TABLE 7

Presentation scores

| Gene | Pathogenic mutation | Reversion mutation | HLA presentation likelihood |
|---|---|---|---|
| BRCA1 | c.68_69delAG | c.85delG | 81 |
| BRCA1 | c.68_69delAG | c.108delC | 66 |
| BRCA1 | c.68_69delAG | c.113delA | 66 |
| BRCA1 | c.68_69delAG | c.65_79delTAGAGTGTCCCATCT [SEQ ID NO: 1219] | 7 |
| BRCA1 | c.5266dupC | c.5272delA | 64 |
| BRCA1 | c.5266dupC | c.5276_5277dupAG | 54 |
| BRCA2 | c.5946delT | c.5994_5999delAGTGTTinsTATC | 98 |
| BRCA2 | c.5946delT | c.5992_6005delCAAGTGTTTTCTGA [SEQ ID NO: 1222] | 97 |
| BRCA2 | c.5946delT | c.5998_6008delTTTTCTGAAAT [SEQ ID NO: 1220] insCAA | 96 |
| BRCA2 | c.5946delT | c.5964_5998del35 | 84 |
| BRCA2 | c.5946delT | c.5946_5990del45 | 75 |
| BRCA2 | c.5946delT | c.5952_5959delATCTGTCC | 69 |
| BRCA2 | c.5946delT | c.5959_5966delCAGGTATC | 69 |
| BRCA2 | c.5946delT | c.5949_5952dupAAAA | 59 |
| BRCA2 | c.5946delT | c.5954_6090del137 | 29 |
| BRCA2 | c.5946delT | c.5944_5952delAGTGGAAAA | 25 |
| BRCA2 | c.5946delT | c.5941_5956delGCAAGTGGAAAATCTG [SEQ ID NO: 1221] insA | 4 |

TABLE 8

Predicted binding level (WB—weak binder, % Rank < 2; SB—strong binder, % Rank < 0.5) of the specified mutations

| MHC | SEQ ID NO: | Identity | % Rank_EL | BindLevel |
|---|---|---|---|---|
| HLA-B*0801 | 3 | B1__185delAG_dow | 0.458 | SB |
| HLA-B*1501 | 4 | B1__185delAG_dow | 0.3 | SB |
| HLA-A*0201 | 1 | B1__185delAG_dow | 0.072 | SB |

TABLE 8-continued

Predicted binding level (WB—weak binder, % Rank < 2; SB—strong binder, % Rank < 0.5) of the specified mutations

| MHC | SEQ ID NO: | Identity | % Rank_EL | BindLevel |
|---|---|---|---|---|
| HLA-B*3801 | 1157 | B1__185delAG_dow | 0.224 | SB |
| HLA-B*0801 | 1158 | B1__185delAG_dow | 1.342 | WB |
| HLA-B*0801 | 1159 | B1__185delAG_dow | 0.683 | WB |

TABLE 8-continued

Predicted binding level (WB—weak binder, % Rank < 2; SB—strong binder, % Rank < 0.5) of the specified mutations

| MHC | SEQ ID NO: | Identity | % Rank_EL | BindLevel |
|---|---|---|---|---|
| HLA-A*0301 | 1160 | B1_185delAG_dow | 0.6 | WB |
| HLA-A*0201 | 1161 | B1_185delAG_dow | 1.687 | WB |
| HLA-B*1501 | 1162 | B1_185delAG_dow | 1.712 | WB |
| HLA-A*0201 | 5 | B1_185delAG_dow | 0.942 | WB |
| HLA-A*0101 | 1163 | B1_185delAG_dow | 1.313 | WB |
| HLA-A*0101 | 1164 | B1_185delAG_dow | 1.478 | WB |
| HLA-A*0101 | 1165 | B1_185delAG_dow | 0.987 | WB |
| HLA-A*0301 | 2 | B1_185delAG_dow | 0.676 | WB |
| HLA-A*0301 | 20 | B1_5382insC_dow | 0.411 | SB |
| HLA-B*4001 | 1166 | B1_5382insC_dow | 0.483 | SB |
| HLA-B*4001 | 7 | B1_5382insC_dow | 0.068 | SB |
| HLA-B*5801 | 13 | B1_5382insC_dow | 0.098 | SB |
| HLA-B*2705 | 6 | B1_5382insC_dow | 0.033 | SB |
| HLA-B*3901 | 14 | B1_5382insC_dow | 0.189 | SB |
| HLA-B*5801 | 12 | B1_5382insC_dow | 0.021 | SB |
| HLA-B*5801 | 8 | B1_5382insC_dow | 0.1 | SB |
| HLA-B*5801 | 9 | B1_5382insC_dow | 0.253 | SB |
| HLA-B*0702 | 1167 | B1_5382insC_dow | 0.941 | WB |
| HLA-B*2705 | 19 | B1_5382insC_dow | 0.764 | WB |
| HLA-B*4001 | 1168 | B1_5382insC_dow | 0.688 | WB |
| HLA-B*1501 | 1169 | B1_5382insC_dow | 1.929 | WB |
| HLA-B*4001 | 27 | B1_5382insC_dow | 1.53 | WB |
| HLA-B*5701 | 1170 | B1_5382insC_dow | 1.566 | WB |
| HLA-B*0801 | 1171 | B1_5382insC_dow | 1.842 | WB |
| HLA-B*5701 | 1172 | B1_5382insC_dow | 0.553 | WB |
| HLA-B*2705 | 1173 | B1_5382insC_dow | 1.321 | WB |
| HLA-B*5701 | 23 | B1_5382insC_dow | 0.612 | WB |
| HLA-B*2705 | 28 | B1_5382insC_dow | 0.621 | WB |
| HLA-B*2705 | 1174 | B1_5382insC_dow | 0.893 | WB |
| HLA-B*2705 | 1175 | B1_5382insC_dow | 1.822 | WB |
| HLA-A*0201 | 1176 | B1_5382insC_dow | 0.72 | WB |
| HLA-B*1501 | 1177 | B1_5382insC_dow | 0.799 | WB |
| HLA-B*0801 | 18 | B1_5382insC_dow | 1.378 | WB |
| HLA-B*5801 | 1178 | B1_5382insC_dow | 0.83 | WB |
| HLA-B*5801 | 1179 | B1_5382insC_dow | 1.352 | WB |
| HLA-B*5801 | 1180 | B1_5382insC_dow | 1.465 | WB |
| HLA-B*5801 | 21 | B1_5382insC_dow | 0.773 | WB |
| HLA-B*5801 | 1181 | B1_5382insC_dow | 0.722 | WB |
| HLA-B*2705 | 1182 | B1_5382insC_dow | 1.764 | WB |
| HLA-B*5701 | 1183 | B1_5382insC_dow | 1.668 | WB |
| HLA-B*5701 | 22 | B1_5382insC_dow | 0.625 | WB |
| HLA-B*2705 | 1184 | B1_5382insC_dow | 1.407 | WB |
| HLA-B*2705 | 24 | B1_5382insC_dow | 0.775 | WB |
| HLA-B*5801 | 1185 | B1_5382insC_dow | 1.756 | WB |
| HLA-B*5801 | 1186 | B1_5382insC_dow | 0.669 | WB |
| HLA-B*5701 | 1187 | B1_5382insC_ups | 0.023 | SB |
| HLA-B*0801 | 1188 | B1_5382insC_ups | 0.13 | SB |
| HLA-B*5801 | 1189 | B1_5382insC_ups | 0.426 | SB |
| HLA-B*5801 | 1190 | B1_5382insC_ups | 0.058 | SB |
| HLA-B*4001 | 1191 | B1_5382insC_ups | 0.397 | SB |
| HLA-B*0801 | 1192 | B1_5382insC_ups | 1.481 | WB |
| HLA-B*5801 | 1193 | B1_5382insC_ups | 1.204 | WB |
| HLA-B*1501 | 1194 | B1_5382insC_ups | 1.767 | WB |
| HLA-B*3901 | 1195 | B1_5382insC_ups | 0.916 | WB |
| HLA-A*0201 | 1196 | B1_5382insC_ups | 1.68 | WB |
| HLA-A*0201 | 1197 | B1_5382insC_ups | 1.791 | WB |
| HLA-B*4001 | 1198 | B1_5382insC_ups | 0.97 | WB |
| HLA-B*4001 | 1199 | B1_5382insC_ups | 1.239 | WB |
| HLA-B*4001 | 1200 | B1_5382insC_ups | 1.289 | WB |
| HLA-B*0801 | 1201 | B1_5382insC_ups | 0.556 | WB |
| HLA-B*0801 | 1202 | B1_5382insC_ups | 0.883 | WB |
| HLA-A*0101 | 1203 | B2_6174delT_dow | 0.46 | SB |
| HLA-A*2601 | 35 | B2_6174delT_dow | 0.075 | SB |
| HLA-A*2601 | 30 | B2_6174delT_dow | 0.125 | SB |
| HLA-B*4001 | 31 | B2_6174delT_dow | 0.134 | SB |
| HLA-B*4001 | 44 | B2_6174delT_dow | 0.367 | SB |
| HLA-B*0801 | 40 | B2_6174delT_dow | 0.226 | SB |
| HLA-B*0801 | 41 | B2_6174delT_dow | 0.423 | SB |
| HLA-B*2705 | 36 | B2_6174delT_dow | 0.466 | SB |
| HLA-B*2705 | 43 | B2_6174delT_dow | 0.056 | SB |
| HLA-B*3801 | 1204 | B2_6174delT_dow | 0.24 | SB |
| HLA-B*3801 | 1205 | B2_6174delT_dow | 0.481 | SB |
| HLA-A*0301 | 32 | B2_6174delT_dow | 0.155 | SB |
| HLA-A*2402 | 34 | B2_6174delT_dow | 0.703 | WB |

TABLE 8-continued

Predicted binding level (WB—weak binder, % Rank < 2; SB—strong binder, % Rank < 0.5) of the specified mutations

| MHC | SEQ ID NO: | Identity | % Rank_EL | BindLevel |
|---|---|---|---|---|
| HLA-A*0301 | 33 | B2_6174delT_dow | 1.35 | WB |
| HLA-A*0101 | 1206 | B2_6174delT_dow | 1.619 | WB |
| HLA-B*2705 | 38 | B2_6174delT_dow | 0.821 | WB |
| HLA-B*2705 | 1207 | B2_6174delT_dow | 1.345 | WB |
| HLA-B*0801 | 1208 | B2_6174delT_dow | 0.936 | WB |
| HLA-A*0101 | 45 | B2_6174delT_dow | 0.905 | WB |
| HLA-B*2705 | 1209 | B2_6174delT_dow | 1.057 | WB |
| HLA-A*0101 | 39 | B2_6174delT_dow | 0.531 | WB |
| HLA-B*2705 | 1210 | B2_6174delT_dow | 0.822 | WB |
| HLA-B*2705 | 1211 | B2_6174delT_dow | 1.14 | WB |
| HLA-B*2705 | 1212 | B2_6174delT_dow | 1.784 | WB |
| HLA-A*0301 | 1213 | B2_6174delT_dow | 1.23 | WB |
| HLA-A*0301 | 1214 | B2_6174delT_dow | 0.67 | WB |
| HLA-B*3901 | 1215 | B2_6174delT_dow | 0.999 | WB |
| HLA-A*2402 | 1216 | B2_6174delT_dow | 0.756 | WB |
| HLA-B*3901 | 1217 | B2_6174delT_dow | 1.299 | WB |
| HLA-B*0801 | 1218 | B2_6174delT_ups | 0.227 | SB |

The amino acid sequence of the neopeptides that result from the BRCA1 and BRCA2 reversion mutations set forth in Table 3 above may be determined from the reversion mutation, sequence of the BRCA1 or BRCA2 gene, the genomic sequences of which are available from the NCBI at the accession numbers disclosed above, respectively. The genetic code can then be used to determine the amino acid sequence of the reading frame following the relevant mutation described above.

For example, the BRCA2 muation c.5998_6008delTTTTCTGAAATinsCAA encodes the out-of-frame amino acid sequence, as shown boxed in FIG. 4B, row three.

Discussion

The inventors have shown that by collating, codifying and analysing >200 HR-gene reversion mutations, a number of principles can be established. These include the unique nature of most reversions, positional "hotspots" and "deserts" in the N- and C-terminal coding regions of BRCA2, the paucity of missense and splice-site pathogenic mutations leading to reversions, and differences in microhomology use in BRCA1 compared to BRCA2-related reversions. Finally, it was found that many reverted alleles were predicted to encode highly immunogenic neo-peptides, suggesting a route to treatment of reverted disease. The inventors believe that by generating, analysing and expanding the reversion dataset, additional principles that govern how therapy resistance emerges in HR-defective cancers could be established.

The inventors noted that the clinical reversion mutations seem to have a more restricted spectrum (<100 bp deletions, close to the pathogenic mutation (FIG. 2A, FIG. 3E, FIG. 7)) compared to those previously seen in cell line and PDX studies, where large deletions predominate (Edwards et al., 2008; Sakai et al., 2008; Ter Brugge et al., 2016). Although some ascertainment bias in the detection of clinical reversions cannot be eliminated, it seems that the types of reversions seen in patients are more likely to preserve the majority of the coding sequence than those seen in preclinical models. Furthermore, in contrast to the ubiquitous microhomology at deletions in cell line studies, the inventors found that microhomology usage in clinical reversions was not universal (66% of the deletion-mediated reversion mutations exhibiting microhomology). Without being bound by theory, the inventors believe that multiple DNA repair processes might drive reversion, implying that the design of therapeutic interventions that limit reversions might be more complex than originally thought. Tumour sequencing studies have assessed microhomology usage in somatic deletion mutations at a genome-wide level, finding, for example, that ≈40% of deletions (IQR, 30-50) showed microhomology in BRCA1/2 mutant breast cancers, compared to ≈20% in BRCA wild-type (Davies et al., 2017)). Thus, the frequency of microhomology-associated BRCA-gene reversions is at the upper end of what might be expected at the genome-wide level in BRCA-gene mutant cancers, but still lower than that seen for reversions isolated from cell line models. Interestingly very few non-microhomology-mediated reversions in breast cancer cases (FIG. 3D) were observed, but this may be due to the relatively low numbers of patients reported.

The observation of a possible hotspot for secondary mutations around position c.750-775 in BRCA2 has potential implications for patients with these mutations. This may indicate that patients with such mutations would be at higher risk of acquiring resistance via reversions mutations, and should be monitored more closely. Conversely, patients with missense and splice site mutations, or mutations in the BRCA2 C-terminal desert (position c.7500 onwards) may be at lower risk of developing resistance via reversion.

As more is understood about the prevalence and nature of reversion mutations, the question of how to treat cancers that acquire drug resistance via secondary mutation can be addressed. After performing this analysis and without being bound by theory, the inventors suggest several possibilities. First, as described above, inhibiting microhomology-mediated end joining may be a way of preventing the emergence of some reversions, although this might not be a completely effective approach, given the frequency of non-microhomology mediated events observed. Targeting the reverted protein in some way may also be possible where this differs from wild type; for example, the mutant proteins may have an increased dependence on chaperones such as heat shock proteins to fold correctly. Where inserted or out-of-frame amino acid sequences are formed by reversion, these may be immunogenic. The inventors have demonstrated that there is a high probability of presentation by the MHC for many of the revertant sequences, including at common founders such as BRCA2:c.5946delT (FIG. 4). Thus, immunotherapies or cancer vaccines may also be an option for direct targeting of the revertant protein. There are other possible approaches that are not related to the revertant protein per se, such as using WEE1 or ATR inhibitors, that have been empirically shown in pre-clinical models to target BRCA-gene mutant tumour cells even after the acquisition of reversion mutations (Dréan et al., 2017), an effect likely mediated by the general replication stress that is likely to still exist in the tumour, despite reversion.

The analysis of all published clinically-occurring reversion events (reversions.icr.ac.uk) indicates that 66% of BRCA1 and 85% of BRCA2 reversion events are of these latter two classes and are mediated by deletions, which in most cases result in a new protein sequence (neopeptide) being encoded as shown in FIG. 4A. Almost all reversion mutations, with the exception of true reversions to wild type, will encode at least one novel amino acid or junction sequence. Using an in silico prediction of how likely these neopeptides are to be presented as antigens by MHC complexes (Punta et al. 2019; Jurtz et al. 2017), the inventors found that for most deletion-mediated reversion events the resulting neopeptides were highly likely to be presented by the MHC, taking population HLA frequencies into account including at common founder mutations such as BRCA2: c.6174delT (FIG. 4B). Across all reversions seen in clinical cases of PARPi or platinum resistance, the inventors found that the median percentage of individuals predicted to present at least one peptide for a reversion mutation was 35% (FIG. 4D). In most cases of reversions the HLA type of the individual they arose was not published, so a more precise estimate cannot be made. However for some specific, and indeed common, BRCA-gene pathogenic mutations, the likelihood of reversion neoantigens being presented by the MHC was even higher. For example, for reversions derived from individuals with pathogenic BRCA2:c.6174delT mutations, up to 91% of individuals were predicted to present neopeptides from the published cases of reversion mutation (FIG. 4B).

Vaccination as a Strategy to Prevent or Treat Drug Resistance Caused by BRCA Reversions Without being bound by theory, the analysis of all published cases of reversion mutations suggested that this novel out of frame sequence often constitutes a potential tumour neoantigen, with a high predicted probability of antigen presentation by the MHC, opening the possibility that PARP inhibitor resistant cancers could be targeted by exploiting the presentation of a BRCA reversion neoantigen. This could be via an anticancer vaccine or immune checkpoint inhibition. The inventors propose to test this theory using: (1) human T-cell priming assays using predicted neoantigens derived from revertant BRCA proteins; (2) the generation of revertant syngeneic mouse tumour models and a matched anticancer vaccine to test whether vaccinated mice reject BRCA-reverted tumours; and (3) treatment of mice bearing established syngeneic reverted tumours with the vaccine and immune checkpoint inhibitors to assess whether this may represent a viable therapeutic strategy to targeting this area of unmet clinical need.

Below, a strategy is described to test the theory that reversion mutations could be targeted by exploiting the formation of BRCA1 or BRCA2 neoepitopes that form when reversion mutations occur. This may provide the pre-clinical rationale for developing novel therapeutics which target cancers in the growing population of people who display PARPi or platinum salt resistant disease caused by reversion mutations.

Without being bound by theory, the inventors believe that if the immune system could be primed to target tumour cells presenting potentially antigenic neopeptides caused by reversion mutations, this may reduce or delay the emergence of PARPi or platinum salt resistance in individuals with pathogenic BRCA-gene mutations. This could be accomplished by using an anticancer vaccine that targets cells presenting antigenic neopeptides, for example, by using peptide, RNA or oncolytic virus-based vaccination. If the reverted BRCA-protein sequences are indeed immunogenic, this may also argue in favour of the use of immune checkpoint inhibitors to further boost the anti-neoantigen T cell response, in patients likely to have antigenic reversions.

These predictions of immunogenicity may be tested experimentally, through validation of the computational predictions described above and the development and use of syngeneic mouse tumour cell line models of drug resistance caused by reversion mutations. If successful, these experiments could form the basis for the clinical development of reversion vaccines. These could take the form of both personalised approaches for rare pathogenic mutations or "off-the-shelf" vaccines that would work in patients with more common founder mutations in either BRCA1 or BRCA2.

Example 8—T-Cell Priming Assays: Are Predicted Reversion Neopeptides Presented by the MHC?

Figure 9:
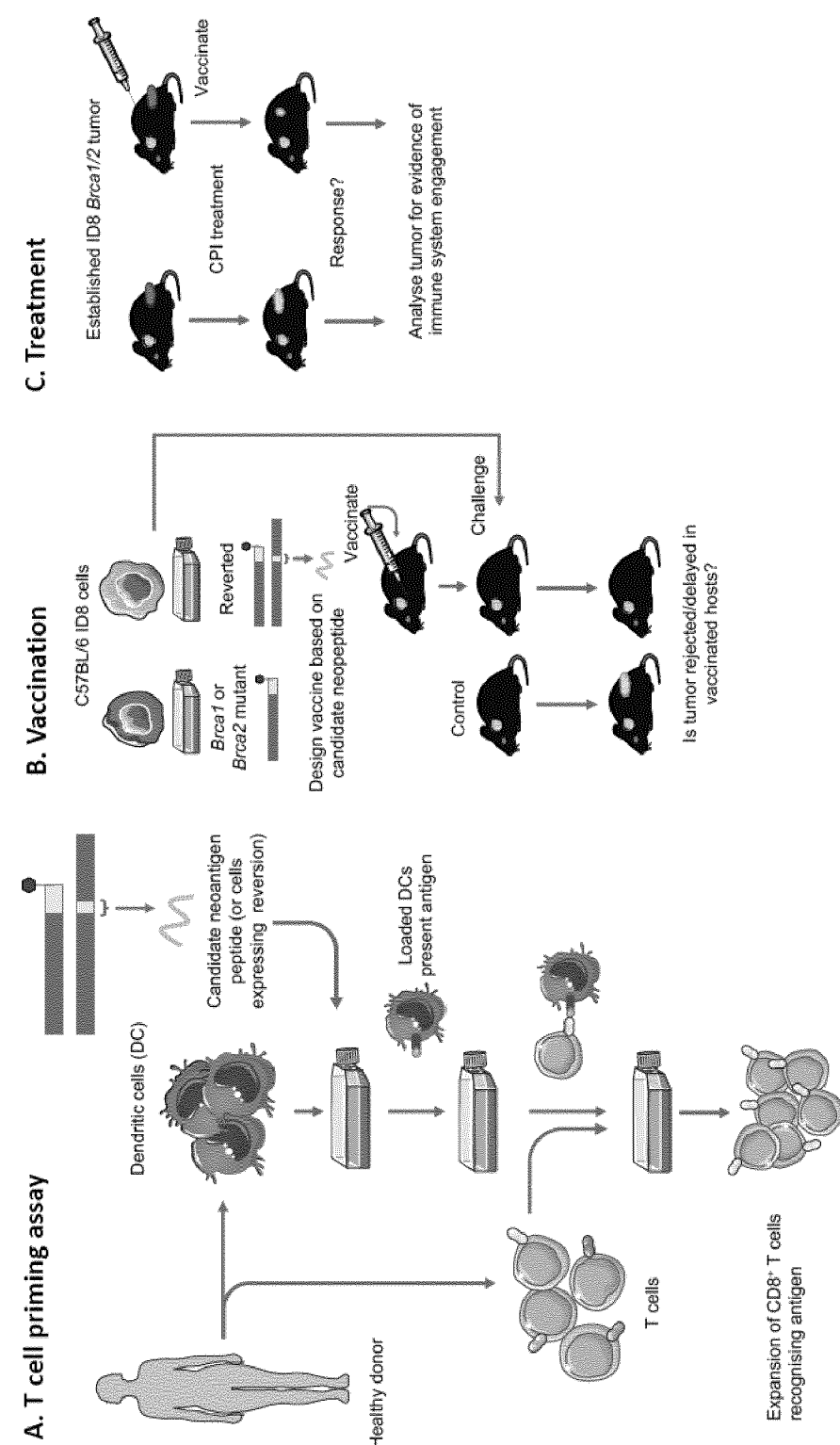
FIG. 9—Research Plan to assess the therapeutic potential of vaccinations against revertant neoantigens. A. Schematic of the T-cell priming assay to assess whether predicted neopeptides are presented as antigens. B. Experimental scheme for vaccination experiment to determine whether the immune system can be primed against reverted tumours. C. Use of vaccines and immune checkpoint inhibitors (CPI—anti-Pd1 or anti-Ctla4) to determine whether an immune-targeted therapeutic strategy would be feasible.
Figure 10:
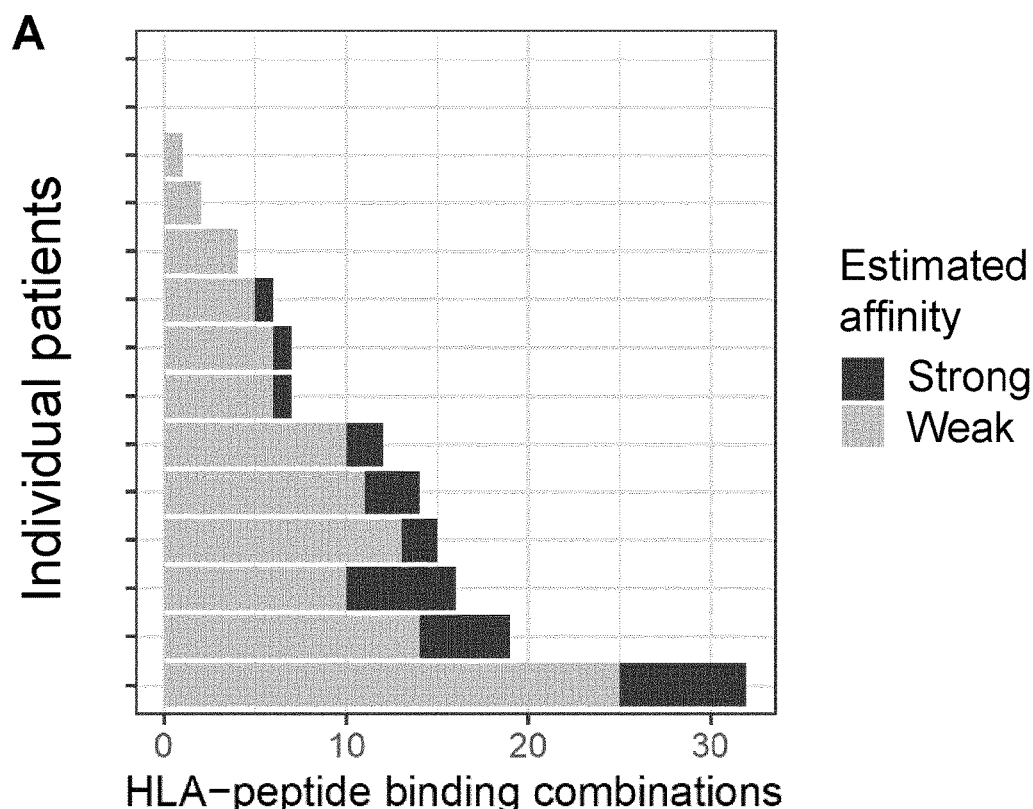
FIG. 10—(a) Individual level, HLA-matched, predictions demonstrate that reversion neopeptides are likely to bind the HLA type of patients they arise in. For each patient, potential neopeptides were identified in the detected reversion mutations and MHC binding predicted using netMHCpan-4.0 and the HLA type of patient. HLA typing used seq2HLA, Polysolver or PCR-SSO from tumour or blood depending on the data/material available. The number of strong and weak binding predictions (HLA-peptide pairs; Strong: % Rank<0.5, Weak<2.0) is plotted for each patient. 12/14 patients are predicted to present at least one neoantigen; the two without predicted presentation have reversions mediated by single nucleotide variants, all others are compensating frameshifts/deletions. (b) Pathogenic mutations in patients modelled in FIG. 10(a). These results demonstrate that reversions are likely to be presented in the patients in which they arise.
Figure 11:
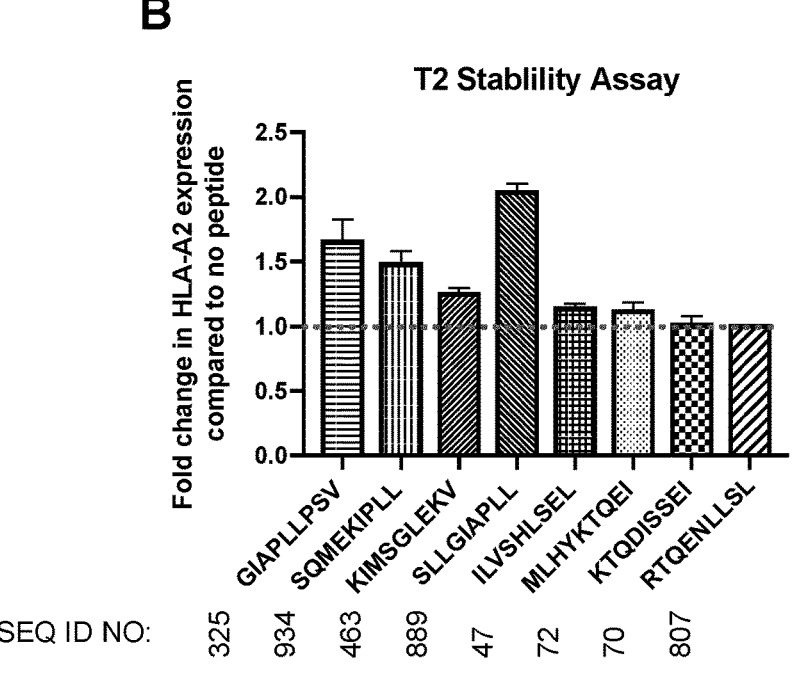
FIG. 11—Presentation of predicted reversion neopeptides by HLA-A2:01. (a) Reversion neopeptides with predicted binding for HLA-A2:01. (b) T2 cells, which express HLA-A2:01 but are defective in processing and presentation of endogenous peptide antigens, were pulsed with the indicated preprocessed synthetic peptides. Binding of these peptides stabilizes the MHC at the cell surface. Several peptides (GIA . . . , SQM . . . , KIM . . . , SLL . . . ) result in stabilization of cell surface MHC. These results provide direct "wet" experimental evidence that the predicted binding translates into actual binding to the relevant MHC.

To assess whether the neopeptides with a high predicted likelihood of MHC presentation are able to be recognised by T-cells, T-cell priming assays will be carried out (FIG. 9A). This assay will be carried out using neoantigens from a number of sources. First, 5-10 peptides for the most highly ranked predictions for candidate neoantigens observed in clinical cases of BRCA-gene reversion will be used. Healthy donor-derived dendritic cells (DC)—which are specialised antigen presenting cells—will be pulsed with synthetic peptides corresponding to the sequences to be tested. Several model systems in the laboratory where pairs of cells with reversions have been matched with their parental cells carrying the pathogenic mutation only. Two of these are cell line models with CRISPR-Cas9 engineered reversion mutations (Dréan et al. 2017) and two are PDX tumours with spontaneously arising reversions (Tutt, Lord, Pettitt et al., unpublished). Cells from these models will be used directly to load DCs from donors, including those with matched HLA types.

These loaded DCs will be mixed with matched donor T-cells. If the dendritic cells are able to prime a T-cell response against the neoantigen, T-cells with T-cell receptors that recognise the antigen will proliferate and expand in number. This can be assessed by analysis of expansion of responder CD8+ cells by FACS or for intracellular IFN-g by ELISPOT. These peptide priming assays can be based on long or shorter, HLA-restricted, peptides as previously published (Prestwich et al. 2008; Jennings et al. 2019). As a complementary approach, the MHC-bound peptides presented in these models will also be profiled directly by mass spectrometry.

Example 9—Anticancer Vaccination: Do Reversion Mutations Result in Tumour Rejection?

Several mouse tumour cell lines from inbred strains exist which can be transplanted back into hosts of the same strain as syngeneic tumour grafts. One of these—ID8, derived from an ovarian tumour—has been modified by CRISPR-Cas9 mutagenesis to make sublines with both Trp53 and Brca1 or Brca2 frameshift mutations, which closely resemble typical human BRCA1 and BRCA2 pathogenic mutations (Walton et al. 2017; Walton et al. 2016). These cells can be transplanted into C57BL/6 host mice and grown as syngeneic tumours, providing a useful model for BRCA1/2 deficient cancer. In theory these mutations should be revertible, providing an opportunity to study reversions in the context of a functional immune system. The neopeptides associated with the engineered frameshift mutations are predicted to bind the C57BL/6 H2b MHC complex.

Reversions in ID8-Brca mutant cells will be generated using an in vitro CRISPR-Cas9 mutagenesis approach that exploits guide RNAs that cause DNA breaks downstream of the pathogenic Brca-gene mutation. The inventors have previously employed this approach to generate reversions in either Capan-1 (BRCA2 mutant) or SUM149 (BRCA1 mutant) human tumour cells (Dréan et al. 2017). After verifying that the reversions retain predicted neoantigens, these tumours will be transplanted into C57BL/6 hosts with or without prior vaccination with a neoantigen epitope (FIG. 9B). If the tumour graft is rejected after vaccination, this would support the idea that vaccination at the outset of treatment could be used as a strategy to prevent establishment of revertant tumour clones. It is also possible that reverted cells will be rejected even without vaccination, as they may be more inherently immunogenic, which would in itself be informative in terms of understanding which reversion events might or might not be tolerated/recognised by the immune system. Vaccines will be mouse dendritic cell (DC) based, generated via loading of purified syngeneic DC with the predicted neopeptide, as this is likely to result in optimal antigen presentation (Hsu et al. 1996). As an alternative strategy, which may be more practical for any future clinical use, the inventors will also consider using the peptide immunised directly along with an adjuvant such as poly(I:C), which has also been a strategy used clinically (Ott et al. 2017). As a back-up strategy, if revertant ID8 cells do not establish as tumour grafts (thus precluding the assessment of vaccines), the inventors will use an alternative strategy, by generating isogenic Brca-gene mutant/revertant 4T1 mouse mammary tumour cells, that can also be used in syngeneic animal experiments.

Example 10—can Tumour Rejection be Improved by Vaccination or Immune Checkpoint Inhibition?

Finally, the inventors will also test treatment of established syngeneic tumours (with reversion mutations) with immune checkpoint inhibitors (anti-Ctla4 or anti-Pd1), with and without the reversion vaccine to further boost the host T cell response against the reverted tumour (FIG. 9C). If established tumours regress, the combination of vaccine and checkpoint inhibitor may also be considered as an effective treatment strategy for reverted tumours.

An important consideration in a vaccination strategy to prevent reversions is whether BRCA carriers might already have central immune tolerance to the out-of-frame sequence associated with reversions. In many reversion mutations there will be at least some sequence unique to the reversion mutation itself; however, most will also retain some of the out-of-frame sequence introduced by the original pathogenic mutation. This sequence would theoretically be shared with the primary tumour (in cases of somatic BRCA mutation) or with heterozygous normal cells in the body in carriers of BRCA germline mutations, and thus may have previously been exposed to the immune system during development of central tolerance. Whether this happens in practice is unknown. There is some evidence that the mutant BRCA-gene transcripts are degraded by nonsense-mediated decay and do not lead to production of stable protein; however some BRCA mutant cell lines such as Capan1 do express a truncated protein (Edwards et al. 2008). In order to unequivocally address this point, the inventors propose to assess whether healthy adult BRCA carriers have central tolerance to out-of-frame peptide sequence encoded by their germline mutant allele. This could be assessed by using the T-cell priming assay with T-cells from a BRCA carrier and peptides for the out-of-frame sequence. If T-cell clones that recognise the out-of-frame sequence have been negatively selected during development, BRCA carriers will not show a response in this assay whereas wild type donors will.

It is possible that stimulation of an immune response against reversions using a vaccine might result in development of auto-immunity in BRCA carriers in cases where the neoantigen sequence is shared between reversion and pathogenic mutations. To address this concern, the inventors will also use a recently developed mouse model carrying the mouse equivalent of the BRCA2:c.6174delT founder mutation (Brca2:c.5096delT). Vaccination of mice carrying this mutation (prior to development of any tumours) with the out-of-frame sequence from the pathogenic allele will allow observation of whether any ill effects occur.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

Afghahi, A., Timms, K. M., Vinayak, S., Jensen, K. C., Kurian, A. W., Carlson, R. W., Chang, P.-J., Schackmann, E., Hartman, A.-R., Ford, J. M., et al. (2017). Tumour BRCA1 Reversion Mutation Arising during Neoadjuvant Platinum-Based Chemotherapy in Triple-Negative Breast Cancer Is Associated with Therapy Resistance. Clin Cancer Res 23, 3365-3370.

Alsop, K., Fereday, S., Meldrum, C., deFazio, A., Emmanuel, C., George, J., Dobrovic, A., Birrer, M. J., Webb, P. M., Stewart, C., et al. (2012). BRCA mutation frequency and patterns of treatment response in BRCA mutation-positive women with ovarian cancer: a report from the Australian Ovarian Cancer Study Group. J Clin Oncol 30, 2654-2663.

Bailey, P., Chang, D. K., Nones, K., Johns, A. L., Patch, A.-M., Gingras, M.-C., Miller, D. K., Christ, A. N., Bruxner, T. J. C., Quinn, M. C., et al. (2016). Genomic analyses identify molecular subtypes of pancreatic cancer. Nature 531, 47-52.

Banda, K., Swisher, E. M., Wu, D., Pritchard, C. C., and Gadi, V. K. (2018). Somatic Reversion of Germline BRCA2 Mutation Confers Resistance to Poly(ADP-ribose) Polymerase Inhibitor Therapy. JCO Precision Oncology, 1-6.

Barber, L. J., Sandhu, S., Chen, L., Campbell, J., Kozarewa, I., Fenwick, K., Assiotis, I., Rodrigues, D. N., Reis Filho, J. S., Moreno, V., et al. (2013). Secondary mutations in BRCA2 associated with clinical resistance to a PARP inhibitor. J Pathol 229, 422-429.

Bhargava, R., Onyango, D. O., and Stark, J. M. (2016). Regulation of Single-Strand Annealing and its Role in Genome Maintenance. Trends in Genetics 32, 566-575.

Cancer Genome Atlas, N. (2012). Comprehensive molecular portraits of human breast tumours. Nature 490, 61-70.

Cancer Genome Atlas Research, N. (2011). Integrated genomic analyses of ovarian carcinoma. Nature 474, 609-615.

Carneiro, B. A., Collier, K. A., Nagy, R. J., Pamarthy, S., Sagar, V., Fairclough, S., Odegaard, J., Lanman, R. B., Costa, R., Taxter, T., et al. (2018). Acquired Resistance to Poly (ADP-ribose) Polymerase Inhibitor Olaparib in BRCA2-Associated Prostate Cancer Resulting From Biallelic BRCA2 Reversion Mutations Restores Both Germline and Somatic Loss-of-Function Mutations. JCO Precision Oncology, 1-8.

Cheng, H. H., Salipante, S. J., Nelson, P. S., Montgomery, B., and Pritchard, C. C. (2018). Polyclonal BRCA2 Reversion Mutations Detected in Circulating Tumour DNA After Platinum Chemotherapy in a Patient With Metastatic Prostate Cancer. JCO Precision Oncology, 1-5.

Christie, E. L., Fereday, S., Doig, K., Pattnaik, S., Dawson, S.-J., and Bowtell, D. D. L. (2017). Reversion of BRCA1/2 Germline Mutations Detected in Circulating Tumour DNA From Patients With High-Grade Serous Ovarian Cancer. J Clin Oncol 35, 1274-1280.

Cline, M. S., Liao, R. G., Parsons, M. T., Paten, B., Alquaddoomi, F., Antoniou, A., Baxter, S., Brody, L., Cook-Deegan, R., Coffin, A., et al. (2018). BRCA Challenge: BRCA Exchange as a global resource for variants in BRCA1 and BRCA2. PLoS Genet 14, e1007752-1007717.

Cruz, C., Castroviejo-Bermejo, M., Gutierrez-Enriquez, S., Llop-Guevara, A., Ibrahim, Y. H., Gris-Oliver, A., Bonache, S., Morancho, B., Bruna, A., Rueda, O. M., et al. (2018). RAD51 foci as a functional biomarker of homologous recombination repair and PARP inhibitor resistance in germline BRCA-mutated breast cancer. Ann Oncol 29, 1203-1210.

Davies, H., Glodzik, D., Morganella, S., Yates, L. R., Staaf, J., Zou, X., Ramakrishna, M., Martin, S., Boyault, S., Sieuwerts, A. M., et al. (2017). HRDetect is a predictor of BRCA1 and BRCA2 deficiency based on mutational signatures. Nat Med 23, 517-525.

Dréan, A., Williamson, C. T., Brough, R., Brandsma, I., Menon, M., Konde, A., Garcia-Murillas, I., Pemberton, H. N., Frankum, J., Rafiq, R., et al. (2017). Modeling Therapy Resistance in BRCA1/2-Mutant Cancers. Mol Cancer Ther 16, 2022-2034.

Edwards, S. L., Brough, R., Lord, C. J., Natrajan, R., Vatcheva, R., Levine, D. A., Boyd, J., Reis-Filho, J. S., and Ashworth, A. (2008). Resistance to therapy caused by intragenic deletion in BRCA2. Nature 451, 1111-1115.

Esashi, F., Galkin, V. E., Yu, X., Egelman, E. H., and West, S. C. (2007). Stabilization of RAD51 nucleoprotein filaments by the C-terminal region of BRCA2. Nat Struct Mol Biol 14, 468-474.

Futreal, P. A., Liu, Q., Shattuck-Eidens, D., Cochran, C., Harshman, K., Tavtigian, S., Bennett, L. M., Haugen-Strano, A., Swensen, J., Miki, Y., et al. (1994). BRCA1 mutations in primary breast and ovarian carcinomas. Science 266, 120-122.

Goodall, J., Mateo, J., Yuan, W., Mossop, H., Porta, N., Miranda, S., Perez-Lopez, R., Dolling, D., Robinson, D. R., Sandhu, S., et al. (2017). Circulating Cell-Free DNA to Guide Prostate Cancer Treatment with PARP Inhibition. Cancer Discov 7, 1006-1017.

Gornstein, E. L., Sandefur, S., Chung, J. H., Gay, L. M., Holmes, O., Erlich, R. L., Soman, S., Martin, L. K., Rose, A. V., Stephens, P. J., et al. (2018). BRCA2 Reversion Mutation Associated With Acquired Resistance to Olaparib in Estrogen Receptor-positive Breast Cancer Detected by Genomic Profiling of Tissue and Liquid Biopsy. Clin Breast Cancer 18, 184-188.

Gourraud, P.-A., Khankhanian, P., Cereb, N., Yang, S. Y., Feolo, M., Maiers, M., Rioux, J. D., Hauser, S., and Oksenberg, J. (2014). HLA diversity in the 1000 genomes dataset. PLoS ONE 9, e97282.

Grasso, C. S., Grasso, C. S., Wu, Y.-M., Wu, Y.-M., Robinson, D. R., Robinson, D. R., Cao, X., Cao, X., Dhanasekaran, S. M., Dhanasekaran, S. M., et al. (2012). The mutational landscape of lethal castration-resistant prostate cancer. Nature 487, 239-243.

Holter, S., Borgida, A., Dodd, A., Grant, R., Semotiuk, K., Hedley, D., Dhani, N., Narod, S., Akbari, M., Moore, M., et al. (2015). Germline BRCAMutations in a Large Clinic-Based Cohort of Patients With Pancreatic Adenocarcinoma. Journal of Clinical Oncology 33, 3124-3129.

Ikeda, H., Matsushita, M., Waisfisz, Q., Kinoshita, A., Oostra, A. B., Nieuwint, A. W. M., De Winter, J. P., Hoatlin, M. E., Kawai, Y., Sasaki, M. S., et al. (2003).

Genetic reversion in an acute myelogenous leukemia cell line from a Fanconi anemia patient with biallelic mutations in BRCA2. Cancer Res 63, 2688-2694.

Jurtz, V., Paul, S., Andreatta, M., Marcatili, P., Peters, B., and Nielsen, M. (2017). NetMHCpan-4.0: Improved Peptide-MHC Class I Interaction Predictions Integrating Eluted Ligand and Peptide Binding Affinity Data. J Immunol 199, 3360-3368.

Khalique, S., Pettitt, S. J., Kelly, G., Tunariu, N., Natrajan, R., Banerjee, S., and Lord, C. J. (2019). Longitudinal analysis of a secondary BRCA2 mutation using digital droplet PCR. J Pathol Clin Res.

Kondrashova, O., Nguyen, M., Shield-Artin, K., Tinker, A. V., Teng, N. N. H., Harrell, M. I., Kuiper, M. J., Ho, G.-Y., Barker, H., Jasin, M., et al. (2017). Secondary Somatic Mutations Restoring and Associated with Acquired Resistance to the PARP Inhibitor Rucaparib in High-Grade Ovarian Carcinoma. Cancer Discov 7, 984-998.

Lancaster, J. M., Wooster, R., Mangion, J., Phelan, C. M., Cochran, C., Gumbs, C., Seal, S., Barfoot, R., Collins, N., Bignell, G., et al. (1996). BRCA2 mutations in primary breast and ovarian cancers. Nat Genet 13, 238-240.

Landrum, M. J., Lee, J. M., Benson, M., Brown, G. R., Chao, C., Chitipiralla, S., Gu, B., Hart, J., Hoffman, D., Jang, W., et al. (2017). ClinVar: improving access to variant interpretations and supporting evidence. Nucleic acids research 46, D1062-D1067.

Lin, K. K., Harrell, M. I., Oza, A. M., Oaknin, A., Ray-Coquard, I., Tinker, A. V., Heiman, E., Radke, M. R., Say, C., Vo, L.-T., et al. (2019). Reversion Mutations in Circulating Tumour DNA Predict Primary and Acquired Resistance to the PARP Inhibitor Rucaparib in High-Grade Ovarian Carcinoma. Cancer Discov 9, 210-219.

Livingstone, C. D., and Barton, G. J. (1993). Protein sequence alignments: a strategy for the hierarchical analysis of residue conservation. Comput Appl Biosci 9, 745-756.

Lord, C. J., and Ashworth, A. (2016). BRCAness revisited. Nat Rev Cancer 16, 110-120.

Lord, C. J., and Ashworth, A. (2017). PARP inhibitors: Synthetic lethality in the clinic. Science 355, 1152-1158.

Marty, R., Kaabinejadian, S., Rossell, D., Slifker, M. J., van de Haar, J., Engin, H. B., de Prisco, N., Ideker, T., Hildebrand, W. H., Font-Burgada, J., et al. (2017). MHC-I Genotype Restricts the Oncogenic Mutational Landscape. Cell 171, 1272-1283.e1215.

Mayor, P., Gay, L. M., Lele, S., and Elvin, J. A. (2017). reversion mutation acquired after treatment identified by liquid biopsy. Gynecol Oncol Rep 21, 57-60.

Meijer, T. G., Verkaik, N. S., van Deurzen, C. H. M., Dubbink, H.-J., den loom, T. D., Sleddens, H. F. B. M., De Hoop, E. O., Dinjens, W. N. M., Kanaar, R., van Gent, D. C., et al. (2019). Direct Ex Vivo Observation of Homologous Recombination Defect Reversal After DNA-Damaging Chemotherapy in Patients With Metastatic Breast Cancer. JCO Precision Oncology, 1-12.

Norquist, B., Wurz, K. A., Pennil, C. C., Garcia, R., Gross, J., Sakai, W., Karlan, B. Y., Taniguchi, T., and Swisher, E. M. (2011). Secondary somatic mutations restoring BRCA1/2 predict chemotherapy resistance in hereditary ovarian carcinomas. J Clin Oncol 29, 3008-3015.

Patch, A.-M., Christie, E. L., Etemadmoghadam, D., Garsed, D. W., George, J., Fereday, S., Nones, K., Cowin, P., Alsop, K., Bailey, P. J., et al. (2015). Whole-genome characterization of chemoresistant ovarian cancer. Nature 521, 489-494.

Patel, J. N., Braicu, I., Timms, K. M., Solimeno, C., Tshiaba, P., Reid, J., Lanchbury, J. S., Darb-Esfahani, S., Ganapathi, M. K., Sehouli, J., et al. (2018). Characterisation of homologous recombination deficiency in paired primary and recurrent high-grade serous ovarian cancer. Br J Cancer 119, 1060-1066.

Pishvaian, M. J., Biankin, A. V., Bailey, P., Chang, D. K., Laheru, D., Wolfgang, C. L., and Brody, J. R. (2017). BRCA2 secondary mutation-mediated resistance to platinum and PARP inhibitor-based therapy in pancreatic cancer. Br J Cancer 116, 1021-1026.

Powell, S., Forslund, K., Szklarczyk, D., Trachana, K., Roth, A., Huerta-Cepas, J., Gabaldón, T., Rattei, T., Creevey, C., Kuhn, M., et al. (2014). eggNOG v4.0: nested orthology inference across 3686 organisms. Nucleic acids research 42, D231-239.

Punta, M., Jennings, V., Melcher, A., and Lise, S. (2019). The immunogenic potential of recurrent cancer drug resistance mutations: an in silico study. bioRxiv, 1-22.

Quigley, D., Alumkal, J. J., Wyatt, A. W., Kothari, V., Foye, A., Lloyd, P., Aggarwal, R., Kim, W., Lu, E., Schwartzman, J., et al. (2017). Analysis of Circulating Cell-Free DNA Identifies Multiclonal Heterogeneity of Reversion Mutations Associated with Resistance to PARP Inhibitors. Cancer Discov 7, 999-1005.

Sakai, W., Swisher, E. M., Jacquemont, C., Chandramohan, K. V., Couch, F. J., Langdon, S. P., Wurz, K., Higgins, J., Villegas, E., and Taniguchi, T. (2009). Functional restoration of BRCA2 protein by secondary BRCA2 mutations in BRCA2-mutated ovarian carcinoma. Cancer Res 69, 6381-6386.

Sakai, W., Swisher, E. M., Karlan, B. Y., Agarwal, M. K., Higgins, J., Friedman, C., Villegas, E., Jacquemont, C., Farrugia, D. J., Couch, F. J., et al. (2008). Secondary mutations as a mechanism of cisplatin resistance in BRCA2-mutated cancers. Nature 451, 1116-1120.

Shroff, R. T., Hendifar, A., McWilliams, R. R., Geva, R., Epelbaum, R., Rolfe, L., Goble, S., Lin, K. K., Biankin, A. V., Giordano, H., et al. (2018). Rucaparib Monotherapy in Patients With Pancreatic Cancer and a Known Deleterious Mutation. JCO Precis Oncol 2018.

Sinha, S., Villarreal, D., Shim, E. Y., and Lee, S. E. (2016). Risky business: Microhomology-mediated end joining. Mutat Res 788, 17-24.

Spurdle, A. B., Healey, S., Devereau, A., Hogervorst, F. B. L., Monteiro, A. N. A., Nathanson, K. L., Radice, P., Stoppa-Lyonnet, D., Tavtigian, S., Wappenschmidt, B., et al. (2011). ENIGMA-Evidence-based network for the interpretation of germline mutant alleles: An international initiative to evaluate risk and clinical significance associated with sequence variation in BRCA1 and BRCA2 genes. Hum Mutat 33, 2-7.

Staaf, J., Glodzik, D., Bosch, A., Vallon-Christersson, J., Reuterswärd, C., Häkkinen, J., Degasperi, A., Amarante, T. D., Saal, L. H., Hegardt, C., et al. (2019). Whole-genome sequencing of triple-negative breast cancers in a population-based clinical study. Nat Med 25, 1526-1533.

Swisher, E. M., Sakai, W., Karlan, B. Y., Wurz, K., Urban, N., and Taniguchi, T. (2008). Secondary BRCA1 mutations in BRCA1-mutated ovarian carcinomas with platinum resistance. Cancer Res 68, 2581-2586.

Ter Brugge, P., Kristel, P., van der Burg, E., Boon, U., de Maaker, M., Lips, E., Mulder, L., de Ruiter, J., Moutinho, C., Gevensleben, H., et al. (2016). Mechanisms of Therapy Resistance in Patient-Derived Xenograft Models of BRCA1-Deficient Breast Cancer. J Natl Cancer Inst 108.

Tutt, A. (2018). Inhibited, trapped or adducted: the optimal selective synthetic lethal mix for BRCAness. Annals of oncology: official journal of the European Society for Medical Oncology/ESMO 29, 18-21.

Tutt, A., Tovey, H., Cheang, M. C. U., Kernaghan, S., Kilburn, L., Gazinska, P., Owen, J., Abraham, J., Barrett, S., Barrett-Lee, P., et al. (2018). Carboplatin in BRCA1/2-mutated and triple-negative breast cancer BRCAness subgroups: the TNT Trial. Nat Med 24, 628-637.

Waddell, N., Pajic, M., Patch, A.-M., Chang, D. K., Kassahn, K. S., Bailey, P., Johns, A. L., Miller, D., Nones, K., Quek, K., et al. (2015). Whole genomes redefine the mutational landscape of pancreatic cancer. Nature 518, 495-501.

Wang, Y., Bernhardy, A. J., Cruz, C., Krais, J. J., Nacson, J., Nicolas, E., Peri, S., van der Gulden, H., van der Heijden, I., O'Brien, S. W., et al. (2016). The BRCA1-Δ11g Alternative Splice Isoform Bypasses Germline Mutations and Promotes Therapeutic Resistance to PARP Inhibition and Cisplatin. Cancer Res 76, 2778-2790.

Weigelt, B., Comino-Mendez, I., de Bruijn, I., Tian, L., Meisel, J. L., Garcia-Murillas, I., Fribbens, C., Cutts, R., Martelotto, L. G., Ng, C. K. Y., et al. (2017). Diverse and Reversion Mutations in Circulating Cell-Free DNA of Therapy-Resistant Breast or Ovarian Cancer. Clin Cancer Res 23, 6708-6720.

Yates, A., Akanni, W., Amode, M. R., Barrell, D., Billis, K., Carvalho-Silva, D., Cummins, C., Clapham, P., Fitzgerald, S., Gil, L., et al. (2016). Ensembl 2016. Nucleic acids research 44, D710-716.

Yun, M. H., and Hiom, K. (2009). CtIP-BRCA1 modulates the choice of DNA double-strand-break repair pathway throughout the cell cycle. Nature 459, 460-463.

Alsop, Kathryn, Sian Fereday, Cliff Meldrum, Anna deFazio, Catherine Emmanuel, Joshy George, Alexander Dobrovic, et al. 2012. "BRCA Mutation Frequency and Patterns of Treatment Response in BRCA Mutation-Positive Women with Ovarian Cancer: A Report from the Australian Ovarian Cancer Study Group." Journal of Clinical Oncology 30 (21): 2654-63.

Christie, Elizabeth L., Sian Fereday, Ken Doig, Swetansu Pattnaik, Sarah-Jane Dawson, and David D. L. Bowtell. 2017. "Reversion of BRCA1/2 Germline Mutations Detected in Circulating Tumour DNA From Patients With High-Grade Serous Ovarian Cancer." Journal of Clinical Oncology 35 (12): 1274-80.

Dréan, Amy, Chris T. Williamson, Rachel Brough, Inger Brandsma, Malini Menon, Asha Konde, Isaac Garcia-Murillas, et al. 2017. "Modeling Therapy Resistance in BRCA1/2-Mutant Cancers." Molecular Cancer Therapeutics 16 (9): 2022-34.

Edwards, Stacey L., Rachel Brough, Christopher J. Lord, Rachael Natrajan, Radost Vatcheva, Douglas A. Levine, Jeff Boyd, Jorge S. Reis-Filho, and Alan Ashworth. 2008. "Resistance to Therapy Caused by Intragenic Deletion in BRCA2." Nature 451 (7182): 1111-15.

Hsu, Frank J., Claudia Benike, Francesco Fagnoni, Tina Marie Liles, Debra Czerwinski, Behnaz Taidi, Edgar G. Engleman, and Ronald Levy. 1996. "Vaccination of Patients with B-cell Lymphoma Using Autologous Antigen-pulsed Dendritic Cells." Nature Medicine 2 (1) 52-58.

Jennings, Victoria A., Gina B. Scott, Ailsa M. S. Rose, Karen J. Scott, Gemma Migneco, Brian Keller, Katrina Reilly, et al. 2019. "Potentiating Oncolytic Virus-Induced Immune-Mediated Tumour Cell Killing Using Histone Deacetylase Inhibition." Molecular Therapy 27 (6): 1139-52.

Jurtz, Vanessa, Sinu Paul, Massimo Andreatta, Paolo Marcatili, Bjoern Peters, and Morten Nielsen. 2017. "NetMHCpan 4.0: Improved Peptide-MHC Class I Interaction Predictions Integrating Eluted Ligand and Peptide Binding Affinity Data." BioRXiv. https://doi.org/10.1101/149518.

Lin, Kevin K., Maria I. Harrell, Amit M. Oza, Ana Oaknin, Isabelle Ray-Coquard, Anna V. Tinker, Elena Helman, et al. 2019. "Reversion Mutations in Circulating Tumour DNA Predict Primary and Acquired Resistance to the PARP Inhibitor Rucaparib in High-Grade Ovarian Carcinoma." Cancer Discovery 9 (2): 210-19.

Lord, Christopher J., and Alan Ashworth. 2017. "PARP Inhibitors: Synthetic Lethality in the Clinic." Science 355 (6330): 1152-58.

Ott, Patrick A., Zhuting Hu, Derin B. Keskin, Sachet A. Shukla, Jing Sun, David J. Bozym, Wandi Zhang, et al. 2017. "An Immunogenic Personal Neoantigen Vaccine for Patients with Melanoma." Nature 547 (7662): 217-21.

Pettitt, Stephen J., and Christopher J. Lord. 2019. "Dissecting PARP Inhibitor Resistance with Functional Genomics." Current Opinion in Genetics & Development 54: 55-63.

Prestwich, Robin J., Fiona Errington, Elizabeth J. Ilett, Ruth S. M. Morgan, Karen J. Scott, Timothy Kottke, Jill Thompson, et al. 2008. "Tumour Infection by Oncolytic Reovirus Primes Adaptive Antitumour Immunity." Clinical Cancer Research 14 (22): 7358-66.

Punta, Marco, Victoria Jennings, Alan Melcher, and Stefano Lise. 2019. "The Immunogenic Potential of Recurrent Cancer Drug Resistance Mutations: An in Silico Study." BioRXiv https://doi.org/10.1101/845784

Sakai, Wataru, Elizabeth M. Swisher, Beth Y. Karlan, Mukesh K. Agarwal, Jake Higgins, Cynthia Friedman, Emily Villegas, et al. 2008. "Secondary Mutations as a Mechanism of Cisplatin Resistance in BRCA2—Mutated Cancers." Nature 451 (7182): 1116-20.

Tutt, Andrew, Holly Tovey, Maggie Chon U. Cheang, Sarah Kernaghan, Lucy Kilburn, Patrycja Gazinska, Julie Owen, et al. 2018. "Carboplatin in BRCA1/2-Mutated and Triple-Negative Breast Cancer BRCAness Subgroups: The TNT Trial." Nature Medicine 24 (5): 628-37.

Walton, Josephine B., Malcolm Farquharson, Susan Mason, Jennifer Port, Bjorn Kruspig, Suzanne Dowson, David Stevenson, et al. 2017. "CRISPR/Cas9-Derived Models of Ovarian High Grade Serous Carcinoma Targeting Brca1, Pten and Nf1, and Correlation with Platinum Sensitivity." Scientific Reports 7 (1): 16827.

Walton, Josephine, Julianna Blagih, Darren Ennis, Elaine Leung, Suzanne Dowson, Malcolm Farquharson, Laura A. Tookman, et al. 2016. "CRISPR/Cas9-Mediated Trp53 and Brca2 Knockout to Generate Improved Murine Models of Ovarian High-Grade Serous Carcinoma." Cancer Research 76 (20): 6118-29.

The invention claimed is:

1. An anti-cancer vaccine comprising:
   (i) at least one peptide comprising the amino acid sequence of SEQ ID NO: 934; and/or
   (ii) at least one polynucleotide encoding the at least one peptide of (i).

2. The anti-cancer vaccine of claim 1, wherein the vaccine comprises a DNA or RNA sequence encoding said peptide.

3. The anti-cancer vaccine of claim 2, wherein the DNA or RNA sequence is provided in the form of a viral vector.

4. The anti-cancer vaccine of claim 3, wherein the viral vector is an oncolytic virus.

5. The anti-cancer vaccine of claim 1, wherein said vaccine is in the form of a plurality of dendritic cells (DCs) that have been pulsed with said at least one peptide and which are capable of presenting said peptide to one or more T cells when administered to a subject.

6. The anti-cancer vaccine of claim 1, wherein the vaccine comprises 2, 3, 4, 5, 6, 7, 8, 9, 10 or more different neoantigens and/or polynucleotide encoding the different neoantigens.

7. The anti-cancer vaccine of claim 1, further comprising at least one adjuvant.

8. The anti-cancer vaccine of claim 7, wherein said at least one adjuvant is selected from: a toll-like receptor (TLR) agonist.

9. The anti-cancer vaccine of claim 1, wherein the vaccine is in the form of or in conjunction with a nanoparticle.

* * * * *